US007829286B2

(12) United States Patent
Wohlgemuth et al.

(10) Patent No.: US 7,829,286 B2
(45) Date of Patent: Nov. 9, 2010

(54) METHODS AND COMPOSITIONS FOR DIAGNOSING AND MONITORING TRANSPLANT REJECTION

(75) Inventors: Jay Wohlgemuth, Menlo Park, CA (US); Kirk Fry, Palo Alto, CA (US); Robert Woodward, Pleasanton, CA (US); Ngoc Ly, San Bruno, CA (US)

(73) Assignee: XDx, Inc., Brisbane, CA (US)

( * ) Notice: Subject to any disclaimer, the term of this patent is extended or adjusted under 35 U.S.C. 154(b) by 38 days.

(21) Appl. No.: 12/329,173

(22) Filed: Dec. 5, 2008

(65) Prior Publication Data

US 2009/0263800 A1 Oct. 22, 2009

Related U.S. Application Data

(60) Division of application No. 10/990,275, filed on Nov. 15, 2004, now abandoned, which is a division of application No. 10/131,831, filed on Apr. 24, 2002, now Pat. No. 7,026,121, which is a continuation-in-part of application No. 10/006,290, filed on Oct. 22, 2001, now abandoned.

(60) Provisional application No. 60/296,764, filed on Jun. 8, 2001.

(51) Int. Cl.
C12Q 1/68 (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 4,190,535 A | 2/1980 | Luderer et al. |
| 4,215,051 A | 7/1980 | Schroeder et al. |
| 4,350,593 A | 9/1982 | Kessler |
| 4,358,535 A | 11/1982 | Falkow et al. |
| 4,376,110 A | 3/1983 | David et al. |
| 4,582,789 A | 4/1986 | Sheldon, III et al. |
| 4,683,195 A | 7/1987 | Mullis et al. |
| 4,683,202 A | 7/1987 | Mullis |
| 4,751,001 A | 6/1988 | Saunders |
| 4,762,780 A | 8/1988 | Spector et al. |
| 4,789,630 A | 12/1988 | Bloch et al. |
| 4,800,159 A | 1/1989 | Mullis et al. |
| 4,818,418 A | 4/1989 | Saunders |
| 4,843,155 A | 6/1989 | Chomczynski |
| 4,889,818 A | 12/1989 | Gelfand et al. |
| 4,908,318 A | 3/1990 | Lerner |
| 4,946,778 A | 8/1990 | Ladner et al. |
| 4,946,952 A | 8/1990 | Kiefer |
| 4,965,188 A | 10/1990 | Mullis et al. |
| 5,053,134 A | 10/1991 | Luderer et al. |
| 5,063,162 A | 11/1991 | Kiefer |
| 5,066,584 A | 11/1991 | Gyllensten et al. |
| 5,075,216 A | 12/1991 | Innis et al. |
| 5,079,352 A | 1/1992 | Gelfand et al. |
| 5,091,310 A | 2/1992 | Innis |
| 5,120,525 A | 6/1992 | Goldenberg |
| 5,142,033 A | 8/1992 | Innis |
| 5,143,854 A | 9/1992 | Pirrung et al. |
| 5,210,015 A | 5/1993 | Gelfand et al. |
| 5,212,071 A | 5/1993 | Fearon et al. |
| 5,215,882 A | 6/1993 | Bahl et al. |
| 5,219,727 A | 6/1993 | Wang et al. |
| 5,264,351 A | 11/1993 | Harley |
| 5,278,043 A | 1/1994 | Bannwarth et al. |
| 5,310,652 A | 5/1994 | Gelfand et al. |
| 5,314,809 A | 5/1994 | Erlich et al. |
| 5,322,770 A | 6/1994 | Gelfand |
| 5,340,720 A | 8/1994 | Stetler |
| 5,346,994 A | 9/1994 | Chomczynski |
| 5,352,600 A | 10/1994 | Gelfand et al. |
| 5,374,553 A | 12/1994 | Gelfand et al. |
| 5,385,824 A | 1/1995 | Hoet et al. |
| 5,389,512 A | 2/1995 | Kwok et al. |
| 5,393,672 A | 2/1995 | Van Ness et al. |
| 5,405,774 A | 4/1995 | Abramson et al. |
| 5,407,800 A | 4/1995 | Gelfand et al. |
| 5,411,876 A | 5/1995 | Bloch et al. |
| 5,418,149 A | 5/1995 | Gelfand et al. |
| 5,420,029 A | 5/1995 | Gelfand et al. |
| 5,426,039 A | 6/1995 | Wallace et al. |

(Continued)

FOREIGN PATENT DOCUMENTS

EP 0 217 102 4/1987

(Continued)

OTHER PUBLICATIONS

European Search Report mailed Dec. 22, 2009, for EP Application No. 06770255.5 filed Dec. 5, 2007, 10 pages.

(Continued)

*Primary Examiner*—James Martinell
(74) *Attorney, Agent, or Firm*—Morrison & Foerster LLP

(57) ABSTRACT

Methods of diagnosing or monitoring transplant rejection or cytomegalovirus infection in a patient by detecting the expression level of one or more genes or surrogates derived therefrom in the patient are described. Diagnostic oligonucleotides for diagnosing or monitoring transplant rejection or cytomegalovirus infection and kits or systems containing the same are also described.

7 Claims, 19 Drawing Sheets

U.S. PATENT DOCUMENTS

| | | | |
|---|---|---|---|
| 5,445,940 A | 8/1995 | Brenner et al. |
| 5,455,170 A | 10/1995 | Abramson et al. |
| 5,459,037 A | 10/1995 | Sutcliffe et al. |
| 5,466,591 A | 11/1995 | Abramson et al. |
| 5,468,613 A | 11/1995 | Erlich et al. |
| 5,476,774 A | 12/1995 | Wang et al. |
| 5,487,970 A | 1/1996 | Rowley et al. |
| 5,487,972 A | 1/1996 | Gelfand et al. |
| 5,491,063 A | 2/1996 | Fisher et al. |
| 5,491,086 A | 2/1996 | Gelfand et al. |
| 5,501,963 A | 3/1996 | Burckhardt et al. |
| 5,506,145 A | 4/1996 | Bull et al. |
| 5,512,462 A | 4/1996 | Cheng |
| 5,514,556 A | 5/1996 | Shearer et al. |
| 5,538,848 A | 7/1996 | Livak et al. |
| 5,561,058 A | 10/1996 | Gelfand et al. |
| 5,565,339 A | 10/1996 | Bloch et al. |
| 5,569,583 A | 10/1996 | Greenberg et al. |
| 5,571,673 A | 11/1996 | Picone |
| 5,573,906 A | 11/1996 | Bannwarth et al. |
| 5,604,099 A | 2/1997 | Erlich et al. |
| 5,618,703 A | 4/1997 | Gelfand et al. |
| 5,618,711 A | 4/1997 | Gelfand et al. |
| 5,624,833 A | 4/1997 | Gelfand et al. |
| 5,635,365 A | 6/1997 | Ansari et al. |
| 5,641,864 A | 6/1997 | Gelfand |
| 5,658,744 A | 8/1997 | Ochoa et al. |
| 5,665,551 A | 9/1997 | Gelfand et al. |
| 5,674,738 A | 10/1997 | Abramson et al. |
| 5,677,152 A | 10/1997 | Birch et al. |
| 5,693,517 A | 12/1997 | Gelfand et al. |
| 5,707,807 A | 1/1998 | Kato |
| 5,716,787 A | 2/1998 | Dunn et al. |
| 5,721,351 A | 2/1998 | Levinson |
| 5,728,822 A | 3/1998 | Macfarlane |
| 5,766,585 A | 6/1998 | Evans et al. |
| 5,773,258 A | 6/1998 | Birch et al. |
| 5,789,224 A | 8/1998 | Gelfand et al. |
| 5,795,762 A | 8/1998 | Abramson et al. |
| 5,804,375 A | 9/1998 | Gelfand et al. |
| 5,807,522 A | 9/1998 | Brown et al. |
| 5,811,284 A | 9/1998 | Chang et al. |
| 5,837,832 A | 11/1998 | Chee et al. |
| 5,939,270 A | 8/1999 | Haunso et al. |
| 5,939,292 A | 8/1999 | Gelfand et al. |
| 5,958,342 A | 9/1999 | Gamble et al. |
| 5,958,688 A | 9/1999 | Eberwine et al. |
| 5,965,366 A | 10/1999 | Ochoa et al. |
| 5,968,799 A | 10/1999 | Gelfand et al. |
| 5,973,137 A | 10/1999 | Heath |
| 5,981,481 A | 11/1999 | Fearon et al. |
| 5,994,056 A | 11/1999 | Higuchi |
| 5,994,076 A | 11/1999 | Chenchik et al. |
| 6,001,611 A | 12/1999 | Will |
| 6,004,755 A | 12/1999 | Wang |
| 6,010,853 A | 1/2000 | Kanteti et al. |
| 6,020,186 A | 2/2000 | Henco et al. |
| 6,033,860 A | 3/2000 | Lockhart et al. |
| 6,040,138 A | 3/2000 | Lockhart et al. |
| 6,040,166 A | 3/2000 | Erlich et al. |
| 6,045,996 A | 4/2000 | Cronin et al. |
| 6,048,695 A | 4/2000 | Bradley et al. |
| 6,048,709 A | 4/2000 | Falb |
| 6,060,240 A | 5/2000 | Kamb et al. |
| 6,066,322 A | 5/2000 | Levinson |
| 6,066,498 A | 5/2000 | Levinson |
| 6,084,083 A | 7/2000 | Levinson |
| 6,087,112 A | 7/2000 | Dale |
| 6,087,477 A | 7/2000 | Falb et al. |
| 6,090,556 A | 7/2000 | Kato |
| 6,099,823 A | 8/2000 | Falb |
| 6,124,433 A | 9/2000 | Falb et al. |
| 6,127,155 A | 10/2000 | Gelfand et al. |
| 6,132,997 A | 10/2000 | Shannon |
| 6,146,828 A | 11/2000 | Lapidus et al. |
| 6,150,121 A | 11/2000 | Hamawy et al. |
| 6,156,887 A | 12/2000 | Levinson |
| 6,162,604 A | 12/2000 | Jacob |
| 6,168,933 B1 | 1/2001 | Kaser et al. |
| 6,171,785 B1 | 1/2001 | Higuchi |
| 6,177,254 B1 | 1/2001 | Rattner et al. |
| 6,187,534 B1 | 2/2001 | Strom et al. |
| 6,190,857 B1 | 2/2001 | Ralph et al. |
| 6,190,872 B1 | 2/2001 | Slotman |
| 6,194,158 B1 | 2/2001 | Kroes et al. |
| 6,197,563 B1 | 3/2001 | Erlich et al. |
| 6,203,987 B1 | 3/2001 | Friend et al. |
| 6,204,371 B1 | 3/2001 | Levinson |
| 6,214,979 B1 | 4/2001 | Gelfand et al. |
| 6,218,122 B1 | 4/2001 | Friend et al. |
| 6,222,093 B1 | 4/2001 | Marton et al. |
| 6,225,084 B1 | 5/2001 | Falb et al. |
| 6,225,093 B1 | 5/2001 | Grant et al. |
| 6,228,628 B1 | 5/2001 | Gelfand et al. |
| 6,242,185 B1 | 6/2001 | Kaser et al. |
| 6,245,334 B1 | 6/2001 | Seilhammer et al. |
| 6,245,526 B1 | 6/2001 | Yue et al. |
| 6,245,527 B1 | 6/2001 | Busfield et al. |
| 6,248,527 B1 | 6/2001 | Chen et al. |
| 6,248,528 B1 | 6/2001 | Chen et al. |
| 6,251,597 B1 | 6/2001 | Shyjan |
| 6,262,244 B1 | 7/2001 | Houchins et al. |
| 6,274,312 B1 | 8/2001 | Gish et al. |
| 6,280,941 B1 | 8/2001 | Tsao et al. |
| 6,303,321 B1 | 10/2001 | Tracey et al. |
| 6,306,602 B1 | 10/2001 | Sillekens et al. |
| 6,365,352 B1 | 4/2002 | Yerramilli et al. |
| 6,403,304 B1 | 6/2002 | Stashenko et al. |
| 6,410,319 B1 | 6/2002 | Raubitschek et al. |
| 6,797,263 B2 | 9/2004 | Strom et al. |
| 6,811,973 B1 | 11/2004 | Reich |
| 6,900,015 B2 | 5/2005 | Avihingsanon et al. |
| 6,905,827 B2 | 6/2005 | Wohlgemuth et al. |
| 6,964,850 B2 | 11/2005 | Bevilacqua et al. |
| 7,026,121 B1 | 4/2006 | Wohlgemuth et al. |
| 7,118,865 B2 | 10/2006 | Behrens et al. |
| 7,235,358 B2 | 6/2007 | Wohlgemuth et al. |
| 7,514,209 B2 | 4/2009 | Dai et al. |
| 2001/0021700 A1 | 9/2001 | Moore et al. |
| 2002/0042386 A1 | 4/2002 | Rosen et al. |
| 2003/0139466 A1 | 7/2003 | Peritt et al. |
| 2004/0023246 A1 | 2/2004 | Meuer et al. |
| 2004/0072181 A1 | 4/2004 | Whitehead et al. |
| 2005/0186637 A1 | 8/2005 | Yu et al. |
| 2005/0281815 A1 | 12/2005 | Eshel et al. |
| 2006/0051803 A1 | 3/2006 | Wohlgemuth et al. |
| 2006/0088836 A1 | 4/2006 | Wohlgemuth et al. |
| 2006/0216707 A1 | 9/2006 | Stuhlmuller et al. |
| 2006/0263813 A1 | 11/2006 | Rosenberg et al. |
| 2007/0037144 A1 | 2/2007 | Wohlgemuth et al. |
| 2007/0037166 A1 | 2/2007 | Wohlgemuth et al. |
| 2007/0037167 A1 | 2/2007 | Wohlgemuth et al. |
| 2007/0248978 A1 | 10/2007 | Lal et al. |
| 2008/0038746 A1 | 2/2008 | Rosenberg et al. |
| 2008/0199853 A1 | 8/2008 | Wohlgemuth et al. |

FOREIGN PATENT DOCUMENTS

| | | |
|---|---|---|
| EP | 0 217 992 | 4/1987 |
| EP | 1 077 254 | 2/2001 |
| EP | 1 162 276 | 12/2001 |
| SG | 200302150-8 | 7/2002 |
| WO | WO-91/18626 | 12/1991 |
| WO | WO-94/23023 A1 | 10/1994 |

| | | |
|---|---|---|
| WO | WO-95/17506 | 6/1995 |
| WO | WO-96/39536 | 12/1996 |
| WO | WO-97/16568 | 5/1997 |
| WO | WO-97/30065 | 8/1997 |
| WO | WO-98/24935 | 6/1998 |
| WO | WO-99/04251 A1 | 1/1999 |
| WO | WO-99/10536 | 3/1999 |
| WO | WO-99/11782 | 3/1999 |
| WO | WO-99/11822 A1 | 3/1999 |
| WO | WO-99/15700 | 4/1999 |
| WO | WO-99/52541 | 10/1999 |
| WO | WO-99/57130 | 11/1999 |
| WO | WO-00/04191 | 1/2000 |
| WO | WO-00/12753 | 3/2000 |
| WO | WO-00/23573 A3 | 4/2000 |
| WO | WO-00/29574 | 5/2000 |
| WO | WO-00/46372 | 8/2000 |
| WO | WO-00/52209 | 9/2000 |
| WO | WO-00/55375 | 9/2000 |
| WO | WO-00/58473 A2 | 10/2000 |
| WO | WO-00/63372 | 10/2000 |
| WO | WO-00/73498 A1 | 12/2000 |
| WO | WO-00/78808 | 12/2000 |
| WO | WO-01/14557 A1 | 3/2001 |
| WO | WO-01/20004 | 3/2001 |
| WO | WO-01/23426 | 4/2001 |
| WO | WO-01/23564 | 4/2001 |
| WO | WO-01/25473 | 4/2001 |
| WO | WO-01/29269 | 4/2001 |
| WO | WO-01/32927 | 5/2001 |
| WO | WO-01/40302 | 6/2001 |
| WO | WO-01/47944 | 7/2001 |
| WO | WO-01/54733 | 8/2001 |
| WO | WO-01/55164 | 8/2001 |
| WO | WO-01/55201 A1 | 8/2001 |
| WO | WO-01/55203 | 8/2001 |
| WO | WO-01/55205 | 8/2001 |
| WO | WO-01/55328 A2 | 8/2001 |
| WO | WO-01/55368 A1 | 8/2001 |
| WO | WO-01/57182 A2 | 8/2001 |
| WO | WO-01/60860 | 8/2001 |
| WO | WO-01/71005 | 9/2001 |
| WO | WO-01/81916 | 11/2001 |
| WO | WO-01/86003 | 11/2001 |
| WO | WO-02/00677 | 1/2002 |
| WO | WO-02/00928 A2 | 1/2002 |
| WO | WO-02/28999 A2 | 4/2002 |
| WO | WO-02/057414 | 7/2002 |
| WO | WO-03/072035 A2 | 9/2003 |
| WO | WO-03/090694 A2 | 11/2003 |
| WO | WO-2004/042346 A2 | 5/2004 |
| WO | WO-2004/074815 A | 9/2004 |
| WO | WO-2004/0108899 | 12/2004 |

OTHER PUBLICATIONS

Japanese Office Action mailed Jan. 15, 2010, for JP Application No. 2003-587333 filed Apr. 24, 2003, English translation 4 pages.
U.S. Appl. No. 12/628,168, filed Nov. 30, 2009 for Lal et al.
U.S. Appl. No. 12/635,438, filed Dec. 10, 2009 for Wohlgemuth et al.
Yeung, K et al. (2004). "From co-expression to co-regulation: how many microarray experiments do we need?," *Genome Biology* 5(7):R48.
Abdallah, A. N. et al. (1997). "Evaluation of Plasma Levels of Tumor Necrosis Factor Alpha and Interleukin-6 as Rejection Markers in a Cohort of 142 Heart-Grafted Patients Followed by Endomyocardial Biopsy," European Heart Journal 18:1024-1029.
Ahern, H. (Jul. 24, 1995). "Biochemical, Reagent Kits Offer Scientists Good Return on Investment," The Scientist 9(15):20-24.
Ajjan, R. A. et al. (1996). "Intrathyroidal Cytokine Gene Expression in Hashimoto's Thyroiditis," Clinical and Experimental Immunology 105:523-528.

Akalin, E. et al. (Sep. 2001). "Gene Expression Analysis in Human Renal Allograft Biopsy Samples Using High-Density Oligoarray Technology," Transplantation 72(5):948-953.
Alizadeh, A. et al. (1998). "Probing Lymphocyte Biology by Genomic-Scale Gene Expression Analysis," Journal of Clinical Immunology 18(6):373-379.
Alizadeh, A. et al. (1999)."The Lymphochip: A Specialized cDNA Microarray for the Genomic-scale Analysis of Gene Expression in Normal and Malignant Lymphocytes," Cold Spring Harbor Symposia on Quantitative Biology 54:71-78.
Alizadeh, A. et al. (2000). "Genomic-Scale Gene Expression Profiling of Normal and Malignant Immune Cells," *Current Opinion in Immunology* 12:219-225.
Alizadeh, A. et al. (Feb. 2000). "Distinct Types of Diffuse Large B-cell Lymphoma Identified by Gene Expression Profiling," Nature 403:503-511.
Alpert, S. et al. (Dec. 1995). "The Relationship of Granzyme A and Perforin Expression to Cardiac Allograft Rejection and Dysfunction," Transplantation 60(12):14781485.
Amaro et al. (1995). "Plasma Leukocyte Elastase Concentration in Angiographically Diagnosed Coronary Artery Disease," Eur Heart J 16(5): 615-622.
Arnett, F. C. et al. (Mar. 1988). "The American Rheumatism Association 1987 Revised Criteria for the Classification of Rheumatoid Arthritis," Arthritis and Rheumatism 31(3):315-324.
Aukrust et al. (1999). "Enhanced Levels of Soluble and Membrane-Bound CD40 Ligand in Patients with Unstable Angina. Possible Reflection of T Lymphocyte and Platelet Involvement in the Pathogenesis of Acute Coronary Syndromes," Circulation 100(6): 614-620.
Australian Written Opinion and Search Report mailed Oct. 7, 2005, for Singapore Application No. SG 200406287-3 filed Apr. 24, 2003, 2 pages.
Autieri, M. V. et al. (2002). "Allograft Inflammatory Factor-1 Expression Correlates with Cardiac Rejection and Development of Cardiac Allograft Vasculopathy," Circulation 106:2218-2223.
Baechler, E. C. et al. (Mar. 2003). "Interferon-Inducible Gene Expression Signature in Peripheral Blood Cells of Patients with Severe Lupus," Proceedings of the National Academy of Sciences 100(5):2610-2615.
Bakke, A. C. et al. (2001). "Neutrophil CD64 Expression Distinguishing Acute Inflammatory Autoimmune Disease from Systemic Infections," Clinical and Applied Immunology Reviews 1:267-275.
Bass, C. A. (Oct. 1993). "Clinical Evaluation of a New Polymerase Chain Reaction Assay for Detection of *Chlamydia trachomatis* in Endocervical Specimens," *Journal of Clinical Microbiology* 31(10):2648-2653.
Bave, U. (2000). "The Combination of Apoptotic U937 Cells and Lupus IgG is a Potent IFN-Alpha Inducer," The Journal of Immunology 165:3519-3526.
Bave, U. (2001). "Activation of Natural Interferon-Alpha Producing Cells by Apoptotic U937 Cells Combined with Lupus IgG and its Regulation by Cytokines," Journal of Autoimmunity 17:71-80.
Belch, J. J. F. et al. (Apr. 1997). "The White Blood Cell Adhesion Molecule E-selectin Predicts Restenosis in Patients With Intermittent Claudication Undergoing Percutaneous Transluminal Angioplasty," Circulation 95(8):2027-2031.
Benner, S. A. et al. (Jul. 2001). "Evolution, Language and Analogy in Functional Genomics," TRENDS in Genetics 17(7):414-418.
Bennett, L. et al. (Mar. 17, 2003). "Interferon and Granulopoiesis Signatures in Systemic Lupus Erythematosus Blood," *The Journal of Experimental Medicine* 197(6):711-723.
Bergholdt, R. et al. (2000). "Characterization of New Polymorphisms in the 5' UTR of the Human Interleukin-1 Receptor Type 1 (IL1R1) Gene: Linkage to Type 1 Diabetes and Correlation to IL-1R1 Plasma Level," *Genes and Immunity* 1:495-500.
Bertone, P. et al. (Dec. 24, 2004). "Global Identification of Human Transcribed Sequences with Genome Tiling Arrays," Science 306:2242-2246.
Bittner, M. et al. (Aug. 2000). "Molecular Classification of Cutaneous Malignant Melanoma by Gene Expression Profiling," Nature 406:536-540.

Boelaert, M. et al. (May 1999). "Latent Class Analysis Permits Unbiased Estimates of the Validity of DAT for the Diagnosis of Visceral Leishmaniasis," *Tropical Medicine & International Health* 4(5):395-401.

Bombardier, C. et al. (Jun. 1992). "Derivation of the SLEDAI- A Disease Activity Index for Lupus Patients," Arthritis and Rheumatism 35(6):630-640.

Bustin, S. A. (2000). "Absolute Quantification of mRNA Using Real-Time Reverse Transcription Polymerase Chain Reaction Assays," *Journal of Molecular Endocrinology* 25:169-193.

Centola, M. et al. (2006). "Genome-Scale Assessment of Molecular Pathology in Systemic Autoimmune Diseases Using Microarray Technology: A Potential Breakthrough Diagnostic and Individualized Therapy-Design Tool," *Scandinavian Journal of Immunology* 64:236-242.

Chang, D. M. et al. (1996). "Cytokines and Cell Surface Markers in Prediction of Cardiac Allograft Rejection," Immunological Investigations 25(1&2):13-21.

Chebath, J. et al. (Mar. 1987). "Four Different Forms of Interferon-induced 2', 5'-Oligo(A) Synthetase Identified by Immunoblotting in Human Cells," The Journal of Biological Chemistry 262(8):3852-2857.

Chen, J. et al. (Aug. 1996). "Identification of Differentially Expressed Genes in Rat Aortic Allograft Vasculopathy," American Journal of Pathology 149(2):597-611.

Cheung, V. et al. (Mar. 2003). "Natural Variation in Human Gene Expression Assessed in Lymphoblastoid Cells," *Nature Genetics* 33:422-425.

Creemers, P. et al. (2002). "Evaluation of Peripheral Blood CD4 and CD8 Lymphocyte Subsets, CD69 Expression and Histologic Rejection Grade as Diagnostic Markers for the Presence of Cardiac Allograft Rejection," Transplant Immunology 10:285-292.

Crow, M. K. et al. (2003). "Microarray Analysis of Gene Expression in Lupus," *Arthritis Research & Therapy* 5(6):279-287.

Damas, J. K. et al. (2001). "Enhanced Gene Expression of Chemokines and their Corresponding Receptors in Mononuclear Blood Cells in Chronic Heart Failure—Modulatory Effect of Intravenous Immunoglobin," Journal of the American College of Cardiology 38(1):187-193.

Davas, E. M. et al. (1999). "Serum IL-6, TNF-alpha, p55 srTNF-alpha, p75srTNF-alpha, srIL2-alpha Levels and Disease Activity in Systemic Lupus Erythematosus," Clinical Rheumatology 18:17-22.

Deng, M. C. et al. (Nov. 1995). "The Relation of Interleukin-6, Tumor Necrosis Factor-Alpha, IL-2, and IL-2 Receptor Levels to Cellular Rejection, Allograft Dysfunction, and Clinical Events Early After Cardiac Transplantation," Transplantation 60(10):1118-1124.

Deuel, T. F. et al. (Jun. 1977). "Amino Acid Sequence of Human Platelet Factor 4," Proceedings of the National Academy of Sciences 74(6):2256-2258.

Deuel, T. F. et al. (Jul. 1981). "Platelet Factor 4 is Chemotactic for Neutrophils and Monocytes," Proceedings of the National Academy of Sciences 78(7):4584-4587.

Dietz, A. B. et al. (2000). "Maturation of Human Monocyte-Derived Dendritic Cells Studied by Microarray Hybridization," Biochemical and Biophysical Research Communications 275:731-738.

Doi, S. et al. (1994). "Polymerase Chain Reaction Quantification of Cytokine Messenger RNA Expression in Peripheral Blood Monoculear Cells of Patients with Acute Exacerbations of Asthma: Effect of Glucocorticoid Therapy," Clinical and Experimental Allergy 24:854-867.

Dozmorov, M. G. et al. (2007). "5α-Androstane-3α,17β-Diol Selectively Activates the Canonical PI3K/AKT Pathway: A Bioinformatics-Based Evidence for Androgen-Activated Cytoplasmic Signaling," *Genomic Medicine* 1:139-146.

Dudek, A. Z. et al. (Jun. 2003). "Platelet Factor 4 Promotes Adhesion of Hennatopoietic Progenitor Cells and Binds IL-8: Novel Mechanisms for Modulation of Hematopoiesis," Blood 101(12):4687-4694.

Dugre, F. J. (Oct. 2000). "Cytokine and Cytotoxic Molecule Gene Expression Determined in Peripheral Blood Mononuclear Cells in the Diagnosis of Acute Renal Rejection," Transplantation 70(7):1074-1080.

Edman, C. F. et al. (1997). "Electric Field Directed Nucleic Acid Hybridization on Microchips," Nucleic Acids Research 25(24):4907-4914.

Eisen, M. B. et al. (Dec. 1998). "Cluster Analysis and Display of Genome-Wide Expression Patterns," Proceedings of the National Academy of Sciences 95:14863-14868.

EMBL-EBI Accession No. AA053887, last updated Aug. 31, 2006, located at <http://www.ebi.ac.uk/cgi-bin/dbfetch?db=embl&id=AA053887&style=raw> visited on Oct. 31, 2007. (3 pages).

EMBL-EBI Accession No. AAC77576, located at <http://www.ebi.ac.uk/cgi-bin/dbfetch?db=emblcds&id=AAC77576&style=raw> visited on Oct. 31, 2007. (1 page).

EMBL-EBI Accession No. AAK80490, located at <http://www.ebi.ac.uk/cgi-bin/dbfetch?db=emblcds&id=AAK80490&style=raw> visited on Oct. 31, 2007. (1 page).

EMBL-EBI Accession No. AI775145, last updated Jun. 21, 2002, located at <http://www.ebi.ac.uk/cgi-bin/dbfetch?db=embl&id=AI755145&style=raw> visited on Oct. 31, 2007. (2 pages).

EMBL-EBI Accession No. AK000354, last updated Sep. 12, 2006, located at <http://www.ebi.ac.uk/cgi-bin/dbfetch?db=embl&id=AK000354&style=raw> visited on Oct. 31, 2007. (3 pages).

EMBL-EBI Accession No. AV742425, last updated Oct. 10, 2000, located at <http://www.ebi.ac.uk/cgi-bin/dbfetch?db=embl&id=AV742425&style=raw> visited on Oct. 31, 2007. (2 pages).

EMBL-EBI Accession No. AW969353, last updated Jun. 8, 2000, located at <http://www.ebi.ac.uk/cgi-bin/dbfetch?db=embl&ic1=AW969353&style=raw> visited on Oct. 31, 2007. (1 page).

EMBL-EBI Accession No. G06338, last updated Mar. 4, 2000, located at <http://www.ebi.ac.uk/cgi-bin/dbfetch?db=embl&id=G06338&style=raw> visited on Oct. 31, 2007. (2 pages).

EMBL-EBI Accession No. L26474, last updated Jan. 9, 2007, located at <http://www.ebi.ac.uk/cgi-bin/dbfetch?db=embl&id=L26474&style=raw> visited on Oct. 31, 2007. (6 pages).

EMBL-EBI Accession No. M23068, last updated Nov. 14, 2006, located at <http://www.ebi.ac.uk/cgi-bin/dbfetch?db=embl&id=M23068&style=raw> visited on Oct. 31, 2007. (2 pages).

EMBL-EBI Accession No. V00497, last updated Nov. 20, 2004, located at <http://www.ebi.ac.uk/cgi-bin/dbfetch?db=embl&id=V00497&style=raw> visited on Oct. 31, 2007. (5 pages).

Fandrey, J. et al. (Feb. 1, 1993). "In Vivo and In Vitro Regulation of Erythropoietin mRNA: Measurement by Competitive Polymerase Chain Reaction," *Blood* 81(3):617-623.

Felson, D. T. et al. (Jun. 1995). "American College of Rheumatology. Preliminary Definition of Improvement in Rheumatoid Arthritis," Arthritis and Rheumatism 38(6):727-735.

Finger, L. R. et al. (1997). "The Human PD-1 Gene: Complete cDNA, Genomic Organization, and Developmentally Regulated Expression in B cell Progenitors," Gene 197:177-187.

Flechner, S. M. et al. (2004). "Kidney Transplant Rejection and Tissue Injury by Gene Profiling of Biopsies and Peripherals Blood Lymphocytes," *American Journal of Transplantation* 4:1475-1489.

Fu, G. et al. (2002). "Representational Difference Analysis in a Lupus-Prone Mouse Strain Results in the Identification of an Unstable Region of the Genome on Chromosome 11," Nucleic Acids Research 30(6):1394-1400.

Fullerton, S. M. et al. (Mar. 1994). "Molecular and Population Genetic Analysis of Allelic Sequence Diversity at the Human Beta-Globin Locus," Proceedings of the National Academy of Sciences 91:1805-1809.

Gabay, C. et al. (1997). "Circulating Levels of Tumor Necrosis Factor Soluble Receptors in Systemic Lupus Erythematosus are Significantly Higher than in other Rheumatic Diseases and Correlate with Disease Activity," The Journal of Rheumatology 24(2):303-308.

Galon, J. et al. (Jan. 2002). "Gene Profiling Reveals Unknown Enhancing and Suppressive Actions of Glucocorticoids on Immune Cells," *The FASEB Journal* 16:61-71.

GenBank Accession No. AL591031 located at http://www.ncbi.nlm.nih.gov/ientrez/viewer.fcgi?db=nuccore&id=16073692 visited on Jun. 27, 2007. (41 pages).

GenBank Accession No. Y10376, last updated May 14, 1997, located at <http://www.ncbi.nlm.nih.govientrez/viewer.fcgi?db=nuccore&id=2052057> visited on Apr. 8, 2008, 3 pages.

Ghosh, A. et al. (Jul. 2001). "A Specific Isozyme of 2'-5' Oligoadenylate Synthetase Is a Dual Function Proapoptotic Protein of the Bcl-2 Family," The Journal of Biological Chemistry 276(27):25477-25455.

Glynne, R. et al. (2000). "B-Lymphocyte Quiescence, Tolerance and Activation as Viewed by Global Gene Expression Profiling on Microarrays," *Immunological Reviews* 176:216-246.

Glynne, R. J. et al. (2000). "Genomic-Scale Gene Expression Analysis of Lymphocyte Growth, Tolerance and Malignancy," *Current Opinion in Immunology* 12:210-214.

Golden-Mason, L. et al. (2000). "Differential Expression of Lymphoid and Myeloid Markers on Differentiating Hematopoietic Stem Cells in Normal and Tumor-Bearing Adult Human Liver," Hepatology 31(6):1251-1256.

Golub, T. R. et al. (Oct. 1999). "Molecular Classification of Cancer: Class Discovery and Class Prediction by Gene Expression Monitoring," Science 286:531-537.

Gorcynski, R. M. (1996). "Correlation of Peripheral Blood Lymphocyte and Intragraft Cytokine mRNA Expression with Rejection in Orthotopic Liver Transplantation," Surgery 120(3):496-502.

Grant, S. C. D. et al. (Aug. 1996). "Serum Cytokines in Human Heart Transplant Recipients," Transplantation 62(4):480-491.

Griffiths, G. M. et al. (1991). "Granzyme A and Perforin as Markers for Rejection in Cardiac Transplantation," European Journal of Immunology 21:687-692.

Gullestad, L. et al. (1999). "Effect of High- Versus Low-Dose Angiotensin Converting Enzyme Inhibition on Cytokine Levels in Chronic Heart Failure," Journal of the American College of Cardiology 34(7):2061-2067.

Harlow, E. et al. (1988). Antibodies: A Laboratory Manual, Cold Spring Harbor Laboratory: New York, NY, 9 pages. (Table of Contents).

Hastie, T. et al. (Aug. 2000). "'Gene Shaving' as a Method for Identifying Distinct Sets of Genes with Similar Expression Patterns," Genome Biology 1(2):research0003.1-0003.21.

Hastie, T. et al. (Jan. 2001). "Supervised Harvesting of Expression Trees," Genome Biology 2(1):research0003.1-0003.12.

Hayward, A. L. et al. (1998). "Modeling and Analysis of Competitive RT-PCR," *Nucleic Acids Research* 26(11):2511-2518.

Hayward-Lester, A. et al. (1995). "Accurate and Absolute Quantitative Measurement of Gene Expression by Single Tube RT-PCR and HPLC," *Genome Research* 5:494-499.

Heller, R. A. et al. (Mar. 1997). "Discovery and Analysis of Inflammatory Disease-Related Genes Using cDNA Microarrays," Proceedings of the National Academy of Sciences 94:2150-2155.

Hendricks, D. A. et al. (Nov. 1995). "Quantitation of HBV DNA in Human Serum Using a Branched DNA (bDNA) Signal Amplification Assay," American Journal of Clinical Pathology 104 (5):537-546.

Higuchi, K. et al. (1998). "Serum 2'-5' Oligoadenylate Synthetase Activity in Children. 2. Serum 2'-5' Oligoadenylate Synthetase in Childhood Collagen Disease," Chemical Abstracts 129(26):406 (342625a).

Hooks, J. J. et al. (1979). "Immune Interferon in the Circulation of Patients with Autoimmune Disease," The New England Journal of Medicine 301(1):5-8.

Hooks, J. J. et al. (Apr. 1982). "Multiple Interferons in the Circulation of Patients with Systemic Lupus Erythematosus and Vasculitis," Arthritis and Rheumatism 25(4):396-400.

Horwitz, P. A. et al. (2004). "Detection of Cardiac Allograft Rejection and Response to Immunosuppressive Therapy with Peripheral Blood Gene Expression," *Circulation* 110:3815-3821.

Hsieh, H.-G. et al. (2001). "IL-17 Expression as a Possible Predictive Parameter for Subclinical Renal Allograft Rejection," Transplant International 14:287-298.

Iida, K. et al. (May 1982). "Complement Receptor (CR1) Deficiency in Erythrocytes from Patients with Systemic Lupus Erythematosus," The Journal of Experimental Medicine 155:1427-1438.

Ing, N. H. (2005). "Steroid Hormones Regulate Gene Expression Posttranscriptionally by Altering the Stabilities of Messenger RNAs," *Biology of Reproduction* 72:1290-1296.

International Search Report and Written Opinion mailed Mar. 27, 2008, for PCT Application No. PCT/US05/31806 filed Sep. 8, 2005, 14 pages.

International Search Report mailed Mar. 1, 2001, for PCT Application No. PCT/US00/17846 filed Jun. 28, 2000, 2 pages.

International Search Report mailed Jul. 18, 2002, for PCT Application No. PCT/US01/47856 filed Oct. 22, 2001, 3 pages.

International Search Report mailed Sep. 30, 2004, for PCT Application No. PCT/US03/13015 filed Apr. 24, 2003, 4 pages.

International Search Report mailed Sep. 23, 2005, for PCT Application No. PCT/US03/12946 filed Apr. 24, 2003, 3 pages.

International Search Report and Written Opinion mailed Aug. 25, 2008, for PCT Application No. PCT/US07/08909 filed Apr. 9, 2007, 10 pages.

International Search Report and Written Opinion mailed Jun. 25, 2008, for PCT Application No. PCT/US06/18381 filed May 11, 2006, 8 pages.

International Search Report and Written Opinion mailed Sep. 10, 2008, for PCT Application No. PCT/US07/18135 filed Aug. 14, 2007, 12 pages.

Invitation to Pay Additional Fees mailed Apr. 27, 2009, for PCT Application No. PCT/US2007/023675 filed Nov. 9, 2007, 6 pages.

Jagota, A. (2000). "Nearest Neighbor Classifiers" Chapter 11 in Data Analysis and Classification for Bioinformatics. Department of Computer Science, University of California, Santa Cruz, pp. 92-93.

Japanese Notice of Reasons for Rejection mailed on Apr. 27, 2009 for Japanese Patent Application No. 2004-549874 filed on Apr. 24, 2003 , 9 pages. [English Translation only].

Japanese Notice of Reasons for Rejection mailed on May 26, 2009 for Japanese Patent Application No. 2003-587333 filed on Apr. 24, 2003, 15 pages.

Jardi, M. et al. (1994). "Urokinase Receptor (UPAR) Expression During Hematopoietic Maturation," Journal of Drug Targeting 8(Suppl 1):51.

Joulin, V. et al. (Oct. 25, 1988). "Isolation and Characterization of the Human 2,3-Bisphosphoglycerate Mutase Gene," The Journal of Biological Chemistry 263(30):15785-15790.

Jude, B. et al. (Oct. 1994). "Evidence for Time-Dependent Activation of Monocytes in the Systemic Circulation in Unstable Angina but Not in Acute Myocardial Infarction or in Stable Angina," Circulation 90(4): 1662-1668.

Kang, J. et al. (2000). "Transcript Quantitation in Total Yeast Cellular RNA Using Kinetic PCR," Nucleic Acids Research 28(2):e2, 8 pages.

Kasprzycka, M. et al. (2002). "Expression of FasL gene in T cells of Renal Allograft Recipients," Immunology Letters 80:9-13.

Kassirer, M. et al. (Sep. 1999). "Increased Expression of the CD11b/CD18 Antigen on the Surface of Peripheral White Blood Cells in Patients with Ischemic Heart Disease: Further Evidence for Smoldering Inflammation in Patients with Atherosclerosis," American Heart Journal 138(3):555-559.

Katz, M. H. (1999). "Assumptions of Multiple Linear Regression, Multiple Logistic Regression, and Proportional Hazards Analysis" Chapter 5 In Multivariable Analysis: A Practical Guide for Clinicians. Cambridge University Press: Cambridge, United Kingdom, pp. 36-42.

Kaufman, D. B. et al. (1997). "Functional Significance of Donor Islet Interleukin-1 Receptor Type 1 (IL-1Rt1) Expression in Islet Transplantation," *Transplantation Proceedings* 29:772773.

Keembiyehetty, C. et al. (Mar. 2006). "Mouse Glucose Transporter 9 Splice Variants Are Expressed in Adult Liver and Kidney and Are Up-regulated in Diabetes," *Molecular Endocrinology* 20(3):686-697.

Kelsen, S. et al. (2004). "The Chemokine Receptor CXCR3 and its Splice Variant are Expressed in Human Airway Epithelial Cells," *American Journal of Physiology-Lung Cellular and Molecular Physiology* 287:L584-L591.

Kendler, K. S. et al. (Jun. 1998). "The Structure of Psychosis Latent Class Analysis of Probands from the Roscommon Family Study," *Archives of General Psychiatry* 55:492-499.

Khan, J. et al. (Jun. 2001). "Classification and Diagnostic Prediction of Cancers Using Gene Expression Profiling and Artificial Neural Networks," Nature Medicine 7(6):673-679.

Kimball, P. et al. (Feb. 1995). "Cytokine Panel Predicts Early Rejection of Therapeutic Response After Cardiac Transplantation," Transplantation Proceedings 27(1):1286-1287.

Kirou, K. A. et al. (Dec. 2004). "Coordinate Overexpression of Interferon-?-Induced Genes in Systemic Lupus Erythematosus," *Arthritis & Rheumatism* 50(12):3958-3967.

Kobashigawa, J. et al. (Aug. 1998). "A Randomized Active-Controlled Trial of Mycophenolate Mofetil in Heart Transplant Recipients," Transplantation 66(4):507-515.

Krause, S. W. (1998). "Carboxypeptidase M as a Marker of Macrophage Maturation," Immunological Reviews 161:119-127.

Kumar, R. et al. (Oct. 1994). "Cell Cycle-Dependent Modulation of Alpha-Interferon-Inducible Gene Expression and Activation of Signaling Components in Daudi Cells," The Journal of Biological Chemistry 269(41):25437-25441.

Kumar, S. et al. (2000). "Expansion and Molecular Evolution of the Interferon-Induced 2'-5' Oligoadenylate Synthetase Gene Family," Molecular Biology and Evolution 17(5):738-750.

Le Naour, F. et al. (May 25, 2001). "Profiling Changes in Gene Expression during Differentiation and Maturation of Monocyte-Derived Dendritic Cells Using Both Oligonucleotide Microarrays and Proteomics," The Journal of Biological Chemistry 276(21):17920-17931.

Lee, M.-T. et al. (Aug. 29, 2000). "Importance of Replication in Microarray Gene Expression Studies: Statistical Methods and Evidence from Repetitive cDNA Hybridizations," *Proceedings of the National Academy of Sciences* 97(18):9834-9839.

Legros-Maida, S. et al. (1994). "Granzyme B and Perforin Can Be Used as Predictive Markers of Acute Rejection in Heart Transplantation," European Journal of Immunology 24:229-233.

Li, B. et al. (Mar. 2001). "Noninvasive Diagnosis of Renal-Allograft Rejection by Measurement of Messenger RNA for Perforin and Granzyme B in Urine," The New England Journal of Medicine 344(13):947-954.

Liossis, S-N. C. (Mar. 2001). "B-cell Kinase Lyn Deficiency in Patients with Systemic Lupus Erythematosus," Journal of Investigative Medicine 49(2):157-165.

Loftus, B. J. et al. (1999). "Genome Duplications and Other Features in 12 Mb of DNA sequence from Human Chromosome 16p and 16q," Genomics 60:295-308.

Magnusson, M. et al. (2001). "Importance of CpG Dinucleotides in Activation of Natural IFN-Alpha-Producing Cells by a Lupus-Related Oligodeoxynucleotide," Scandinavian Journal of Immunology 54:543-550.

Mandel, M. et al. (2006). "Gene Expression Studies in Systemic Lupus Erythematosus," Lupus 15:451-456.

Mansfield, E. S. et al. (2004). "Arraying the Orchestration of Allograft Pathology," *American Journal of Transplantation* 4:853-862.

Marcelin, A.-G. et al. (Nov. 2001). "Effects of Cyclosporine and Hydrocortisone on Kaposi's Sarcoma-Associated Herpesvirus Genome Replication and Cell Apoptosis Induction," Transplantation 72(10):1700-1708.

Marrack, P. et al. (2000). "Genomic-Scale Analysis of Gene Expression in Resting and Activated T Cells," *Current Opinion in Immunology* 12:208-209.

Metler, M. et al. (Nov. 2001). "Expression of the Chemokine Receptor CXCR3 and Its Ligand IP-10 During Human Cardiac Allograft Rejection," Circulation 104:2558-2564.

Mohler III, E. R. et al. (Jul. 1997). "Role of Cytokines in the Mechanism of Action of Amlodipine: The PRAISE Heart Failure Trial," Journal of the American College of Cardiology 30(1):35-41.

Morita, K. et al. (2001). "Early Chemokine Cascades in Murine Cardiac Grafts Regulate T Cell Recruitment and Progression of Acute Allograft Rejection," The Journal of Immunology 167:2979-2984.

Morris, D. L. et al. (Feb. 1997). "Immunophenotyping Analysis of Peripheral Blood, Splenic, and Thymic Lymphocytes in Male and Female Rats," Journal of Pharmacological and Toxicological Methods 37(1): 37-46.

Neto, E. D. et al. (Mar. 2000). "Shotgun Sequencing of the Human Transcriptome with ORF Expressed Sequences Tags," Proceedings of the National Academy of Sciences 97(7):3491-3496.

Newton, M. A. et al. (2001). "On Differential Variability of Expression Ratios: Improving Statistical Inference about Gene Expression Changes from Microarray Data," *Journal of Computational Biology* 8(1):37-52.

Nickel, P. et al. (Sep. 2001). "Cytotoxic Effector Molecule Gene Expression in Acute Renal Allograft Rejection" Transplantation 72(6):1158-1161.

OH, S.-I. et al. (Apr. 2001). "Correlation of Fas and Fas Ligand Expression with Rejection Status of Transplanted Heart in Human," Transplantation 71(7):906-909.

Perou, C. M. et al. (Aug. 2000). "Molecular Portraits of Human Breast Tumours," Nature 406:747-752.

Pickles, A. et al. (1995). "Latent-Class Analysis of Recurrence Risks for Complex Phenotypes with Selection and Measurement Error: A Twin and Family History Study of Autism," *American Journal of Human Genetics* 57:717-726.

Preble, O. T. et al. (Apr. 1982). "Systemic Lupus Erythematosus: Presence in Human Serum of an Unusual Acid-Labile Leukocyte Interferon," Science 216:429-431.

Pruitt, K. D. et al. (Jan. 2000). "Introducing RefSeq and LocusLink: Curated Human Genome Resources at the NCBI," Trends in Genetics 16(1):44-47.

Quattrone, A. et al. (1995). "Quantitation of bcl-2 Oncogene in Cultured Lymphoma/Leukemia Cell Lines and in Primary Leukemia B-Cells by a Highly Sensitive RT-PCR Method," *Haematologica* 80:495-504.

Raychaudhuri, S. et al. (May 2001). "Basic Microarray Analysis: Grouping and Feature Reduction," Trends in Biotechnology 19(5):189-193.

Rebouillat, D. et al. (Jan. 1999). "The 100-kDa 2',5'-Oligoadenylate Synthase Catalyzing Preferentially the Synthesis of Dimeric pppA2'p5'A Molecules Is Composed of Three Homologous Domains," The Journal of Biological Chemistry 274(3):1557-1565.

Ross, S. D. et al. (1999). "Reduced Neutrophil Infiltration Protects Against Lung Reperfusion Injury After Transplantation," The Annals of Thoracic Surgery 67: 1428-1434.

Rus, V. et al. (Mar. 2002). "Expression of Cytokine- and Chemokine-Related Genes in Peripheral Blood Mononuclear Cells from Lupus Patients by cDNA Array," Clinical Immunology 102(3):283-290.

Saiura, A. et al. (Jul. 2001). "A Comparison of Gene Expression in Murine Cardiac Allografts and Isografts by Means DNA Microarray Analysis," Transplantation 72(2):320-329.

Salmon, J. E. et al. (Mar. 1996). "Fc-gamma-RIIA Alleles are Heritable Risk Factors for Lupus Nephritis in African Americans," The Journal of Clinical Investigation 97(5):1348-1354.

Schena, M. et al. (Oct. 1995). "Quantitative Monitoring of Gene Expression Patterns with a Complementary DNA Microarray," Science 270:467-470.

Schena, M. et al. (Oct. 1996). "Parallel Human Genome Analysis: Microarray-based Expression Monitoring of 1000 Genes," Proceedings of the National Academy of Sciences 93:10614-10619.

Schowengerdt, K. O. et al. (May 2000). "Increased Expression of the Lymphocyte Early Activation Marker CD69 in Peripheral Blood Correlates with Histologic Evidence of Cardiac Allograft Rejection," Transplantation 69(10):2102-2107.

Seiter, S. et al. (1998). "CD44 Variant Isoform Expression in a Variety of Skin-Associated Autoimmune Diseases," *Clinical Immunology and Immunopathology* 89(1):79-93.

Sharma, V. K. et al. (Dec. 1996). "Molecular Executors of Cell Death-Differential Intrarenal Expression of Fas Ligand, Fas, Granzyme B, and Perforin During Acute and/or Chronic Rejection of Human Renal Allografts," Transplantation 62(12):1860-1866.

Shin, Y. K. et al. (Apr. 2001). "Expression of Leukemia-Associated Antigen, JL1, in Bone Marrow and Thymus," American Journal of Pathology 158(4):1473-1480.

Shirali, G. S. et al. (May 2001). "Association of Viral Genome with Graft Loss in Children after Cardiac Transplantation," The New England Journal of Medicine 344(20):1498-1503.

Shoker, A. et al. (Aug. 2000). "Heightened CD40 Ligand Gene Expression in Peripheral CD4+ T Cells from Patients with Kidney Allograft Rejection" Transplantation 70(3):497-505.

Shou-Nee, S. et al. (1987). "Serum Interferon in Systemic Lupus Erythematosus," British Journal of Dermatology 117:155-159.

Shulzhenko, N. et al. (2001). "Monitoring of Intragraft and Peripheral Blood TIRC7 Expression as a Diagnostic Tool for Acute Cardiac Rejection in Humans," Human Immunology 62:342-347.

Shulzhenko, N. et al. (Nov. 2001). "Intragraft Activation of Genes Encoding Cytotoxic T Lymphocyte Effector Molecules Precedes the Histological Evidence of Rejection in Human Cardiac Transplantation," Transplantation 72(10):1705-1708.

Smith, A. D. et al. eds. (1997). Oxford Dictionary of Biochemistry and Molecular Biology. Oxford University Press, Oxford, New York, p. 618.

Smith-Norowitz, T. A. et al. (Nov. 1999). "Lymphocyte Activation in Angina Pectoris," Clinical Immunology 93(2):168-175.

Staudt, L. M. et al. (2000). "Genomic Views of the Immune System," Annual Review of Immunology 18:829-859.

Stellrecht, C. M. et al. (1991). "Expression Pattern of a Hematopoietic Proteoglycan Core Protein Gene During Human Hematopoiesis," Differentiation 48:127-135.

Stites, D. P. et al. eds. (1991). Basic and Clinical Immunology. 7th Edition, Appleton & Lange: East Norwalk, CT, 6 pages (Table of Contents).

Strehlau, J. et al. (Jan. 1997). "Quantitative Detection of Immune Activation Transcripts as a Diagnostic Tool in Kidney Transplantation," Proceedings of the National Academy of Sciences 94:695-700.

Supplemental Partial European Search Report mailed Jul. 9, 2007, for EP Application No. 01997055.7 filed Oct. 22, 2001, 6 pages.

Supplementary European Search Report mailed Oct. 18, 2007, for EP Application No. 03799755.8 filed Apr. 24, 2003, 17 pages.

Tamayo, P. et al. (Mar. 1999). "Interpreting Patterns of Gene Expression with Self-Organizing Maps: Methods and Application to Hematopoietic Differentiation," Proceedings of the National Academy of Sciences 96:2907-2912.

Tan, E. M. et al. (Nov. 1982). "The 1982 Revised Criteria for the Classification of Systemic Lupus Erythematosus," Arthritis and Rheumatism 25(2):1271-1277.

Tan, L. et al. (Mar. 2001). "Sequential Monitoring of Peripheral T-Lymphocyte Cytokine Gene Expression in the Early Post Renal Allograft Period," Transplantation 71(6): 751-759.

Tanaka, J. et al. (1995). "Cytokine Receptor Gene Expression in Peripheral Blood Mononuclear Cells During Graft-Versus-Host Disease After Allogeneic Bone Marrow Transplantation," Leukemia and Lymphoma 19:281-287.

Thomas, E. et al. (Jul. 2000). "Subtyping of Juvenile Idiopathic Arthritis Using Latent Class Analysis," Arthritis & Rheumatism 43(7):1496-1503.

Tibshirani, R. et al. (May 2002). "Diagnosis of Multiple Cancer Types by Shrunken Centroids of Gene Expression," Proceedings of the National Academy of Sciences 99(1):6567-6572.

Toogood, G. J. et al. (Sep. 1996). "The Immune Response Following Small Bowel Transplantation," Transplantation 62(6):851-855.

Toronen, P. et al. (1999). "Analysis of Gene Expression Data Using Self-Organizing Maps," FEBS Letters 451:142-146.

Torre-Amione, G. et al. (Apr. 1996). "Proinflammatory Cytokine Levels in Patients with Depressed Left Ventricular Ejection Fraction: A Report from the Studies of Left Ventricular Dysfunction (SOLVD)," Journal of the American College of Cardiology 27(5):1201-1206.

Tsutamoto, T. et al. (Mar. 2000). "Angiotensin II Type 1 Receptor Antagonist Decreases Plasma Levels of Tumor Necrosis Factor Alpha, Interleukin-6 and Soluble Adhesion Molecules in Patients with Chronic Heart Failure," Journal of the American College of Cardiology 35(3):714-721.

Tusher, V. G. et al. (Apr. 2001). "Significance Analysis of Microarrays Applied to the Ionizing Radiation Response," Proceedings of the National Academy of Sciences 98(9):5116-5121.

Umek, R. M. et al. (May 2001). "Electronic Detection of Nucleic Acids: A Versatile Platform for Molecular Diagnostics," Journal of Molecular. Diagnostics 3(2):74-84.

U.S. Appl. No. 10/512,028, filed Apr. 14, 2006 for Wohlgemuth et al.
U.S. Appl. No. 11/938,227, filed Nov. 9, 2007 for Lal et al. (17.00).
U.S. Appl. No. 12/235,969, filed Sep. 23, 2008 for Wohlgemuth et al. (1.12).
U.S. Appl. No. 12/544,182, filed Aug. 19, 2009 for Wohlgemuth et al. (1.06).
U.S. Appl. No. 12/561,213, filed Sep. 16, 2009 for Wohlgemuth et al. (1.14).
U.S. Appl. No. 12/584,615, filed Sep. 8, 2009 for Wohlgemuth et al. (1.23).
U.S. Office Action mailed Jun. 15, 2007, for U.S. Appl. No. 11/223,492, filed Sep. 8, 2005, 20 pages.
U.S. Office Action mailed Oct. 3, 2007, for U.S. Appl. No. 10/990,275, filed Nov. 15, 2004, 6 pages.
U.S. Office Action mailed Oct. 5, 2007, for U.S. Appl. No. 10/990,298, filed Nov. 15, 2004, 5 pages.
U.S. Office Action mailed Mar. 5, 2008, for U.S. Appl. No. 11/223,492, filed Sep. 8, 2005, 13 pages.
U.S. Office Action mailed Jul. 18, 2008, for U.S. Appl. No. 10/990,275, filed Nov. 15, 2004, 4 pages.
U.S. Office Action mailed Oct. 8, 2008, for U.S. Appl. No. 10/511,937, filed Jul. 22, 2005, 4 pages.
U.S. Office Action mailed Sep. 19, 2008, for U.S. Appl. No. 10/512,028, filed Jul. 21, 2005, 6 pages.
U.S. Office Action mailed Dec. 4, 2008, for U.S. Appl. No. 11/223,492, filed Sep. 8, 2005, 18 pages.
U.S. Office Action mailed May 29, 2009, for U.S. Appl. No. 11/893,236, filed Aug. 14, 2007, 12 pages.
U.S. Office Action mailed May 29, 2009, for U.S. Appl. No. 11/784,998, filed Apr. 9, 2007, 28 pages.

Vallin, H. et al. (1999). "Anti-Double-Stranded DNA Antibodies and Immunostimulatory Plasmid DNA in Combination Mimic the Endogenous IFN-Alpha Inducer in Systemic Lupus Erythematosus," The Journal of Immunology 163:6306-6313.

Vamvakopoulos, J. et al. (2002). "Genetic Control of IL-1βBioactivity Through Differential Regulation of the IL-1 Receptor Antagonist," European Journal of Immunology 32:2988-2996.

Vandevyver, C. et al. (1998). "Cytokine mRNA Profile of Myelin Basic Protein Reactive T-Cell Clones in Patients with Multiple Sclerosis," Autoimmunity 28:77-89.

Vasconcellos, L. M. et al. (Sep. 1998). "Cytotoxic Lymphocyte Gene Expression in Peripheral Blood Leukocytes Correlates with Rejecting Renal Allografts," Transplantation 66(5):562-566.

Vignali, D. A. A. (2000). "Multiplexed Particle-Based Flow Cytometric Assays," Journal of Immunological Methods 243:243-255.

Vincenti, F. et al. (May 2001). "Multicenter Trial Exploring Calcineurin Inhibitors Avoidance in Renal Transplantation," Transplantation 71(9):1282-1287.

Vu, H. K. (2000). "A Method for Quantification of Absolute Amounts of Nucleic Acids by (RT)-PCR and a New Mathematical Model for Data Analysis," Nucleic Acids Research 28(7):e18, 9 pages.

Watanabe-Fukunaga, R. et al. (Mar. 1992). "Lymphoproliferation Disorder in Mice Explained by Defects in Fas Antigen that Mediates Apoptosis," Nature 356:314-317.

Weast, R. C. ed. (1968). Handbook of Chemistry and Physics. 49th Edition, The Chemical Rubber Co.: Cleveland, Ohio, p. A-245.

Welsh, J. B. et al. (Jan. 2001). "Analysis of Gene Expression Profiles in Normal and Neoplastic Ovarian Tissue Samples Identifies Candidate Molecular Markers of Epithelial Ovarian Cancer," Proceedings of the National Academy of Sciences 98(3):1176-1181.

Westin, L. et al. (Feb. 2000). "Anchored Multiplex Amplification on a Microelectronic Chip Array," Nature Biotechnology 18:199-204.

Whitehead, J. (Date Unknown). "An Introduction to Logistic Regression," Department of Economics, Edast Carolina University, 48 pages, located at <http://arts.uwaterloo.ca/~wnrr/Soc710_421/Whitehead%20Logistic%20Regression.ppt>.

Willems, R. et al. (May 29, 1998). "Decrease in Nucleoside Diphosphate Kinase (NDPK/nm23) Expression During Hematopoietic Maturation," The Journal of Biological Chemistry 273(22):13663-13668.

Wu, T. (2001). "Analysing Gene Expression Data from DNA Microarrays to Identify Candidate Genes," Journal of Pathology 195:53-65.

Wu, J. et al. (Sep. 1996). "Fas Ligand Mutation in a Patient with Systemic Lupus Erythematosus and Lymphoproliferative Disease," The Journal of Clinical Investigation 98(3):1107-1113.

Xia, D. et al. (Sep. 2001). "Real-Time Polymerase Chain Reaction Analysis Reveals an Evolution of Cytokine mRNA Production in Allograft Acceptor Mice," Transplantation 72(5):907-914.

Yu, F. et al. (Oct. 1999). "Protein Synthesis-Dependent and Independent Induction of p69 2'-5'-Oligoadenylate Synthetase by Interferon-Alpha," Cytokine 11(10):744-750.

Zanders, E. et al. (2000). "Analysis of Immune System Gene Expression in Small Rheumatoid Arthritis Biopsies Using a Combination of Subtractive Hybridization and High-Density cDNA Arrays," *Journal of Immunological Methods* 233(1-2):131-140.

Zhang, L. et al. (Oct. 1997). "IRF-7, A New Interferon Regulatory Factor Associated with Epstein-Barr Virus Latency," Molecular and Cellular Biology 17(10):5748-5757.

Zhu, H. et al. (Nov. 2005). "The Role of Hyaluronan Receptor CD44 in MSC Migration in The Extracellular Matrix," *Stem Cells Express*, pp. 1-32.

Zucker, S. et al. (1999). "Increased Serum Stromelysin-1 Levels in Systemic Lupus Erythematosus: Lack of Correlation with Disease Activity," Journal of Rheumatology 26(1):78-80.

U.S. Office Action mailed Mar. 23, 2010 for U.S. Appl. No. 12/635,438 filed Dec. 10, 2009, 8 pages.

Deng, M. C. et al. (Jan. 2006). "Noninvasive discrimination of rejection in cardiac allograft recipients using gene expression profiling," *American Journal of Transplantation* 6(1):150-160.

European Search Report and Written Opinion mailed Apr. 28, 2010, for EP Application No. 08016970 filed Sep. 26, 2008, 10 pages.

Morgun, A. et al. (Feb. 1, 2001). "Cytokine and TLRC7 MRNA expression during acute rejection in cardiac allograft recipients," *Transplantation Proceedings*, Orlando, Florida, USA 33:1610-1611.

Nishimura, H. et al. (Aug. 1999). "Development of Lupus-like autoimmune diseases by distruption of the PD-1 gene encoding an ITIM motif-carrying immunoreceptor," *Immunity* 11(2):141-151.

Figure 1: Novel Gene Sequence Analysis
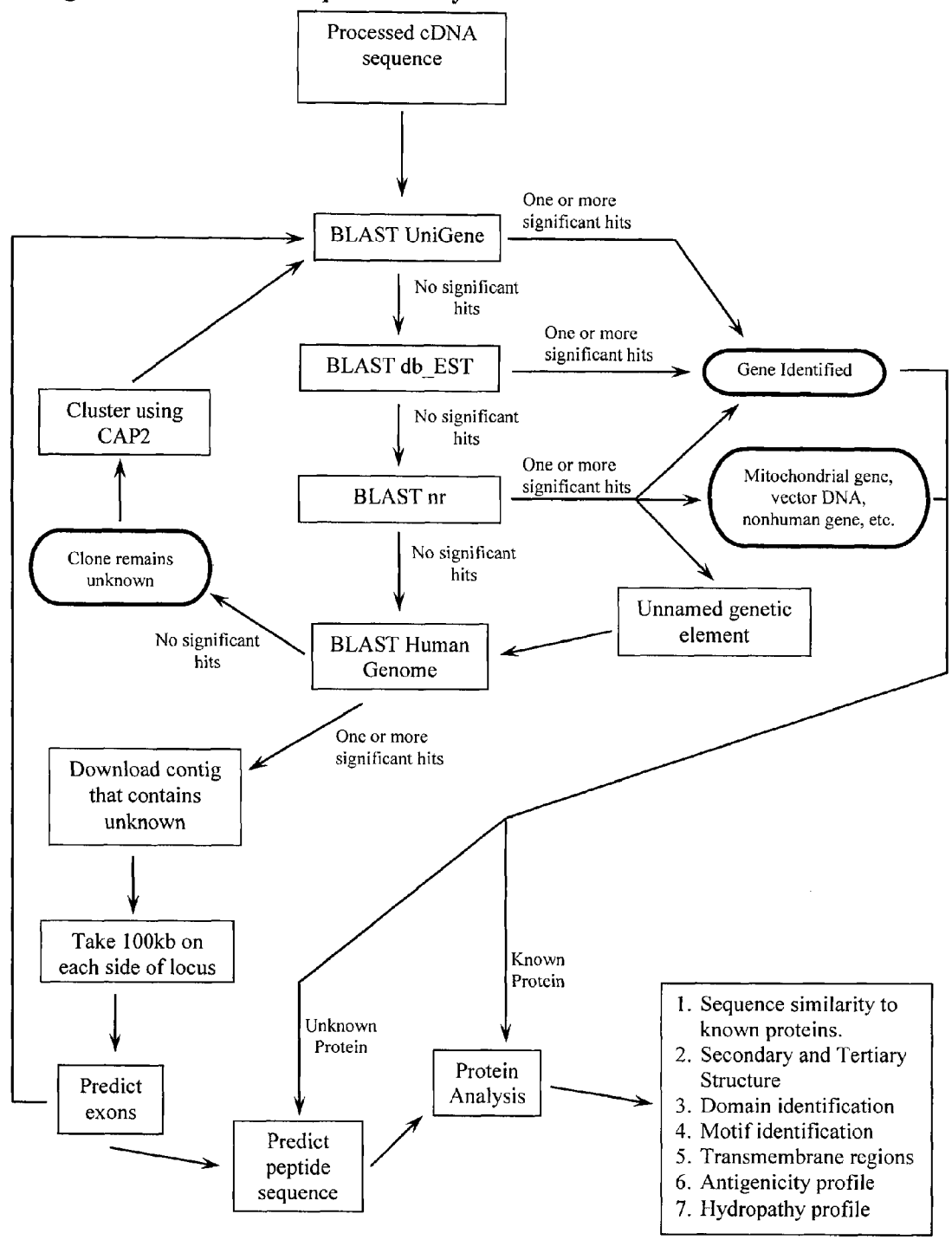

Figure 2. Automated Mononuclear Cell RNA Isolation Device
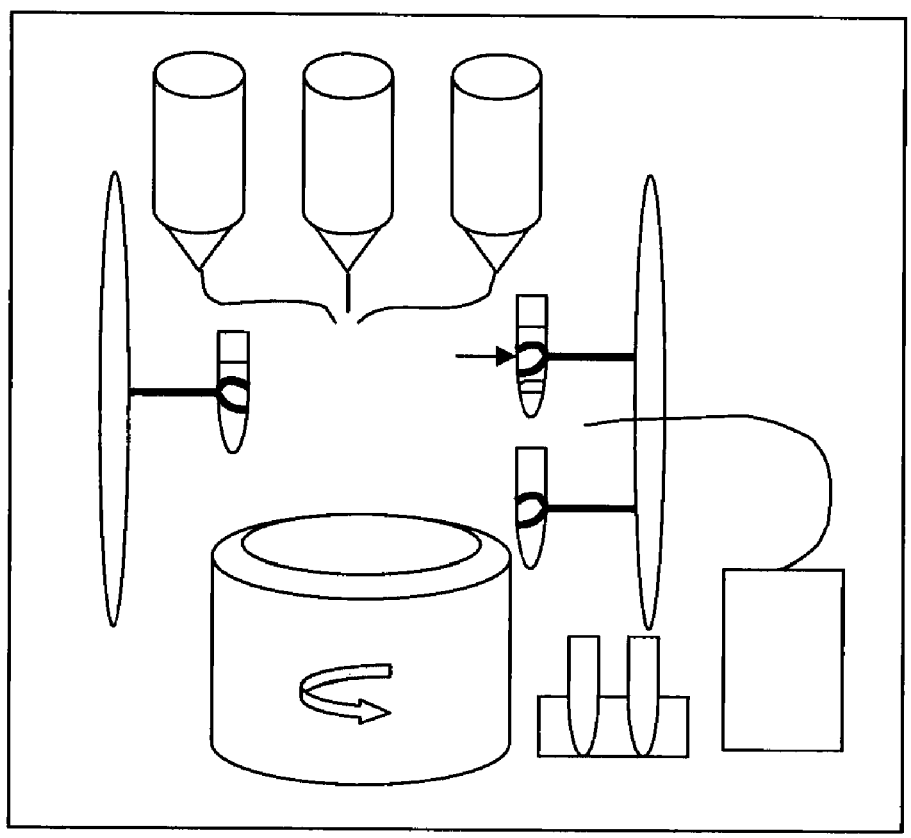

(Fig.3 pg 1 of 3)

Figure 3: Kits for discovery of, or application of diagnostic gene sets

A. Contents of kit for discovery of diagnostic gene sets using microarrays

1. Sterile, endotoxin and RNAse free blood collection tubes
2. Alcohol swabs, tourniquet, blood collection set
3. -PBS (phosphate buffer saline; needed when method of example 8 is used to derived mononuclear RNA)
4. Cell lysis buffer
5. RNA isolation kit
6. Substrates for labeling of RNA (may vary for various expression profiling techniques)
   For fluorescence microarray expression profiling:
   Reverse transcriptase and 10x RT buffer
   T7(dT)24 primer (primer with T7 promoter at 5' end)
   DTT
   Deoxynucleotides 100mM each
   RNAse inhibitor
   $2^{nd}$ strand cDNA buffer
   DNA polymerase
   Rnase H
   T7 RNA polymerase
   Ribonucleotides
   In Vitro transcription buffer
   Cy3 and Cy5 labeled ribonucleotides
7. Microarrays containing candidate gene libraries
8. Cover slips for slides
9. Hybridization chambers
10. Software package for identification of diagnostic gene set from data
    Contains statistical methods.
    Allows alteration in desired sensitivity and specificity of gene set.
    Software facilitates access to and data analysis by centrally located database server.
11. Password and account number to access central database server.
12. Kit User Manual

B. Contents of kit for application of diagnostic gene sets using microarrays 1. Sterile, endotoxin and RNAse free blood collection tubes
2. Alcohol swabs, tourniquet, blood collection set
3. -PBS (phosphate buffer saline; needed when method of example 7 is used to derived mononuclear RNA)

(Fig.3 pg 2 of 3)

4. Cell lysis buffer
5. RNA isolation kit
6. Substrates for labeling of RNA (may vary for various expression profiling techniques)
    For fluorescence microarray expression profiling:
    Reverse transcriptase and 10x RT buffer
    T7(dT)24 primer (primer with T7 promoter at 5' end)
    DTT
    Deoxynucleotides 100mM each
    RNAse inhibitor
    $2^{nd}$ strand cDNA buffer
    DNA polymerase
    Rnase H
    T7 RNA polymerase
    Ribonucleotides
    In Vitro transcription buffer
    Cy3 and Cy5 labeled ribonucleotides
7. Microarrays containing candidate gene libraries
8. Cover slips for slides
9. Hybridization chambers
10. Software package for identification of diagnostic gene set from data
    Contains statistical methods.
    Allows alteration in desired sensitivity and specificity of gene set.
    Software facilitates access to and data analysis by centrally located database server.
11. Password and account number to access central database server.
12. Kit User Manual

C. Contents of kit for application of diagnostic gene sets using Real-time RT-PCR 1. Sterile, endotoxin and RNAse free blood collection tubes
2. Alcohol swabs, tourniquet, blood collection set
3. -PBS (phosphate buffer saline; needed when method of example 7 is used to derived mononuclear RNA)
4. Cell lysis buffer
5. RNA isolation kit
6. Substrates for real time RT-PCR (may vary for various real-time PCR techniques:
    poly dT primers, random hexamer primers
    Reverse Transcriptase and RT buffer
    DTT
    Deoxynucleotides 100 mM
    RNase H
    primer pairs for diagnostic and control gene set
    10x PCR reaction buffer (Fig.3 pg 3 of 3)

Taq DNA polymerase
    Fluorescent probes for diagnostic and control gene set
    (alternatively, fluorescent dye that binds to only double stranded DNA)
    reaction tubes with or without barcode for sample tracking
    96-well plates with barcode for sample identification, one barcode for entire set, or individual barcode per reaction tube in plate 7. Software package for identification of diagnostic gene set from data
    Contains statistical methods.
    Allows alteration in desired sensitivity and specificity of gene set.
    Software facilitates access to and data analysis by centrally located database server 8. Password and account number to access central database server.

9. Kit User Manual

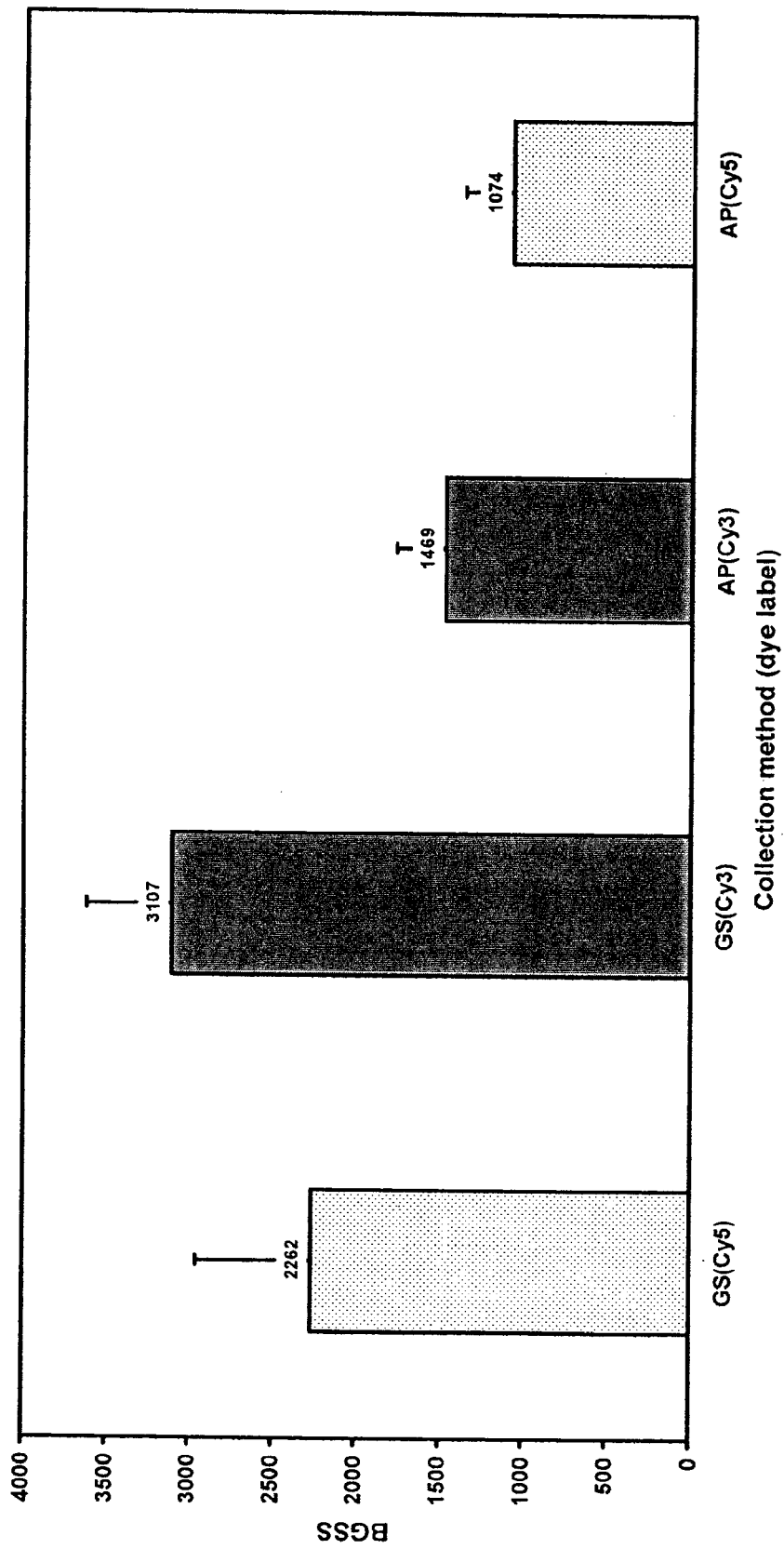

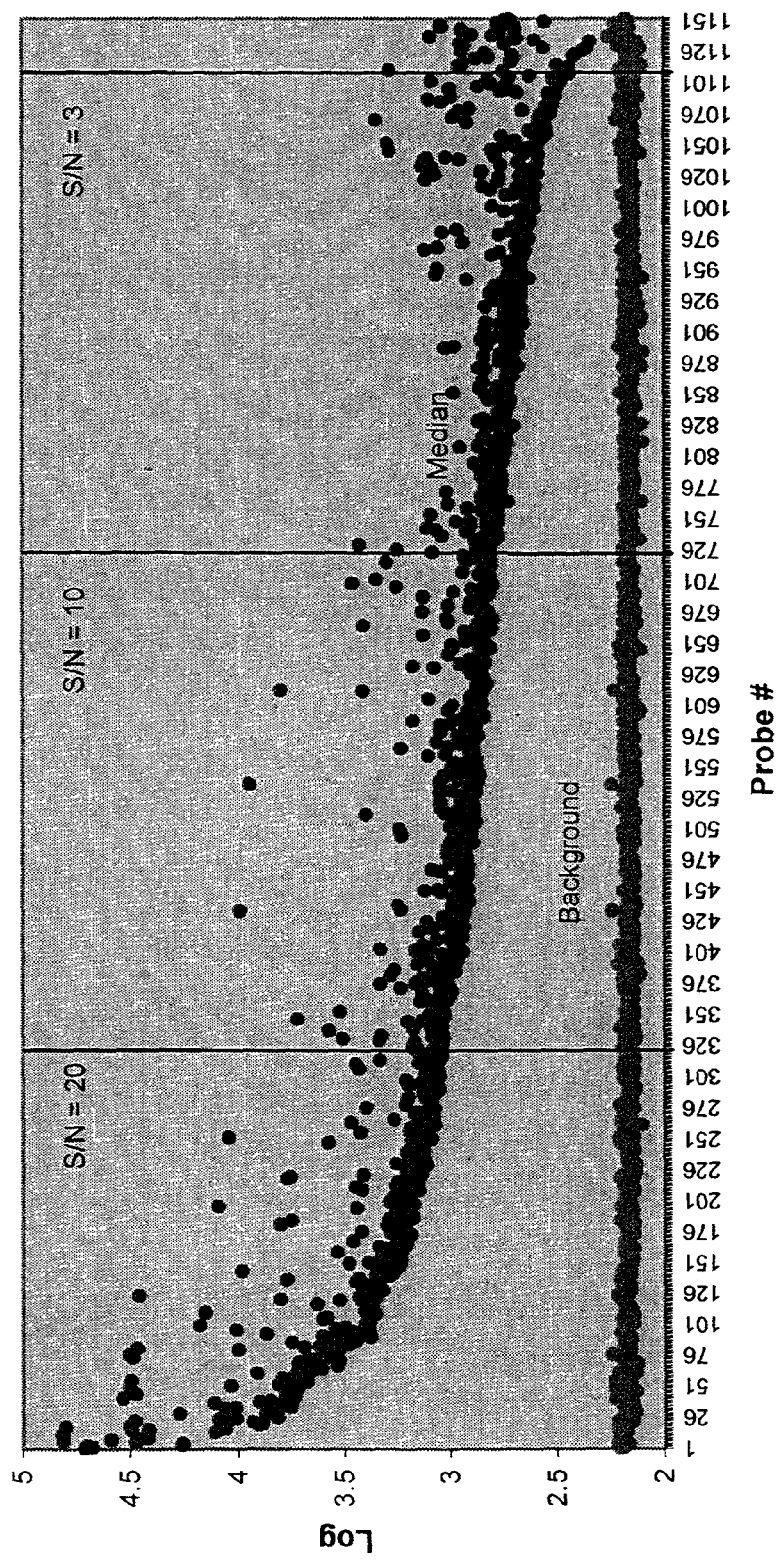
Figure 8: Log expression of each probe using the R50 reference RNA. Probe expression is ordered by Signal to noise, S/N, decreasing from left to right.

Figure 9A: Cardiac Allograft rejection diagnostic genes.
| | | Marker Gene Expression Ratios | | | | |
|---|---|---|---|---|---|---|
| Sample | Grade | 6514 | 6091 | 792 | 5280 | 4460 |
| 12-0025-02 | 0 | 3.90 | 3.69 | 5.49 | 3.24 | 3.34 |
| 12-0024-04 | 0 | 3.66 | 4.05 | 5.89 | 3.75 | 3.03 |
| 15-0024-01 | 0 | 3.55 | 4.01 | 5.61 | 2.90 | 3.23 |
| 12-0029-03 | 0 | 3.44 | 3.12 | 4.25 | 3.55 | 3.07 |
| 12-0024-03 | 0 | 2.88 | 2.54 | 2.56 | 2.20 | 2.38 |
| 14-0021-05 | 0 | 1.31 | 1.03 | 1.07 | 0.91 | 0.99 |
| 14-0005-06 | 3A | 0.42 | 0.27 | 0.51 | 0.22 | 0.26 |
| 14-0012-07 | 3A | 0.60 | 0.62 | 0.70 | 0.42 | 0.61 |
| 14-0001-06 | 3A | 0.93 | 0.71 | 0.58 | 0.37 | 0.44 |
| 14-0009-01 | 3A | 0.71 | 0.63 | 0.68 | 0.61 | 0.66 |
| 12-0012-02 | 3A | 0.86 | 0.85 | 0.73 | 0.41 | 0.72 |
| 12-0001-01 | 3A | 1.08 | 0.97 | 1.01 | 0.40 | 1.06 |
| Average Grade 0: | | 3.13 | 3.07 | 4.14 | 2.76 | 2.67 |
| Average Grade 3A: | | 0.77 | 0.68 | 0.70 | 0.40 | 0.62 |
| Fold Difference: | | 4.08 | 4.55 | 5.91 | 6.82 | 4.28 |
Figure 9B: CART classification model.
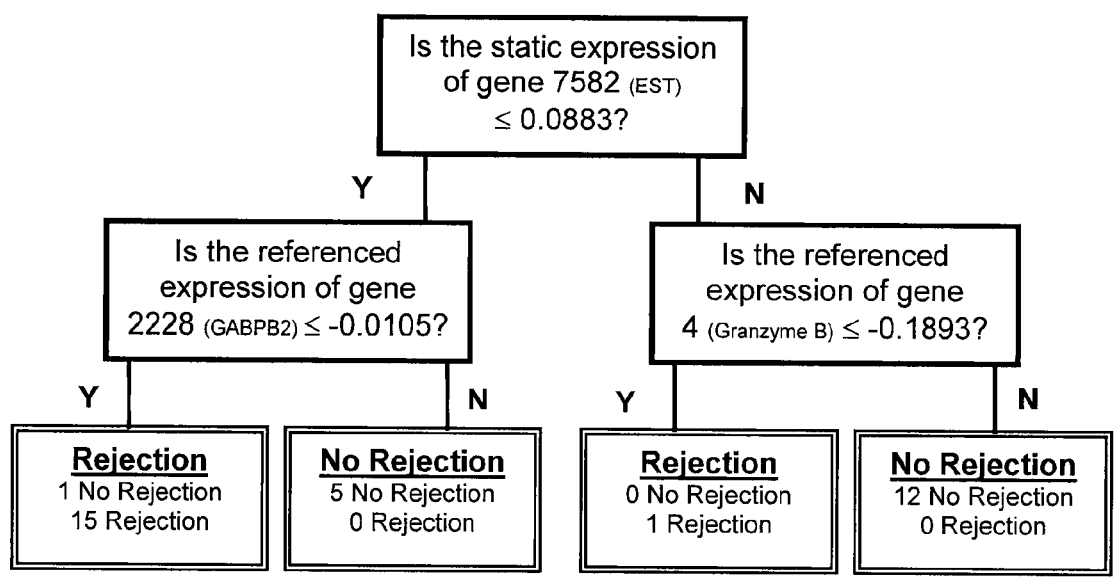

Figure 9C: Surrogates for the CART classification model.

| Primary Splitter | static 7582 | ref 2228 | ref 4 |
|---|---|---|---|
| Surrogate 1 | ref 1512 | ref 2287 | ref 797 |
| Surrogate 2 | ref 99 | static 1956 | ref 801 |
| Surrogate 3 | ref 792 | ref 841 | ref 99 |
| Surrogate 4 | ref 4460 | ref 441 | ref 214 |
| Surrogate 5 | ref 820 | ref 797 | ref 241 |
| Primary Splitter | static 223 | ref 3017 | ref 4 |
| Surrogate 1 | ref 167 | ref 102 | ref 2761 |
| Surrogate 2 | ref 3016 | static 36 | ref 2762 |
| Surrogate 3 | ref 1760 | ref 2764 | ref 3016 |
| Surrogate 4 | ref 85 | ref 2759 | ref 2757 |
| Surrogate 5 | ref 2763 | ref 2761 | ref 2758 |

Validation of differential expression of Granzyme B in CMV patients using Real-time PCR

Figure 13: Validation of differential expression of Granzyme B in CMV patients using Real-time PCR
A.
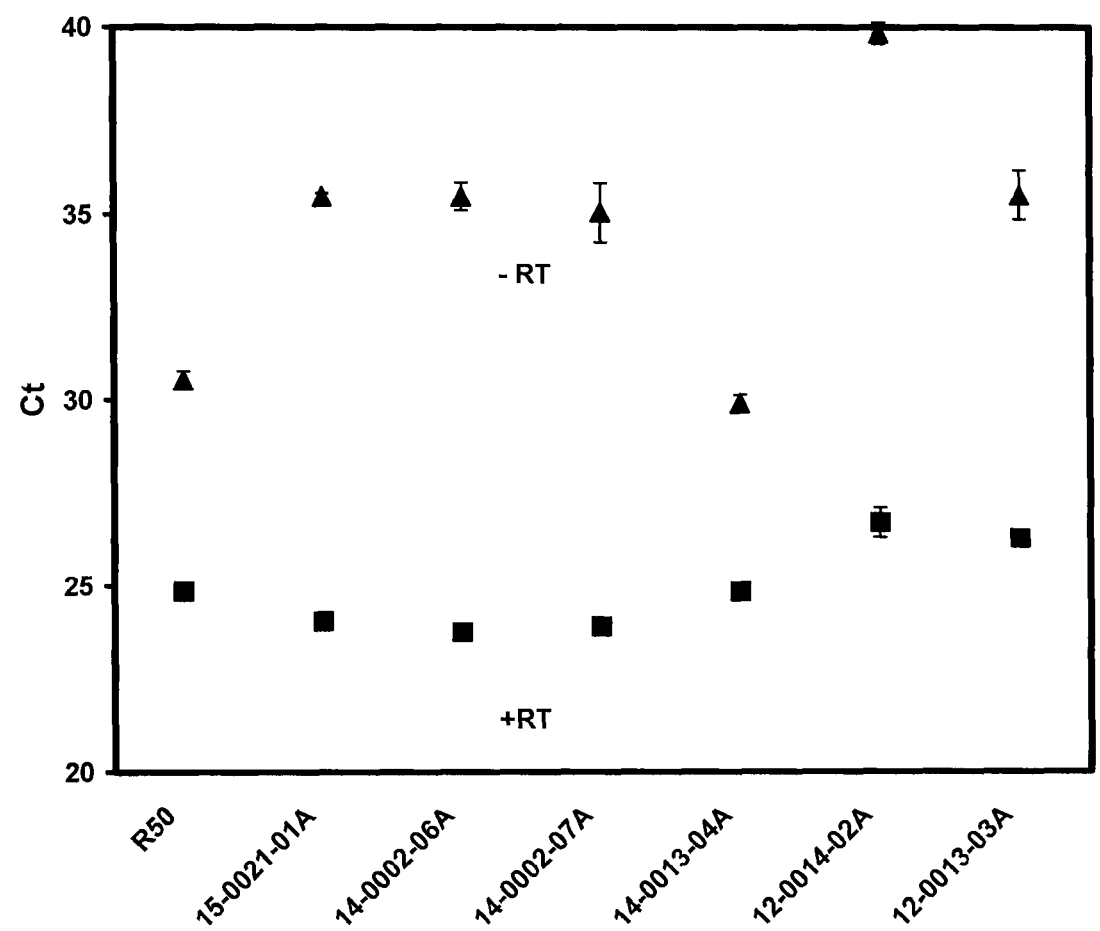

(Figure 13 cont'd)
B.
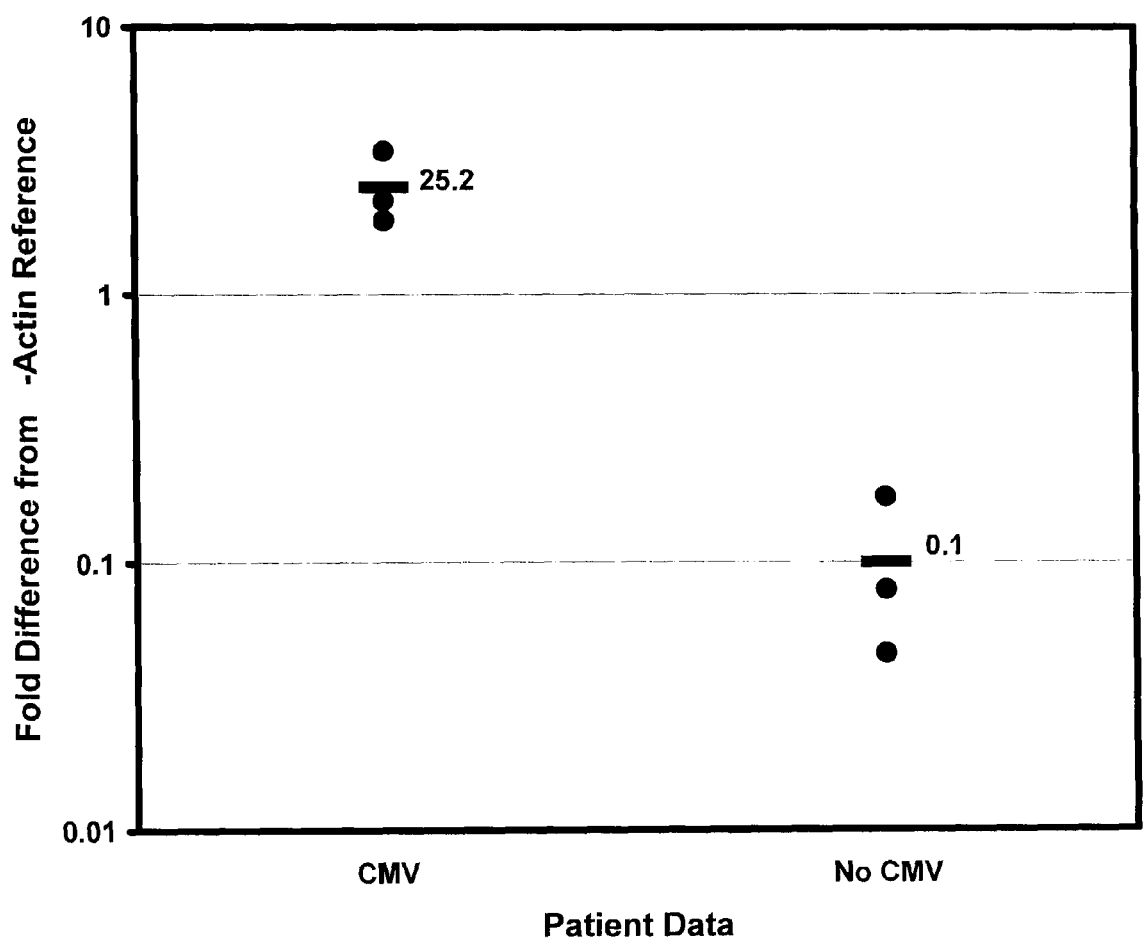

METHODS AND COMPOSITIONS FOR DIAGNOSING AND MONITORING TRANSPLANT REJECTION

RELATED APPLICATIONS

This application is a divisional of application Ser. No. 10/990,275, filed Nov. 15, 2004, which is a divisional of application Ser. No. 10/131,831, filed Apr. 24, 2002, now U.S. Pat. No. 7,026,121, which is a continuation-in-part of application Ser. No. 10/006,290, filed Oct. 22, 2001, now abandoned, which claims the benefit of U.S. Provisional Application No. 60/296,764, filed Jun. 8, 2001, all of which are hereby incorporated by reference in their entirety.

SUBMISSION ON COMPACT DISC

The content of the following submission on compact discs is incorporated herein by reference in its entirety: A computer readable form (CRF) of the Sequence Listing on compact disc (file name: SUBSTITUTESEQLIST506612000111.txt, date recorded: Apr. 3, 2008, size: 1,818 kBytes); a duplicate compact disc copy of the Sequence Listing (COPY 1) (file name: SUBSTITUTESEQLIST506612000111.txt, date recorded: Apr. 3, 2008, size: 1,818 kBytes); and a duplicate compact disc copy of the Sequence Listing (COPY 2) (file name: SUBSTITUTESEQLIST506612000111.txt, date recorded: Apr. 3, 2008, size: 1,818 kBytes).

FIELD OF THE INVENTION

This invention is in the field of expression profiling. In particular, this invention is in the field of leukocyte expression profiling.

BACKGROUND OF THE INVENTION

Many of the current shortcomings in diagnosis, prognosis, risk stratification and treatment of disease can be approached through the identification of the molecular mechanisms underlying a disease and through the discovery of nucleotide sequences (or sets of nucleotide sequences) whose expression patterns predict the occurrence or progression of disease states, or predict a patient's response to a particular therapeutic intervention. In particular, identification of nucleotide sequences and sets of nucleotide sequences with such predictive value from cells and tissues that are readily accessible would be extremely valuable. For example, peripheral blood is attainable from all patients and can easily be obtained at multiple time points at low cost. This is a desirable contrast to most other cell and tissue types, which are less readily accessible, or accessible only through invasive and aversive procedures. In addition, the various cell types present in circulating blood are ideal for expression profiling experiments as the many cell types in the blood specimen can be easily separated if desired prior to analysis of gene expression. While blood provides a very attractive substrate for the study of diseases using expression profiling techniques, and for the development of diagnostic technologies and the identification of therapeutic targets, the value of expression profiling in blood samples rests on the degree to which changes in gene expression in these cell types are associated with a predisposition to, and pathogenesis and progression of a disease.

There is an extensive literature supporting the role of leukocytes, e.g., T- and B-lymphocytes, monocytes and granulocytes, including neutrophils, in a wide range of disease processes, including such broad classes as cardiovascular diseases, inflammatory, autoimmune and rheumatic diseases, infectious diseases, transplant rejection, cancer and malignancy, and endocrine diseases. For example, among cardiovascular diseases, such commonly occurring diseases as atherosclerosis, restenosis, transplant vasculopathy and acute coronary syndromes all demonstrate significant T cell involvement (Smith-Norowitz et al. (1999) Clin Immunol 93:168-175; Jude et al. (1994) Circulation 90:1662-8; Belch et al. (1997) Circulation 95:2027-31). These diseases are now recognized as manifestations of chronic inflammatory disorders resulting from an ongoing response to an injury process in the arterial tree (Ross et al. (1999) Ann Thorac Surg 67:1428-33). Differential expression of lymphocyte, monocyte and neutrophil genes and their products has been demonstrated clearly in the literature. Particularly interesting are examples of differential expression in circulating cells of the immune system that demonstrate specificity for a particular disease, such as arteriosclerosis, as opposed to a generalized association with other inflammatory diseases, or for example, with unstable angina rather than quiescent coronary disease.

A number of individual genes, e.g., CD11b/CD18 (Kassirer et al. (1999) Am Heart J 138:555-9); leukocyte elastase (Amaro et al. (1995) Eur Heart J 16:615-22; and CD40L (Aukrust et al. (1999) Circulation 100:614-20) demonstrate some degree of sensitivity and specificity as markers of various vascular diseases. In addition, the identification of differentially expressed target and fingerprint genes isolated from purified populations of monocytes manipulated in various in vitro paradigms has been proposed for the diagnosis and monitoring of a range of cardiovascular diseases, see, e.g., U.S. Pat. Nos. 6,048,709; 6,087,477; 6,099,823; and 6,124,433 "COMPOSITIONS AND METHODS FOR THE TREATMENT AND DIAGNOSIS OF CARDIOVASCULAR DISEASE" to Falb (see also, WO 97/30065). Lockhart, in U.S. Pat. No. 6,033,860 "EXPRESSION PROFILES IN ADULT AND FETAL ORGANS" proposes the use of expression profiles for a subset of identified genes in the identification of tissue samples, and the monitoring of drug effects.

The accuracy of technologies based on expression profiling for the diagnosis, prognosis, and monitoring of disease would be dramatically increased if numerous differentially expressed nucleotide sequences, each with a measure of specificity for a disease in question, could be identified and assayed in a concerted manner. In order to achieve this improved accuracy, the appropriate sets of nucleotide sequences need to be identified and validated against numerous samples in combination with relevant clinical data. The present invention addresses these and other needs, and applies to any disease or disease state for which differential regulation of genes, or other nucleotide sequences, of peripheral blood can be demonstrated.

SUMMARY OF THE INVENTION

The present invention is thus directed to a system for detecting differential gene expression. In one format, the system has one or more isolated DNA molecules wherein each isolated DNA molecule detects expression of a gene selected from the group of genes corresponding to the oligonucleotides depicted in the Sequence Listing. It is understood that the DNA sequences and oligonucleotides of the invention may have slightly different sequences that those identified herein. Such sequence variations are understood to those of ordinary skill in the art to be variations in the sequence which do not significantly affect the ability of the sequences to detect gene expression.

The sequences encompassed by the invention have at least 40-50, 50-60, 70-80, 80-85, 85-90, 90-95 or 95-100% sequence identity to the sequences disclosed herein. In some embodiments, DNA molecules are less than about any of the following lengths (in bases or base pairs): 10,000; 5,000; 2500; 2000; 1500; 1250; 1000; 750; 500; 300; 250; 200; 175; 150; 125; 100; 75; 50; 25; 10. In some embodiments, DNA molecule is greater than about any of the following lengths (in bases or base pairs): 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, a DNA molecule can be any of a range of sizes having an upper limit of 10,000; 5,000; 2500; 2000; 1500; 1250; 1000; 750; 500; 300; 250; 200; 175; 150; 125; 100; 75; 50; 25; or 10 and an independently selected lower limit of 10; 15; 20; 25; 30; 40; 50; 60; 75; 100; 125; 150; 175; 200; 250; 300; 350; 400; 500; 750; 1000; 2000; 5000; 7500 wherein the lower limit is less than the upper limit.

The gene expression system may be a candidate library, a diagnostic agent, a diagnostic oligonucleotide set or a diagnostic probe set. The DNA molecules may be genomic DNA, protein nucleic acid (PNA), cDNA or synthetic oligonucleotides.

In one format, the gene expression system is immobilized on an array. The array may be a chip array, a plate array, a bead array, a pin array, a membrane array, a solid surface array, a liquid array, an oligonucleotide array, a polynucleotide array, a cDNA array, a microfilter plate, a membrane or a chip.

The present invention is further directed to a method of diagnosing or monitoring transplant rejection in a patient, comprising detecting the expression level of one or more genes or surrogates derived therefrom in the patient to diagnose or monitor transplant rejection in said patient wherein said one or more genes include a nucleotide sequence selected from SEQ ID NO:4; SEQ ID NO:26; SEQ ID NO:60; SEQ ID NO:130; SEQ ID NO:176; SEQ ID NO:184; SEQ ID NO:261; SEQ ID NO:707; SEQ ID NO:792; SEQ ID NO:841; SEQ ID NO:1024; SEQ ID NO:1128; SEQ ID NO:1140; SEQ ID NO:1333; SEQ ID NO:1345; SEQ ID NO:1435; SEQ ID NO:1749; SEQ ID NO:1778; SEQ ID NO:1956; SEQ ID NO:2086; SEQ ID NO:2228; SEQ ID NO:2518; SEQ ID NO:2519; SEQ ID NO:2770; SEQ ID NO:2801; SEQ ID NO:3134; SEQ ID NO:3263; SEQ ID NO:3842; SEQ ID NO:4092; SEQ ID NO:4191; SEQ ID NO:4460; SEQ ID NO:4515; SEQ ID NO:5108; SEQ ID NO:5280; SEQ ID NO:5573; SEQ ID NO:5673; SEQ ID NO:5834; SEQ ID NO:6091; SEQ ID NO:6112; SEQ ID NO:6221; SEQ ID NO:6309; SEQ ID NO:6347; SEQ ID NO:6514; SEQ ID NO:6573; SEQ ID NO:7094; SEQ ID NO:7199; SEQ ID NO:7481; SEQ ID NO:7482; SEQ ID NO:7605; SEQ ID NO:8076 and SEQ ID NO:8089.

The present invention is further directed to a method of diagnosing or monitoring cytomegolovirus infection in a patient, by detecting the expression level of one or more genes or surrogates derived therefrom in the patient to diagnose or monitor cytomegolovirus infection in the patient wherein the genes include a nucleotide sequence selected from: SEQ ID NO:4; SEQ ID NO:26; SEQ ID NO:60; SEQ ID NO:130; SEQ ID NO:176; SEQ ID NO:184; SEQ ID NO:261; SEQ ID NO:707; SEQ ID NO:792; SEQ ID NO:841; SEQ ID NO:1024; SEQ ID NO:1128; SEQ ID NO:1140; SEQ ID NO:1333; SEQ ID NO:1345; SEQ ID NO:1435; SEQ ID NO:1749; SEQ ID NO:1778; SEQ ID NO:1956; SEQ ID NO:2086; SEQ ID NO:2228; SEQ ID NO:2518; SEQ ID NO:2519; SEQ ID NO:2770; SEQ ID NO:2801; SEQ ID NO:3134; SEQ ID NO:3263; SEQ ID NO:3842; SEQ ID NO:4092; SEQ ID NO:4191; SEQ ID NO:4460; SEQ ID NO:4515; SEQ ID NO:5108; SEQ ID NO:5280; SEQ ID NO:5573; SEQ ID NO:5673; SEQ ID NO:5834; SEQ ID NO:6091; SEQ ID NO:6112; SEQ ID NO:6221; SEQ ID NO:6309; SEQ ID NO:6347; SEQ ID NO:6514; SEQ ID NO:6573; SEQ ID NO:7094; SEQ ID NO:7199; SEQ ID NO:7481; SEQ ID NO:7482; SEQ ID NO:7605; SEQ ID NO:8076; SEQ ID NO:8089; SEQ ID NO: 4132; SEQ ID NO:4604; SEQ ID NO:2630; SEQ ID NO:3305; SEQ ID NO:3717; SEQ ID NO:5471; SEQ ID NO:5559; SEQ ID NO:6308; SEQ ID NO:1983; SEQ ID NO:4761; SEQ ID NO:5509; SEQ ID NO:2004; SEQ ID NO:1685; SEQ ID NO:2428; SEQ ID NO:4113; SEQ ID NO:6059; SEQ ID NO:1754 and SEQ ID NO:375.

The present invention is further directed to a diagnostic agent comprising an oligonucleotide wherein the oligonucleotide has a nucleotide sequence selected from the Sequence Listing wherein the oligonucleotide detects expression of a gene that is differentially expressed in leukocytes in an individual over time.

The present invention is further directed to a system for detecting gene expression in leukocytes comprising an isolated DNA molecule wherein the isolated DNA molecule detects expression of a gene wherein the gene is selected from the group of genes corresponding to the oligonucleotides depicted in the Sequence Listing and the gene is differentially expressed in the leukocytes in an individual with at least one disease criterion for a disease selected from Table 1 as compared to the expression of the gene in leukocytes in an individual without the at least one disease criterion.

The present invention is further directed to a gene expression candidate library comprising at least two oligonucleotides wherein the oligonucleotides have a sequence selected from those oligonucleotide sequences listed in Table 2, Table 3, and the Sequence Listing. Table 3 encompasses Tables 3A, 3B and 3C. The oligonucleotides of the candidate library may comprise deoxyribonucleic acid (DNA), ribonucleic acid (RNA), protein nucleic acid (PNA), synthetic oligonucleotides, or genomic DNA.

In one embodiment, the candidate library is immobilized on an array. The array may comprises one or more of: a chip array, a plate array, a bead array, a pin array, a membrane array, a solid surface array, a liquid array, an oligonucleotide array, a polynucleotide array or a cDNA array, a microtiter plate, a pin array, a bead array, a membrane or a chip. Individual members of the libraries are may be separately immobilized.

The present invention is further directed to a diagnostic oligonucleotide set for a disease having at least two oligonucleotides wherein the oligonucleotides have a sequence selected from those oligonucleotide sequences listed in Table 2, Table 3, or the Sequence Listing which are differentially expressed in leukocytes genes in an individual with at least one disease criterion for at least one leukocyte-related disease as compared to the expression in leukocytes in an individual without the at least one disease criterion, wherein expression of the two or more genes of the gene expression library is correlated with at least one disease criterion.

The present invention is further directed to a diagnostic oligonucleotide set for a disease having at least one oligonucleotide wherein the oligonucleotide has a sequence selected from those sequences listed in Table 2, Table 3, or the sequence listing which is differentially expressed in leukocytes in an individual with at least one disease criterion for a disease selected from Table 1 as compared to leukocytes in an individual without at least one disease criterion, wherein expression of the at least one gene from the gene expression library is correlated with at least one disease criterion, wherein the differential expression of the at least one gene has not previously been described. In one format, two or more oligonucleotides are utilized.

In the diagnostic oligonucleotide sets of the invention the disease criterion may include data selected from patient historic, diagnostic, prognostic, risk prediction, therapeutic progress, and therapeutic outcome data. This includes lab results, radiology results, pathology results such as histology, cytology and the like, physical examination findings, and medication lists.

In the diagnostic oligonucleotide sets of the invention the leukocytes comprise peripheral blood leukocytes or leukocytes derived from a non-blood fluid. The non-blood fluid may be selected from colon, sinus, spinal fluid, saliva, lymph fluid, esophagus, small bowel, pancreatic duct, biliary tree, ureter, vagina, cervix uterus and pulmonary lavage fluid.

In the diagnostic oligonucleotide sets of the invention the leukocytes may include leukocytes derived from urine or a joint biopsy sample or biopsy of any other tissue or may be T-lymphocytes.

In the diagnostic oligonucleotide sets of the invention the disease may be selected from cardiac allograft rejection, kidney allograft rejection, liver allograft rejection, atherosclerosis, congestive heart failure, systemic lupus erythematosis (SLE), rheumatoid arthritis, osteoarthritis, and cytomegalovirus infection.

The diagnostic oligonucleotide sets of the invention may further include one or more cytomegalovirus (CMV) nucleotide sequences, wherein expression of the CMV nucleotide sequence is correlated with CMV infection.

The diagnostic nucleotide sets of the invention may further include one or more Epstein-Barr virus (EBV) nucleotide sequences, wherein expression of the one or more EBV nucleotide sequences is correlated with EBV infection.

In the present invention, expression may be differential expression, wherein the differential expression is one or more of a relative increase in expression, a relative decrease in expression, presence of expression or absence of expression, presence of disease or absence of disease. The differential expression may be RNA expression or protein expression. The differential expression may be between two or more samples from the same patient taken on separate occasions or between two or more separate patients or between two or more genes relative to each other.

The present invention is further directed to a diagnostic probe set for a disease where the probes correspond to at least one oligonucleotide wherein the oligonucleotides have a sequence such as those listed in Table 2, Table 3, or the Sequence Listing which is differentially expressed in leukocytes in an individual with at least one disease criterion for a disease selected from Table 1 as compared to leukocytes in an individual without the at least one disease criterion, wherein expression of the oligonucleotide is correlated with at least one disease criterion, and further wherein the differential expression of the at least one nucleotide sequence has not previously been described.

The present invention is further directed to a diagnostic probe set wherein the probes include one or more of probes useful for proteomics and probes for nucleic acids cDNA, or synthetic oligonucleotides.

The present invention is further directed to an isolated nucleic acid having a sequences such as those listed in Table 3B or Table 3C or the Sequence Listing.

The present invention is further directed to polypeptides wherein the polypeptides are encoded by the nucleic acid sequences in Tables 3B, 3C and the Sequence Listing.

The present invention is further directed to a polynucleotide expression vector containing the polynucleotide of Tables 3B-3C or the Sequence Listing in operative association with a regulatory element which controls expression of the polynucleotide in a host cell. The present invention is further directed to host cells transformed with the expression vectors of the invention. The host cell may be prokaryotic or eukaryotic.

The present invention is further directed to fusion proteins produced by the host cells of the invention. The present invention is further directed to antibodies directed to the fusion proteins of the invention. The antibodies may be monoclonal or polyclonal antibodies.

The present invention is further directed to kits comprising the diagnostic oligonucleotide sets of the invention. The kits may include instructions for use of the kit.

The present invention is further directed to a method of diagnosing a disease by obtaining a leukocyte sample from an individual, hybridizing nucleic acid derived from the leukocyte sample with a diagnostic oligonucleotide set, and comparing the expression of the diagnostic oligonucleotide set with a molecular signature indicative of the presence or absence of the disease.

The present invention is further directed to a method of detecting gene expression by a) isolating RNA and b) hybridizing the RNA to isolated DNA molecules wherein the isolated DNA molecules detect expression of a gene wherein the gene corresponds to one of the oligonucleotides depicted in the Sequence Listing.

The present invention is further directed to a method of detecting gene expression by a) isolating RNA; b) converting the RNA to nucleic acid derived from the RNA and c) hybridizing the nucleic acid derived from the RNA to isolated DNA molecules wherein the isolated DNA molecules detect expression of a gene wherein the gene corresponds to one of the oligonucleotides depicted in the Sequence Listing. In one format, the nucleic acid derived from the RNA is cDNA.

The present invention is further directed to a method of detecting gene expression by a) isolating RNA; b) converting the RNA to cRNA or aRNA and c) hybridizing the cRNA or aRNA to isolated DNA molecules wherein the isolated DNA molecules detect expression of a gene corresponding to one of the oligonucleotides depicted in the Sequence Listing.

The present invention is further directed to a method of monitoring progression of a disease by obtaining a leukocyte sample from an individual, hybridizing the nucleic acid derived from leukocyte sample with a diagnostic oligonucleotide set, and comparing the expression of the diagnostic oligonucleotide set with a molecular signature indicative of the presence or absence of disease progression.

The present invention is further directed to a method of monitoring the rate of progression of a disease by obtaining a leukocyte sample from an individual, hybridizing the nucleic acid derived from leukocyte sample with a diagnostic oligonucleotide set, and comparing the expression of the diagnostic oligonucleotide set with a molecular signature indicative of the presence or absence of disease progression.

The present invention is further directed to a method of predicting therapeutic outcome by obtaining a leukocyte sample from an individual, hybridizing the nucleic acid derived from leukocyte sample with a diagnostic oligonucleotide set, and comparing the expression of the diagnostic oligonucleotide set with a molecular signature indicative of the predicted therapeutic outcome.

The present invention is further directed to a method of determining prognosis by obtaining a leukocyte sample from an individual, hybridizing the nucleic acid derived from leukocyte sample with a diagnostic oligonucleotide set, and comparing the expression of the diagnostic oligonucleotide set with a molecular signature indicative of the prognosis.

The present invention is further directed to a method of predicting disease complications by obtaining a leukocyte sample from an individual, hybridizing nucleic acid derived from the leukocyte sample with a diagnostic oligonucleotide set, and comparing the expression of the diagnostic oligonucleotide set with a molecular signature indicative of the presence or absence of disease complications.

The present invention is further directed to a method of monitoring response to treatment, by obtaining a leukocyte sample from an individual, hybridizing the nucleic acid derived from leukocyte sample with a diagnostic oligonucleotide set, and comparing the expression of the diagnostic oligonucleotide set with a molecular signature indicative of the presence or absence of response to treatment.

In the methods of the invention the invention may further include characterizing the genotype of the individual, and comparing the genotype of the individual with a diagnostic genotype, wherein the diagnostic genotype is correlated with at least one disease criterion. The genotype may be analyzed by one or more methods selected from the group consisting of Southern analysis, RFLP analysis, PCR, single stranded conformation polymorphism and SNP analysis.

The present invention is further directed to a method of non-invasive imaging by providing an imaging probe for a nucleotide sequence that is differentially expressed in leukocytes from an individual with at least one disease criterion for at least one leukocyte-implicated disease where leukocytes localize at the site of disease, wherein the expression of the at least one nucleotide sequence is correlated with the at least one disease criterion by (a) contacting the probe with a population of leukocytes; (b) allowing leukocytes to localize to the site of disease or injury and (c) detecting an image.

The present invention is further directed to a control RNA for use in expression profile analysis, where the RNA extracted from the buffy coat samples is from at least four individuals.

The present invention is further directed to a method of collecting expression profiles, comprising comparing the expression profile of an individual with the expression profile of buffy coat control RNA, and analyzing the profile.

The present invention is further directed to a method of RNA preparation suitable for diagnostic expression profiling by obtaining a leukocyte sample from a subject, adding actinomycin-D to a final concentration of 1 ug/ml, adding cycloheximide to a final concentration of 10 ug/ml, and extracting RNA from the leukocyte sample. In the method of RNA preparation of the invention the actinomycin-D and cycloheximide may be present in a sample tube to which the leukocyte sample is added. The method may further include centrifuging the sample at 4° C. to separate mononuclear cells.

The present invention is further directed to a leukocyte oligonucleotide set including at least two oligonucleotides which are differentially expressed in leukocytes undergoing adhesion to an endothelium relative to expression in leukocytes not undergoing adhesion to an endothelium, wherein expression of the two oligonucleotides is correlated with the at least one indicator of adhesion state.

The present invention is further directed to a method of identifying at least one diagnostic probe set for assessing atherosclerosis by (a) providing a library of candidate oligonucleotides, which candidate oligonucleotides are differentially expressed in leukocytes which are undergoing adhesion to an endothelium relative to their expression in leukocytes that are not undergoing adhesion to an endothelium; (b) assessing expression of two or more oligonucleotides, which two or more oligonucleotides correspond to components of the library of candidate oligonucleotides, in a subject sample of leukocytes; (c) correlating expression of the two or more oligonucleotides with at least one criterion, which criterion includes one or more indicators of adhesion to an endothelium; and, (d) recording the molecular signature in a database.

The present invention is further directed to a method of identifying at least one diagnostic probe set for assessing atherosclerosis by (a) providing a library of candidate oligonucleotides, which candidate oligonucleotides are differentially expressed in leukocytes which are undergoing adhesion to an endothelium relative to their expression in leukocytes that are not undergoing adhesion to an endothelium; (b) assessing expression of two or more oligonucleotides, which two or more oligonucleotides correspond to components of the library of candidate nucleotide sequences, in a subject sample of epithelial cells; (c) correlating expression of the two or more nucleotide sequences with at least one criterion, which criterion comprises one or more indicator of adhesion to an endothelium; and (d) recording the molecular signature in a database.

The present invention is further directed to methods of leukocyte expression profiling including methods of analyzing longitudinal clinical and expression data. The rate of change and/or magnitude and direction of change of gene expression can be correlated with disease states and the rate of change of clinical conditions/data and/or the magnitude and direction of changes in clinical data. Correlations may be discovered by examining these expression or clinical changes that are not found in the absence of such changes.

The present invention is further directed to methods of leukocyte profiling for analysis and/or detection of one or more viruses. The virus may be CMV, HIV, hepatitis or other viruses. Both viral and human leukocyte genes can be subjected to expression profiling for these purposes.

BRIEF DESCRIPTION OF THE SEQUENCE LISTING

The table below gives a description of the sequence listing. There are 8830 entries. The Sequence Listing presents 50 mer oligonucleotide sequences derived from human leukocyte, plant and viral genes. These are listed as SEQ IDs 1-8143. The 50 mer sequences and their sources are also displayed in Table 8. Most of these 50 mers were designed from sequences of genes in Tables 2, 3A, B and C, Tables 8, 11-12, 14 and the Sequence listing.

SEQ IDs 8144-8766 are the cDNA sequences derived from human leukocytes that were not homologous to UniGene sequences or sequences found in dbEST at the time they were searched. Some of these sequences match human genomic sequences and are listed in Tables 3B and C. The remaining clones are putative cDNA sequences that contained less than 50% masked nucleotides when submitted to RepeatMasker, were longer than 147 nucleotides, and did not have significant similarity to the UniGene Unique database, dbEST, the NR nucleotide database of Genbank or the assembled human genome of Genbank.

SEQ IDs 8767-8770, 8828-8830 and 8832 are sequences that appear in the text and examples (primer, masked sequences, exemplary sequences, etc.).

SEQ IDs 8771-8827 are CMV PCR primers described in Example 17.

BRIEF DESCRIPTION OF THE FIGURES

FIG. 1: FIG. 1 is a schematic flow chart illustrating a schematic instruction set for characterization of the nucleotide sequence and/or the predicted protein sequence of novel nucleotide sequences.

FIG. 2: FIG. 2 depicts the components of an automated RNA preparation machine.

FIG. 3: FIG. 3 describes kits useful for the practice of the invention. FIG. 3A describes the contents of a kit useful for the discovery of diagnostic nucleotide sets using microarrays. FIG. 3B describes the contents of a kit useful for the application of diagnostic nucleotide sets using microarrays. FIG. 3C describes contents of a kit useful for the application of diagnostic nucleotide sets using real-time PCR.

FIG. 4 shows the results of six hybridizations on a mini array graphed (n=6 for each column). The error bars are the SEM. This experiment shows that the average signal from AP prepared RNA is 47% of the average signal from GS prepared RNA for both Cy3 and Cy5.

FIG. 8 shows data from an array hybridization.

FIG. 9: Cardiac Allograft rejection diagnostic genes.

A. Example of rejection and no-rejection samples expression data for 5 marker genes. For each sample, the associated rejection grades are shown as are the expression ratios for 5 differentially expressed genes. The genes are identified by the SEQ ID number for the oligonucleotide. The average fold difference between grade 0 and grade 3A samples is calculated at the bottom.

B. CART classification model. Decision tree for a 3 gene classification model for diagnosis of cardiac rejection. In the first step, expression of gene 7582 is used to divide the patients to 2 branches. The remaining samples in each branch are then further divided by one remaining gene. The samples are classified as either rejection or no rejection. 1 no rejection sample is misclassified as a rejection sample.

C. Surrogates for the CART classification model. For each of the 3 splitter genes in the CART rejection model described in the example, 5 top surrogate genes are listed that were identified by the CART algorithm.

Figure 10A:
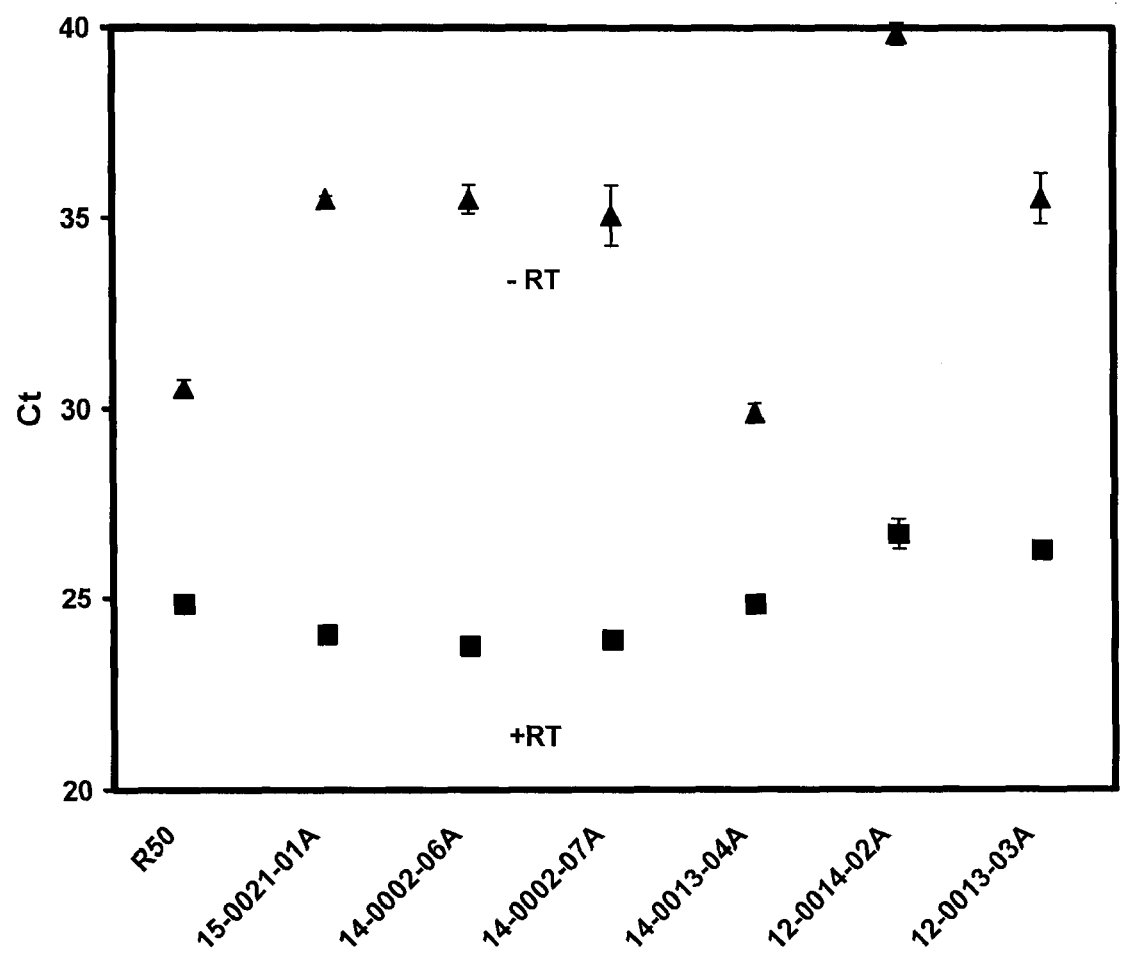

FIG. 10: Validation of differential expression of a gene discovered using microarrays using real-time PCR FIG. 10A. The Ct for each patient sample on multiple assays is shown along with the Ct in the R50 control RNA. Triangles represent –RT (reverse transcriptase) controls.

Figure 10B:
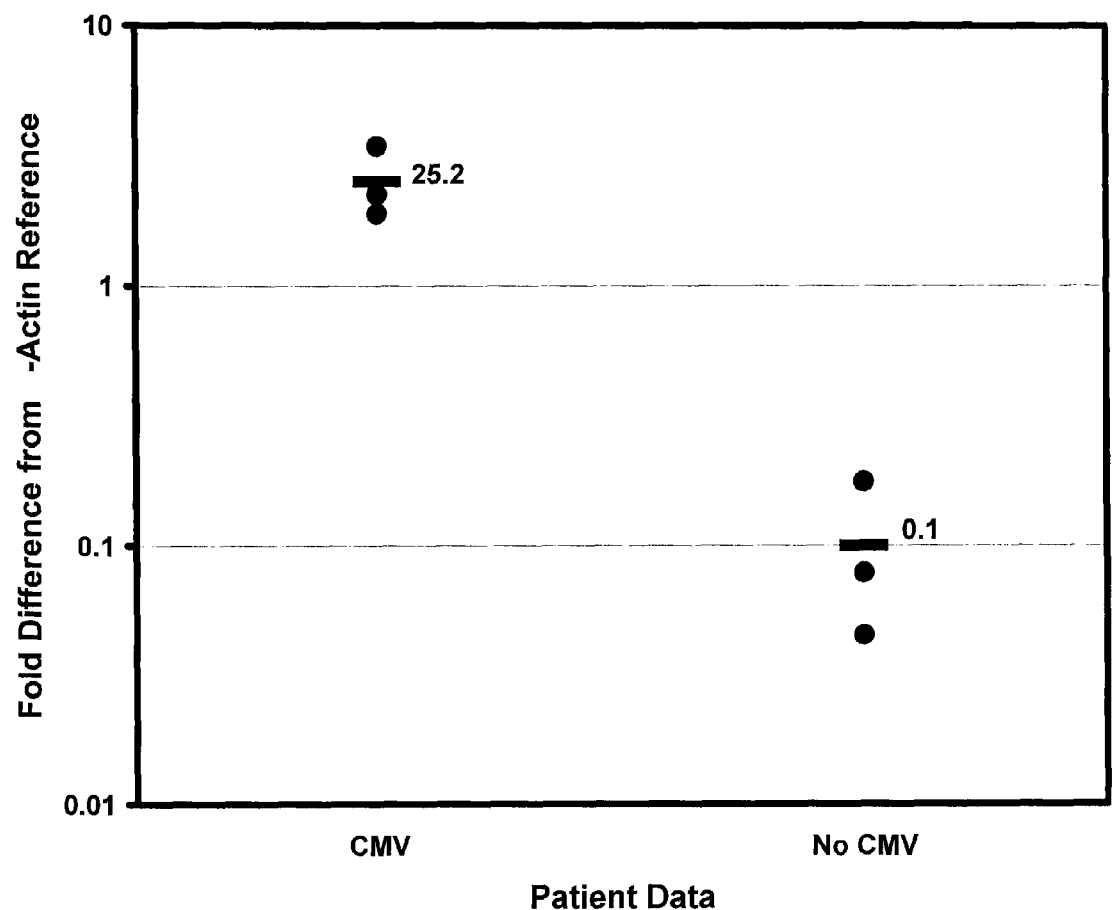

FIG. 10B. The fold difference between the expression of Granzyme B and an Actin reference is shown for 3 samples from patients with and without CMV disease.

Figure 11:
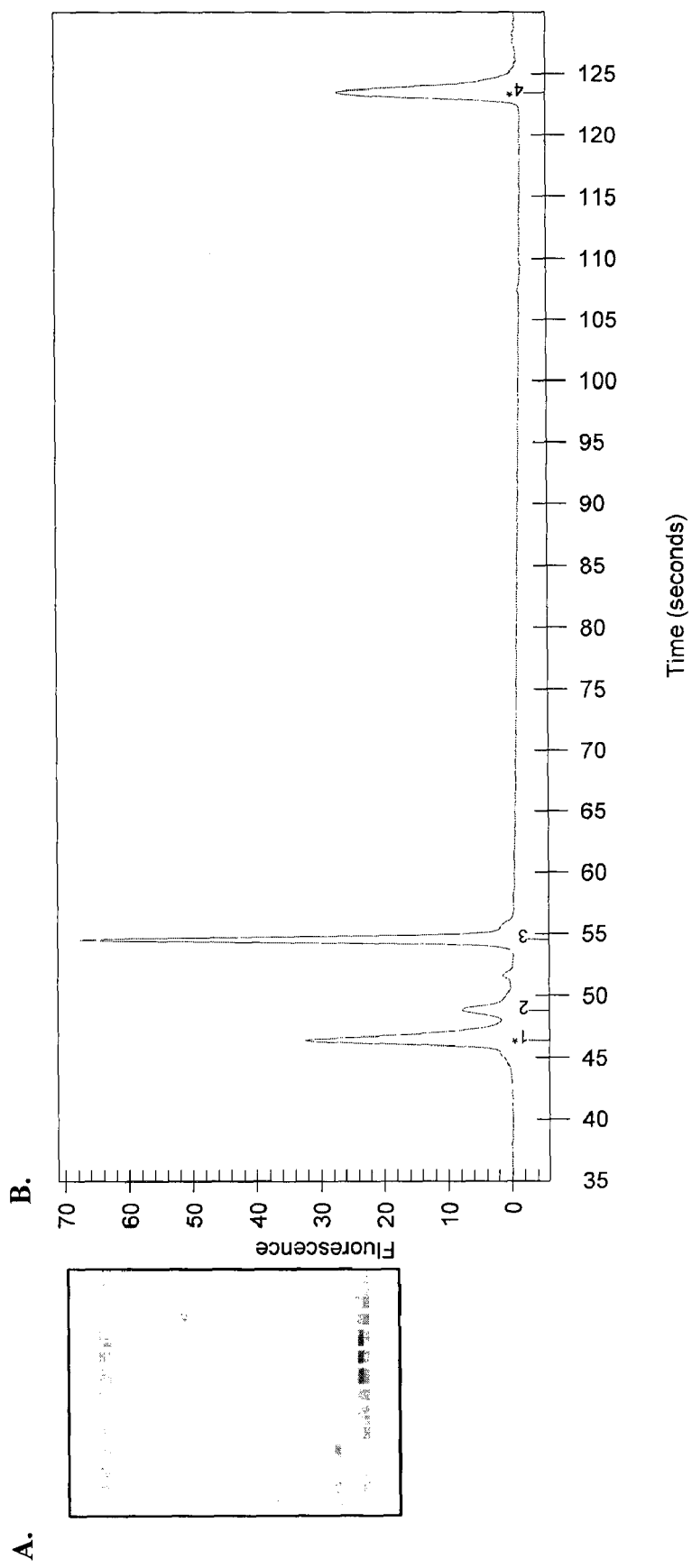
Figure 11:
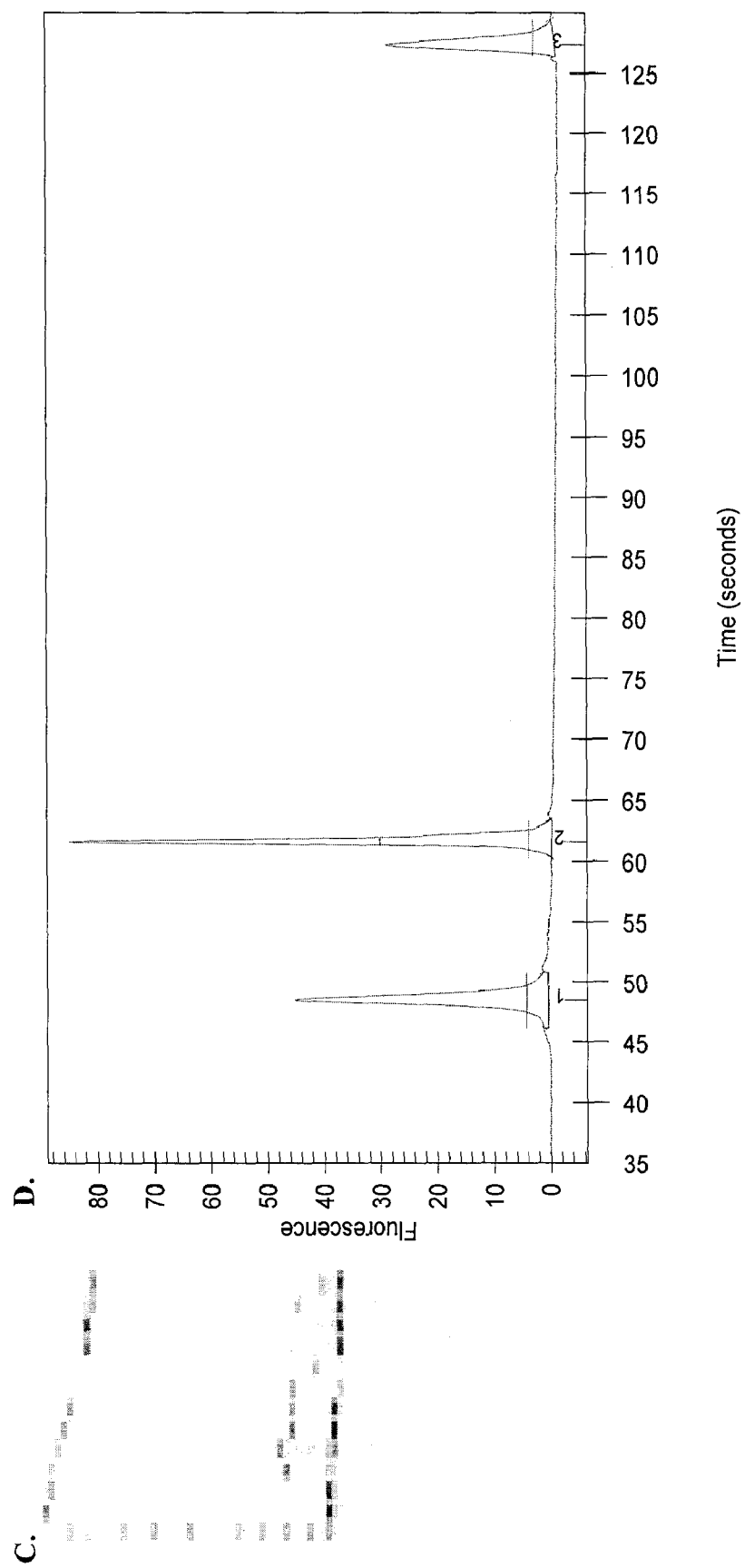

FIG. 11: Endpoint testing of PCR primers.

Electrophoresis and microfluidics are used to assess the product of gene specific PCR primers.

A. β-GUS gel image. Lane 3 is the image for primers F178 and R242. Lanes 2 and 1 correspond to the no-template control and –RT control, respectively.

B. The electropherogram of β-GUS primers F178 and R242, a graphical representation of Lane 3 from the gel image.

C. β-Actin gel image. Lane 3 is the image for primers F75 and R178. Lanes 2 and 1 correspond to the no-template control and –RT control, respectively.

D. The electropherogram of β-Actin primers F75 and R178, a graphical representation of Lave 3 from the gel image.

Figure 12:
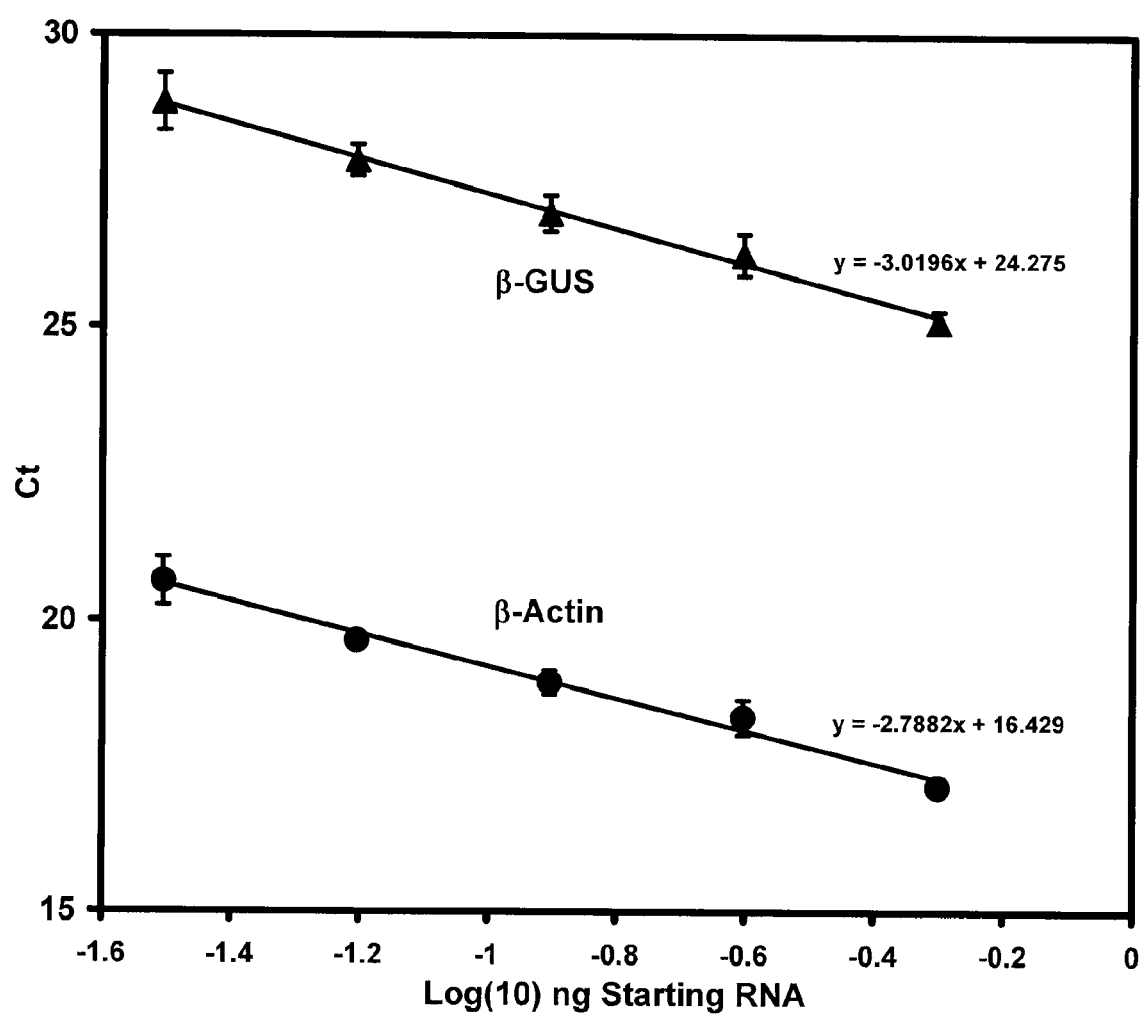

FIG. 12: PCR Primer efficiency testing. A standard curve of Ct versus log of the starting RNA amount is shown for 2 genes.

FIGS. 13A-B Validation of differential expression of Granzyme B in CMV patients using Real-time PCR

BRIEF DESCRIPTION OF THE TABLES

Table 1: Table 1 lists diseases or conditions amenable to study by leukocyte profiling.

Table 2: Table 2 describes genes and other nucleotide sequences identified using data mining of publicly available publication databases and nucleotide sequence databases. Corresponding Unigene (build 133) cluster numbers are listed with each gene or other nucleotide sequence.

Table 3A: Table 3A describes differentially expressed nucleotide sequences useful for the prediction of clinical outcomes. This table contains 4517 identified cDNAs and cDNA regions of genes that are members of a leukocyte candidate library, for use in measuring the expression of nucleotide sequences that could subsequently be correlated with human clinical conditions. The regions of similarity were found by searching three different databases for pair wise similarity using blastn. The three databases were Uni-Gene Unique build Mar. 30, 2001, file Hs.seq.uniq.Z; the downloadable database at ftp.ncbi.nlm.nih.com/blast/db/est human.Z with date Apr. 8, 2001 which is a section of Genbank version 122; and the non-redundant section of Genbank ver 123. The Hs.XXXXX numbers represent UniGene accession numbers from the Hs.seq.uniq.Z file of Mar. 30, 2001. The clone sequences are not in the sequence listing.

Table 3B: Table 3B describes Identified Genomic Regions that code for novel mRNAs. The table contains 591 identified genomic regions that are highly similar to the cDNA clones. Those regions that are within ~100 to 200 Kb of each other on the same contig are likely to represent exons of the same gene. The indicated clone is exemplary of the cDNA clones that match the indicated genomic region. The "number clones" column indicates how many clones were isolated from the libraries that are similar to the indicated region of the chromosome. The probability number is the likelihood that region of similarity would occur by chance on a random sequence. The Accession numbers are from the Mar. 15, 2001 build of the human genome. The file date for the downloaded data was Apr. 17, 2001. These sequences may prove useful for the prediction of clinical outcomes.

Table 3C: Table 3C describes 48 clones whose sequences align to two or more non-contiguous sequences on the same assembled human contig of genomic sequence. The Accession numbers are from the Mar. 15, 2001 build of the human genome. The file date for the downloaded data was Apr. 17, 2001. The alignments of the clone and the contig are indicated in the table. The start and stop offset of each matching region is indicated in the table. The sequence of the clones themselves is included in the sequence listing. The alignments of these clones strongly suggest that they are novel nucleotide sequences. Furthermore, no EST or mRNA aligning to the clone was found in the database. These sequences may prove useful for the prediction of clinical outcomes.

Table 4: Table 4 describes patient groups and diagnostic gene sets

Table 5: Table 5 describes the nucleotide sequence databases used in the sequence analysis described herein.

Table 6: Table 6 describes the algorithms and software packages used for exon and polypeptide prediction used in the sequence analysis described herein.

Table 7: Table 7 describes the databases and algorithms used for the protein sequence analysis described herein.

Table 8: Table 8 provides a listing of all oligonucleotides designed for the arrays and their associated genes. In this table, the sequence ID is given which corresponds to the sequence listing. The origin of the sequence for inclusion on the array is noted as coming from one of the cDNA libraries described in example 1, mining from databases as described in examples 2 and 20 or identification from the published literature. The unigene number, genebank accession and GI number are also given for each sequence when known. These data were obtained from the Unigene unique database, build 137. The name of the gene associated with the accession number is noted. The strand is noted as –1 or 1, meaning that the probe was designed from the complement of the sequence (–1) or directly from the sequence (1). Finally, the nucleotide sequence of each probe is also given.

Table 9: Database mining. The Library Browser at the NCBI UniGene web site was used to identify genes that are specifically expressed in leukocyte cell populations. The table lists the library name and type, the number of sequences in each library and the number used for the array.

Table 10: Viral gene for arrays. Viral genomes were used to design oligonucleotides for the microarrays. The accession numbers for the viral genomes used are given, along with the gene name and location of the region used for oligonucleotide design.

Table 11A. CMV gene expression markers. This table lists the oligonucleotides and associated genes identified as having value for the diagnosis and monitoring of CMV infection. The first column gives the SEQ ID that corresponds to the oligonucleotide in the sequence listing. The origin of the sequence for inclusion on the array is noted as coming from one of the cDNA libraries described in example 1, mining from databases as described in examples 2 and 20 or identification from the published literature. The unigene number, genebank accession and GI number are also given for each sequence when known. The SEQ ID for the sequence listing for the full-length genes corresponding to the accession numbers in the table are also given (SEQ ID Acc). These data were obtained from the Unigene unique database, build 149, and the Genbank Version 129. The full length sequences are presented in Table 14A. The name of the gene associated with the accession number is noted. The strand is noted as –1 or 1, meaning that the probe was designed from the complement of the sequence (–1) or directly from the sequence (1). Next, the nucleotide sequence of each probe is also given. For each gene, the false detection rate (FDR) from the significance analysis described in example 17 is given if applicable. WBC is the white blood cell count. WPT is the number of weeks past transplant.

Table 11B. Primers for PCR. For each of the CMV gene expression markers identified in Table 11A, 2 sets of PCR primer pairs are shown that were derived by the methods described in example 25. The first column gives the SEQ ID of the oligonucleotide probe used on the microarrays. The melting temperature (Tm) for each primer is shown, as is the corresponding SEQ ID for the primer in the sequence listing.

Table 12A. Cardiac rejection gene expression markers. This table lists the oligonucleotides and associated genes identified as having value for the diagnosis and monitoring of cardiac rejection. The first column gives the SEQ ID that corresponds to the oligonucleotide in the sequence listing. The origin of the sequence for inclusion on the array is noted as coming from one of the cDNA libraries described in example 1, mining from databases as described in examples 2 and 20 or identification from the published literature. The unigene number, genebank accession and GI number are also given for each sequence when known. The full length sequence for the accession number given is in the sequence listing. The SEQ ID for the sequence listing for the full-length genes corresponding to the accession numbers in the table are also given (SEQ ID ACC). These data were obtained from the Unigene unique database, build 149, and the Genbank Version 129. The full length sequences are presented in Table 14B. The name of the gene associated with the accession number is noted. The strand is noted as –1 or 1, meaning that the probe was designed from the complement of the sequence (–1) or directly from the sequence (1). Next, the nucleotide sequence of each probe is given. The remaining columns give data from the significance analysis and classification analysis that identified each gene as a rejection marker. Data is reported from 2 types of data: static data or referenced data, as described in the example. For each gene, the false detection rate (FDR) from the significance analysis described in example 24 is given if applicable. The FDR is given as a %. The final columns report the criteria for selection of each gene as a rejection marker from either the static or referenced data sets:

A1: Low FDR (<20) in two independent data sets with SAM

A2: Occurred greater than 50% of the time in the top 20 genes with low FDR (<20) by SAM AND occurred at all in Isolator or CART analyses B1: Occurred greater than 50% of the time in the top 5 terms with Isolator B2: Identified among the top 10 based on Isolator term occurrences C1: A primary splitter in a CART analysis of ~6000 genes C2: Identified among the top 10 based on CART splitter occurrences D: Part of a logistic regression model E: Part of a K-nearest neighbor model Table 12B. Primers for PCR. For each of the rejection gene expression markers identified in Table 12A, 2 sets of PCR primer pairs are shown that were derived by the methods described in example 25. The first column gives the SEQ ID of the oligonucleotide probe used on the microarrays. The melting temperature (Tm) for each primer is shown, as is the corresponding SEQ ID for each primer in the sequence listing.

Table 12C. Surrogates for rejection gene expression markers. For some of the rejection marker genes identified in Table 12A, genes are identified by the SEQ ID number as surrogates. The surrogates are identified as such by the CART algorithm or by hierarchical clustering (see text). Surrogates identified by hierarchical clustering are static expression values and those identified by CART are either static or referenced (see example 24).

Table 13. Dependent variables for discovery of gene expression markers of cardiac allograft rejection. A stable Grade 0 is a Grade 0 biopsy in a patient who does not experience rejection with the subsequent biopsy. HG or highest grade means that the higher of the biopsy grades from the centralized and local pathologists was used for a definition of the dependent variable.

Table 14A shows the full length CMV gene sequences referred to in Table 11A.

Table 14B shows the full length gene sequences for genes related to transplant rejection referred to in Table 12A.

DETAILED DESCRIPTION OF THE INVENTION

Definitions

Unless defined otherwise, all scientific and technical terms are understood to have the same meaning as commonly used in the art to which they pertain. For the purpose of the present invention, the following terms are defined below.

In the context of the invention, the term "gene expression system" refers to any system, device or means to detect gene expression and includes diagnostic agents, candidate libraries, oligonucleotide sets or probe sets.

The term "monitoring" is used herein to describe the use of gene sets to provide useful information about an individual or an individual's health or disease status. "Monitoring" can include, determination of prognosis, risk-stratification, selection of drug therapy, assessment of ongoing drug therapy, prediction of outcomes, determining response to therapy, diagnosis of a disease or disease complication, following progression of a disease or providing any information relating to a patients health status.

The term "diagnostic oligonucleotide set" generally refers to a set of two or more oligonucleotides that, when evaluated for differential expression of their products, collectively yields predictive data. Such predictive data typically relates to diagnosis, prognosis, monitoring of therapeutic outcomes, and the like. In general, the components of a diagnostic oligonucleotide set are distinguished from nucleotide sequences that are evaluated by analysis of the DNA to directly determine the genotype of an individual as it correlates with a specified trait or phenotype, such as a disease, in that it is the pattern of expression of the components of the diagnostic nucleotide set, rather than mutation or polymorphism of the DNA sequence that provides predictive value. It will be understood that a particular component (or member) of a diagnostic nucleotide set can, in some cases, also present one or more mutations, or polymorphisms that are amenable to direct genotyping by any of a variety of well known analysis methods, e.g., Southern blotting, RFLP, AFLP, SSCP, SNP, and the like.

A "disease specific target oligonucleotide sequence" is a gene or other oligonucleotide that encodes a polypeptide, most typically a protein, or a subunit of a multi-subunit protein, that is a therapeutic target for a disease, or group of diseases.

A "candidate library" or a "candidate oligonucleotide library" refers to a collection of oligonucleotide sequences (or gene sequences) that by one or more criteria have an increased probability of being associated with a particular disease or group of diseases. The criteria can be, for example, a differential expression pattern in a disease state or in activated or resting leukocytes in vitro as reported in the scientific or technical literature, tissue specific expression as reported in a sequence database, differential expression in a tissue or cell type of interest, or the like. Typically, a candidate library has at least 2 members or components; more typically, the library has in excess of about 10, or about 100, or about 1000, or even more, members or components.

The term "disease criterion" is used herein to designate an indicator of a disease, such as a diagnostic factor, a prognostic factor, a factor indicated by a medical or family history, a genetic factor, or a symptom, as well as an overt or confirmed diagnosis of a disease associated with several indicators such as those selected from the above list. A disease criterion includes data describing a patient's health status, including retrospective or prospective health data, e.g. in the form of the patient's medical history, laboratory test results, diagnostic test result, clinical events, medications, lists, response(s) to treatment and risk factors, etc.

The terms "molecular signature" or "expression profile" refers to the collection of expression values for a plurality (e.g., at least 2, but frequently about 10, about 100, about 1000, or more) of members of a candidate library. In many cases, the molecular signature represents the expression pattern for all of the nucleotide sequences in a library or array of candidate or diagnostic nucleotide sequences or genes. Alternatively, the molecular signature represents the expression pattern for one or more subsets of the candidate library. The term "oligonucleotide" refers to two or more nucleotides. Nucleotides may be DNA or RNA, naturally occurring or synthetic.

The term "healthy individual," as used herein, is relative to a specified disease or disease criterion. That is, the individual does not exhibit the specified disease criterion or is not diagnosed with the specified disease. It will be understood, that the individual in question, can, of course, exhibit symptoms, or possess various indicator factors for another disease.

Similarly, an "individual diagnosed with a disease" refers to an individual diagnosed with a specified disease (or disease criterion). Such an individual may, or may not, also exhibit a disease criterion associated with, or be diagnosed with another (related or unrelated) disease.

An "array" is a spatially or logically organized collection, e.g., of oligonucleotide sequences or nucleotide sequence products such as RNA or proteins encoded by an oligonucleotide sequence. In some embodiments, an array includes antibodies or other binding reagents specific for products of a candidate library.

When referring to a pattern of expression, a "qualitative" difference in gene expression refers to a difference that is not assigned a relative value. That is, such a difference is designated by an "all or nothing" valuation. Such an all or nothing variation can be, for example, expression above or below a threshold of detection (an on/off pattern of expression). Alternatively, a qualitative difference can refer to expression of different types of expression products, e.g., different alleles (e.g., a mutant or polymorphic allele), variants (including sequence variants as well as post-translationally modified variants), etc.

In contrast, a "quantitative" difference, when referring to a pattern of gene expression, refers to a difference in expression that can be assigned a value on a graduated scale, (e.g., a 0-5 or 1-10 scale, a +−++ scale, a grade 1-grade 5 scale, or the like; it will be understood that the numbers selected for illustration are entirely arbitrary and in no-way are meant to be interpreted to limit the invention).

Gene Expression Systems of the Invention

The invention is directed to a gene expression system having one or more DNA molecules wherein the one or more DNA molecules has a nucleotide sequence which detects expression of a gene corresponding to the oligonucleotides depicted in the Sequence Listing. In one format, the oligonucleotide detects expression of a gene that is differentially expressed in leukocytes. The gene expression system may be a candidate library, a diagnostic agent, a diagnostic oligonucleotide set or a diagnostic probe set. The DNA molecules may be genomic DNA, protein nucleic acid (PNA), cDNA or synthetic oligonucleotides. Following the procedures taught herein, one can identity sequences of interest for analyzing gene expression in leukocytes. Such sequences may be predictive of a disease state.

Diagnostic Oligonucleotides of the Invention

The invention relates to diagnostic nucleotide set(s) comprising members of the leukocyte candidate library listed in Table 2, Table 3 and in the Sequence Listing, for which a correlation exists between the health status of an individual, and the individual's expression of RNA or protein products corresponding to the nucleotide sequence. In some instances, only one oligonucleotide is necessary for such detection. Members of a diagnostic oligonucleotide set may be identified by any means capable of detecting expression of RNA or protein products, including but not limited to differential expression screening, PCR, RT-PCR, SAGE analysis, high-throughput sequencing, microarrays, liquid or other arrays, protein-based methods (e.g., western blotting, proteomics, and other methods described herein), and data mining methods, as further described herein.

In one embodiment, a diagnostic oligonucleotide set comprises at least two oligonucleotide sequences listed in Table 2 or Table 3 or the Sequence Listing which are differentially expressed in leukocytes in an individual with at least one disease criterion for at least one leukocyte-implicated disease relative to the expression in individual without the at least one disease criterion, wherein expression of the two or more nucleotide sequences is correlated with at least one disease criterion, as described below.

In another embodiment, a diagnostic nucleotide set comprises at least one oligonucleotide having an oligonucleotide sequence listed in Table 2 or 3 or the Sequence Listing which is differentially expressed, and further wherein the differential expression/correlation has not previously been described. In some embodiments, the diagnostic nucleotide set is immobilized on an array.

In another embodiment, diagnostic nucleotides (or nucleotide sets) are related to the members of the leukocyte candidate library listed in Table 2, Table 3 and in the Sequence Listing, for which a correlation exists between the health status (or disease criterion) of an individual. The diagnostic nucleotides are partially or totally contained in (or derived from) full-length gene sequences (or predicted full-length gene sequences) for the members of the candidate library listed in Table 2, 3, Tables 8, 11-12, 14. This includes sequences from accession numbers and unigene numbers from Table 8. Table 8 shows the accession and unigene number (when known) for each oligonucleotide used on the 8134 gene leukocyte array described in examples 11-13. In some cases, oligonucleotide sequences are designed from EST or Chromosomal sequences from a public database. In these cases the full-length gene sequences may not be known. Full-length sequences in these cases can be predicted using gene prediction algorithms (examples 4-6). Alternatively the full-length can be determined by cloning and sequencing the full-length gene or genes that contain the sequence of interest using standard molecular biology approaches described here. The same is true for oligonucleotides designed from our sequencing of cDNA libraries (see examples 1-4) where the cDNA does not match any sequence in the public databases.

The diagnostic nucleotides may also be derived from other genes that are coexpressed with the correlated sequence or full-length gene. Genes may share expression patterns because they are regulated in the same molecular pathway. Because of the similarity of expression behavior genes are identified as surrogates in that they can substitute for a diagnostic gene in a diagnostic gene set. Example 10 demonstrates the discovery of surrogates from the data and the sequence listing identify and give the sequence for surrogates for lupus diagnostic genes.

As used herein the term "gene cluster" or "cluster" refers to a group of genes related by expression pattern. In other words, a cluster of genes is a group of genes with similar regulation across different conditions, such as graft non-rejection versus graft rejection. The expression profile for each gene in a cluster should be correlated with the expression profile of at least one other gene in that cluster. Correlation may be evaluated using a variety of statistical methods. As used herein the term "surrogate" refers to a gene with an expression profile such that it can substitute for a diagnostic gene in a diagnostic assay. Such genes are often members of the same gene cluster as the diagnostic gene. For each member of a diagnostic gene set, a set of potential surrogates can be identified through identification of genes with similar expression patterns as described below.

Many statistical analyses produce a correlation coefficient to describe the relatedness between two gene expression patterns. Patterns may be considered correlated if the correlation coefficient is greater than or equal to 0.8. In preferred embodiments, the correlation coefficient should be greater than 0.85, 0.9 or 0.95. Other statistical methods produce a measure of mutual information to describe the relatedness between two gene expression patterns. Patterns may be considered correlated if the normalized mutual information value is greater than or equal to 0.7. In preferred embodiments, the normalized mutual information value should be greater than 0.8, 0.9 or 0.95. Patterns may also be considered similar if they cluster closely upon hierarchical clustering of gene expression data (Eisen et al. 1998). Similar patterns may be those genes that are among the 1, 2, 5, 10, 20, 50 or 100 nearest neighbors in a hierarchical clustering or have a similarity score (Eisen et al. 1998) of >0.5, 0.7, 0.8, 0.9, 0.95 or 0.99. Similar patterns may also be identified as those genes found to be surrogates in a classification tree by CART (Breiman et al. 1994). Often, but not always, members of a gene cluster have similar biological functions in addition to similar gene expression patterns.

Correlated genes, clusters and surrogates are identified for the diagnostic genes of the invention. These surrogates may be used as diagnostic genes in an assay instead of, or in addition to, the diagnostic genes for which they are surrogates.

The invention also provides diagnostic probe sets. It is understood that a probe includes any reagent capable of specifically identifying a nucleotide sequence of the diagnostic nucleotide set, including but not limited to amplified DNA, amplified RNA, cDNA, synthetic oligonucleotide, partial or full-length nucleic acid sequences. In addition, the probe may identify the protein product of a diagnostic nucleotide sequence, including, for example, antibodies and other affinity reagents.

It is also understood that each probe can correspond to one gene, or multiple probes can correspond to one gene, or both, or one probe can correspond to more than one gene.

Homologs and variants of the disclosed nucleic acid molecules may be used in the present invention. Homologs and variants of these nucleic acid molecules will possess a relatively high degree of sequence identity when aligned using standard methods. The sequences encompassed by the invention have at least 40-50, 50-60, 70-80, 80-85, 85-90, 90-95 or 95-100% sequence identity to the sequences disclosed herein.

It is understood that for expression profiling, variations in the disclosed sequences will still permit detection of gene expression. The degree of sequence identity required to detect gene expression varies depending on the length of the oligomer. For a 60 mer, 6-8 random mutations or 6-8 random deletions in a 60 mer do not affect gene expression detection. Hughes, T R, et al. "Expression profiling using microarrays fabricated by an ink-jet oligonucleotide synthesizer. Nature Biotechnology, 19:343-347 (2001). As the length of the DNA sequence is increased, the number of mutations or deletions permitted while still allowing gene expression detection is increased.

As will be appreciated by those skilled in the art, the sequences of the present invention may contain sequencing errors. That is, there may be incorrect nucleotides, frameshifts, unknown nucleotides, or other types of sequencing errors in any of the sequences; however, the correct sequences will fall within the homology and stringency definitions herein.

The minimum length of an oligonucleotide probe necessary for specific hybridization in the human genome can be estimated using two approaches. The first method uses a statistical argument that the probe will be unique in the human genome by chance. Briefly, the number of independent perfect matches (Po) expected for an oligonucleotide of length L in a genome of complexity C can be calculated from the equation (Laird C D, Chromosoma 32:378 (1971):

$$Po=(1/4)^{L}*2C$$

In the case of mammalian genomes, $2C=\sim3.6\times10^9$, and an oligonucleotide of 14-15 nucleotides is expected to be represented only once in the genome. However, the distribution of nucleotides in the coding sequence of mammalian genomes is nonrandom (Lathe, R. J. Mol. Biol. 183:1 (1985) and longer oligonucleotides may be preferred in order to in increase the specificity of hybridization. In practical terms, this works out to probes that are 19-40 nucleotides long (Sambrook J et al., infra). The second method for estimating the length of a specific probe is to use a probe long enough to hybridize under the chosen conditions and use a computer to search for that sequence or close matches to the sequence in the human genome and choose a unique match. Probe sequences are chosen based on the desired hybridization properties as described in Chapter 11 of Sambrook et al, infra. The PRIMER3 program is useful for designing these probes (S. Rozen and H. Skaletsky 1996, 1997; Primer3 code available at the web site located at genome.wi.mit.edu/genome_software/other/primer3.html). The sequences of these probes are then compared pair wise against a database of the human genome sequences using a program such as BLAST or MEGABLAST (Madden, T. L et al. (1996) Meth. Enzymol. 266:131-141). Since most of the human genome is now contained in the database, the number of matches will be determined. Probe sequences are chosen that are unique to the desired target sequence.

In some embodiments, a diagnostic probe set is immobilized on an array. The array is optionally comprises one or more of: a chip array, a plate array, a bead array, a pin array, a membrane array, a solid surface array, a liquid array, an oligonucleotide array, a polynucleotide array or a cDNA array, a microtiter plate, a pin array, a bead array, a membrane or a chip.

In some embodiments, the leukocyte-implicated disease is selected from the diseases listed in Table 1. In other embodiments, the disease is atherosclerosis or cardiac allograft rejection. In other embodiments, the disease is congestive heart failure, angina, myocardial infarction, systemic lupus erythematosis (SLE) and rheumatoid arthritis.

In some embodiments, diagnostic nucleotides of the invention are used as a diagnostic gene set in combination with genes that are know to be associated with a disease state ("known markers"). The use of the diagnostic nucleotides in combination with the known markers can provide information that is not obtainable through the known markers alone. The known markers include those identified by the prior art listing provided.

General Molecular Biology References

In the context of the invention, nucleic acids and/or proteins are manipulated according to well known molecular biology techniques. Detailed protocols for numerous such procedures are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Q-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company (mcrc@oligos.com), The Great American Gene Company ExpressGen, Inc., Operon Technologies, Inc. and many others.

Similarly, commercial sources for nucleic acid and protein microarrays are available, and include, e.g., Agilent Technologies, Palo Alto, Calif. Affymetrix, Santa Clara, Calif.; and others.

Identification of Diagnostic Nucleotide Sets

Candidate Library

Libraries of candidates that are differentially expressed in leukocytes are substrates for the identification and evaluation of diagnostic oligonucleotide sets and disease specific target nucleotide sequences.

The term leukocyte is used generically to refer to any nucleated blood cell that is not a nucleated erythrocyte. More specifically, leukocytes can be subdivided into two broad classes. The first class includes granulocytes, including, most prevalently, neutrophils, as well as eosinophils and basophils at low frequency. The second class, the non-granular or mononuclear leukocytes, includes monocytes and lymphocytes (e.g., T cells and B cells). There is an extensive literature in the art implicating leukocytes, e.g., neutrophils, monocytes and lymphocytes in a wide variety of disease processes, including inflammatory and rheumatic diseases, neurodegenerative diseases (such as Alzheimer's dementia), cardiovascular disease, endocrine diseases, transplant rejection, malignancy and infectious diseases, and other diseases listed in Table 1. Mononuclear cells are involved in the chronic immune response, while granulocytes, which make up approximately 60% of the leukocytes, have a non-specific and stereotyped response to acute inflammatory stimuli and often have a life span of only 24 hours.

In addition to their widespread involvement and/or implication in numerous disease related processes, leukocytes are particularly attractive substrates for clinical and experimental evaluation for a variety of reasons. Most importantly, they are readily accessible at low cost from essentially every potential subject. Collection is minimally invasive and associated with little pain, disability or recovery time. Collection can be performed by minimally trained personnel (e.g., phlebotomists, medical technicians, etc.) in a variety of clinical and non-clinical settings without significant technological expenditure. Additionally, leukocytes are renewable, and thus available at multiple time points for a single subject.

Assembly of Candidate Libraries

At least two conceptually distinct approaches to the assembly of candidate libraries exist. Either, or both, or other, approaches can be favorably employed. The method of assembling, or identifying, candidate libraries is secondary to the criteria utilized for selecting appropriate library members. Most importantly, library members are assembled based on differential expression of RNA or protein products in leukocyte populations. More specifically, candidate nucleotide sequences are induced or suppressed, or expressed at increased or decreased levels in leukocytes from a subject with one or more disease or disease state (a disease criterion) relative to leukocytes from a subject lacking the specified disease criterion. Alternatively, or in addition, library members can be assembled from among nucleotide sequences that are differentially expressed in activated or resting leukocytes relative to other cell types.

Firstly, publication and sequence databases can be "mined" using a variety of search strategies, including, e.g., a variety of genomics and proteomics approaches. For example, currently available scientific and medical publication databases such as Medline, Current Contents, OMIM (online Mendelian inheritance in man) various Biological and Chemical Abstracts, Journal indexes, and the like can be searched using term or key-word searches, or by author, title, or other relevant search parameters. Many such databases are publicly available, and one of skill is well versed in strategies and procedures for identifying publications and their contents, e.g., genes, other nucleotide sequences, descriptions, indications, expression pattern, etc. Numerous databases are available through the internet for free or by subscription, see, e.g., at the web sites located at ncbi.nlm.nih.gov/PubMed/; 3.infotrieve.com/; isinet.com/; sciencemag.org/. Additional or alternative publication or citation databases are also available that provide identical or similar types of information, any of which are favorable employed in the context of the invention. These databases can be searched for publications describing differential gene expression in leukocytes between patient with and without diseases or conditions listed in Table 1. We identified the nucleotide sequences listed in Table 2 and some of the sequences listed in Table 8 (Example 20), using data mining methods.

Alternatively, a variety of publicly available and proprietary sequence databases (including GenBank, dbEST, UniGene, and TIGR and SAGE databases) including sequences corresponding to expressed nucleotide sequences, such as expressed sequence tags (ESTs) are available. For example, Genbank™ ncbi.nlm.nih.gov/Genbank/) among others can be readily accessed and searched via the internet. These and other sequence and clone database resources are currently available; however, any number of additional or alternative databases comprising nucleotide sequence sequences, EST sequences, clone repositories, PCR primer sequences, and the like corresponding to individual nucleotide sequence sequences are also suitable for the purposes of the invention. Sequences from nucleotide sequences can be identified that are only found in libraries derived from leukocytes or subpopulations of leukocytes, for example see Table 2.

Alternatively, the representation, or relative frequency, of a nucleotide sequence may be determined in a leukocyte-derived nucleic acid library and compared to the representation of the sequence in non-leukocyte derived libraries. The representation of a nucleotide sequence correlates with the relative expression level of the nucleotide sequence in leukocytes and non-leukocytes. An oligonucleotide sequence which has increased or decreased representation in a leukocyte-derived nucleic acid library relative to a non-leukocyte-derived libraries is a candidate for a leukocyte-specific gene.

Nucleotide sequences identified as having specificity to activated or resting leukocytes or to leukocytes from patients or patient samples with a variety of disease types can be isolated for use in a candidate library for leukocyte expression profiling through a variety of mechanisms. These include, but are not limited to, the amplification of the nucleotide sequence from RNA or DNA using nucleotide sequence specific primers for PCR or RT-PCR, isolation of the nucleotide sequence using conventional cloning methods, the purchase of an IMAGE consortium cDNA clone (EST) with complimentary sequence or from the same expressed nucleotide sequence, design of oligonucleotides, preparation of synthetic nucleic acid sequence, or any other nucleic-acid based method. In addition, the protein product of the nucleotide sequence can be isolated or prepared, and represented in a candidate library, using standard methods in the art, as described further below.

While the above discussion related primarily to "genomics" approaches, it is appreciated that numerous, analogous "proteomics" approaches are suitable to the present invention. For example, a differentially expressed protein product can, for example, be detected using western analysis, two-dimensional gel analysis, chromatographic separation, mass spectrometric detection, protein-fusion reporter constructs, colorometric assays, binding to a protein array, or by characterization of polysomal mRNA. The protein is further characterized and the nucleotide sequence encoding the protein is identified using standard techniques, e.g. by screening a cDNA library using a probe based on protein sequence information.

The second approach involves the construction of a differential expression library by any of a variety of means. Any one or more of differential screening, differential display or subtractive hybridization procedures, or other techniques that preferentially identify, isolate or amplify differentially expressed nucleotide sequences can be employed to produce a library of differentially expressed candidate nucleotide sequences, a subset of such a library, a partial library, or the like. Such methods are well known in the art. For example, peripheral blood leukocytes, (i.e., a mixed population including lymphocytes, monocytes and neutrophils), from multiple donor samples are pooled to prevent bias due to a single-donor's unique genotype. The pooled leukocytes are cultured in standard medium and stimulated with individual cytokines or growth factors e.g., with IL-2, IL-1, MCP1, TNFα, and/or IL8 according to well known procedures (see, e.g., Tough et al. (1999); Winston et al. (1999); Hansson et al. (1989)). Typically, leukocytes are recovered from Buffy coat preparations produced by centrifugation of whole blood. Alternatively, mononuclear cells (monocytes and lymphocytes) can be obtained by density gradient centrifugation of whole blood, or specific cell types (such as a T lymphocyte) can be isolated using affinity reagents to cell specific surface markers. Leukocytes may also be stimulated by incubation with ionomycin, and phorbol myristate acetate (PMA). This stimulation protocol is intended to non-specifically mimic "activation" of numerous pathways due to variety of disease conditions rather than to simulate any single disease condition or paradigm.

Using well known subtractive hybridization procedures (as described in, e.g., U.S. Pat. Nos. 5,958,738; 5,589,339; 5,827,658; 5,712,127; 5,643,761) each of which are hereby incorporated by reference, a library is produced that is enriched for RNA species (messages) that are differentially expressed between test and control leukocyte populations. In some embodiments, the test population of leukocytes are simply stimulated as described above to emulate non-specific activation events, while in other embodiments the test population can be selected from subjects (or patients) with a specified disease or class of diseases. Typically, the control leukocyte population lacks the defining test condition, e.g., stimulation, disease state, diagnosis, genotype, etc. Alternatively, the total RNA from control and test leukocyte populations are prepared by established techniques, treated with DNAseI, and selected for messenger RNA with an intact 3' end (i.e., polyA (+) messenger RNA) e.g., using commercially available kits according to the manufacturer's instructions e.g. Clontech. Double stranded cDNA is synthesized utilizing reverse transcriptase. Double stranded cDNA is then cut with a first restriction enzyme (e.g., NlaIII, that cuts at the recognition site: CATG, and cuts the cDNA sequence at approximately 256 bp intervals) that cuts the cDNA molecules into conveniently sized fragments.

The cDNAs prepared from the test population of leukocytes are divided into (typically 2) "tester" pools, while cDNAs prepared from the control population of leukocytes are designated the "driver" pool. Typically, pooled populations of cells from multiple individual donors are utilized and in the case of stimulated versus unstimulated cells, the corresponding tester and driver pools for any single subtraction reaction are derived from the same donor pool.

A unique double-stranded adapter is ligated to each of the tester cDNA populations using unphosphorylated primers so that only the sense strand is covalently linked to the adapter. An initial hybridization is performed consisting of each of the tester pools of cDNA (each with its corresponding adapter) and an excess of the driver cDNA. Typically, an excess of about 10-100 fold driver relative to tester is employed, although significantly lower or higher ratios can be empirically determined to provide more favorable results. The initial hybridization results in an initial normalization of the cDNAs such that high and low abundance messages become more equally represented following hybridization due to a failure of driver/tester hybrids to amplify.

A second hybridization involves pooling un-hybridized sequences from initial hybridizations together with the addition of supplemental driver cDNA. In this step, the expressed sequences enriched in the two tester pools following the initial hybridization can hybridize. Hybrids resulting from the hybridization between members of each of the two tester pools are then recovered by amplification in a polymerase chain reaction (PCR) using primers specific for the unique adapters. Again, sequences originating in a tester pool that form hybrids with components of the driver pool are not amplified. Hybrids resulting between members of the same tester pool are eliminated by the formation of "panhandles" between their common 5' and 3' ends. For additional details, see, e.g., Lukyanov et al. (1997) *Biochem Biophys Res Commun* 230:285-8.

Typically, the tester and driver pools are designated in the alternative, such that the hybridization is performed in both directions to ensure recovery of messenger RNAs that are differentially expressed in either a positive or negative manner (i.e., that are turned on or turned off, up-regulated or down-regulated). Accordingly, it will be understood that the designation of test and control populations is to some extent arbitrary, and that a test population can just as easily be compared to leukocytes derived from a patient with the same of another disease of interest.

If so desired, the efficacy of the process can be assessed by such techniques as semi-quantitative PCR of known (i.e., control) nucleotide sequences, of varying abundance such as β-actin. The resulting PCR products representing partial cDNAs of differentially expressed nucleotide sequences are then cloned (i.e., ligated) into an appropriate vector (e.g., a commercially available TA cloning vector, such as pGEM from Promega) and, optionally, transformed into competent bacteria for selection and screening.

Either of the above approaches, or both in combination, or indeed, any procedure, which permits the assembly of a collection of nucleotide sequences that are expressed in leukocytes, is favorably employed to produce the libraries of candidates useful for the identification of diagnostic nucleotide sets and disease specific target nucleotides of the invention. Additionally, any method that permits the assembly of a collection of nucleotides that are expressed in leukocytes and preferentially associated with one or more disease or condition, whether or not the nucleotide sequences are differentially expressed, is favorably employed in the context of the invention. Typically, libraries of about 2,000-10,000 members are produced (although libraries in excess of 10,000 are not uncommon). Following additional evaluation procedures, as described below, the proportion of unique clones in the candidate library can approximate 100%.

A candidate oligonucleotide sequence may be represented in a candidate library by a full-length or partial nucleic acid sequence, deoxyribonucleic acid (DNA) sequence, cDNA sequence, RNA sequence, synthetic oligonucleotides, etc. The nucleic acid sequence can be at least 19 nucleotides in length, at least 25 nucleotides, at least 40 nucleotides, at least 100 nucleotides, or larger. Alternatively, the protein product of a candidate nucleotide sequence may be represented in a candidate library using standard methods, as further described below.

Characterization of Candidate Oligonucleotide Sequences

The sequence of individual members (e.g., clones, partial sequence listing in a database such as an EST, etc.) of the candidate oligonucleotide libraries is then determined by conventional sequencing methods well known in the art, e.g., by the dideoxy-chain termination method of Sanger et al. (1977) Proc Natl Acad Sci USA 74:5463-7; by chemical procedures, e.g., Maxam and Gilbert (1977) Proc Natl Acad Sci USA 74:560-4; or by polymerase chain reaction cycle sequencing methods, e.g., Olsen and Eckstein (1989) Nuc Acid Res 17:9613-20, DNA chip based sequencing techniques or variations, including automated variations (e.g., as described in Hunkapiller et al. (1991) Science 254:59-67; Pease et al. (1994) Proc Natl Acad Sci USA 91:5022-6), thereof. Numerous kits for performing the above procedures are commercially available and well known to those of skill in the art. Character strings corresponding to the resulting nucleotide sequences are then recorded (i.e., stored) in a database. Most commonly the character strings are recorded on a computer readable medium for processing by a computational device.

Generally, to facilitate subsequent analysis, a custom algorithm is employed to query existing databases in an ongoing fashion, to determine the identity, expression pattern and potential function of the particular members of a candidate library. The sequence is first processed, by removing low quality sequence. Next the vector sequences are identified and removed and sequence repeats are identified and masked. The remaining sequence is then used in a Blast algorithm against multiple publicly available, and/or proprietary databases, e.g., NCBI nucleotide, EST and protein databases, Unigene, and Human Genome Sequence. Sequences are also compared to all previously sequenced members of the candidate libraries to detect redundancy.

In some cases, sequences are of high quality, but do not match any sequence in the NCBI nr, human EST or Unigene databases. In this case the sequence is queried against the human genomic sequence. If a single chromosomal site is matched with a high degree of confidence, that region of genomic DNA is identified and subjected to further analysis with a gene prediction program such as GRAIL. This analysis may lead to the identification of a new gene in the genomic sequence. This sequence can then be translated to identify the protein sequence that is encoded and that sequence can be further analyzed using tools such as Pfam, Blast P, or other protein structure prediction programs, as illustrated in Table 7. Typically, the above analysis is directed towards the identification of putative coding regions, e.g., previously unidentified open reading frames, confirming the presence of known coding sequences, and determining structural motifs or sequence similarities of the predicted protein (i.e., the conceptual translation product) in relation to known sequences. In addition, it has become increasingly possible to assemble "virtual cDNAs" containing large portions of coding region, simply through the assembly of available expressed sequence tags (ESTs). In turn, these extended nucleic acid and amino acid sequences allow the rapid expansion of substrate sequences for homology searches and structural and functional motif characterization. The results of these analysis permits the categorization of sequences according to structural characteristics, e.g., as structural proteins, proteins involved in signal transduction, cell surface or secreted proteins etc.

It is understood that full-length nucleotide sequences may also be identified using conventional methods, for example, library screening, RT-PCR, chromosome walking, etc., as described in Sambrook and Ausubel, infra.

Candidate Nucleotide Library of the Invention

We identified members of a candidate nucleotide library that are differentially expressed in activated leukocytes and resting leukocytes. Accordingly, the invention provides the candidate leukocyte nucleotide library comprising the nucleotide sequences listed in Table 2, Table 3 and in the sequence listing. In another embodiment, the invention provides a candidate library comprising at least two nucleotide sequences listed in Table 2, Table 3, Tables 8, 11-12, 14 and the sequence listing. In another embodiment, the at least two nucleotide sequence are at least 19 nucleotides in length, at least 35 nucleotides, at least 40 nucleotides or at least 100 nucleotides. In some embodiments, the nucleotide sequences comprises deoxyribonucleic acid (DNA) sequence, ribonucleic acid (RNA) sequence, synthetic oligonucleotide sequence, or genomic DNA sequence. It is understood that the nucleotide sequences may each correspond to one gene, or that several nucleotide sequences may correspond to one gene, or both.

The invention also provides probes to the candidate nucleotide library. In one embodiment of the invention, the probes comprise at least two nucleotide sequences listed in Table 2, Table 3, or the sequence listing which are differentially expressed in leukocytes in an individual with a least one disease criterion for at least one leukocyte-related disease and in leukocytes in an individual without the at least one disease criterion, wherein expression of the two or more nucleotide sequences is correlated with at least one disease criterion. It is understood that a probe may detect either the RNA expression or protein product expression of the candidate nucleotide library. Alternatively, or in addition, a probe can detect a genotype associated with a candidate nucleotide sequence, as further described below. In another embodiment, the probes for the candidate nucleotide library are immobilized on an array.

The candidate nucleotide library of the invention is useful in identifying diagnostic nucleotide sets of the invention, as described below. The candidate nucleotide sequences may be further characterized, and may be identified as a disease target nucleotide sequence and/or a novel nucleotide sequence, as described below. The candidate nucleotide sequences may also be suitable for use as imaging reagents, as described below.

Generation of Expression Patterns

RNA, DNA or Protein Sample Procurement

Following identification or assembly of a library of differentially expressed candidate nucleotide sequences, leukocyte expression profiles corresponding to multiple members of the candidate library are obtained. Leukocyte samples from one or more subjects are obtained by standard methods. Most typically, these methods involve trans-cutaneous venous sampling of peripheral blood. While sampling of circulating leukocytes from whole blood from the peripheral vasculature is generally the simplest, least invasive, and lowest cost alternative, it will be appreciated that numerous alternative sampling procedures exist, and are favorably employed in some circumstances. No pertinent distinction exists, in fact, between leukocytes sampled from the peripheral vasculature, and those obtained, e.g., from a central line, from a central artery, or indeed from a cardiac catheter, or during a surgical procedure which accesses the central vasculature. In addition, other body fluids and tissues that are, at least in part, composed of leukocytes are also desirable leukocyte samples. For example, fluid samples obtained from the lung during bronchoscopy may be rich in leukocytes, and amenable to expression profiling in the context of the invention, e.g., for the diagnosis, prognosis, or monitoring of lung transplant rejection, inflammatory lung diseases or infectious lung disease. Fluid samples from other tissues, e.g., obtained by endoscopy of the colon, sinuses, esophagus, stomach, small bowel, pancreatic duct, biliary tree, bladder, ureter, vagina, cervix or uterus, etc., are also suitable. Samples may also be obtained other sources containing leukocytes, e.g., from urine, bile, cerebrospinal fluid, feces, gastric or intestinal secretions, semen, or solid organ or joint biopsies.

Most frequently, mixed populations of leukocytes, such as are found in whole blood are utilized in the methods of the present invention. A crude separation, e.g., of mixed leukocytes from red blood cells, and/or concentration, e.g., over a sucrose, percoll or ficoll gradient, or by other methods known in the art, can be employed to facilitate the recovery of RNA or protein expression products at sufficient concentrations, and to reduce non-specific background. In some instances, it can be desirable to purify sub-populations of leukocytes, and methods for doing so, such as density or affinity gradients, flow cytometry, fluorescence Activated Cell Sorting (FACS), immuno-magnetic separation, "panning," and the like, are described in the available literature and below.

Obtaining DNA, RNA and Protein Samples for Expression Profiling

Expression patterns can be evaluated at the level of DNA, or RNA or protein products. For example, a variety of techniques are available for the isolation of RNA from whole blood. Any technique that allows isolation of mRNA from cells (in the presence or absence of rRNA and tRNA) can be utilized. In brief, one method that allows reliable isolation of total RNA suitable for subsequent gene expression analysis, is described as follows. Peripheral blood (either venous or arterial) is drawn from a subject, into one or more sterile, endotoxin free, tubes containing an anticoagulant (e.g., EDTA, citrate, heparin, etc.). Typically, the sample is divided into at least two portions. One portion, e.g., of 5-8 ml of whole blood is frozen and stored for future analysis, e.g., of DNA or protein. A second portion, e.g., of approximately 8 ml whole blood is processed for isolation of total RNA by any of a variety of techniques as described in, e.g., Sambook, Ausubel, below, as well as U.S. Pat. Nos. 5,728,822 and 4,843,155.

Typically, a subject sample of mononuclear leukocytes obtained from about 8 ml of whole blood, a quantity readily available from an adult human subject under most circumstances, yields 5-20 μg of total RNA. This amount is ample, e.g., for labeling and hybridization to at least two probe arrays. Labeled probes for analysis of expression patterns of nucleotides of the candidate libraries are prepared from the subject's sample of RNA using standard methods. In many cases, cDNA is synthesized from total RNA using a polyT primer and labeled, e.g., radioactive or fluorescent, nucleotides. The resulting labeled cDNA is then hybridized to probes corresponding to members of the candidate nucleotide library, and expression data is obtained for each nucleotide sequence in the library. RNA isolated from subject samples (e.g., peripheral blood leukocytes, or leukocytes obtained from other biological fluids and samples) is next used for analysis of expression patterns of nucleotides of the candidate libraries.

In some cases, however, the amount of RNA that is extracted from the leukocyte sample is limiting, and amplification of the RNA is desirable. Amplification may be accomplished by increasing the efficiency of probe labeling, or by amplifying the RNA sample prior to labeling. It is appreciated that care must be taken to select an amplification procedure that does not introduce any bias (with respect to gene expression levels) during the amplification process.

Several methods are available that increase the signal from limiting amounts of RNA, e.g. use of the Clontech (Glass Fluorescent Labeling Kit) or Stratagene (Fairplay Microarray Labeling Kit), or the Micromax kit (New England Nuclear, Inc.). Alternatively, cDNA is synthesized from RNA using a T7-polyT primer, in the absence of label, and DNA dendrimers from Genisphere (3DNA Submicro) are hybridized to the poly T sequence on the primer, or to a different "capture sequence" which is complementary to a fluorescently labeled sequence. Each 3DNA molecule has 250 fluorescent molecules and therefore can strongly label each cDNA.

Alternatively, the RNA sample is amplified prior to labeling. For example, linear amplification may be performed, as described in U.S. Pat. No. 6,132,997. A T7-polyT primer is used to generate the cDNA copy of the RNA. A second DNA strand is then made to complete the substrate for amplification. The T7 promoter incorporated into the primer is used by a T7 polymerase to produce numerous antisense copies of the original RNA. Fluorescent dye labeled nucleotides are directly incorporated into the RNA. Alternatively, amino allyl labeled nucleotides are incorporated into the RNA, and then fluorescent dyes are chemically coupled to the amino allyl groups, as described in Hughes. Other exemplary methods for amplification are described below.

It is appreciated that the RNA isolated must contain RNA derived from leukocytes, but may also contain RNA from other cell types to a variable degree. Additionally, the isolated RNA may come from subsets of leukocytes, e.g. monocytes and/or T-lymphocytes, as described above. Such consideration of cell type used for the derivation of RNA depend on the method of expression profiling used.

DNA samples may be obtained for analysis of the presence of DNA mutations, single nucleotide polymorphisms (SNPs), or other polymorphisms. DNA is isolated using standard techniques, e.g. Maniatus, supra.

Expression of products of candidate nucleotides may also be assessed using proteomics. Protein(s) are detected in samples of patient serum or from leukocyte cellular protein. Serum is prepared by centrifugation of whole blood, using standard methods. Proteins present in the serum may have been produced from any of a variety of leukocytes and non-leukocyte cells, and include secreted proteins from leukocytes. Alternatively, leukocytes or a desired sub-population of leukocytes are prepared as described above. Cellular protein is prepared from leukocyte samples using methods well known in the art, e.g., Trizol (Invitrogen Life Technologies, cat # 15596108; Chomczynski, P. and Sacchi, N. (1987) Anal. Biochem. 162, 156; Simms, D., Cizdziel, P. E., and Chomczynski, P. (1993) Focus® 15, 99; Chomczynski, P., Bowers-Finn, R., and Sabatini, L. (1987) J. of NIH Res. 6, 83; Chomczynski, P. (1993) Bio/Techniques 15, 532; Bracete, A. M., Fox, D. K., and Simms, D. (1998) Focus 20, 82; Sewall, A. and McRae, S. (1998) Focus 20, 36; Anal Biochem 1984 April; 138(1):141-3, A method for the quantitative recovery of protein in dilute solution in the presence of detergents and lipids; Wessel D, Flugge U I. (1984) Anal Biochem. 1984 April; 138(1):141-143.

Obtaining Expression Patterns

Expression patterns, or profiles, of a plurality of nucleotides corresponding to members of the candidate library are then evaluated in one or more samples of leukocytes. Typically, the leukocytes are derived from patient peripheral blood samples, although, as indicated above, many other sample sources are also suitable. These expression patterns constitute a set of relative or absolute expression values for a some number of RNAs or protein products corresponding to the plurality of nucleotide sequences evaluated, which is referred to herein as the subject's "expression profile" for those nucleotide sequences. While expression patterns for as few as one independent member of the candidate library can be obtained, it is generally preferable to obtain expression patterns corresponding to a larger number of nucleotide sequences, e.g., about 2, about 5, about 10, about 20, about 50, about 100, about 200, about 500, or about 1000, or more. The expression pattern for each differentially expressed component member of the library provides a finite specificity and sensitivity with respect to predictive value, e.g., for diagnosis, prognosis, monitoring, and the like.

Clinical Studies, Data and Patient Groups

For the purpose of discussion, the term subject, or subject sample of leukocytes, refers to an individual regardless of health and/or disease status. A subject can be a patient, a study participant, a control subject, a screening subject, or any other class of individual from whom a leukocyte sample is obtained and assessed in the context of the invention. Accordingly, a subject can be diagnosed with a disease, can present with one or more symptom of a disease, or a predisposing factor, such as a family (genetic) or medical history (medical) factor, for a disease, or the like. Alternatively, a subject can be healthy with respect to any of the aforementioned factors or criteria. It will be appreciated that the term "healthy" as used herein, is relative to a specified disease, or disease factor, or disease criterion, as the term "healthy" cannot be defined to correspond to any absolute evaluation or status. Thus, an individual defined as healthy with reference to any specified disease or disease criterion, can in fact be diagnosed with any other one or more disease, or exhibit any other one or more disease criterion.

Furthermore, while the discussion of the invention focuses, and is exemplified using human sequences and samples, the invention is equally applicable, through construction or selection of appropriate candidate libraries, to non-human animals, such as laboratory animals, e.g., mice, rats, guinea pigs, rabbits; domesticated livestock, e.g., cows, horses, goats, sheep, chicken, etc.; and companion animals, e.g., dogs, cats, etc.

Methods for Obtaining Expression Data

Numerous methods for obtaining expression data are known, and any one or more of these techniques, singly or in combination, are suitable for determining expression profiles in the context of the present invention. For example, expression patterns can be evaluated by northern analysis, PCR, RT-PCR, Taq Man analysis, FRET detection, monitoring one or more molecular beacon, hybridization to an oligonucleotide array, hybridization to a cDNA array, hybridization to a polynucleotide array, hybridization to a liquid microarray, hybridization to a microelectric array, molecular beacons, cDNA sequencing, clone hybridization, cDNA fragment fingerprinting, serial analysis of gene expression (SAGE), subtractive hybridization, differential display and/or differential screening (see, e.g., Lockhart and Winzeler (2000) *Nature* 405:827-836, and references cited therein).

For example, specific PCR primers are designed to a member(s) of a candidate nucleotide library. cDNA is prepared from subject sample RNA by reverse transcription from a poly-dT oligonucleotide primer, and subjected to PCR. Double stranded cDNA may be prepared using primers suitable for reverse transcription of the PCR product, followed by amplification of the cDNA using in vitro transcription. The product of in vitro transcription is a sense-RNA corresponding to the original member(s) of the candidate library. PCR product may be also be evaluated in a number of ways known in the art, including real-time assessment using detection of labeled primers, e.g. TaqMan or molecular beacon probes. Technology platforms suitable for analysis of PCR products include the ABI 7700, 5700, or 7000 Sequence Detection Systems (Applied Biosystems, Foster City, Calif.), the MJ Research Opticon (MJ Research, Waltham, Mass.), the Roche Light Cycler (Roche Diagnositics, Indianapolis, Ind.), the Stratagene MX4000 (Stratagene, La Jolla, Calif.), and the Bio-Rad iCycler (Bio-Rad Laboratories, Hercules, Calif.). Alternatively, molecular beacons are used to detect presence of a nucleic acid sequence in an unamplified RNA or cDNA sample, or following amplification of the sequence using any method, e.g. IVT (In Vitro transcription) or NASBA (nucleic acid sequence based amplification). Molecular beacons are designed with sequences complementary to member(s) of a candidate nucleotide library, and are linked to fluorescent labels. Each probe has a different fluorescent label with non-overlapping emission wavelengths. For example, expression of ten genes may be assessed using ten different sequence-specific molecular beacons.

Alternatively, or in addition, molecular beacons are used to assess expression of multiple nucleotide sequences at once. Molecular beacons with sequence complimentary to the members of a diagnostic nucleotide set are designed and linked to fluorescent labels. Each fluorescent label used must have a non-overlapping emission wavelength. For example, 10 nucleotide sequences can be assessed by hybridizing 10 sequence specific molecular beacons (each labeled with a different fluorescent molecule) to an amplified or un-amplified RNA or cDNA sample. Such an assay bypasses the need for sample labeling procedures.

Alternatively, or in addition bead arrays can be used to assess expression of multiple sequences at once. See, e.g, LabMAP 100, Luminex Corp, Austin, Tex.). Alternatively, or in addition electric arrays are used to assess expression of multiple sequences, as exemplified by the e-Sensor technology of Motorola (Chicago, Ill.) or Nanochip technology of Nanogen (San Diego, Calif.)

Of course, the particular method elected will be dependent on such factors as quantity of RNA recovered, practitioner preference, available reagents and equipment, detectors, and the like. Typically, however, the elected method(s) will be appropriate for processing the number of samples and probes of interest. Methods for high-throughput expression analysis are discussed below.

Alternatively, expression at the level of protein products of gene expression is performed. For example, protein expression, in a sample of leukocytes, can be evaluated by one or more method selected from among: western analysis, two-dimensional gel analysis, chromatographic separation, mass spectrometric detection, protein-fusion reporter constructs, calorimetric assays, binding to a protein array and characterization of polysomal mRNA. One particularly favorable approach involves binding of labeled protein expression products to an array of antibodies specific for members of the candidate library. Methods for producing and evaluating antibodies are widespread in the art, see, e.g., Coligan, supra; and Harlow and Lane (1989) *Antibodies: A Laboratory Manual*, Cold Spring Harbor Press, NY ("Harlow and Lane"). Additional details regarding a variety of immunological and immunoassay procedures adaptable to the present invention by selection of antibody reagents specific for the products of candidate nucleotide sequences can be found in, e.g., Stites and Terr (eds.) (1991) *Basic and Clinical Immunology*, $7^{th}$ ed., and Paul, supra. Another approach uses systems for performing desorption spectrometry. Commercially available systems, e.g., from Ciphergen Biosystems, Inc. (Fremont, Calif.)

are particularly well suited to quantitative analysis of protein expression. Indeed, Protein Chip® arrays (see, e.g., the web site ciphergen.com) used in desorption spectrometry approaches provide arrays for detection of protein expression. Alternatively, affinity reagents, e.g., antibodies, small molecules, etc.) are developed that recognize epitopes of the protein product. Affinity assays are used in protein array assays, e.g. to detect the presence or absence of particular proteins. Alternatively, affinity reagents are used to detect expression using the methods described above. In the case of a protein that is expressed on the cell surface of leukocytes, labeled affinity reagents are bound to populations of leukocytes, and leukocytes expressing the protein are identified and counted using fluorescent activated cell sorting (FACS).

It is appreciated that the methods of expression evaluation discussed herein, although discussed in the context of discovery of diagnostic nucleotide sets, are equally applicable for expression evaluation when using diagnostic nucleotide sets for, e.g. diagnosis of diseases, as further discussed below.

High Throughput Expression Assays

A number of suitable high throughput formats exist for evaluating gene expression. Typically, the term high throughput refers to a format that performs at least about 100 assays, or at least about 500 assays, or at least about 1000 assays, or at least about 5000 assays, or at least about 10,000 assays, or more per day. When enumerating assays, either the number of samples or the number of candidate nucleotide sequences evaluated can be considered. For example, a northern analysis of, e.g., about 100 samples performed in a gridded array, e.g., a dot blot, using a single probe corresponding to a candidate nucleotide sequence can be considered a high throughput assay. More typically, however, such an assay is performed as a series of duplicate blots, each evaluated with a distinct probe corresponding to a different member of the candidate library. Alternatively, methods that simultaneously evaluate expression of about 100 or more candidate nucleotide sequences in one or more samples, or in multiple samples, are considered high throughput.

Numerous technological platforms for performing high throughput expression analysis are known. Generally, such methods involve a logical or physical array of either the subject samples, or the candidate library, or both. Common array formats include both liquid and solid phase arrays. For example, assays employing liquid phase arrays, e.g., for hybridization of nucleic acids, binding of antibodies or other receptors to ligand, etc., can be performed in multiwell, or microtiter, plates. Microtiter plates with 96, 384 or 1536 wells are widely available, and even higher numbers of wells, e.g, 3456 and 9600 can be used. In general, the choice of microtiter plates is determined by the methods and equipment, e.g., robotic handling and loading systems, used for sample preparation and analysis. Exemplary systems include, e.g., the ORCA™ system from Beckman-Coulter, Inc. (Fullerton, Calif.) and the Zymate systems from Zymark Corporation (Hopkinton, Mass.).

Alternatively, a variety of solid phase arrays can favorably be employed in to determine expression patterns in the context of the invention. Exemplary formats include membrane or filter arrays (e.g, nitrocellulose, nylon), pin arrays, and bead arrays (e.g., in a liquid "slurry"). Typically, probes corresponding to nucleic acid or protein reagents that specifically interact with (e.g., hybridize to or bind to) an expression product corresponding to a member of the candidate library are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In a preferred embodiment, the array is a "chip" composed, e.g., of one of the above specified materials. Polynucleotide probes, e.g., RNA or DNA, such as cDNA, synthetic oligonucleotides, and the like, or binding proteins such as antibodies, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Detailed discussion of methods for linking nucleic acids and proteins to a chip substrate, are found in, e.g., U.S. Pat. No. 5,143,854 "LARGE SCALE PHOTOLITHOGRAPHIC SOLID PHASE SYNTHESIS OF POLYPEPTIDES AND RECEPTOR BINDING SCREENING THEREOF" to Pirrung et al., issued, Sep. 1, 1992; U.S. Pat. No. 5,837,832 "ARRAYS OF NUCLEIC ACID PROBES ON BIOLOGICAL CHIPS" to Chee et al., issued Nov. 17, 1998; U.S. Pat. No. 6,087,112 "ARRAYS WITH MODIFIED OLIGONUCLEOTIDE AND POLYNUCLEOTIDE COMPOSITIONS" to Dale, issued Jul. 11, 2000; U.S. Pat. No. 5,215,882 "METHOD OF IMMOBILIZING NUCLEIC ACID ON A SOLID SUBSTRATE FOR USE IN NUCLEIC ACID HYBRIDIZATION ASSAYS" to Bahl et al., issued Jun. 1, 1993; U.S. Pat. No. 5,707,807 "MOLECULAR INDEXING FOR EXPRESSED GENE ANALYSIS" to Kato, issued Jan. 13, 1998; U.S. Pat. No. 5,807,522 "METHODS FOR FABRICATING MICROARRAYS OF BIOLOGICAL SAMPLES" to Brown et al., issued Sep. 15, 1998; U.S. Pat. No. 5,958,342 "JET DROPLET DEVICE" to Gamble et al., issued Sep. 28, 1999; U.S. Pat. No. 5,994,076 "METHODS OF ASSAYING DIFFERENTIAL EXPRESSION" to Chenchik et al., issued Nov. 30, 1999; U.S. Pat. No. 6,004,755 "QUANTITATIVE MICROARRAY HYBRIDIZATION ASSAYS" to Wang, issued Dec. 21, 1999; U.S. Pat. No. 6,048,695 "CHEMICALLY MODIFIED NUCLEIC ACIDS AND METHOD FOR COUPLING NUCLEIC ACIDS TO SOLID SUPPORT" to Bradley et al., issued Apr. 11, 2000; U.S. Pat. No. 6,060,240 "METHODS FOR MEASURING RELATIVE AMOUNTS OF NUCLEIC ACIDS IN A COMPLEX MIXTURE AND RETRIEVAL OF SPECIFIC SEQUENCES THEREFROM" to Kamb et al., issued May 9, 2000; U.S. Pat. No. 6,090,556 "METHOD FOR QUANTITATIVELY DETERMINING THE EXPRESSION OF A GENE" to Kato, issued Jul. 18, 2000; and U.S. Pat. No. 6,040,138 "EXPRESSION MONITORING BY HYBRIDIZATION TO HIGH DENSITY OLIGONUCLEOTIDE ARRAYS" to Lockhart et al., issued Mar. 21, 2000 each of which are hereby incorporated by reference in their entirety.

For example, cDNA inserts corresponding to candidate nucleotide sequences, in a standard TA cloning vector are amplified by a polymerase chain reaction for approximately 30-40 cycles. The amplified PCR products are then arrayed onto a glass support by any of a variety of well known techniques, e.g., the VSLIPS™ technology described in U.S. Pat. No. 5,143,854. RNA, or cDNA corresponding to RNA, isolated from a subject sample of leukocytes is labeled, e.g., with a fluorescent tag, and a solution containing the RNA (or cDNA) is incubated under conditions favorable for hybridization, with the "probe" chip. Following incubation, and washing to eliminate non-specific hybridization, the labeled nucleic acid bound to the chip is detected qualitatively or quantitatively, and the resulting expression profile for the corresponding candidate nucleotide sequences is recorded. It is appreciated that the probe used for diagnostic purposes may be identical to the probe used during diagnostic nucleotide sequence discovery and validation. Alternatively, the probe sequence may be different than the sequence used in diagnostic nucleotide sequence discovery and validation. Multiple cDNAs from a nucleotide sequence that are non-overlapping or partially overlapping may also be used.

In another approach, oligonucleotides corresponding to members of a candidate nucleotide library are synthesized and spotted onto an array. Alternatively, oligonucleotides are synthesized onto the array using methods known in the art, e.g. Hughes, et al. supra. The oligonucleotide is designed to be complementary to any portion of the candidate nucleotide sequence. In addition, in the context of expression analysis for, e.g. diagnostic use of diagnostic nucleotide sets, an oligonucleotide can be designed to exhibit particular hybridization characteristics, or to exhibit a particular specificity and/or sensitivity, as further described below.

Hybridization signal may be amplified using methods known in the art, and as described herein, for example use of the Clontech kit (Glass Fluorescent Labeling Kit), Stratagene kit (Fairplay Microarray Labeling Kit), the Micromax kit (New England Nuclear, Inc.), the Genisphere kit (3DNA Submicro), linear amplification, e.g. as described in U.S. Pat. No. 6,132,997 or described in Hughes, T R, et al., Nature Biotechnology, 19:343-347 (2001) and/or Westin et al. *Nat Biotech.* 18:199-204.

Alternatively, fluorescently labeled cDNA are hybridized directly to the microarray using methods known in the art. For example, labeled cDNA are generated by reverse transcription using Cy3- and Cy5-conjugated deoxynucleotides, and the reaction products purified using standard methods. It is appreciated that the methods for signal amplification of expression data useful for identifying diagnostic nucleotide sets are also useful for amplification of expression data for diagnostic purposes.

Microarray expression may be detected by scanning the microarray with a variety of laser or CCD-based scanners, and extracting features with numerous software packages, for example, Imagene (Biodiscovery), Feature Extraction (Agilent), Scanalyze (Eisen, M. 1999. SCANALYZE User Manual; Stanford Univ., Stanford, Calif. Ver 2.32.), GenePix (Axon Instruments).

In another approach, hybridization to microelectric arrays is performed, e.g. as described in Umek et al (2001) *J Mol Diagn.* 3:74-84. An affinity probe, e.g. DNA, is deposited on a metal surface. The metal surface underlying each probe is connected to a metal wire and electrical signal detection system. Unlabelled RNA or cDNA is hybridized to the array, or alternatively, RNA or cDNA sample is amplified before hybridization, e.g. by PCR. Specific hybridization of sample RNA or cDNA results in generation of an electrical signal, which is transmitted to a detector. See Westin (2000) *Nat Biotech.* 18:199-204 (describing anchored multiplex amplification of a microelectronic chip array); Edman (1997) *NAR* 25:4907-14; Vignali (2000) *J Immunol Methods* 243:243-55.

In another approach, a microfluidics chip is used for RNA sample preparation and analysis. This approach increases efficiency because sample preparation and analysis are streamlined. Briefly, microfluidics may be used to sort specific leukocyte sub-populations prior to RNA preparation and analysis. Microfluidics chips are also useful for, e.g., RNA preparation, and reactions involving RNA (reverse transcription, RT-PCR). Briefly, a small volume of whole, anti-coagulated blood is loaded onto a microfluidics chip, for example chips available from Caliper (Mountain View, Calif.) or Nanogen (San Diego, Calif.) A microfluidics chip may contain channels and reservoirs in which cells are moved and reactions are performed. Mechanical, electrical, magnetic, gravitational, centrifugal or other forces are used to move the cells and to expose them to reagents. For example, cells of whole blood are moved into a chamber containing hypotonic saline, which results in selective lysis of red blood cells after a 20-minute incubation. Next, the remaining cells (leukocytes) are moved into a wash chamber and finally, moved into a chamber containing a lysis buffer such as guanidine isothyocyanate. The leukocyte cell lysate is further processed for RNA isolation in the chip, or is then removed for further processing, for example, RNA extraction by standard methods. Alternatively, the microfluidics chip is a circular disk containing ficoll or another density reagent. The blood sample is injected into the center of the disc, the disc is rotated at a speed that generates a centrifugal force appropriate for density gradient separation of mononuclear cells, and the separated mononuclear cells are then harvested for further analysis or processing.

It is understood that the methods of expression evaluation, above, although discussed in the context of discovery of diagnostic nucleotide sets, are also applicable for expression evaluation when using diagnostic nucleotide sets for, e.g. diagnosis of diseases, as further discussed below.

Evaluation of Expression Patterns

Expression patterns can be evaluated by qualitative and/or quantitative measures. Certain of the above described techniques for evaluating gene expression (as RNA or protein products) yield data that are predominantly qualitative in nature. That is, the methods detect differences in expression that classify expression into distinct modes without providing significant information regarding quantitative aspects of expression. For example, a technique can be described as a qualitative technique if it detects the presence or absence of expression of a candidate nucleotide sequence, i.e., an on/off pattern of expression. Alternatively, a qualitative technique measures the presence (and/or absence) of different alleles, or variants, of a gene product.

In contrast, some methods provide data that characterizes expression in a quantitative manner. That is, the methods relate expression on a numerical scale, e.g., a scale of 0-5, a scale of 1-10, a scale of +–+++, from grade 1 to grade 5, a grade from a to z, or the like. It will be understood that the numerical, and symbolic examples provided are arbitrary, and that any graduated scale (or any symbolic representation of a graduated scale) can be employed in the context of the present invention to describe quantitative differences in nucleotide sequence expression. Typically, such methods yield information corresponding to a relative increase or decrease in expression.

Any method that yields either quantitative or qualitative expression data is suitable for evaluating expression of candidate nucleotide sequence in a subject sample of leukocytes. In some cases, e.g., when multiple methods are employed to determine expression patterns for a plurality of candidate nucleotide sequences, the recovered data, e.g., the expression profile, for the nucleotide sequences is a combination of quantitative and qualitative data.

In some applications, expression of the plurality of candidate nucleotide sequences is evaluated sequentially. This is typically the case for methods that can be characterized as low- to moderate-throughput. In contrast, as the throughput of the elected assay increases, expression for the plurality of candidate nucleotide sequences in a sample or multiple samples of leukocytes, is assayed simultaneously. Again, the methods (and throughput) are largely determined by the individual practitioner, although, typically, it is preferable to employ methods that permit rapid, e.g. automated or partially automated, preparation and detection, on a scale that is time-efficient and cost-effective.

It is understood that the preceding discussion, while directed at the assessment of expression of the members of candidate libraries, is also applies to the assessment of the expression of members of diagnostic nucleotide sets, as further discussed below.

Genotyping

In addition to, or in conjunction with the correlation of expression profiles and clinical data, it is often desirable to correlate expression patterns with the subject's genotype at one or more genetic loci. The selected loci can be, for example, chromosomal loci corresponding to one or more member of the candidate library, polymorphic alleles for marker loci, or alternative disease related loci (not contributing to the candidate library) known to be, or putatively associated with, a disease (or disease criterion). Indeed, it will be appreciated, that where a (polymorphic) allele at a locus is linked to a disease (or to a predisposition to a disease), the presence of the allele can itself be a disease criterion.

Numerous well known methods exist for evaluating the genotype of an individual, including southern analysis, restriction fragment length polymorphism (RFLP) analysis, polymerase chain reaction (PCR), amplification length polymorphism (AFLP) analysis, single stranded conformation polymorphism (SSCP) analysis, single nucleotide polymorphism (SNP) analysis (e.g., via PCR, Taqman or molecular beacons), among many other useful methods. Many such procedures are readily adaptable to high throughput and/or automated (or semi-automated) sample preparation and analysis methods. Most, can be performed on nucleic acid samples recovered via simple procedures from the same sample of leukocytes as yielded the material for expression profiling. Exemplary techniques are described in, e.g., Sambrook, and Ausubel, supra.

Identification of the Diagnostic Nucleotide Sets of the Invention

Identification of diagnostic nucleotide sets and disease specific target nucleotide sequence proceeds by correlating the leukocyte expression profiles with data regarding the subject's health status to produce a data set designated a "molecular signature." Examples of data regarding a patient's health status, also termed "disease criteria(ion)", is described below and in the Section titled "selected diseases," below. Methods useful for correlation analysis are further described elsewhere in the specification.

Generally, relevant data regarding the subject's health status includes retrospective or prospective health data, e.g., in the form of the subject's medical history, as provided by the subject, physician or third party, such as, medical diagnoses, laboratory test results, diagnostic test results, clinical events, or medication lists, as further described below. Such data may include information regarding a patient's response to treatment and/or a particular medication and data regarding the presence of previously characterized "risk factors." For example, cigarette smoking and obesity are previously identified risk factors for heart disease. Further examples of health status information, including diseases and disease criteria, is described in the section titled Selected diseases, below.

Typically, the data describes prior events and evaluations (i.e., retrospective data). However, it is envisioned that data collected subsequent to the sampling (i.e., prospective data) can also be correlated with the expression profile. The tissue sampled, e.g., peripheral blood, bronchial lavage, etc., can be obtained at one or more multiple time points and subject data is considered retrospective or prospective with respect to the time of sample procurement.

Data collected at multiple time points, called "longitudinal data", is often useful, and thus, the invention encompasses the analysis of patient data collected from the same patient at different time points. Analysis of paired samples, such as samples from a patient at different time, allows identification of differences that are specifically related to the disease state since the genetic variability specific to the patient is controlled for by the comparison. Additionally, other variables that exist between patients may be controlled for in this way, for example, the presence or absence of inflammatory diseases (e.g., rheumatoid arthritis) the use of medications that may effect leukocyte gene expression, the presence or absence of co-morbid conditions, etc. Methods for analysis of paired samples are further described below. Moreover, the analysis of a pattern of expression profiles (generated by collecting multiple expression profiles) provides information relating to changes in expression level over time, and may permit the determination of a rate of change, a trajectory, or an expression curve. Two longitudinal samples may provide information on the change in expression of a gene over time, while three longitudinal samples may be necessary to determine the "trajectory" of expression of a gene. Such information may be relevant to the diagnosis of a disease. For example, the expression of a gene may vary from individual to individual, but a clinical event, for example, a heart attack, may cause the level of expression to double in each patient. In this example, clinically interesting information is gleaned from the change in expression level, as opposed to the absolute level of expression in each individual.

When a single patient sample is obtained, it may still be desirable to compare the expression profile of that sample to some reference expression profile. In this case, one can determine the change of expression between the patient's sample and a reference expression profile that is appropriate for that patient and the medical condition in question. For example, a reference expression profile can be determined for all patients without the disease criterion in question who have similar characteristics, such as age, sex, race, diagnoses etc.

Generally, small sample sizes of 10-40 samples from 10-20 individuals are used to identify a diagnostic nucleotide set. Larger sample sizes are generally necessary to validate the diagnostic nucleotide set for use in large and varied patient populations, as further described below. For example, extension of gene expression correlations to varied ethnic groups, demographic groups, nations, peoples or races may require expression correlation experiments on the population of interest.

Expression Reference Standards

Expression profiles derived from a patient (i.e., subjects diagnosed with, or exhibiting symptoms of, or exhibiting a disease criterion, or under a doctor's care for a disease) sample are compared to a control or standard expression RNA to facilitate comparison of expression profiles (e.g. of a set of candidate nucleotide sequences) from a group of patients relative to each other (i.e., from one patient in the group to other patients in the group, or to patients in another group).

The reference RNA used should have desirable features of low cost and simplicity of production on a large scale. Additionally, the reference RNA should contain measurable amounts of as many of the genes of the candidate library as possible.

For example, in one approach to identifying diagnostic nucleotide sets, expression profiles derived from patient samples are compared to a expression reference "standard." Standard expression reference can be, for example, RNA derived from resting cultured leukocytes or commercially available reference RNA, such as Universal reference RNA from Stratagene. See Nature, V406, 8-17-00, p. 747-752. Use of an expression reference standard is particularly useful when the expression of large numbers of nucleotide sequences is assayed, e.g. in an array, and in certain other applications, e.g. qualitative PCR, RT-PCR, etc., where it is desirable to compare a sample profile to a standard profile, and/or when large numbers of expression profiles, e.g. a patient population, are to be compared. Generally, an expression reference standard should be available in large quantities, should be a good substrate for amplification and labeling reactions, and should be capable of detecting a large percentage of candidate nucleic acids using suitable expression profiling technology.

Alternatively, or in addition, the expression profile derived from a patient sample is compared with the expression of an internal reference control gene, for example, β-actin or CD4. The relative expression of the profiled genes and the internal reference control gene (from the same individual) is obtained. An internal reference control may also be used with a reference RNA. For example, an expression profile for "gene 1" and the gene encoding CD4 can be determined in a patient sample and in a reference RNA. The expression of each gene can be expressed as the "relative" ratio of expression the gene in the patient sample compared with expression of the gene in the reference RNA. The expression ratio (sample/reference) for gene 1 may be divided by the expression ration for CD4 (sample/reference) and thus the relative expression of gene 1 to CD4 is obtained.

The invention also provides a buffy coat control RNA useful for expression profiling, and a method of using control RNA produced from a population of buffy coat cells, the white blood cell layer derived from the centrifugation of whole blood. Buffy coat contains all white blood cells, including granulocytes, mononuclear cells and platelets. The invention also provides a method of preparing control RNA from buffy coat cells for use in expression profile analysis of leukocytes. Buffy coat fractions are obtained, e.g. from a blood bank or directly from individuals, preferably from a large number of individuals such that bias from individual samples is avoided and so that the RNA sample represents an average expression of a healthy population. Buffy coat fractions from about 50 or about 100, or more individuals are preferred. 10 ml buffy coat from each individual is used. Buffy coat samples are treated with an erthythrocyte lysis buffer, so that erthythrocytes are selectively removed. The leukocytes of the buffy coat layer are collected by centrifugation. Alternatively, the buffy cell sample can be further enriched for a particular leukocyte sub-populations, e.g. mononuclear cells, T-lymphocytes, etc. To enrich for mononuclear cells, the buffy cell pellet, above, is diluted in PBS (phosphate buffered saline) and loaded onto a non-polystyrene tube containing a polysucrose and sodium diatrizoate solution adjusted to a density of 1.077+/−0.001 g/ml. To enrich for T-lymphocytes, 45 ml of whole blood is treated with RosetteSep (Stem Cell Technologies), and incubated at room temperature for 20 minutes. The mixture is diluted with an equal volume of PBS plus 2% FBS and mixed by inversion. 30 ml of diluted mixture is layered on top of 15 ml DML medium (Stem Cell Technologies). The tube is centrifuged at 1200×g, and the enriched cell layer at the plasma: medium interface is removed, washed with PBS+2% FBS, and cells collected by centrifugation at 1200×g. The cell pellet is treated with 5 ml of erythrocyte lysis buffer (EL buffer, Qiagen) for 10 minutes on ice, and enriched T-lymphocytes are collected by centrifugation.

In addition or alternatively, the buffy cells (whole buffy coat or sub-population, e.g. mononuclear fraction) can be cultured in vitro and subjected to stimulation with cytokines or activating chemicals such as phorbol esters or ionomycin. Such stimuli may increase expression of nucleotide sequences that are expressed in activated immune cells and might be of interest for leukocyte expression profiling experiments.

Following sub-population selection and/or further treatment, e.g. stimulation as described above, RNA is prepared using standard methods. For example, cells are pelleted and lysed with a phenol/guanidinium thiocyanate and RNA is prepared. RNA can also be isolated using a silica gel-based purification column or the column method can be used on RNA isolated by the phenol/guanidinium thiocyanate method. RNA from individual buffy coat samples can be pooled during this process, so that the resulting reference RNA represents the RNA of many individuals and individual bias is minimized or eliminated. In addition, a new batch of buffy coat reference RNA can be directly compared to the last batch to ensure similar expression pattern from one batch to another, using methods of collecting and comparing expression profiles described above/below. One or more expression reference controls are used in an experiment. For example, RNA derived from one or more of the following sources can be used as controls for an experiment: stimulated or unstimulated whole buffy coat, stimulated or unstimulated peripheral mononuclear cells, or stimulated or unstimulated T-lymphocytes.

Alternatively, the expression reference standard can be derived from any subject or class of subjects including healthy subjects or subjects diagnosed with the same or a different disease or disease criterion. Expression profiles from subjects in two distinct classes are compared to determine which subset of nucleotide sequences in the candidate library best distinguish between the two subject classes, as further discussed below. It will be appreciated that in the present context, the term "distinct classes" is relevant to at least one distinguishable criterion relevant to a disease of interest, a "disease criterion." The classes can, of course, demonstrate significant overlap (or identity) with respect to other disease criteria, or with respect to disease diagnoses, prognoses, or the like. The mode of discovery involves, e.g., comparing the molecular signature of different subject classes to each other (such as patient to control, patients with a first diagnosis to patients with a second diagnosis, etc.) or by comparing the molecular signatures of a single individual taken at different time points. The invention can be applied to a broad range of diseases, disease criteria, conditions and other clinical and/or epidemiological questions, as further discussed above/below.

It is appreciated that while the present discussion pertains to the use of expression reference controls while identifying diagnostic nucleotide sets, expression reference controls are also useful during use of diagnostic nucleotide sets, e.g. use of a diagnostic nucleotide set for diagnosis of a disease, as further described below.

Analysis of Expression Profiles

In order to facilitate ready access, e.g., for comparison, review, recovery, and/or modification, the molecular signatures/expression profiles are typically recorded in a database. Most typically, the database is a relational database accessible by a computational device, although other formats, e.g., manually accessible indexed files of expression profiles as photographs, analogue or digital imaging readouts, spreadsheets, etc. can be used. Further details regarding preferred embodiments are provided below. Regardless of whether the expression patterns initially recorded are analog or digital in nature and/or whether they represent quantitative or qualitative differences in expression, the expression patterns, expression profiles (collective expression patterns), and molecular signatures (correlated expression patterns) are stored digitally and accessed via a database. Typically, the database is compiled and maintained at a central facility, with access being available locally and/or remotely.

As additional samples are obtained, and their expression profiles determined and correlated with relevant subject data, the ensuing molecular signatures are likewise recorded in the database. However, rather than each subsequent addition being added in an essentially passive manner in which the data from one sample has little relation to data from a second (prior or subsequent) sample, the algorithms optionally additionally query additional samples against the existing database to further refine the association between a molecular signature and disease criterion. Furthermore, the data set comprising the one (or more) molecular signatures is optionally queried against an expanding set of additional or other disease criteria. The use of the database in integrated systems and web embodiments is further described below.

Analysis of Expression Profile Data from Arrays

Expression data is analyzed using methods well known in the art, including the software packages Imagene (Biodiscovery, Marina del Rey, Calif.), Feature Extraction Software (Agilent, Palo Alto, Calif.), and Scanalyze (Stanford University). In the discussion that follows, a "feature" refers to an individual spot of DNA on an array. Each gene may be represented by more than one feature. For example, hybridized microarrays are scanned and analyzed on an Axon Instruments scanner using GenePix 3.0 software (Axon Instruments, Union City, Calif.). The data extracted by GenePix is used for all downstream quality control and expression evaluation. The data is derived as follows. The data for all features flagged as "not found" by the software is removed from the dataset for individual hybridizations. The "not found" flag by GenePix indicates that the software was unable to discriminate the feature from the background. Each feature is examined to determine the value of its signal. The median pixel intensity of the background ($B_n$) is subtracted from the median pixel intensity of the feature ($F_n$) to produce the background-subtracted signal (hereinafter, "BGSS"). The BGSS is divided by the standard deviation of the background pixels to provide the signal-to-noise ratio (hereinafter, "S/N"). Features with a S/N of three or greater in both the Cy3 channel (corresponding to the sample RNA) and Cy5 channel (corresponding to the reference RNA) are used for further analysis (hereinafter denoted "useable features"). Alternatively, different S/Ns are used for selecting expression data for an analysis. For example, only expression data with signal to noise ratios>3 might be used in an analysis. Alternatively, features with S/N values<3 may be flagged as such and included in the analysis. Such flagged data sets include more values and may allow one to discover expression markers that would be missed otherwise. However, such data sets may have a higher variablilty than filtered data, which may decrease significance of findings or performance of correlation statistics.

For each usable feature (i), the expression level (e) is expressed as the logarithm of the ratio (R) of the Background Subtracted Signal (hereinafter "BGSS") for the Cy3 (sample RNA) channel divided by the BGSS for the Cy5 channel (reference RNA). This "log ratio" value is used for comparison to other experiments.

$$R_i = \frac{BGSS_{sample}}{BGSS_{reference}} \quad (0.1)$$

$$e_i = \log r_i \quad (0.2)$$

Variation in signal across hybridizations may be caused by a number of factors affecting hybridization, DNA spotting, wash conditions, and labeling efficiency.

A single reference RNA may be used with all of the experimental RNAs, permitting multiple comparisons in addition to individual comparisons. By comparing sample RNAs to the same reference, the gene expression levels from each sample are compared across arrays, permitting the use of a consistent denominator for our experimental ratios.

Scaling

The data may be scaled (normalized) to control for labeling and hybridization variability within the experiment, using methods known in the art. Scaling is desirable because it facilitates the comparison of data between different experiments, patients, etc. Generally the BGSS are scaled to a factor such as the median, the mean, the trimmed mean, and percentile. Additional methods of scaling include: to scale between 0 and 1, to subtract the mean, or to subtract the median.

Scaling is also performed by comparison to expression patterns obtained using a common reference RNA, as described in greater detail above. As with other scaling methods, the reference RNA facilitates multiple comparisons of the expression data, e.g., between patients, between samples, etc. Use of a reference RNA provides a consistent denominator for experimental ratios.

In addition to the use of a reference RNA, individual expression levels may be adjusted to correct for differences in labeling efficiency between different hybridization experiments, allowing direct comparison between experiments with different overall signal intensities, for example. A scaling factor (a) may be used to adjust individual expression levels as follows. The median of the scaling factor (a), for example, BGSS, is determined for the set of all features with a S/N greater than three. Next, the $BGSS_i$ (the BGSS for each feature "i") is divided by the median for all features (a), generating a scaled ratio. The scaled ration is used to determine the expression value for the feature ($e_i$), or the log ratio.

$$S_i = \frac{BGSS_i}{a} \quad (0.3)$$

$$e_i = \log\left(\frac{Cy3S_i}{Cy5S_i}\right) \quad (0.4)$$

In addition, or alternatively, control features are used to normalize the data for labeling and hybridization variability within the experiment. Control feature may be cDNA for genes from the plant, *Arabidopsis thaliana*, that are included when spotting the mini-array. Equal amounts of RNA complementary to control cDNAs are added to each of the samples before they were labeled. Using the signal from these control genes, a normalization constant (L) is determined according to the following formula:

$$L_j = \frac{\frac{\sum_{i=1}^{N} BGSS_{j,i}}{N}}{\sum_{j=1}^{K} \frac{\sum_{i=1}^{N} BGSS_{j,i}}{N}}$$

where $BGSS_i$ is the signal for a specific feature, N is the number of *A. thaliana* control features, K is the number of hybridizations, and $L_j$ is the normalization constant for each individual hybridization.

Using the formula above, the mean for all control features of a particular hybridization and dye (e.g., Cy3) is calculated. The control feature means for all Cy3 hybridizations are averaged, and the control feature mean in one hybridization divided by the average of all hybridizations to generate a normalization constant for that particular Cy3 hybridization ($L_j$), which is used as a in equation (0.3). The same normalization steps may be performed for Cy3 and Cy5 values.

Many additional methods for normalization exist and can be applied to the data. In one method, the average ratio of Cy3 BGSS/Cy5 BGSS is determined for all features on an array. This ratio is then scaled to some arbitrary number, such as 1 or some other number. The ratio for each probe is then multiplied by the scaling factor required to bring the average ratio to the chosen level. This is performed for each array in an analysis. Alternatively, the ratios are normalized to the average ratio across all arrays in an analysis.

If multiple features are used per gene sequence or oligonucleotide, these repeats can be used to derive an average expression value for each gene. If some of the replicate features are of poor quality and don't meet requirements for analysis, the remaining features can be used to represent the gene or gene sequence.

Correlation Analysis

Correlation analysis is performed to determine which array probes have expression behavior that best distinguishes or serves as markers for relevant groups of samples representing a particular clinical condition. Correlation analysis, or comparison among samples representing different disease criteria (e.g., clinical conditions), is performed using standard statistical methods. Numerous algorithms are useful for correlation analysis of expression data, and the selection of algorithms depends in part on the data analysis to be performed. For example, algorithms can be used to identify the single most informative gene with expression behavior that reliably classifies samples, or to identify all the genes useful to classify samples. Alternatively, algorithms can be applied that determine which set of 2 or more genes have collective expression behavior that accurately classifies samples. The use of multiple expression markers for diagnostics may overcome the variability in expression of a gene between individuals, or overcome the variability intrinsic to the assay. Multiple expression markers may include redundant markers (surrogates), in that two or more genes or probes may provide the same information with respect to diagnosis. This may occur, for example, when two or more genes or gene probes are coordinately expressed. For diagnostic application, it may be appropriate to utilize a gene and one or more of its surrogates in the assay. This redundancy may overcome failures (technical or biological) of a single marker to distinguish samples. Alternatively, one or more surrogates may have properties that make them more suitable for assay development, such as a higher baseline level of expression, better cell specificity, a higher fold change between sample groups or more specific sequence for the design of PCR primers or complimentary probes. It will be appreciated that while the discussion above pertains to the analysis of RNA expression profiles the discussion is equally applicable to the analysis of profiles of proteins or other molecular markers.

Prior to analysis, expression profile data may be formatted or prepared for analysis using methods known in the art. For example, often the log ratio of scaled expression data for every array probe is calculated using the following formula: log(Cy 3 BGSS/Cy5 BGSS), where Cy 3 signal corresponds to the expression of the gene in the clinical sample, and Cy5 signal corresponds to expression of the gene in the reference RNA.

Data may be further filtered depending on the specific analysis to be done as noted below. For example, filtering may be aimed at selecting only samples with expression above a certain level, or probes with variability above a certain level between sample sets.

The following non-limiting discussion consider several statistical methods known in the art. Briefly, the t-test and ANOVA are used to identify single genes with expression differences between or among populations, respectively. Multivariate methods are used to identify a set of two or more genes for which expression discriminates between two disease states more specifically than expression of any single gene.

T-Test

The simplest measure of a difference between two groups is the Student's t test. See, e.g., Welsh et al. (2001) *Proc Natl Acad Sci USA* 98:1176-81 (demonstrating the use of an unpaired Student's t-test for the discovery of differential gene expression in ovarian cancer samples and control tissue samples). The t-test assumes equal variance and normally distributed data. This test identifies the probability that there is a difference in expression of a single gene between two groups of samples. The number of samples within each group that is required to achieve statistical significance is dependent upon the variation among the samples within each group. The standard formula for a t-test is:

$$t(e_i) = \frac{\bar{e}_{i,c} - \bar{e}_{i,t}}{\sqrt{(s_{i,c}^2/n_c) + (s_{i,t}^2/n_t)}}, \quad (0.5)$$

where $\bar{e}_i$ is the difference between the mean expression level of gene i in groups c and t, $s_{i,c}$ is the variance of gene x in group c and $s_{i,t}$ is the variance of gene x in group t. $n_c$ and $n_t$ are the numbers of samples in groups c and t.

The combination of the t statistic and the degrees of freedom [min($n_t$, $n_c$)−1] provides a p value, the probability of rejecting the null hypothesis. A p-value of $\leq 0.01$, signifying a 99 percent probability the mean expression levels are different between the two groups (a 1% chance that the mean expression levels are in fact not different and that the observed difference occurred by statistical chance), is often considered acceptable.

When performing tests on a large scale, for example, on a large dataset of about 8000 genes, a correction factor must be included to adjust for the number of individual tests being performed. The most common and simplest correction is the Bonferroni correction for multiple tests, which divides the p-value by the number of tests run. Using this test on an 8000 member dataset indicates that a p value of $\leq 0.00000125$ is required to identify genes that are likely to be truly different between the two test conditions.

Significance Analysis for Microarrays (SAM)

Significance analysis for microarrays (SAM) (Tusher 2001) is a method through which genes with a correlation between their expression values and the response vector are statistically discovered and assigned a statistical significance. The ratio of false significant to significant genes is the False Discovery Rate (FDR). This means that for each threshold there are a set of genes which are called significant, and the FDR gives a confidence level for this claim. If a gene is called differentially expressed between 2 classes by SAM, with a FDR of 5%, there is a 95% chance that the gene is actually differentially expressed between the classes. SAM takes into account the variability and large number of variables of microarrays. SAM will identity genes that are most globally differentially expressed between the classes. Thus, important genes for identifying and classifying outlier samples or patients may not be identified by SAM.

Wilcoxon's Signed Ranks Test

This method is non-parametric and is utilized for paired comparisons. See e.g., Sokal and Rohlf (1987) *Introduction to Biostatistics* 2$^{nd}$ edition, WH Freeman, New York. At least 6 pairs are necessary to apply this statistic. This test is useful for analysis of paired expression data (for example, a set of patients who have cardiac transplant biopsy on 2 occasions and have a grade 0 on one occasion and a grade 3A on another).

ANOVA

Differences in gene expression across multiple related groups may be assessed using an Analysis of Variance (ANOVA), a method well known in the art (Michelson and Schofield, 1996).

Multivariate Analysis

Many algorithms suitable for multivariate analysis are known in the art. Generally, a set of two or more genes for which expression discriminates between two disease states more specifically than expression of any single gene is identified by searching through the possible combinations of genes using a criterion for discrimination, for example the expression of gene X must increase from normal 300 percent, while the expression of genes Y and Z must decrease from normal by 75 percent. Ordinarily, the search starts with a single gene, then adds the next best fit at each step of the search. Alternatively, the search starts with all of the genes and genes that do not aid in the discrimination are eliminated step-wise.

Paired Samples

Paired samples, or samples collected at different timepoints from the same patient, are often useful, as described above. For example, use of paired samples permits the reduction of variation due to genetic variation among individuals. In addition, the use of paired samples has a statistical significance, in that data derived from paired samples can be calculated in a different manner that recognizes the reduced variability. For example, the formula for a t-test for paired samples is:

$$t(e_x) = \frac{\overline{D}_{ex}}{\sqrt{\frac{\sum D^2 - (\sum D)^2/b}{b-1}}}, \qquad (0.5)$$

where D is the difference between each set of paired samples and b is the number of sample pairs. $\overline{D}$ is the mean of the differences between the members of the pairs. In this test, only the differences between the paired samples are considered, then grouped together (as opposed to taking all possible differences between groups, as would be the case with an ordinary t-test). Additional statistical tests useful with paired data, e.g., ANOVA and Wilcoxon's signed rank test, are discussed above.

Diagnostic Classification

Once a discriminating set of genes is identified, the diagnostic classifier (a mathematical function that assigns samples to diagnostic categories based on expression data) is applied to unknown sample expression levels.

Methods that can be used for this analysis include the following non-limiting list:

CLEAVER is an algorithm used for classification of useful expression profile data. See Raychaudhuri et al. (2001) *Trends Biotechnol* 19:189-193. CLEAVER uses positive training samples (e.g., expression profiles from samples known to be derived from a particular patient or sample diagnostic category, disease or disease criteria), negative training samples (e.g., expression profiles from samples known not to be derived from a particular patient or sample diagnostic category, disease or disease criteria) and test samples (e.g., expression profiles obtained from a patient), and determines whether the test sample correlates with the particular disease or disease criteria, or does not correlate with a particular disease or disease criteria. CLEAVER also generates a list of the 20 most predictive genes for classification.

Artificial neural networks (hereinafter, "ANN") can be used to recognize patterns in complex data sets and can discover expression criteria that classify samples into more than 2 groups. The use of artificial neural networks for discovery of gene expression diagnostics for cancers using expression data generated by oligonucleotide expression microarrays is demonstrated by Khan et al. (2001) *Nature Med.* 7:673-9. Khan found that 96 genes provided 0% error rate in classification of the tumors. The most important of these genes for classification was then determined by measuring the sensitivity of the classification to a change in expression of each gene. Hierarchical clustering using the 96 genes results in correct grouping of the cancers into diagnostic categories.

Golub uses cDNA microarrays and a distinction calculation to identify genes with expression behavior that distinguishes myeloid and lymphoid leukemias. See Golub et al. (1999) *Science* 286:531-7. Self organizing maps were used for new class discovery. Cross validation was done with a "leave one out" analysis. 50 genes were identified as useful markers. This was reduced to as few as 10 genes with equivalent diagnostic accuracy.

Hierarchical and non-hierarchical clustering methods are also useful for identifying groups of genes that correlate with a subset of clinical samples such as with transplant rejection grade. Alizadeh used hierarchical clustering as the primary tool to distinguish different types of diffuse B-cell lymphomas based on gene expression profile data. See Alizadeh et al. (2000) *Nature* 403:503-11. Alizadeh used hierarchical clustering as the primary tool to distinguish different types of diffuse B-cell lymphomas based on gene expression profile data. A cDNA array carrying 17856 probes was used for these experiments, 96 samples were assessed on 128 arrays, and a set of 380 genes was identified as being useful for sample classification.

Perou demonstrates the use of hierarchical clustering for the molecular classification of breast tumor samples based on expression profile data. See Perou et al. (2000) *Nature* 406: 747-52. In this work, a cDNA array carrying 8102 gene probes was used. 1753 of these genes were found to have high variation between breast tumors and were used for the analysis.

Hastie describes the use of gene shaving for discovery of expression markers. Hastie et al. (2000) *Genome Biol.* 1(2): RESEARCH 0003.1-0003.21. The gene shaving algorithm identifies sets of genes with similar or coherent expression patterns, but large variation across conditions (RNA samples, sample classes, patient classes). In this manner, genes with a tight expression pattern within a transplant rejection grade, but also with high variability across rejection grades are grouped together. The algorithm takes advantage of both characteristics in one grouping step. For example, gene shaving can identify useful marker genes with co-regulated expression. Sets of useful marker genes can be reduced to a smaller set, with each gene providing some non-redundant value in classification. This algorithm was used on the data set described in Alizadeh et al., supra, and the set of 380 informative gene markers was reduced to 234.

Supervised harvesting of expression trees (Hastie 2001) identifies genes or clusters that best distinguish one class from all the others on the data set. The method is used to identify the genes/clusters that can best separate one class versus all the others for datasets that include two or more classes or all classes from each other. This algorithm can be used for discovery or testing of a diagnostic gene set.

CART is a decision tree classification algorithm (Breiman 1984). From gene expression and or other data, CART can develop a decision tree for the classification of samples. Each node on the decision tree involves a query about the expression level of one or more genes or variables. Samples that are above the threshold go down one branch of the decision tree and samples that are not go down the other branch. See examples 10 and 16 for further description of its use in classification analysis and examples of its usefulness in discovering and implementing a diagnostic gene set. CART identifies surrogates for each splitter (genes that are the next best substitute for a useful gene in classification.

Once a set of genes and expression criteria for those genes have been established for classification, cross validation is done. There are many approaches, including a 10 fold cross validation analysis in which 10% of the training samples are left out of the analysis and the classification algorithm is built with the remaining 90%. The 10% are then used as a test set for the algorithm. The process is repeated 10 times with 10% of the samples being left out as a test set each time. Through this analysis, one can derive a cross validation error which helps estimate the robustness of the algorithm for use on prospective (test) samples.

Clinical data are gathered for every patient sample used for expression analysis. Clinical variables can be quantitative or non-quantitative. A clinical variable that is quantitative can be used as a variable for significance or classification analysis. Non-quantitative clinical variables, such as the sex of the patient, can also be used in a significance analysis or classification analysis with some statistical tool. It is appreciated that the most useful diagnostic gene set for a condition may be optimal when considered along with one or more predictive clinical variables. Clinical data can also be used as supervising vectors for a correlation analysis. That is to say that the clinical data associated with each sample can be used to divide the samples into meaningful diagnostic categories for analysis. For example, samples can be divided into 2 or more groups based on the presence or absence of some diagnostic criterion (a). In addition, clinical data can be utilized to select patients for a correlation analysis or to exclude them based on some undesirable characteristic, such as an ongoing infection, a medicine or some other issue. Clinical data can also be used to assess the pre-test probability of an outcome. For example, patients who are female are much more likely to be diagnosed as having systemic lupus erythematosis than patients who are male.

Once a set of genes are identified that classify samples with acceptable accuracy. These genes are validated as a set using new samples that were not used to discover the gene set. These samples can be taken from frozen archives from the discovery clinical study or can be taken from new patients prospectively. Validation using a "test set" of samples can be done using expression profiling of the gene set with microarrays or using real-time PCR for each gene on the test set samples. Alternatively, a different expression profiling technology can be used.

Selected Diseases

In principle, diagnostic nucleotide sets of the invention may be developed and applied to essentially any disease, or disease criterion, as long as at least one subset of nucleotide sequences is differentially expressed in samples derived from one or more individuals with a disease criteria or disease and one or more individuals without the disease criteria or disease, wherein the individual may be the same individual sampled at different points in time, or the individuals may be different individuals (or populations of individuals). For example, the subset of nucleotide sequences may be differentially expressed in the sampled tissues of subjects with the disease or disease criterion (e.g., a patient with a disease or disease criteria) as compared to subjects without the disease or disease criterion (e.g., patients without a disease (control patients)). Alternatively, or in addition, the subset of nucleotide sequence(s) may be differentially expressed in different samples taken from the same patient, e.g at different points in time, at different disease stages, before and after a treatment, in the presence or absence of a risk factor, etc.

Expression profiles corresponding to sets of nucleotide sequences that correlate not with a diagnosis, but rather with a particular aspect of a disease can also be used to identify the diagnostic nucleotide sets and disease specific target nucleotide sequences of the invention. For example, such an aspect, or disease criterion, can relate to a subject's medical or family history, e.g., childhood illness, cause of death of a parent or other relative, prior surgery or other intervention, medications, symptoms (including onset and/or duration of symptoms), etc. Alternatively, the disease criterion can relate to a diagnosis, e.g., hypertension, diabetes, atherosclerosis, or prognosis (e.g., prediction of future diagnoses, events or complications), e.g., acute myocardial infarction, restenosis following angioplasty, reperfusion injury, allograft rejection, rheumatoid arthritis or systemic lupus erythematosis disease activity or the like. In other cases, the disease criterion corresponds to a therapeutic outcome, e.g., transplant rejection, bypass surgery or response to a medication, restenosis after stent implantation, collateral vessel growth due to therapeutic angiogenesis therapy, decreased angina due to revascularization, resolution of symptoms associated with a myriad of therapies, and the like. Alternatively, the disease criteria corresponds with previously identified or classic risk factors and may correspond to prognosis or future disease diagnosis. As indicated above, a disease criterion can also correspond to genotype for one or more loci. Disease criteria (including patient data) may be collected (and compared) from the same patient at different points in time, from different patients, between patients with a disease (criterion) and patients representing a control population, etc. Longitudinal data, i.e., data collected at different time points from an individual (or group of individuals) may be used for comparisons of samples obtained from an individual (group of individuals) at different points in time, to permit identification of differences specifically related to the disease state, and to obtain information relating to the change in expression over time, including a rate of change or trajectory of expression over time. The usefulness of longitudinal data is further discussed in the section titled "Identification of diagnostic nucleotide sets of the invention".

It is further understood that diagnostic nucleotide sets may be developed for use in diagnosing conditions for which there is no present means of diagnosis. For example, in rheumatoid arthritis, joint destruction is often well under way before a patient experience symptoms of the condition. A diagnostic nucleotide set may be developed that diagnoses rheumatic joint destruction at an earlier stage than would be possible using present means of diagnosis, which rely in part on the presentation of symptoms by a patient. Diagnostic nucleotide sets may also be developed to replace or augment current diagnostic procedures. For example, the use of a diagnostic nucleotide set to diagnose cardiac allograft rejection may replace the current diagnostic test, a graft biopsy.

It is understood that the following discussion of diseases is exemplary and non-limiting, and further that the general criteria discussed above, e.g. use of family medical history, are generally applicable to the specific diseases discussed below.

In addition to leukocytes, as described throughout, the general method is applicable to nucleotide sequences that are differentially expressed in any subject tissue or cell type, by the collection and assessment of samples of that tissue or cell type. However, in many cases, collection of such samples presents significant technical or medical problems given the current state of the art.

Organ Transplant Rejection and Success

A frequent complication of organ transplantation is recognition of the transplanted organ as foreign by the immune system resulting in rejection. Diagnostic nucleotide sets can be identified and validated for monitoring organ transplant success, rejection and treatment. Medications currently exist that suppress the immune system, and thereby decrease the rate of and severity of rejection. However, these drugs also suppress the physiologic immune responses, leaving the patient susceptible to a wide variety of opportunistic infections and cancers. At present there is no easy, reliable way to diagnose transplant rejection. Organ biopsy is the preferred method, but this is expensive, painful and associated with significant risk and has inadequate sensitivity for focal rejection.

Diagnostic nucleotide sets of the present invention can be developed and validated for use as diagnostic tests for transplant rejection and success. It is appreciated that the methods of identifying diagnostic nucleotide sets are applicable to any organ transplant population. For example, diagnostic nucleotide sets are developed for cardiac allograft rejection and success.

In some cases, disease criteria correspond to acute stage rejection diagnosis based on organ biopsy and graded using the International Society for Heart and Lung Transplantation ("ISHLT") criteria. This grading system classifies endomyocardial biopsies on the histological level as Grade 0, 1A, 1B, 2, 3A, 3B, or 4. Grade 0 biopsies have no evidence of rejection, while each successive grade has increased severity of leukocyte infiltration and/or damage to the graft myocardial cells. It is appreciated that there is variability in the Grading systems between medical centers and pathologists and between repeated readings of the same pathologist at different times. When using the biopsy grade as a disease criterion for leukocyte gene expression correlation analysis, it may be desirable to have a single pathologist read all biopsy slides or have multiple pathologists read all slides to determine the variability in this disease criterion. It is also appreciated that cardiac biopsy, in part due to variability, is not 100% sensitive or 100% specific for diagnosing acute rejection. When using the cardiac biopsy grade as a disease criterion for the discovery of diagnostic gene sets, it may be desirable to divide patient samples into diagnostic categories based on the grades. Examples of such classes are those patients with: Grade 0 vs. Grades 1A-4, Grade 0 vs. Grades 1B-4, Grade 0 vs. Grades 2-4, Grade 0-1 vs. Grade 2-4, Grade 0-1 vs. Grade 3A-4, or Grade 0 vs. Grade 3A-4.

Other disease criteria correspond to the cardiac biopsy results and other criteria, such as the results of cardiac function testing by echocardiography, hemodynamics assessment by cardiac catheterization, CMV infection, weeks post transplant, medication regimen, demographics and/or results of other diagnostic tests.

Other disease criteria correspond to information from the patient's medical history and information regarding the organ donor. Alternatively, disease criteria include the presence or absence of cytomegalovirus (CMV) infection, Epstein-Barr virus (EBV) infection, allograft dysfunction measured by physiological tests of cardiac function (e.g., hemodynamic measurements from catheterization or echocardiograph data), and symptoms of other infections. Alternatively, disease criteria correspond to therapeutic outcome, e.g. graft failure, re-transplantation, death, hospitalization, need for intravenous immunosuppression, transplant vasculopathy, response to immunosuppressive medications, etc. Disease criteria may further correspond to a rejection episode of at least moderate histologic grade, which results in treatment of the patient with additional corticosteroids, anti-T cell antibodies, or total lymphoid irradiation; a rejection with histologic grade 2 or higher; a rejection with histologic grade<2; the absence of histologic rejection and normal or unchanged allograft function (based on hemodynamic measurements from catheterization or on echocardiographic data); the presence of severe allograft dysfunction or worsening allograft dysfunction during the study period (based on hemodynamic measurements from catheterization or on echocardiographic data); documented CMV infection by culture, histology, or PCR, and at least one clinical sign or symptom of infection; specific graft biopsy rejection grades; rejection of mild to moderate histologic severity prompting augmentation of the patient's chronic immunosuppressive regimen; rejection of mild to moderate severity with allograft dysfunction prompting plasmaphoresis or a diagnosis of "humoral" rejection; infections other than CMV, especially infection with Epstein Barr virus (EBV); lymphoproliferative disorder (also called post-transplant lymphoma); transplant vasculopathy diagnosed by increased intimal thickness on intravascular ultrasound (IVUS), angiography, or acute myocardial infarction; graft failure or retransplantation; and all cause mortality. Further specific examples of clinical data useful as disease criteria are provided in Example 9.

In another example, diagnostic nucleotide sets are developed and validated for use in diagnosis and treatment of kidney allograft recipients. Disease criteria correspond to, e.g., results of biopsy analysis for kidney allograft rejection, serum creatine level, creatinine clearance, radiological imaging results for the kidney and urinalysis results. Another disease criterion corresponds to the need for hemodialysis, retransplantation, death or other renal replacement therapy. Diagnostic nucleotide sets are developed and validated for use in diagnosis and treatment of bone marrow transplant and liver transplantation patients, respectively. Disease criteria for bone marrow transplant correspond to the diagnosis and monitoring of graft rejection and/or graft versus host disease, the recurrence of cancer, complications due to immunosuppression, hematologic abnormalities, infection, hospitalization and/or death. Disease criteria for liver transplant rejection include levels of serum markers for liver damage and liver function such as AST (aspartate aminotransferase), ALT (alanine aminotransferase), Alkaline phosphatase, GGT, (gamma-glutamyl transpeptidase) Bilirubin, Albumin and Prothrombin time. Further disease criteria correspond to hepatic encephalopathy, medication usage, ascites, graft failure, retransplantation, hospitalization, complications of immunosuppression, results of diagnostic tests, results of radiological testing, death and histological rejection on graft biopsy. In addition, urine can be utilized for at the target tissue for profiling in renal transplant, while biliary and intestinal secretions and feces may be used favorably for hepatic or intestinal organ allograft rejection.

In another example, diagnostic nucleotide sets are developed and validated for use in diagnosis and treatment of xenograft recipients. This can include the transplantation of any organ from a non-human animal to a human or between non-human animals. Considerations for discovery and application of diagnostics and therapeutics and for disease criterion are substantially similar to those for allograft transplantation between humans.

In another example, diagnostic nucleotide sets are developed and validated for use in diagnosis and treatment of artificial organ recipients. This includes, but is not limited to mechanical circulatory support, artificial hearts, left ventricular assist devices, renal replacement therapies, organ prostheses and the like. Disease criteria are thrombosis (blood clots), infection, death, hospitalization, and worsening measures of organ function (e.g., hemodynamics, creatinine, liver function testing, renal function testing, functional capacity).

In another example, diagnostic nucleotide sets are developed and validated for use in matching donor organs to appropriate recipients. Diagnostic gene set can be discovered that correlate with successful matching of donor organ to recipient. Disease criteria include graft failure, acute and chronic rejection, death, hospitalization, immunosuppressive drug use, and complications of immunosuppression. Gene sets may be assayed from the donor or recipient's peripheral blood, organ tissue or some other tissue.

In another example, diagnostic nucleotide sets are developed and validated for use in diagnosis and induction of patient immune tolerance (decrease rejection of an allograft by the host immune system). Disease criteria include rejection, assays of immune activation, need for immunosuppression and all disease criteria noted above for transplantation of each organ.

Viral Diseases

Diagnostic leukocyte nucleotide sets may be developed and validated for use in diagnosing viral disease. In another aspect, viral nucleotide sequences may be added to a leukocyte nucleotide set for use in diagnosis of viral diseases. Alternatively, viral nucleotide sets and leukocyte nucleotides sets may be used sequentially.

Epstein-Barr Virus (EBV)

EBV causes a variety of diseases such as mononucleosis, B-cell lymphoma, and pharyngeal carcinoma. It infects mononuclear cells and circulating atypical lymphocytes are a common manifestation of infection. Peripheral leukocyte gene expression is altered by infection. Transplant recipients and patients who are immunosuppressed are at increased risk for EBV-associated lymphoma.

Diagnostic nucleotide sets may be developed and validated for use in diagnosis and monitoring of EBV. In one aspect, the diagnostic nucleotide set is a leukocyte nucleotide set. Alternatively, EBV nucleotide sequences are added to a leukocyte nucleotide set, for use in diagnosing EBV. Disease criteria correspond with diagnosis of EBV, and, in patients who are EBV-sero-positive, presence (or prospective occurrence) of EBV-related illnesses such as mononucleosis, and EBV-associated lymphoma. Diagnostic nucleotide sets are useful for diagnosis of EBV, and prediction of occurrence of EBV-related illnesses.

Cytomegalovirus (CMV)

Cytomegalovirus cause inflammation and disease in almost any tissue, particularly the colon, lung, bone marrow and retina, and is a very important cause of disease in immunosuppressed patients, e.g. transplant, cancer, AIDS. Many patients are infected with or have been exposed to CMV, but not all patients develop clinical disease from the virus. Also, CMV negative recipients of allografts that come from CMV positive donors are at high risk for CMV infection. As immunosuppressive drugs are developed and used, it is increasingly important to identify patients with current or impending clinical CMV disease, because the potential benefit of immunosuppressive therapy must be balanced with the increased rate of clinical CMV infection and disease that may result from the use of immunosuppression therapy. CMV may also play a role in the occurrence of atherosclerosis or restenosis after angioplasty.

Diagnostic nucleotide sets are developed for use in diagnosis and monitoring of CMV infection or re-activation of CMV infection. In one aspect, the diagnostic nucleotide set is a leukocyte nucleotide set. In another aspect, CMV nucleotide sequences are added to a leukocyte nucleotide set, for use in diagnosing CMV. Disease criteria correspond to diagnosis of CMV (e.g., sero-positive state) and presence of clinically active CMV. Disease criteria may also correspond to prospective data, e.g. the likelihood that CMV will become clinically active or impending clinical CMV infection. Antiviral medications are available and diagnostic nucleotide sets can be used to select patients for early treatment, chronic suppression or prophylaxis of CMV activity.

Hepatitis B and C

These chronic viral infections affect about 1.25 and 2.7 million patients in the US, respectively. Many patients are infected, but suffer no clinical manifestations. Some patients with infection go on to suffer from chronic liver failure, cirrhosis and hepatic carcinoma.

Diagnostic nucleotide sets are developed for use in diagnosis and monitoring of HBV or HCV infection. In one aspect, the diagnostic nucleotide set is a leukocyte nucleotide set. In another aspect, viral nucleotide sequences are added to a leukocyte nucleotide set, for use in diagnosing the virus and monitoring progression of liver disease. Disease criteria correspond to diagnosis of the virus (e.g., sero-positive state or other disease symptoms). Alternatively, disease criteria correspond to liver damage, e.g., elevated alkaline phosphatase, ALT, AST or evidence of ongoing hepatic damage on liver biopsy. Alternatively, disease criteria correspond to serum liver tests (AST, ALT, Alkaline Phosphatase, GGT, PT, bilirubin), liver biopsy, liver ultrasound, viral load by serum PCR, cirrhosis, hepatic cancer, need for hospitalization or listing for liver transplant. Diagnostic nucleotide sets are used to diagnose HBV and HCV, and to predict likelihood of disease progression. Antiviral therapeutic usage, such as Interferon gamma and Ribavirin, can also be disease criteria.

HIV

HIV infects T cells and certainly causes alterations in leukocyte expression. Diagnostic nucleotide sets are developed for diagnosis and monitoring of HIV. In one aspect, the diagnostic nucleotide set is a leukocyte nucleotide set. In another aspect, viral nucleotide sequences are added to a leukocyte nucleotide set, for use in diagnosing the virus. Disease criteria correspond to diagnosis of the virus (e.g., sero-positive state). In addition, disease criteria correspond to viral load, CD4 T cell counts, opportunistic infection, response to antiretroviral therapy, progression to AIDS, rate of progression and the occurrence of other HIV related outcomes (e.g., malignancy, CNS disturbance). Response to antiretrovirals may also be disease criteria.

Pharmacogenomics

Pharmacogenomics is the study of the individual propensity to respond to a particular drug therapy (combination of therapies). In this context, response can mean whether a particular drug will work on a particular patient, e.g. some patients respond to one drug but not to another drug. Response can also refer to the likelihood of successful treatment or the assessment of progress in treatment. Titration of drug therapy to a particular patient is also included in this description, e.g. different patients can respond to different doses of a given medication. This aspect may be important when drugs with side-effects or interactions with other drug therapies are contemplated.

Diagnostic nucleotide sets are developed and validated for use in assessing whether a patient will respond to a particular therapy and/or monitoring response of a patient to drug therapy(therapies). Disease criteria correspond to presence or absence of clinical symptoms or clinical endpoints, presence of side-effects or interaction with other drug(s). The diagnostic nucleotide set may further comprise nucleotide sequences that are targets of drug treatment or markers of active disease.

Validation and Accuracy of Diagnostic Nucleotide Sets

Prior to widespread application of the diagnostic probe sets of the invention the predictive value of the probe set is validated. When the diagnostic probe set is discovered by microarray based expression analysis, the differential expression of the member genes may be validated by a less variable and more quantitative and accurate technology such as real time PCR. In this type of experiment the amplification product is measured during the PCR reaction. This enables the researcher to observe the amplification before any reagent becomes rate limiting for amplification. In kinetic PCR the measurement is of $C_T$ (threshold cycle) or $C_P$ (crossing point). This measurement ($C_T=C_P$) is the point at which an amplification curve crosses a threshold fluorescence value. The threshold is set to a point within the area where all of the reactions were in their linear phase of amplification. When measuring $C_T$, a lower $C_T$ value is indicative of a higher amount of starting material since an earlier cycle number means the threshold was crossed more quickly.

Several fluorescence methodologies are available to measure amplification product in real-time PCR. Taqman (Applied BioSystems, Foster City, Calif.) uses fluorescence resonance energy transfer (FRET) to inhibit signal from a probe until the probe is degraded by the sequence specific binding and Taq 3' exonuclease activity. Molecular Beacons (Stratagene, La Jolla, Calif.) also use FRET technology, whereby the fluorescence is measured when a hairpin structure is relaxed by the specific probe binding to the amplified DNA. The third commonly used chemistry is Sybr Green, a DNA-binding dye (Molecular Probes, Eugene, Oreg.). The more amplified product that is produced, the higher the signal. The Sybr Green method is sensitive to non-specific amplification products, increasing the importance of primer design and selection. Other detection chemistries can also been used, such as ethedium bromide or other DNA-binding dyes and many modifications of the fluorescent dye/quencher dye Taqman chemistry, for example scorpions.

Real-time PCR validation can be done as described in Example 15.

Typically, the oligonucleotide sequence of each probe is confirmed, e.g. by DNA sequencing using an oligonucleotide-specific primer. Partial sequence obtained is generally sufficient to confirm the identity of the oligonucleotide probe. Alternatively, a complementary polynucleotide is fluorescently labeled and hybridized to the array, or to a different array containing a resynthesized version of the oligo nucleotide probe, and detection of the correct probe is confirmed.

Typically, validation is performed by statistically evaluating the accuracy of the correspondence between the molecular signature for a diagnostic probe set and a selected indicator. For example, the expression differential for a nucleotide sequence between two subject classes can be expressed as a simple ratio of relative expression. The expression of the nucleotide sequence in subjects with selected indicator can be compared to the expression of that nucleotide sequence in subjects without the indicator, as described in the following equations.

$$\Sigma E_x ai/N = E_x A$$

the average expression of nucleotide sequence x in the members of group A;

$$\Sigma E_x bi/M = E_x B$$

the average expression of nucleotide sequence x in the members of group B;

$$E_x A / ExB = \Delta E_x AB$$

the average differential expression of nucleotide sequence x between groups A and B:

where $\Sigma$ indicates a sum; Ex is the expression of nucleotide sequence x relative to a standard; ai are the individual members of group A, group A has N members; bi are the individual members of group B, group B has M members.

The expression of at least two nucleotide sequences, e.g., nucleotide sequence X and nucleotide sequence Y are measured relative to a standard in at least one subject of group A (e.g., with a disease) and group B (e.g., without the disease). Ideally, for purposes of validation the indicator is independent from (i.e., not assigned based upon) the expression pattern. Alternatively, a minimum threshold of gene expression for nucleotide sequences X and Y, relative to the standard, are designated for assignment to group A. For nucleotide sequence x, this threshold is designated $\Delta Ex$, and for nucleotide sequence y, the threshold is designated $\Delta Ey$.

The following formulas are used in the calculations below:

Sensitivity=(true positives/true positives+false negatives)

Specificity=(true negatives/true negatives+false positives)

If, for example, expression of nucleotide sequence x above a threshold: $x > \Delta Ex$, is observed for 80/100 subjects in group A and for 10/100 subjects in group B, the sensitivity of nucleotide sequence x for the assignment to group A, at the given expression threshold $\Delta Ex$, is 80%, and the specificity is 90%.

If the expression of nucleotide sequence y is $>\Delta Ey$ in 80/100 subjects in group A, and in 10/100 subjects in group B, then, similarly the sensitivity of nucleotide sequence y for the assignment to group A at the given threshold $\Delta Ey$ is 80% and the specificity is 90%. If in addition, 60 of the 80 subjects in group A that meet the expression threshold for nucleotide sequence y also meet the expression threshold $\Delta Ex$ and that 5 of the 10 subjects in group B that meet the expression threshold for nucleotide sequence y also meet the expression threshold $\Delta Ex$, the sensitivity of the test ($x > \Delta Ex$ and $y > \Delta Ey$) for assignment of subjects to group A is 60% and the specificity is 95%.

Alternatively, if the criteria for assignment to group A are change to: Expression of $x > \Delta Ex$ or expression of $y > \Delta Ey$, the sensitivity approaches 100% and the specificity is 85%.

Clearly, the predictive accuracy of any diagnostic probe set is dependent on the minimum expression threshold selected. The expression of nucleotide sequence X (relative to a standard) is measured in subjects of groups A (with disease) and B (without disease). The minimum threshold of nucleotide sequence expression for x, required for assignment to group A is designated $\Delta Ex$ 1.

If 90/100 patients in group A have expression of nucleotide sequence $x > \Delta Ex$ 1 and 20/100 patients in group B have expression of nucleotide sequence $x > \Delta Ex$ 1, then the sensitivity of the expression of nucleotide sequence x (using $\Delta Ex$ 1 as a minimum expression threshold) for assignment of patients to group A will be 90% and the specificity will be 80%.

Altering the minimum expression threshold results in an alteration in the specificity and sensitivity of the nucleotide sequences in question. For example, if the minimum expression threshold of nucleotide sequence x for assignment of subjects to group A is lowered to $\Delta Ex$ 2, such that 100/100 subjects in group A and 40/100 subjects in group B meet the threshold, then the sensitivity of the test for assignment of subjects to group A will be 100% and the specificity will be 60%.

Thus, for 2 nucleotide sequences X and Y: the expression of nucleotide sequence x and nucleotide sequence y (relative to a standard) are measured in subjects belonging to groups A (with disease) and B (without disease). Minimum thresholds of nucleotide sequence expression for nucleotide sequences X and Y (relative to common standards) are designated for assignment to group A. For nucleotide sequence x, this threshold is designated $\Delta Ex1$ and for nucleotide sequence y, this threshold is designated $\Delta Ey1$.

If in group A, 90/100 patients meet the minimum requirements of expression $\Delta Ex1$ and $\Delta Ey1$, and in group B, 10/100 subjects meet the minimum requirements of expression $\Delta Ex1$ and $\Delta Ey1$, then the sensitivity of the test for assignment of subjects to group A is 90% and the specificity is 90%.

Increasing the minimum expression thresholds for X and Y to $\Delta Ex2$ and $\Delta Ey2$, such that in group A, 70/100 subjects meet the minimum requirements of expression $\Delta Ex2$ and $\Delta Ey2$, and in group B, 3/100 subjects meet the minimum requirements of expression $\Delta Ex2$ and $\Delta Ey2$. Now the sensitivity of the test for assignment of subjects to group A is 70% and the specificity is 97%.

If the criteria for assignment to group A is that the subject in question meets either threshold, $\Delta Ex2$ or $\Delta Ey2$, and it is found that 100/100 subjects in group A meet the criteria and 20/100 subjects in group B meet the criteria, then the sensitivity of the test for assignment to group A is 100% and the specificity is 80%.

Individual components of a diagnostic probe set each have a defined sensitivity and specificity for distinguishing between subject groups. Such individual nucleotide sequences can be employed in concert as a diagnostic probe set to increase the sensitivity and specificity of the evaluation. The database of molecular signatures is queried by algorithms to identify the set of nucleotide sequences (i.e., corresponding to members of the probe set) with the highest average differential expression between subject groups. Typically, as the number of nucleotide sequences in the diagnostic probe set increases, so does the predictive value, that is, the sensitivity and specificity of the probe set. When the probe sets are defined they may be used for diagnosis and patient monitoring as discussed below. The diagnostic sensitivity and specificity of the probe sets for the defined use can be determined for a given probe set with specified expression levels as demonstrated above. By altering the expression threshold required for the use of each nucleotide sequence as a diagnostic, the sensitivity and specificity of the probe set can be altered by the practitioner. For example, by lowering the magnitude of the expression differential threshold for each nucleotide sequence in the set, the sensitivity of the test will increase, but the specificity will decrease. As is apparent from the foregoing discussion, sensitivity and specificity are inversely related and the predictive accuracy of the probe set is continuous and dependent on the expression threshold set for each nucleotide sequence. Although sensitivity and specificity tend to have an inverse relationship when expression thresholds are altered, both parameters can be increased as nucleotide sequences with predictive value are added to the diagnostic nucleotide set. In addition a single or a few markers may not be reliable expression markers across a population of patients. This is because of the variability in expression and measurement of expression that exists between measurements, individuals and individuals over time. Inclusion of a large number of candidate nucleotide sequences or large numbers of nucleotide sequences in a diagnostic nucleotide set allows for this variability as not all nucleotide sequences need to meet a threshold for diagnosis. Generally, more markers are better than a single marker. If many markers are used to make a diagnosis, the likelihood that all expression markers will not meet some thresholds based upon random variability is low and thus the test will give fewer false negatives.

It is appreciated that the desired diagnostic sensitivity and specificity of the diagnostic nucleotide set may vary depending on the intended use of the set. For example, in certain uses, high specificity and high sensitivity are desired. For example, a diagnostic nucleotide set for predicting which patient population may experience side effects may require high sensitivity so as to avoid treating such patients. In other settings, high sensitivity is desired, while reduced specificity may be tolerated. For example, in the case of a beneficial treatment with few side effects, it may be important to identify as many patients as possible (high sensitivity) who will respond to the drug, and treatment of some patients who will not respond is tolerated. In other settings, high specificity is desired and reduced sensitivity may be tolerated. For example, when identifying patients for an early-phase clinical trial, it is important to identify patients who may respond to the particular treatment. Lower sensitivity is tolerated in this setting as it merely results in reduced patients who enroll in the study or requires that more patients are screened for enrollment.

Methods of Using Diagnostic Nucleotide Sets.

The invention also provide methods of using the diagnostic nucleotide sets to: diagnose disease; assess severity of disease; predict future occurrence of disease; predict future complications of disease; determine disease prognosis; evaluate the patient's risk, or "stratify" a group of patients; assess response to current drug therapy; assess response to current non-pharmacological therapy; determine the most appropriate medication or treatment for the patient; predict whether a patient is likely to respond to a particular drug; and determine most appropriate additional diagnostic testing for the patient, among other clinically and epidemiologically relevant applications.

The nucleotide sets of the invention can be utilized for a variety of purposes by physicians, healthcare workers, hospitals, laboratories, patients, companies and other institutions. As indicated previously, essentially any disease, condition, or status for which at least one nucleotide sequence is differentially expressed in leukocyte populations (or sub-populations) can be evaluated, e.g., diagnosed, monitored, etc. using the diagnostic nucleotide sets and methods of the invention. In addition to assessing health status at an individual level, the diagnostic nucleotide sets of the present invention are suitable for evaluating subjects at a "population level," e.g., for epidemiological studies, or for population screening for a condition or disease.

Collection and Preparation of Sample

RNA, protein and/or DNA is prepared using methods well-known in the art, as further described herein. It is appreciated that subject samples collected for use in the methods of the invention are generally collected in a clinical setting, where delays may be introduced before RNA samples are prepared from the subject samples of whole blood, e.g. the blood sample may not be promptly delivered to the clinical lab for further processing. Further delay may be introduced in the clinical lab setting where multiple samples are generally being processed at any given time. For this reason, methods which feature lengthy incubations of intact leukocytes at room temperature are not preferred, because the expression profile of the leukocytes may change during this extended time period. For example, RNA can be isolated from whole blood using a phenol/guanidine isothiocyanate reagent or another direct whole-blood lysis method, as described in, e.g., U.S. Pat. Nos. 5,346,994 and 4,843,155. This method may be less preferred under certain circumstances because the large majority of the RNA recovered from whole blood RNA extraction comes from erythrocytes since these cells outnumber leukocytes 1000:1. Care must be taken to ensure that the presence of erythrocyte RNA and protein does not introduce bias in the RNA expression profile data or lead to inadequate sensitivity or specificity of probes.

Alternatively, intact leukocytes may be collected from whole blood using a lysis buffer that selectively lyses erythrocytes, but not leukocytes, as described, e.g., in (U.S. Pat. Nos. 5,973,137, and 6,020,186). Intact leukocytes are then collected by centrifugation, and leukocyte RNA is isolated using standard protocols, as described herein. However, this method does not allow isolation of sub-populations of leukocytes, e.g. mononuclear cells, which may be desired. In addition, the expression profile may change during the lengthy incubation in lysis buffer, especially in a busy clinical lab where large numbers of samples are being prepared at any given time.

Alternatively, specific leukocyte cell types can be separated using density gradient reagents (Boyum, A, 1968). For example, mononuclear cells may be separated from whole blood using density gradient centrifugation, as described, e.g., in U.S. Pat. Nos. 4,190,535, 4,350,593, 4,751,001, 4,818,418, and 5,053,134. Blood is drawn directly into a tube containing an anticoagulant and a density reagent (such as Ficoll or Percoll). Centrifugation of this tube results in separation of blood into an erythrocyte and granulocyte layer, a mononuclear cell suspension, and a plasma layer. The mononuclear cell layer is easily removed and the cells can be collected by centrifugation, lysed, and frozen. Frozen samples are stable until RNA can be isolated. Density centrifugation, however, must be conducted at room temperature, and if processing is unduly lengthy, such as in a busy clinical lab, the expression profile may change.

The quality and quantity of each clinical RNA sample is desirably checked before amplification and labeling for array hybridization, using methods known in the art. For example, one microliter of each sample may be analyzed on a Bioanalyzer (Agilent 2100 Palo Alto, Calif. USA) using an RNA 6000 nano LabChip (Caliper, Mountain View, Calif. USA). Degraded RNA is identified by the reduction of the 28S to 18S ribosomal RNA ratio and/or the presence of large quantities of RNA in the 25-100 nucleotide range.

It is appreciated that the RNA sample for use with a diagnostic nucleotide set may be produced from the same or a different cell population, sub-population and/or cell type as used to identify the diagnostic nucleotide set. For example, a diagnostic nucleotide set identified using RNA extracted from mononuclear cells may be suitable for analysis of RNA extracted from whole blood or mononuclear cells, depending on the particular characteristics of the members of the diagnostic nucleotide set. Generally, diagnostic nucleotide sets must be tested and validated when used with RNA derived from a different cell population, sub-population or cell type than that used when obtaining the diagnostic gene set. Factors such as the cell-specific gene expression of diagnostic nucleotide set members, redundancy of the information provided by members of the diagnostic nucleotide set, expression level of the member of the diagnostic nucleotide set, and cell-specific alteration of expression of a member of the diagnostic nucleotide set will contribute to the usefulness of using a different RNA source than that used when identifying the members of the diagnostic nucleotide set. It is appreciated that it may be desirable to assay RNA derived from whole blood, obviating the need to isolate particular cell types from the blood.

Rapid Method of RNA Extraction Suitable for Production in a Clinical Setting of High Quality RNA for Expression Profiling In a clinical setting, obtaining high quality RNA preparations suitable for expression profiling, from a desired population of leukocytes poses certain technical challenges, including: the lack of capacity for rapid, high-throughput sample processing in the clinical setting, and the possibility that delay in processing (in a busy lab or in the clinical setting) may adversely affect RNA quality, e.g. by a permitting the expression profile of certain nucleotide sequences to shift. Also, use of toxic and expensive reagents, such as phenol, may be disfavored in the clinical setting due to the added expense associated with shipping and handling such reagents.

A useful method for RNA isolation for leukocyte expression profiling would allow the isolation of monocyte and lymphocyte RNA in a timely manner, while preserving the expression profiles of the cells, and allowing inexpensive production of reproducible high-quality RNA samples. Accordingly, the invention provides a method of adding inhibitor(s) of RNA transcription and/or inhibitor(s) of protein synthesis, such that the expression profile is "frozen" and RNA degradation is reduced. A desired leukocyte population or sub-population is then isolated, and the sample may be frozen or lysed before further processing to extract the RNA. Blood is drawn from subject population and exposed to ActinomycinD (to a final concentration of 10 ug/ml) to inhibit transcription, and cycloheximide (to a final concentration of 10 ug/ml) to inhibit protein synthesis. The inhibitor(s) can be injected into the blood collection tube in liquid form as soon as the blood is drawn, or the tube can be manufactured to contain either lyophilized inhibitors or inhibitors that are in solution with the anticoagulant. At this point, the blood sample can be stored at room temperature until the desired leukocyte population or sub-population is isolated, as described elsewhere. RNA is isolated using standard methods, e.g., as described above, or a cell pellet or extract can be frozen until further processing of RNA is convenient.

The invention also provides a method of using a low-temperature density gradient for separation of a desired leukocyte sample. In another embodiment, the invention provides the combination of use of a low-temperature density gradient and the use of transcriptional and/or protein synthesis inhibitor(s). A desired leukocyte population is separated using a density gradient solution for cell separation that maintains the required density and viscosity for cell separation at 0-4° C. Blood is drawn into a tube containing this solution and may be refrigerated before and during processing as the low temperatures slow cellular processes and minimize expression profile changes. Leukocytes are separated, and RNA is isolated using standard methods. Alternately, a cell pellet or extract is frozen until further processing of RNA is convenient. Care must be taken to avoid rewarming the sample during further processing steps.

Alternatively, the invention provides a method of using low-temperature density gradient separation, combined with the use of actinomycin A and cyclohexamide, as described above.

Assessing Expression for Diagnostics

Expression profiles for the set of diagnostic nucleotide sequences in a subject sample can be evaluated by any technique that determines the expression of each component nucleotide sequence. Methods suitable for expression analysis are known in the art, and numerous examples are discussed in the Sections titled "Methods of obtaining expression data" and "high throughput expression Assays", above.

In many cases, evaluation of expression profiles is most efficiently, and cost effectively, performed by analyzing RNA expression. Alternatively, the proteins encoded by each component of the diagnostic nucleotide set are detected for diagnostic purposes by any technique capable of determining protein expression, e.g., as described above. Expression profiles can be assessed in subject leukocyte sample using the same or different techniques as those used to identify and validate the diagnostic nucleotide set. For example, a diagnostic nucleotide set identified as a subset of sequences on a cDNA microarray can be utilized for diagnostic (or prognostic, or monitoring, etc.) purposes on the same array from which they were identified. Alternatively, the diagnostic nucleotide sets for a given disease or condition can be organized onto a dedicated sub-array for the indicated purpose. It is important to note that if diagnostic nucleotide sets are discovered using one technology, e.g. RNA expression profiling, but applied as a diagnostic using another technology, e.g. protein expression profiling, the nucleotide sets must generally be validated for diagnostic purposes with the new technology. In addition, it is appreciated that diagnostic nucleotide sets that are developed for one use, e.g. to diagnose a particular disease, may later be found to be useful for a different application, e.g. to predict the likelihood that the particular disease will occur. Generally, the diagnostic nucleotide set will need to be validated for use in the second circumstance. As discussed herein, the sequence of diagnostic nucleotide set members may be amplified from RNA or cDNA using methods known in the art providing specific amplification of the nucleotide sequences.

Identification of Novel Nucleotide Sequences that are Differentially Expressed in Leukocytes Novel nucleotide sequences that are differentially expressed in leukocytes are also part of the invention. Previously unidentified open reading frames may be identified in a library of differentially expressed candidate nucleotide sequences, as described above, and the DNA and predicted protein sequence may be identified and characterized as noted above. We identified unnamed (not previously described as corresponding to a gene, or an expressed gene) nucleotide sequences in the our candidate nucleotide library, depicted in Table 3A, 3B, Tables 8, 11-12, 14 and the sequence listing. Accordingly, further embodiments of the invention are the isolated nucleic acids described in Tables 3A and 3B, and in the sequence listing. The novel differentially expressed nucleotide sequences of the invention are useful in the diagnostic nucleotide set of the invention described above, and are further useful as members of a diagnostic nucleotide set immobilized on an array. The novel partial nucleotide sequences may be further characterized using sequence tools and publicly or privately accessible sequence databases, as is well known in the art: Novel differentially expressed nucleotide sequences may be identified as disease target nucleotide sequences, described below. Novel nucleotide sequences may also be used as imaging reagent, as further described below.

As used herein, "nucleotide sequence" refers to (a) a nucleotide sequence containing at least one of the DNA sequences disclosed herein (as shown in FIGS. Table 3A, 3B, Tables 8, 11-12, 14 and the sequence listing); (b) any DNA sequence that encodes the amino acid sequence encoded by the DNA sequences disclosed herein; (c) any DNA sequence that hybridizes to the complement of the coding sequences disclosed herein, contained within the coding region of the nucleotide sequence to which the DNA sequences disclosed herein (as shown in Table 3A, 3B, Tables 8, 11-12, 14 and the sequence listing) belong, under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3), (d) any DNA sequence that hybridizes to the complement of the coding sequences disclosed herein, (as shown in Table 3A, 3B, Tables 8, 11-12, 14 and the sequence listing) contained within the coding region of the nucleotide sequence to which DNA sequences disclosed herein (as shown in TABLES 3A, 3B, Tables 8, 11-12, 14) belong, under less stringent conditions, such as moderately stringent conditions, e.g., washing in 0.2×SSC/0.1% SDS at 42° C. (Ausubel et al., 1989, supra), yet which still encodes a functionally equivalent gene product; and/or (e) any DNA sequence that is at least 90% identical, at least 80% identical or at least 70% identical to the coding sequences disclosed herein (as shown in TABLES 3A, 3B and the sequence listing), wherein % identity is determined using standard algorithms known in the art.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target nucleotide sequence antisense molecules, useful, for example, in target nucleotide sequence regulation and/or as antisense primers in amplification reactions of target nucleotide sequence nucleic acid sequences. Further, such sequences may be used as part of ribozyme and/or triple helix sequences, also useful for target nucleotide sequence regulation. Still further, such molecules may be used as components of diagnostic methods whereby the presence of a disease-causing allele, may be detected.

The invention also encompasses nucleic acid molecules contained in full-length gene sequences that are related to or derived from sequences in Tables 2, 3, Tables 8, 11-12, 14 and the sequence listing. One sequence may map to more than one full-length gene.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. The invention includes fragments of any of the DNA sequences disclosed herein. Fragments of the DNA sequences may be at least 5, at least 10, at least 15, at least 19 nucleotides, at least 25 nucleotides, at least 50 nucleotides, at least 100 nucleotides, at least 200, at least 500, or larger.

In addition to the nucleotide sequences described above, homologues of such sequences, as may, for example be present in other species, may be identified and may be readily isolated, without undue experimentation, by molecular biological techniques well known in the art, as well as use of gene analysis tools described above, and e.g., in Example 4. Further, there may exist nucleotide sequences at other genetic loci within the genome that encode proteins which have extensive homology to one or more domains of such gene products. These nucleotide sequences may also be identified via similar techniques.

For example, the isolated differentially expressed nucleotide sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Novel nucleotide products include those proteins encoded by the novel nucleotide sequences described, above. Specifically, novel gene products may include polypeptides encoded by the novel nucleotide sequences contained in the coding regions of the nucleotide sequences to which DNA sequences disclosed herein (in TABLES 3A, 3B, Tables 8, 11-12, 14 and the sequence listing).

In addition, novel protein products of novel nucleotide sequences may include proteins that represent functionally equivalent gene products. Such an equivalent novel gene product may contain deletions, additions or substitutions of amino acid residues within the amino acid sequence encoded by the novel nucleotide sequences described, above, but which result in a silent change, thus producing a functionally equivalent novel nucleotide sequence product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous novel gene products encoded by the novel nucleotide described, above.

The novel gene products (protein products of the novel nucleotide sequences) may be produced by recombinant DNA technology using techniques well known in the art. Thus, methods for preparing the novel gene polypeptides and peptides of the invention by expressing nucleic acid encoding novel nucleotide sequences are described herein. Methods which are well known to those skilled in the art can be used to construct expression vectors containing novel nucleotide sequence protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding novel nucleotide sequence protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety A variety of host-expression vector systems may be utilized to express the novel nucleotide sequence coding sequences of the invention. Such host-expression systems represent vehicles by which the coding sequences of interest may be produced and subsequently purified, but also represent cells which may, when transformed or transfected with the appropriate nucleotide coding sequences, exhibit the novel protein encoded by the novel nucleotide sequence of the invention in situ. These include but are not limited to microorganisms such as bacteria (e.g., *E. coli, B. subtilis*) transformed with recombinant bacteriophage DNA, plasmid DNA or cosmid DNA expression vectors containing novel nucleotide sequence protein coding sequences; yeast (e.g. *Saccharomyces, Pichia*) transformed with recombinant yeast expression vectors containing the novel nucleotide sequence protein coding sequences; insect cell systems infected with recombinant virus expression vectors (e.g., baculovirus) containing the novel nucleotide sequence protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing novel nucleotide sequence protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5 K promoter).

In bacterial systems, a number of expression vectors may be advantageously selected depending upon the use intended for the novel nucleotide sequence protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited to, the E. coli expression vector pUR278 (Ruther et al., 1983, EMBO J. 2:1791), in which the novel nucleotide sequence protein coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 264:5503-5509); and the likes of pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target nucleotide sequence protein can be released from the GST moiety. Other systems useful in the invention include use of the FLAG epitope or the 6-HIS systems.

In an insect system, Autographa californica nuclear polyhedrosis virus (AcNPV) is used as a vector to express foreign nucleotide sequences. The virus grows in Spodoptera frugiperda cells. The novel nucleotide sequence coding sequence may be cloned individually into non-essential regions (for example the polyhedrin gene) of the virus and placed under control of an AcNPV promoter (for example the polyhedrin promoter). Successful insertion of novel nucleotide sequence coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted nucleotide sequence is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the novel nucleotide sequence coding sequence of interest may be ligated to an adenovirus transcription/translation control complex, e.g., the late promoter and tripartite leader sequence. This chimeric nucleotide sequence may then be inserted in the adenovirus genome by in vitro or in vivo recombination. Insertion in a non-essential region of the viral genome (e.g., region E1 or E3) will result in a recombinant virus that is viable and capable of expressing novel nucleotide sequence encoded protein in infected hosts. (E.g., See Logan & Shenk, 1984, Proc. Natl. Acad. Sci. USA 81:3655-3659). Specific initiation signals may also be required for efficient translation of inserted novel nucleotide sequence coding sequences. These signals include the ATG initiation codon and adjacent sequences. In cases where an entire novel nucleotide sequence, including its own initiation codon and adjacent sequences, is inserted into the appropriate expression vector, no additional translational control signals may be needed. However, in cases where only a portion of the novel nucleotide sequence coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

In addition, a host cell strain may be chosen which modulates the expression of the inserted sequences, or modifies and processes the product of the nucleotide sequence in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, etc.

For long-term, high-yield production of recombinant proteins, stable expression is preferred. For example, cell lines which stably express the novel nucleotide sequence encoded protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express novel nucleotide sequence encoded protein. Such engineered cell lines may be particularly useful in screening and evaluation of compounds that affect the endogenous activity of the novel nucleotide sequence encoded protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

An alternative fusion protein system allows for the ready purification of non-denatured fusion proteins expressed in human cell lines (Janknecht, et al., 1991, Proc. Natl. Acad. Sci. USA 88: 8972-8976). In this system, the nucleotide sequence of interest is subcloned into a vaccinia recombination plasmid such that the nucleotide sequence's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

Where recombinant DNA technology is used to produce the protein encoded by the novel nucleotide sequence for such assay systems, it may be advantageous to engineer fusion proteins that can facilitate labeling, immobilization and/or detection.

Indirect labeling involves the use of a protein, such as a labeled antibody, which specifically binds to the protein encoded by the novel nucleotide sequence. Such antibodies include but are not limited to polyclonal, monoclonal, chimeric, single chain, Fab fragments and fragments produced by an Fab expression library.

The invention also provides for antibodies to the protein encoded by the novel nucleotide sequences. Described herein are methods for the production of antibodies capable of specifically recognizing one or more novel nucleotide sequence epitopes. Such antibodies may include, but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Such antibodies may be used, for example, in the detection of a novel nucleotide sequence in a biological sample, or, alternatively, as a method for the inhibition of abnormal gene activity, for example, the inhibition of a disease target nucleotide sequence, as further described below. Thus, such antibodies may be utilized as part of cardiovascular or other disease treatment method, and/or may be used as part of diagnostic techniques whereby patients may be tested for abnormal levels of novel nucleotide sequence encoded proteins, or for the presence of abnormal forms of the such proteins.

For the production of antibodies to a novel nucleotide sequence, various host animals may be immunized by injection with a novel protein encoded by the novel nucleotide sequence, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as novel gene product, or an antigenic functional derivative thereof. For the production of polyclonal antibodies, host animals such as those described above, may be immunized by injection with novel gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo.

In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334: 544-546) can be adapted to produce novel nucleotide sequence-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries may be constructed (Huse et al., 1989, Science, 246:1275-1281) to allow rapid and easy identification of monoclonal Fab fragments with the desired specificity.

Disease Specific Target Nucleotide Sequences

The invention also provides disease specific target nucleotide sequences, and sets of disease specific target nucleotide sequences. The diagnostic nucleotide sets, subsets thereof, novel nucleotide sequences, and individual members of the diagnostic nucleotide sets identified as described above are also disease specific target nucleotide sequences. In particular, individual nucleotide sequences that are differentially regulated or have predictive value that is strongly correlated with a disease or disease criterion are especially favorable as disease specific target nucleotide sequences. Sets of genes that are co-regulated may also be identified as disease specific target nucleotide sets. Such nucleotide sequences and/or nucleotide sequence products are targets for modulation by a variety of agents and techniques. For example, disease specific target nucleotide sequences (or the products of such nucleotide sequences, or sets of disease specific target nucleotide sequences) can be inhibited or activated by, e.g., target specific monoclonal antibodies or small molecule inhibitors, or delivery of the nucleotide sequence or gene product of the nucleotide sequence to patients. Also, sets of genes can be inhibited or activated by a variety of agents and techniques. The specific usefulness of the target nucleotide sequence(s) depends on the subject groups from which they were discovered, and the disease or disease criterion with which they correlate.

Imaging

The invention also provides for imaging reagents. The differentially expressed leukocyte nucleotide sequences, diagnostic nucleotide sets, or portions thereof, and novel nucleotide sequences of the invention are nucleotide sequences expressed in cells with or without disease. Leukocytes expressing a nucleotide sequence(s) that is differentially expressed in a disease condition may localize within the body to sites that are of interest for imaging purposes. For example, a leukocyte expressing a nucleotide sequence(s) that are differentially expressed in an individual having atherosclerosis may localize or accumulate at the site of an atherosclerotic plaque. Such leukocytes, when labeled, may provide a detection reagent for use in imaging regions of the body where labeled leukocyte accumulate or localize, for example, at the atherosclerotic plaque in the case of atherosclerosis. For example, leukocytes are collected from a subject, labeled in vitro, and reintroduced into a subject. Alternatively, the labeled reagent is introduced into the subject individual, and leukocyte labeling occurs within the patient.

Imaging agents that detect the imaging targets of the invention are produced by well-known molecular and immunological methods (for exemplary protocols, see, e.g., Ausubel, Berger, and Sambrook, as well as Harlow and Lane, supra).

For example, a full-length nucleic acid sequence, or alternatively, a gene fragment encoding an immunogenic peptide or polypeptide fragments, is cloned into a convenient expression vector, for example, a vector including an in-frame epitope or substrate binding tag to facilitate subsequent purification. Protein is then expressed from the cloned cDNA sequence and used to generate antibodies, or other specific binding molecules, to one or more antigens of the imaging target protein. Alternatively, a natural or synthetic polypeptide (or peptide) or small molecule that specifically binds (or is specifically bound to) the expressed imaging target can be identified through well established techniques (see, e.g., Mendel et al. (2000) *Anticancer Drug Des* 15:29-41; Wilson (2000) *Curr Med Chem* 7:73-98; Hamby and Showwalter (1999) *Pharmacol Ther* 82:169-93; and Shimazawa et al. (1998) *Curr Opin Struct Biol* 8:451-8). The binding molecule, e.g., antibody, small molecule ligand, etc., is labeled with a contrast agent or other detectable label, e.g., gadolinium, iodine, or a gamma-emitting source. For in-vivo imaging of a disease process that involved leukocytes, the labeled antibody is infused into a subject, e.g., a human patient or animal subject, and a sufficient period of time is passed to permit binding of the antibody to target cells. The subject is then imaged with appropriate technology such as MRI (when the label is gadolinium) or with a gamma counter (when the label is a gamma emitter).

Identification of Nucleotide Sequence Involved in Leukocyte Adhesion

The invention also encompasses a method of identifying nucleotide sequences involved in leukocyte adhesion. The interaction between the endothelial cell and leukocyte is a fundamental mechanism of all inflammatory disorders, including the diseases listed in Table 1. For example, the first visible abnormality in atherosclerosis is the adhesion to the endothelium and diapedesis of mononuclear cells (e.g., T-cell and monocyte). Insults to the endothelium (for example, cytokines, tobacco, diabetes, hypertension and many more) lead to endothelial cell activation. The endothelium then expresses adhesion molecules, which have counter receptors on mononuclear cells. Once the leukocyte receptors have bound the endothelial adhesion molecules, they stick to the endothelium, roll a short distance, stop and transmigrate across the endothelium. A similar set of events occurs in both acute and chronic inflammation. When the leukocyte binds the endothelial adhesion molecule, or to soluble cytokines secreted by endothelial or other cells, a program of gene expression is activated in the leukocyte. This program of expression leads to leukocyte rolling, firm adhesion and transmigration into the vessel wall or tissue parenchyma. Inhibition of this process is highly desirable goal in anti-inflammatory drug development. In addition, leukocyte nucleotide sequences and epithelial cell nucleotide sequences, that are differentially expressed during this process may be disease-specific target nucleotide sequences.

Human endothelial cells, e.g. derived from human coronary arteries, human aorta, human pulmonary artery, human umbilical vein or microvascular endothelial cells, are cultured as a confluent monolayer, using standard methods. Some of the endothelial cells are then exposed to cytokines or another activating stimuli such as oxidized LDL, hyperglycemia, shear stress, or hypoxia (Moser et al. 1992). Some endothelial cells are not exposed to such stimuli and serve as controls. For example, the endothelial cell monolayer is incubated with culture medium containing 5 U/ml of human recombinant IL-1alpha or 10 ng/ml TNF (tumor necrosis factor), for a period of minutes to overnight. The culture medium composition is changed or the flask is sealed to induce hypoxia. In addition, tissue culture plate is rotated to induce sheer stress.

Human T-cells and/or monocytes are cultured in tissue culture flasks or plates, with LGM-3 media from Clonetics. Cells are incubated at 37 degree C., 5% CO2 and 95% humidity. These leukocytes are exposed to the activated or control endothelial layer by adding a suspension of leukocytes on to the endothelial cell monolayer. The endothelial cell monolayer is cultured on a tissue culture treated plate/flask or on a microporous membrane. After a variable duration of exposures, the endothelial cells and leukocytes are harvested separately by treating all cells with trypsin and then sorting the endothelial cells from the leukocytes by magnetic affinity reagents to an endothelial cell specific marker such as PECAM-1 (Stem Cell Technologies). RNA is extracted from the isolated cells by standard techniques. Leukocyte RNA is labeled as described above, and hybridized to leukocyte candidate nucleotide library. Epithelial cell RNA is also labeled and hybridized to the leukocyte candidate nucleotide library. Alternatively, the epithelial cell RNA is hybridized to a epithelial cell candidate nucleotide library, prepared according to the methods described for leukocyte candidate libraries, above.

Hybridization to candidate nucleotide libraries will reveal nucleotide sequences that are up-regulated or down-regulated in leukocyte and/or epithelial cells undergoing adhesion. The differentially regulated nucleotide sequences are further characterized, e.g. by isolating and sequencing the full-length sequence, analysis of the DNA and predicted protein sequence, and functional characterization of the protein product of the nucleotide sequence, as described above. Further characterization may result in the identification of leukocyte adhesion specific target nucleotide sequences, which may be candidate targets for regulation of the inflammatory process. Small molecule or antibody inhibitors can be developed to inhibit the target nucleotide sequence function. Such inhibitors are tested for their ability to inhibit leukocyte adhesion in the in vitro test described above.

Integrated Systems

Integrated systems for the collection and analysis of expression profiles, and molecular signatures, as well as for the compilation, storage and access of the databases of the invention, typically include a digital computer with software including an instruction set for sequence searching and analysis, and, optionally, high-throughput liquid control software, image analysis software, data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises an image scanner for digitizing label signals from labeled assay components, e.g., labeled nucleic acid hybridized to a candidate library microarray. The image scanner can interface with image analysis software to provide a measurement of the presence or intensity of the hybridized label, i.e., indicative of an on/off expression pattern or an increase or decrease in expression.

Readily available computational hardware resources using standard operating systems are fully adequate, e.g., a PC (Intel x86 or Pentium chip-compatible DOS™, OS2™, WINDOWS™, WINDOWS NT™, WINDOWS95™, WINDOWS98™, LINUX, or even Macintosh, Sun or PCs will suffice) for use in the integrated systems of the invention. Current art in software technology is similarly adequate (i.e., there are a multitude of mature programming languages and source code suppliers) for design, e.g., of an upgradeable open-architecture object-oriented heuristic algorithm, or instruction set for expression analysis, as described herein. For example, software for aligning or otherwise manipulating molecular signatures can be constructed by one of skill using a standard programming language such as Visual basic, Fortran, Basic, Java, or the like, according to the methods herein.

Various methods and algorithms, including genetic algorithms and neural networks, can be used to perform the data collection, correlation, and storage functions, as well as other desirable functions, as described herein. In addition, digital or analog systems such as digital or analog computer systems can control a variety of other functions such as the display and/or control of input and output files.

For example, standard desktop applications such as word processing software (e.g., Corel WordPerfect™ or Microsoft Word™) and database software (e.g., spreadsheet software such as Corel Quattro Pro™, Microsoft Excel™, or database programs such as Microsoft Access™ or Paradox™) can be adapted to the present invention by inputting one or more character string corresponding, e.g., to an expression pattern or profile, subject medical or historical data, molecular signature, or the like, into the software which is loaded into the memory of a digital system, and carrying out the operations indicated in an instruction set, e.g., as exemplified in FIG. 2. For example, systems can include the foregoing software having the appropriate character string information, e.g., used in conjunction with a user interface in conjunction with a standard operating system such as a Windows, Macintosh or LINUX system. For example, an instruction set for manipulating strings of characters, either by programming the required operations into the applications or with the required operations performed manually by a user (or both). For example, specialized sequence alignment programs such as PILEUP or BLAST can also be incorporated into the systems of the invention, e.g., for alignment of nucleic acids or proteins (or corresponding character strings).

Software for performing the statistical methods required for the invention, e.g., to determine correlations between expression profiles and subsets of members of the diagnostic nucleotide libraries, such as programmed embodiments of the statistical methods described above, are also included in the computer systems of the invention. Alternatively, programming elements for performing such methods as principle component analysis (PCA) or least squares analysis can also be included in the digital system to identify relationships between data. Exemplary software for such methods is provided by Partek, Inc., St. Peter, Mo.; at the web site partek.com.

Any controller or computer optionally includes a monitor which can include, e.g., a flat panel display (e.g., active matrix liquid crystal display, liquid crystal display), a cathode ray tube ("CRT") display, or another display system which serves as a user interface, e.g., to output predictive data. Computer circuitry, including numerous integrated circuit chips, such as a microprocessor, memory, interface circuits, and the like, is often placed in a casing or box which optionally also includes a hard disk drive, a floppy disk drive, a high capacity removable drive such as a writeable CD-ROM, and other common peripheral elements.

Inputting devices such as a keyboard, mouse, or touch sensitive screen, optionally provide for input from a user and for user selection, e.g., of sequences or data sets to be compared or otherwise manipulated in the relevant computer system. The computer typically includes appropriate software for receiving user instructions, either in the form of user input into a set parameter or data fields (e.g., to input relevant subject data), or in the form of preprogrammed instructions, e.g., preprogrammed for a variety of different specific operations. The software then converts these instructions to appropriate language for instructing the system to carry out any desired operation.

The integrated system may also be embodied within the circuitry of an application specific integrated circuit (ASIC) or programmable logic device (PLD). In such a case, the invention is embodied in a computer readable descriptor language that can be used to create an ASIC or PLD. The integrated system can also be embodied within the circuitry or logic processors of a variety of other digital apparatus, such as PDAs, laptop computer systems, displays, image editing equipment, etc.

The digital system can comprise a learning component where expression profiles, and relevant subject data are compiled and monitored in conjunction with physical assays, and where correlations, e.g., molecular signatures with predictive value for a disease, are established or refined. Successful and unsuccessful combinations are optionally documented in a database to provide justification/preferences for user-base or digital system based selection of diagnostic nucleotide sets with high predictive accuracy for a specified disease or condition.

The integrated systems can also include an automated workstation. For example, such a workstation can prepare and analyze leukocyte RNA samples by performing a sequence of events including: preparing RNA from a human blood sample; labeling the RNA with an isotopic or non-isotopic label; hybridizing the labeled RNA to at least one array comprising all or part of the candidate library; and detecting the hybridization pattern. The hybridization pattern is digitized and recorded in the appropriate database.

Automated RNA Preparation Tool

The invention also includes an automated RNA preparation tool for the preparation of mononuclear cells from whole blood samples, and preparation of RNA from the mononuclear cells. In a preferred embodiment, the use of the RNA preparation tool is fully automated, so that the cell separation and RNA isolation would require no human manipulations. Full automation is advantageous because it minimizes delay, and standardizes sample preparation across different laboratories. This standardization increases the reproducibility of the results.

FIG. 2 depicts the processes performed by the RNA preparation tool of the invention. A primary component of the device is a centrifuge (A). Tubes of whole blood containing a density gradient solution, transcription/translation inhibitors, and a gel barrier that separates erythrocytes from mononuclear cells and serum after centrifugation are placed in the centrifuge (B). The barrier is permeable to erythrocytes and granulocytes during centrifugation, but does not allow mononuclear cells to pass through (or the barrier substance has a density such that mononuclear cells remain above the level of the barrier during the centrifugation). After centrifugation, the erythrocytes and granulocytes are trapped beneath the barrier, facilitating isolation of the mononuclear cell and serum layers. A mechanical arm removes the tube and inverts it to mix the mononuclear cell layer and the serum (C). The arm next pours the supernatant into a fresh tube (D), while the erythrocytes and granulocytes remained below the barrier. Alternatively, a needle is used to aspirate the supernatant and transfer it to a fresh tube. The mechanical arms of the device opens and closes lids, dispenses PBS to aid in the collection of the mononuclear cells by centrifugation, and moves the tubes in and out of the centrifuge. Following centrifugation, the supernatant is poured off or removed by a vacuum device (E), leaving an isolated mononuclear cell pellet. Purification of the RNA from the cells is performed automatically, with lysis buffer and other purification solutions (F) automatically dispensed and removed before and after centrifugation steps. The result is a purified RNA solution. In another embodiment, RNA isolation is performed using a column or filter method. In yet another embodiment, the invention includes an on-board homogenizer for use in cell lysis.

Other Automated Systems

Automated and/or semi-automated methods for solid and liquid phase high-throughput sample preparation and evaluation are available, and supported by commercially available devices. For example, robotic devices for preparation of nucleic acids from bacterial colonies, e.g., to facilitate production and characterization of the candidate library include, for example, an automated colony picker (e.g., the Q-bot, Genetix, U.K.) capable of identifying, sampling, and inoculating up to 10,000/4 hrs different clones into 96 well microtiter dishes. Alternatively, or in addition, robotic systems for liquid handling are available from a variety of sources, e.g., automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual operations performed by a scientist. Any of the above devices are suitable for use with the present invention, e.g., for high-throughput analysis of library components or subject leukocyte samples. The nature and implementation of modifications to these devices (if any) so that they can operate as discussed herein will be apparent to persons skilled in the relevant art.

High throughput screening systems that automate entire procedures, e.g., sample and reagent pipetting, liquid dispensing, timed incubations, and final readings of the microplate in detector(s) appropriate for the relevant assay are commercially available. (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These configurable systems provide high throughput and rapid start up as well as a high degree of flexibility and customization. Similarly, arrays and array readers are available, e.g., from Affymetrix, PE Biosystems, and others.

The manufacturers of such systems provide detailed protocols the various high throughput. Thus, for example, Zymark Corp. provides technical bulletins describing screening systems for detecting the modulation of gene transcription, ligand binding, and the like.

A variety of commercially available peripheral equipment, including, e.g., optical and fluorescent detectors, optical and fluorescent microscopes, plate readers, CCD arrays, phosphorimagers, scintillation counters, phototubes, photodiodes, and the like, and software is available for digitizing, storing and analyzing a digitized video or digitized optical or other assay results, e.g., using PC (Intel x86 or pentium chip-compatible DOS™, OS2™ WINDOWS™, WINDOWS NT™ or WINDOWS95™ based machines), MACINTOSH™, or UNIX based (e.g., SUN™ work station) computers.

Embodiment in a Web Site.

The methods described above can be implemented in a localized or distributed computing environment. For example, if a localized computing environment is used, an array comprising a candidate nucleotide library, or diagnostic nucleotide set, is configured in proximity to a detector, which is, in turn, linked to a computational device equipped with user input and output features.

In a distributed environment, the methods can be implemented on a single computer with multiple processors or, alternatively, on multiple computers. The computers can be linked, e.g. through a shared bus, but more commonly, the computer(s) are nodes on a network. The network can be generalized or dedicated, at a local level or distributed over a wide geographic area. In certain embodiments, the computers are components of an intra-net or an internet.

The predictive data corresponding to subject molecular signatures (e.g., expression profiles, and related diagnostic, prognostic, or monitoring results) can be shared by a variety of parties. In particular, such information can be utilized by the subject, the subject's health care practitioner or provider, a company or other institution, or a scientist. An individual subject's data, a subset of the database or the entire database recorded in a computer readable medium can be accessed directly by a user by any method of communication, including, but not limited to, the internet. With appropriate computational devices, integrated systems, communications networks, users at remote locations, as well as users located in proximity to, e.g., at the same physical facility, the database can access the recorded information. Optionally, access to the database can be controlled using unique alphanumeric passwords that provide access to a subset of the data. Such provisions can be used, e.g., to ensure privacy, anonymity, etc.

Typically, a client (e.g., a patient, practitioner, provider, scientist, or the like) executes a Web browser and is linked to a server computer executing a Web server. The Web browser is, for example, a program such as IBM's Web Explorer, Internet explorer, NetScape or Mosaic, or the like. The Web server is typically, but not necessarily, a program such as IBM's HTTP Daemon or other WWW daemon (e.g., LINUX-based forms of the program). The client computer is bi-directionally coupled with the server computer over a line or via a wireless system. In turn, the server computer is bi-directionally coupled with a website (server hosting the website) providing access to software implementing the methods of this invention.

A user of a client connected to the Intranet or Internet may cause the client to request resources that are part of the web site(s) hosting the application(s) providing an implementation of the methods described herein. Server program(s) then process the request to return the specified resources (assuming they are currently available). A standard naming convention has been adopted, known as a Uniform Resource Locator ("URL"). This convention encompasses several types of location names, presently including subclasses such as Hypertext Transport Protocol ("http"), File Transport Protocol ("ftp"), gopher, and Wide Area Information Service ("WAIS"). When a resource is downloaded, it may include the URLs of additional resources. Thus, the user of the client can easily learn of the existence of new resources that he or she had not specifically requested.

Methods of implementing Intranet and/or Intranet embodiments of computational and/or data access processes are well known to those of skill in the art and are documented, e.g., in ACM Press, pp. 383-392; ISO-ANSI, Working Draft, "Information Technology-Database Language SQL", Jim Melton, Editor, International Organization for Standardization and American National Standards Institute, July 1992; ISO Working Draft, "Database Language SQL-Part 2:Foundation (SQL/Foundation)", CD9075-2:199.chi.SQL, Sep. 11, 1997; and Cluer et al. (1992) A General Framework for the Optimization of Object-Oriented Queries, Proc SIGMOD International Conference on Management of Data, San Diego, Calif., Jun. 2-5, 1992, SIGMOD Record, vol. 21, Issue 2, June, 1992; Stonebraker, M., Editor. Other resources are available, e.g., from Microsoft, IBM, Sun and other software development companies.

Using the tools described above, users of the reagents, methods and database as discovery or diagnostic tools can query a centrally located database with expression and subject data. Each submission of data adds to the sum of expression and subject information in the database. As data is added, a new correlation statistical analysis is automatically run that incorporates the added clinical and expression data. Accordingly, the predictive accuracy and the types of correlations of the recorded molecular signatures increases as the database grows.

For example, subjects, such as patients, can access the results of the expression analysis of their leukocyte samples and any accrued knowledge regarding the likelihood of the patient's belonging to any specified diagnostic (or prognostic, or monitoring, or risk group), i.e., their expression profiles, and/or molecular signatures. Optionally, subjects can add to the predictive accuracy of the database by providing additional information to the database regarding diagnoses, test results, clinical or other related events that have occurred since the time of the expression profiling. Such information can be provided to the database via any form of communication, including, but not limited to, the internet. Such data can be used to continually define (and redefine) diagnostic groups. For example, if 1000 patients submit data regarding the occurrence of myocardial infarction over the 5 years since their expression profiling, and 300 of these patients report that they have experienced a myocardial infarction and 700 report that they have not, then the 300 patients define a new "group A." As the algorithm is used to continually query and revise the database, a new diagnostic nucleotide set that differentiates groups A and B (i.e., with and without myocardial infarction within a five year period) is identified. This newly defined nucleotide set is then be used (in the manner described above) as a test that predicts the occurrence of myocardial infarction over a five-year period. While submission directly by the patient is exemplified above, any individual with access and authority to submit the relevant data e.g., the patient's physician, a laboratory technician, a health care or study administrator, or the like, can do so.

As will be apparent from the above examples, transmission of information via the internet (or via an intranet) is optionally bi-directional. That is, for example, data regarding expression profiles, subject data, and the like are transmitted via a communication system to the database, while information regarding molecular signatures, predictive analysis, and the like, are transmitted from the database to the user. For example, using appropriate configurations of an integrated system including a microarray comprising a diagnostic nucleotide set, a detector linked to a computational device can directly transmit (locally or from a remote workstation at great distance, e.g., hundreds or thousands of miles distant from the database) expression profiles and a corresponding individual identifier to a central database for analysis according to the methods of the invention. According to, e.g., the algorithms described above, the individual identifier is assigned to one or more diagnostic (or prognostic, or monitoring, etc.) categories. The results of this classification are then relayed back, via, e.g., the same mode of communication, to a recipient at the same or different internet (or intranet) address.

Kits

The present invention is optionally provided to a user as a kit. Typically, a kit contains one or more diagnostic nucleotide sets of the invention. Alternatively, the kit contains the candidate nucleotide library of the invention. Most often, the kit contains a diagnostic nucleotide probe set, or other subset of a candidate library, e.g., as a cDNA or antibody microarray packaged in a suitable container. The kit may further comprise, one or more additional reagents, e.g., substrates, labels, primers, for labeling expression products, tubes and/or other accessories, reagents for collecting blood samples, buffers, e.g., erythrocyte lysis buffer, leukocyte lysis buffer, hybridization chambers, cover slips, etc., as well as a software package, e.g., including the statistical methods of the invention, e.g., as described above, and a password and/or account number for accessing the compiled database. The kit optionally further comprises an instruction set or user manual detailing preferred methods of using the diagnostic nucleotide sets in the methods of the invention. Exemplary kits are described in FIG. 3.

This invention will be better understood by reference to the following non-limiting Examples:

EXAMPLES

List of Example Titles

Example 1: Generation of subtracted leukocyte candidate nucleotide library

Example 2: Identification of nucleotide sequences for candidate library using data mining techniques Example 3: DNA Sequencing and Processing of raw sequence data.

Example 4: Further sequence analysis of novel nucleotide sequences identified by subtractive hybridization screening Example 5: Further sequence analysis of novel Clone 596H6

Example 6: Further sequence analysis of novel Clone 486E11

Example 7: Preparation of a Leukocyte cDNA Array Comprising a Candidate Gene Library Example 8: Preparation of RNA from Mononuclear Cells for Expression Profiling Example 9: Preparation of Universal Control RNA for Use in Leukocyte Expression profiling Example 10: RNA Labeling and hybridization to a leukocyte cDNA array of candidate nucleotide sequences.

Example 11: Clinical study for the Identification of diagnostic gene sets useful in diagnosis and treatment of Cardiac allograft rejection Example 12: Identification of diagnostic nucleotide sets for kidney and liver allograft rejection Example 13: Identification of diagnostic nucleotide sequences sets for use in the diagnosis and treatment of Atherosclerosis, Stable Angina Pectoris, and acute coronary syndrome.

Example 14: Identification of diagnostic nucleotide sets for use in diagnosing and treating Restenosis Example 15: Identification of diagnostic nucleotide sets for use in monitoring treatment and/or progression of Congestive Heart Failure Example 16: Identification of diagnostic nucleotide sets for use in diagnosis of rheumatoid arthritis.

Example 17: Identification of diagnostic nucleotide sets for diagnosis of cytomegalovirus Example 18: Identification of diagnostic nucleotide sets for diagnosis of Epstein Barr Virus Example 19: Identification of diagnostic nucleotides sets for monitoring response to statin drugs.

Example 20: Probe selection for a 24,000 feature Array.

Example 21: Design of oligonucleotide probes.

Example 22: Production of an array of 8,000 spotted 50 mer oligonucleotides.

Example 23: Amplification, labeling and hybridization of total RNA to an oligonucleotide microarray.

Example 24: Analysis of Human Transplant Patient Mononuclear cell RNA Hybridized to a 24,000 Feature Microarray.

Example 25: Real-time PCR validation of array expression results

Example 26: Correlation and Classification Analysis

EXAMPLES

Example 1

Generation of Subtracted Leukocyte Candidate Nucleotide Library

To produce a candidate nucleotide library with representatives from the spectrum of nucleotide sequences that are differentially expressed in leukocytes, subtracted hybridization libraries were produced from the following cell types and conditions:

1. Buffy Coat leukocyte fractions—stimulated with ionomycin and PMA
2. Buffy Coat leukocyte fractions—un-stimulated
3. Peripheral blood mononuclear cells—stimulated with ionomycin and PMA
4. Peripheral blood mononuclear cells—un-stimulated
5. T lymphocytes—stimulated with PMA and ionomycin
6. T lymphocytes—resting Cells were obtained from multiple individuals to avoid introduction of bias by using only one person as a cell source.

Buffy coats (platelets and leukocytes that are isolated from whole blood) were purchased from Stanford Medical School Blood Center. Four buffy coats were used, each of which was derived from about 350 ml of whole blood from one donor individual 10 ml of buffy coat sample was drawn from the sample bag using a needle and syringe. 40 ml of Buffer EL (Qiagen) was added per 10 ml of buffy coat to lyse red blood cells. The sample was placed on ice for 15 minutes, and cells were collected by centrifugation at 2000 rpm for 10 minutes. The supernatant was decanted and the cell pellet was re-suspended in leukocyte growth media supplemented with DNase (LGM-3 from Clonetics supplemented with Dnase at a final concentration of 30 U/ml). Cell density was determined using a hemocytometer. Cells were plated in media at a density of $1\times10^6$ cells/ml in a total volume of 30 ml in a T-75 flask (Corning). Half of the cells were stimulated with ionomycin and phorbol myristate acetate (PMA) at a final concentration of 1 µg/ml and 62 ng/ml, respectively. Cells were incubated at 37° C. and at 5% $CO_2$ for 3 hours, then cells were scraped off the flask and collected into 50 ml tubes. Stimulated and resting cell populations were kept separate. Cells were centrifuged at 2000 rpm for 10 minutes and the supernatant was removed. Cells were lysed in 6 ml of phenol/guanidine isothyocyanate (Trizol reagent, GibcoBRL), homogenized using a rotary homogenizer, and frozen at 80°. Total RNA and mRNA were isolated as described below.

Two frozen vials of $5\times10^6$ human peripheral blood mononuclear cells (PBMCs) were purchased from Clonetics (catalog number cc-2702). The cells were rapidly thawed in a 37° C. water bath and transferred to a 15 ml tube containing 10 ml of leukocyte growth media supplemented with DNase (prepared as described above). Cells were centrifuged at 200 µg for 10 minutes. The supernatant was removed and the cell pellet was resuspended in LGM-3 media supplemented with DNase. Cell density was determined using a hemocytometer. Cells were plated at a density of $1\times10^6$ cells/ml in a total volume of 30 ml in a T-75 flask (Corning). Half of the cells were stimulated with ionomycin and PMA at a final concentration of 1 µg/ml and 62 ng/ml, respectively. Cells were incubated at 37° C. and at 5% $CO_2$ for 3 hours, then cells were scraped off the flask and collected into 50 ml tubes. Stimulated and resting cell populations were kept separate. Cells were centrifuged at 2000 rpm and the supernatant was removed. Cells were lysed in 6 ml of phenol/guanidine isothyocyanate solution (TRIZOL reagent, GibcoBRL)), homogenized using a rotary homogenizer, and frozen at 80°. Total RNA and mRNA were isolated from these samples using the protocol described below.

45 ml of whole blood was drawn from a peripheral vein of four healthy human subjects into tubes containing anticoagulant. 50 µl RosetteSep (Stem Cell Technologies) cocktail per ml of blood was added, mixed well, and incubated for 20 minutes at room temperature. The mixture was diluted with an equal volume of PBS+2% fetal bovine serum (FBS) and mixed by inversion. 30 ml of diluted mixture sample was layered on top of 15 ml DML medium (Stem Cell Technologies). The sample tube was centrifuged for 20 minutes at 1200×g at room temperature. The enriched T-lymphocyte cell layer at the plasma: medium interface was removed. Enriched cells were washed with PBS+2% FBS and centrifuged at 1200×g. The cell pellet was treated with 5 ml of erythrocyte lysis buffer (EL buffer, Qiagen) for 10 minutes on ice. The sample was centrifuged for 5 min at 1200 g. Cells were plated at a density of x10$^6$ cells/ml in a total volume of 30 ml in a T-75 flask (Corning). Half of the cells were stimulated with ionomycin and PMA at a final concentration of 1 µg/ml and 62 ng/ml, respectively. Cells were incubated at 37° C. and at 5% $CO_2$ for 3 hours, then cells were scraped off the flask and collected into 50 ml tubes. Stimulated and resting cell populations were kept separate. Cells were centrifuged at 2000 rpm and the supernatant was removed. Cells were lysed in 6 ml of phenol/guanidine isothyocyanate solution (TRIZOL reagent, GibcoBRL), homogenized using a rotary homogenizer, and frozen at 80°. Total RNA and mRNA were isolated as described below.

Total RNA and mRNA were isolated using the following procedure: the homogenized samples were thawed and mixed by vortexing. Samples were lysed in a 1:0.2 mixture of Trizol and chloroform, respectively. For some samples, 6 ml of Trizol-chloroform was added. Variable amounts of Trizol-chloroform was added to other samples. Following lysis, samples were centrifuged at 3000 g for 15 min at 4° C. The aqueous layer was removed into a clean tube and 4 volumes of Buffer RLT Qiagen) was added for every volume of aqueous layer. The samples were mixed thoroughly and total RNA was prepared from the sample by following the Qiagen Rneasy midi protocol for RNA cleanup (October 1999 protocol, Qiagen). For the final step, the RNA was eluted from the column twice with 250 µl Rnase-free water. Total RNA was quantified using a spectrophotometer. Isolation of mRNA from total RNA sample was done using The Oligotex mRNA isolation protocol (Qiagen) was used to isolate mRNA from total RNA, according to the manufacturer's instructions (Qiagen, 7/99 version). mRNA was quantified by spectrophotometry.

Subtracted cDNA libraries were prepared using Clontech's PCR-Select cDNA Subtraction Kit (protocol number PT-1117-1) as described in the manufacturer's protocol. The protocol calls for two sources of RNA per library, designated "Driver" and "Tester." The following 6 libraries were made:

| Library | Driver RNA | Tester RNA |
| --- | --- | --- |
| Buffy Coat Stimulated | Un-stimulated Buffy Coat | Stimulated Buffy Coat |
| Buffy Coat Resting | Stimulated Buffy Coat | Un-stimulated Buffy Coat |
| PBMC Stimulated | Un-stimulated PBMCs | Stimulated PBMCs |
| PBMC Resting | Stimulated PBMCs | Un-stimulated PBMCs |
| T-cell Stimulated | Un-stimulated T-cells | Stimulated T-cells |
| T-cell Resting | Stimulated T-cells | Un-stimulated T-cells |

The Clontech protocol results in the PCR amplification of cDNA products. The PCR products of the subtraction protocol were ligated to the pGEM T-easy bacterial vector as described by the vector manufacturer (Promega 6/99 version). Ligated vector was transformed into competent bacteria using well-known techniques, plated, and individual clones are picked, grown and stored as a glycerol stock at −80C. Plasmid DNA was isolated from these bacteria by standard techniques and used for sequence analysis of the insert. Unique cDNA sequences were searched in the Unigene database (build 133), and Unigene cluster numbers were identified that corresponded to the DNA sequence of the cDNA. Unigene cluster numbers were recorded in an Excel spreadsheet.

Example 2

Identification of Nucleotide Sequences for Candidate Library Using Data Mining Techniques Existing and publicly available gene sequence databases were used to identify candidate nucleotide sequences for leukocyte expression profiling. Genes and nucleotide sequences with specific expression in leukocytes, for example, lineage specific markers, or known differential expression in resting or activated leukocytes were identified. Such nucleotide sequences are used in a leukocyte candidate nucleotide library, alone or in combination with nucleotide sequences isolated through cDNA library construction, as described above.

Leukocyte candidate nucleotide sequences were identified using three primary methods. First, the publicly accessible publication database PubMed was searched to identify nucleotide sequences with known specific or differential expression in leukocytes. Nucleotide sequences were identified that have been demonstrated to have differential expression in peripheral blood leukocytes between subjects with and without particular disease(s) selected from Table 1. Additionally, genes and gene sequences that were known to be specific or selective for leukocytes or sub-populations of leukocytes were identified in this way.

Next, two publicly available databases of DNA sequences, Unigenea at the web site ncbi.nlm.nih.gov/UniGene/) and BodyMap (bodymap.ims.u-tokyo.ac.jp/), were searched for sequenced DNA clones that showed specificity to leukocyte lineages, or subsets of leukocytes, or resting or activated leukocytes.

The human Unigene database (build 133) was used to identify leukocyte candidate nucleotide sequences that were likely to be highly or exclusively expressed in leukocytes. We used the Library Differential Display utility of Unigene, which uses statistical methods (The Fisher Exact Test) to identify nucleotide sequences that have relative specificity for a chosen library or group of libraries relative to each other. We compared the following human libraries from Unigene release 133:

546 NCI_CGAP_HSC1 (399)
848 Human_mRNA_from_cd34+_stem_cells (122)
105 CD34+DIRECTIONAL (150)
3587 KRIBB_Human_CD4_intrathymic_T-cell_cDNA_library (134)
3586 KRIBB_Human_DP_intrathymic_T-cell_cDNA_library (179)
3585 KRIBB_Human_TN_intrathymic_T-cell_cDNA_library (127)
3586 323 Activated_T-cells_I (740)
376 Activated_T-cells_XX (1727)
327 Monocytes,_stimulated_II (110)
824 Proliferating_Erythroid_Cells_(LCB:ad_library) (665)
825 429 Macrophage_II (105)
387 Macrophage_I (137)
669 NCI_CGAP_CLL1 (11626)
129 Human_White_blood_cells (922)
1400 NIH_MGC_2 (422)
55 Human_promyelocyte (1220)
1010 NCI_CGAP_CML1 (2541)
2217 NCI_CGAP_Sub7 (218)
1395 NCI_CGAP_Sub6 (2764)
4874 NIH_MGC_48 (2524)

BodyMap, like Unigene, contains cell-specific libraries that contain potentially useful information about genes that may serve as lineage-specific or leukocyte specific markers (Okubo et al. 1992). We compared three leukocyte specific libraries, Granulocyte, CD4 T cell, and CD8 T cell, with the other libraries. Nucleotide sequences that were found in one or more of the leukocyte-specific libraries, but absent in the others, were identified. Clones that were found exclusively in one of the three leukocyte libraries were also included in a list of nucleotide sequences that could serve as lineage-specific markers.

Next, the sequence of the nucleotide sequences identified in PubMed or BodyMap were searched in Unigene (version 133), and a human Unigene cluster number was identified for each nucleotide sequence. The cluster number was recorded in a Microsoft Excel™ spreadsheet, and a non-redundant list of these clones was made by sorting the clones by UniGene number, and removing all redundant clones using Microsoft Excel™ tools. The non-redundant list of UniGene cluster numbers was then compared to the UniGene cluster numbers of the cDNAs identified using differential cDNA hybridization, as described above in Example 1 (listed in Table 3, Tables 8, 11-12, 14 and the sequence listing). Only UniGene clusters that were not contained in the cDNA libraries were retained. Unigene clusters corresponding to 1911 candidate nucleotide sequences for leukocyte expression profiling were identified in this way and are listed in Table 3 and the sequence listing.

DNA clones corresponding to each UniGene cluster number are obtained in a variety of ways. First, a cDNA clone with identical sequence to part of, or all of the identified UniGene cluster is bought from a commercial vendor or obtained from the IMAGE consortium (http://image.llnl.gov/, the Integrated Molecular Analysis of Genomes and their Expression). Alternatively, PCR primers are designed to amplify and clone any portion of the nucleotide sequence from cDNA or genomic DNA using well-known techniques. Alternatively, the sequences of the identified UniGene clusters are used to design and synthesize oligonucleotide probes for use in microarray based expression profiling.

Example 3

DNA Sequencing and Processing of Raw Sequence Data

Clones of differentially expressed cDNAs (identified by subtractive hybridization, described above) were sequenced on an MJ Research BaseStation™ slab gel based fluorescent detection system, using BigDye™ (Applied Biosystems, Foster City, Calif.) terminator chemistry was used (Heiner et al., Genome Res 1998 May; 8(5):557-61).

The fluorescent profiles were analyzed using the Phred sequence analysis program (Ewing et al, (1998), Genome Research 8: 175-185). Analysis of each clone results in a one pass nucleotide sequence and a quality file containing a number for each base pair with a score based on the probability that the determined base is correct. Each sequence files and its respective quality files were initially combined into single fasta format (Pearson, W R. Methods Mol Biol. 2000; 132: 185-219), multi-sequence file with the appropriate labels for each clone in the headers for subsequent automated analysis.

Initially, known sequences were analyzed by pair wise similarity searching using the blastn option of the blastall program obtained from the National Center for Biological Information, National Library of Medicine, National Institutes of Health (NCBI) to determine the quality score that produced accurate matching (Altschul S F, et al. J Mol Biol. 1990 Oct. 5; 215(3):403-10). Empirically, it was determined that a raw score of 8 was the minimum that contained useful information. Using a sliding window average for 16 base pairs, an average score was determined. The sequence was removed (trimmed) when the average score fell below 8. Maximum reads were 950 nucleotides long.

Next, the sequences were compared by similarity matching against a database file containing the flanking vector sequences used to clone the cDNA, using the blastall program with the blastn option. All regions of vector similarity were removed, or "trimmed" from the sequences of the clones using scripts in the GAWK programming language, a variation of AWK (Aho A V et al, The Awk Programming Language (Addison-Wesley, Reading Mass., 1988); Robbins, A D, "Effective AWK Programming" (Free Software Foundation, Boston Mass., 1997). It was found that the first 45 base pairs of all the sequences were related to vector; these sequences were also trimmed and thus removed from consideration. The remaining sequences were then compared against the NCBI vector database (Kitts, P. A. et al. National Center for Biological Information, National Library of Medicine, National Institutes of Health, Manuscript in preparation (2001) using blastall with the blastn option. Any vector sequences that were found were removed from the sequences.

Messenger RNA contains repetitive elements that are found in genomic DNA. These repetitive elements lead to false positive results in similarity searches of query mRNA sequences versus known mRNA and EST databases. Additionally, regions of low information content (long runs of the same nucleotide, for example) also result in false positive results. These regions were masked using the program RepeatMasker2 found at http://repeatmasker.genome.washington.edu (Smit, A F A & Green, P "RepeatMasker" at http://ftp.genome.washington.edu/RM/RepeatMasker.html). The trimmed and masked files were then subjected to further sequence analysis.

Example 4

Further Sequence Analysis of Novel Nucleotide Sequences Identified by Subtractive Hybridization Screening cDNA sequences were further characterized using BLAST analysis. The BLASTN program was used to compare the sequence of the fragment to the UniGene, dbEST, and nr databases at NCBI (GenBank release 123.0; see Table 5). In the BLAST algorithm, the expect value for an alignment is used as the measure of its significance. First, the cDNA sequences were compared to sequences in Unigene. If no alignments were found with an expect value less than $10^{-25}$, the sequence was compared to the sequences in the dbEST database using BLASTN. If no alignments were found with an expect value less than $10^{-25}$, the sequence was compared to sequences in the nr database.

The BLAST analysis produced the following categories of results: a) a significant match to a known or predicted human gene, b) a significant match to a nonhuman DNA sequence, such as vector DNA or E. coli DNA, c) a significant match to an unidentified GenBank entry (a sequence not previously identified or predicted to be an expressed sequence or a gene), such as a cDNA clone, mRNA, or cosmid, or d) no significant alignments. If a match to a known or predicted human gene was found, analysis of the known or predicted protein product was performed as described below. If a match to an unidentified GenBank entry was found, or if no significant alignments were found, the sequence was searched against all known sequences in the human genome database see Table 5).

If many unknown sequences were to be analyzed with BLASTN, the clustering algorithm CAP2 (Contig Assembly Program, version 2) was used to cluster them into longer, contiguous sequences before performing a BLAST search of the human genome. Sequences that can be grouped into contigs are likely to be cDNA from expressed genes rather than vector DNA, *E. coli* DNA or human chromosomal DNA from a noncoding region, any of which could have been incorporated into the library. Clustered sequences provide a longer query sequence for database comparisons with BLASTN, increasing the probability of finding a significant match to a known gene. When a significant alignment was found, further analysis of the putative gene was performed, as described below. Otherwise, the sequence of the original cDNA fragment or the CAP2 contig is used to design a probe for expression analysis and further approaches are taken to identify the gene or predicted gene that corresponds to the cDNA sequence, including similarity searches of other databases, molecular cloning, and Rapid Amplification of cDNA Ends (RACE).

In some cases, the process of analyzing many unknown sequences with BLASTN was automated by using the BLAST network-client program blastc13, which was downloaded from ftp://ncbi.nlm.nih.gov/blast/network/netblast.

When a cDNA sequence aligned to the sequence of one or more chromosomes, a large piece of the genomic region around the loci was used to predict the gene containing the cDNA. To do this, the contig corresponding to the mapped locus, as assembled by the RefSeq project at NCBI, was downloaded and cropped to include the region of alignment plus 100,000 bases preceding it and 100,000 bases following it on the chromosome. The result was a segment 200 kb in length, plus the length of the alignment. This segment, designated a putative gene, was analyzed using an exon prediction algorithm to determine whether the alignment area of the unknown sequence was contained within a region predicted to be transcribed (see Table 6).

This putative gene was characterized as follows: all of the exons comprising the putative gene and the introns between them were taken as a unit by noting the residue numbers on the 200 kb+ segment that correspond to the first base of the first exon and the last base of the last exon, as given in the data returned by the exon prediction algorithm. The truncated sequence was compared to the UniGene, dbEST, and nr databases to search for alignments missed by searching with the initial fragment.

The predicted amino acid sequence of the gene was also analyzed. The peptide sequence of the gene predicted from the exons was used in conjunction with numerous software tools for protein analysis (see Table 7). These were used to classify or identify the peptide based on similarities to known proteins, as well as to predict physical, chemical, and biological properties of the peptides, including secondary and tertiary structure, flexibility, hydrophobicity, antigenicity (hydrophilicity), common domains and motifs, and localization within the cell or tissues. The peptide sequence was compared to protein databases, including SWISS-PROT, TrEMBL, GenPept, PDB, PIR, PROSITE, Propom, PROSITE, Blocks, PRINTS, and Pfam, using BLASTP and other algorithms to determine similarities to known proteins or protein subunits.

Example 5

Further Sequence Analysis of Novel Clone 596H6

The sequence of clone 596H6 is provided below:

```
                                                    (SEQ ID NO: 8767)
ACTATATTTA GGCACCACTG CCATAAACTA CCAAAAAAAA AATGTAATTC      50

CTAGAAGCTG TGAAGAATAG TAGTGTAGCT AAGCACGGTG TGTGGACAGT     100

GGGACATCTG CCACCTGCAG TAGGTCTCTG CACTCCCAAA AGCAAATTAC     150

ATTGGCTTGA ACTTCAGTAT GCCCGGTTCC ACCCTCCAGA AACTTTTGTG     200

TTCTTTGTAT AGAATTTAGG AACTTCTGAG GGCCACAAAT ACACACATTA     250

AAAAAGGTAG AATTTTTGAA GATAAGATTC TTCTAAAAAA GCTTCCCAAT     300

GCTTGAGTAG AAAGTATCAG TAGAGGTATC AAGGGAGGAG AGACTAGGTG     350

ACCACTAAAC TCCTTCAGAC TCTTAAAATT ACGATTCTTT TCTCAAAGGG     400

GAAGAACGTC AGTGCAGCGA TCCCTTCACC TTTAGCTAAA GAATTGGACT     450

GTGCTGCTCA AAATAAAGAT CAGTTGGAGG TANGATGTCC AAGACTGAAG     500

GTAAAGGACT AGTGCAAACT GAAAGTGATG GGGAAACAGA CCTACGTATG     550

GAAGCCATGT AGTGTTCTTC ACAGGCTGCT GTTGACTGAA ATTCCTATCC     600

TCAAATTACT CTAGACTGAA GCTGCTTCCC TTCAGTGAGC AGCCTCTCCT     650

TCCAAGATTC TGGAAAGCAC ACCTGACTCC AAACAAAGAC TTAGAGCCCT     700

GTGTCAGTGC TGCTGCTGCT TTTACCAGAT TCTCTAACCT TCCGGGTAGA     750

AGAG
```

This sequence was used as input for a series of BLASTN searches. First, it was used to search the UniGene database, build 132 at the web site located at ncbi.nlm.nih.gov/BLAST/). No alignments were found with an expect value less than the threshold value of $10^{-25}$. A BLASTN search of the database dbEST, release 041001, was then performed on the sequence and 21 alignments were found a the web site ncbi.nlm.nih.gov/BLAST/). Ten of these had expect values less than $10^{-25}$, but all were matches to unidentified cDNA clones. Next, the sequence was used to run a BLASTN search of the nr database, release 123.0. No significant alignment to any sequence in nr was found. Finally, a BLASTN search of the human genome was performed on the sequence located at the web site cbi.nlm.nih.gov/genome/seq/page.cgi?F=HsBlast.html&&ORG=Hs.

A single alignment to the genome was found on contig NT_004698.3 (e=0.0). The region of alignment on the contig was from base 1,821,298 to base 1,822,054, and this region was found to be mapped to chromosome 1, from base 105,552,694 to base 105,553,450. The sequence containing the aligned region, plus 100 kilobases on each side of the aligned region, was downloaded. Specifically, the sequence of chromosome 1 from base 105,452,694 to 105,653,450 was downloaded from the web site located at ncbi.nlm.nih.gov/cgi-bin/Entrez/seq_reg.cgi?chr=1&from=105452694&to=105653450).

This 200,757 bp segment of the chromosome was used to predict exons and their peptide products as follows. The sequence was used as input for the Genscan algorithm, using the following Genscan settings:

Organism: vertebrate
Suboptimal exon cutoff: 1.00 (no suboptimal exons)
Print options: Predicted CDS and peptides The region matching the sequence of clone 596H6 was known to span base numbers 100,001 to 100,757 of the input sequence. An exon was predicted by the algorithm, with a probability of 0.695, covering bases 100,601 to 101,094 (designated exon 4.14 of the fourth predicted gene). This exon was part of a predicted cistron that is 24,195 bp in length. The sequence corresponding to the cistron was noted and saved separately from the 200,757 bp segment. BLASTN searches of the Unigene, dbEST, and nr databases were performed on it.

At least 100 significant alignments to various regions of the sequence were found in the dbEST database, although most appeared to be redundant representations of a few exons. All matches were to unnamed cDNAs and mRNAs (unnamed cDNAs and mRNAs are cDNAs and mRNAs not previously identified, or shown to correspond to a known or predicted human gene) from various tissue types. Most aligned to a single region on the sequence and spanned 500 bp or less, but several consisted of five or six regions separated by gaps, suggesting the locations of exons in the gene. Several significant matches to entries in the UniGene database were found, as well, even after masking low-complexity regions and short repeats in the sequence. All matches were to unnamed cDNA clones.

At least 100 significant alignments were found in the nr database, as well. A similarity to hypothetical protein FLJ22457 (UniGene cluster Hs.238707) was found (e=0.0). The cDNA of this predicted protein has been isolated from B lymphocytes located at the web site ncbi.nlm.nih.gov/entrez/viewer.cgi?save=0&cmd=&cfm=on&f=1&view=gp&txt=0&val=13637988).

Other significant alignments were to unnamed cDNAs and mRNAs.

Using Genscan, the following 730 residue peptide sequence was predicted from the putative gene:

```
                                                    SEQ ID NO: 8768
MDGLGRRLRA  SLRLKRGHGG  HWRLNEMPYM  KHEFDGGPPQ  DNSGEALKEP      50

ERAQEHSLPN  FAGGQHFFEY  LLVVSLKKKR  SEDDYEPIIT  YQFPKRENLL     100

RGQQEEEERL  LKAIPLFCFP  DGNEWASLTE  YPSLSCKTPG  LLAALVVEKA     150

QPRTCCHASA  PSAAPQARGP  DAPSPAAGQA  LPAGPGPRLP  KVYCIISCIG     200

CFGLFSKILD  EVEKRHQISM  AVIYPFMQGL  REAAFPAPGK  TVTLKSFIPD     250

SGTEFISLTR  PLDSHLEHVD  FSSLLHCLSF  EQILQIFASA  VLERKIIFLA     300

EGLREEEKDV  RDSTEVRGAG  ECHGFQRKGN  LGKQWGLCVE  DSVKMGDNQR     350

GTSCSTLSQC  IHAAAALLYP  FSWAHTYIPV  VPESLLATVC  CPTPFMVGVQ     400

MRFQQEVMDS  PMEEIQPQAE  IKTVNPLGVY  EERGPEKASL  CLFQVLLVNL     450

CEGTFLMSVG  DEKDILPPKL  QDDILDSLGQ  GINELKTAEQ  INEHVSGPFV     500

QFFVKIVGHY  ASYIKREANG  QGHFQERSFC  KALTSKTNRR  FVKKFVKTQL     550

FSLFIQEAEK  SKNPPAEVTQ  VGNSSTCVVD  TWLEAAATAL  SHHYNIFNTE     600

HTLWSKGSAS  LHEVCGHVRT  RVKRKILFLY  VSLAFTMGKS  IFLVENKAMN     650

MTIKWTTSGR  PGHGDMFGVI  ESWGAAALLL  LTGRVRDTGK  SSSSTGHRAS     700

KSLVWSQVCF  PESWEERLLT  EGKQLQSRVI
```

Multiple analyses were performed using this prediction. First, a pairwise comparison of the sequence above and the sequence of FLJ22457, the hypothetical protein mentioned above, using BLASTP version 2.1.2, resulted in a match with an expect value of 0.0. The peptide sequence predicted from clone 596H6 was longer and 19% of the region of alignment between the two resulted from gaps in hypothetical protein FLJ22457. The cause of the discrepancy might be alternative mRNA splicing, alternative post-translational processing, or differences in the peptide-predicting algorithms used to create the two sequences, but the homology between the two is significant.

BLASTP and TBLASTN were also used to search for sequence similarities in the SWISS-PROT, TrEMBL, GenBank Translated, and PDB databases. Matches to several proteins were found, among them a tumor cell suppression protein, HTS1. No matches aligned to the full length of the peptide sequence, however, suggesting that similarity is limited to a few regions of the peptide.

TBLASTN produced matches to several proteins—both identified and theoretical—but again, no matches aligned to the full length of the peptide sequence. The best alignment was to the same hypothetical protein found in GenBank before (FLJ22457).

To discover similarities to protein families, comparisons of the domains (described above) were carried out using the Pfam and Blocks databases. A search of the Pfam database identified two regions of the peptide domains as belonging the DENN protein family (e=2.1×10$^{-33}$). The human DENN protein possesses an RGD cellular adhesion motif and a leucine-zipper-like motif associated with protein dimerization, and shows partial homology to the receptor binding domain of tumor necrosis factor alpha. DENN is virtually identical to MADD, a human MAP kinase-activating death domain protein that interacts with type I tumor necrosis factor receptor (http://srs.ebi.ac.uk/srs6bin/cgi-bin/wgetz?-id+fS5n1GQsHf+-e+[INTERPRO:'IPR001194']). The search of the Blocks database also revealed similarities between regions of the peptide sequence and known protein groups, but none with a satisfactory degree of confidence. In the Blocks scoring system, scores over 1,100 are likely to be relevant. The highest score of any match to the predicted peptide was 1,058.

The Prosite, Propom, PRINTS databases (all publicly available) were used to conduct further domain and motif analysis. The Prosite search generated many recognized protein domains. A BLASTP search was performed to identify areas of similarity between the protein query sequence and PRINTS, a protein database of protein fingerprints, groups of motifs that together form a characteristic signature of a protein family. In this case, no groups were found to align closely to any section of the submitted sequence. The same was true when the Propom database was searched with BLASTP.

A prediction of protein structure was done by performing a BLAST search of the sequence against PDB, a database in which every member has tertiary structure information. No significant alignments were found by this method. Secondary and super-secondary structure was examined using the Garnier algorithm. Although it is only considered to be 60-65% accurate, the algorithm provided information on the locations and lengths of alpha-helices, beta-sheets, turns and coils.

The antigenicity of the predicted peptide was modeled by graphing hydrophilicity vs. amino acid number. This produced a visual representation of trends in hydrophilicity along the sequence. Many locations in the sequence showed antigenicity and five sites had antigenicity greater than 2. This information can be used in the design of affinity reagents to the protein.

Membrane-spanning regions were predicted by graphing hydrophobicity vs. amino acid number. Thirteen regions were found to be somewhat hydrophobic. The algorithm TMpred predicted a model with 6 strong transmembrane heliceslocated at the web site at ch.embnet.org/software/TMPRED_form.html).

NNPSL is a neural network algorithm developed by the Sanger Center. It uses amino acid composition and sequence to predict cellular location. For the peptide sequence submitted, its first choice was mitochondrial (51.1% expected accuracy). Its second choice was cytoplasmic (91.4% expected accuracy).

Example 6

Further Sequence Analysis of Novel Clone 486E11

The sequence of clone 486E11 is provided below:

```
                                                      SEQ ID NO: 8769
         TAAAAGCAGG CTGTGCACTA GGGACCTAGT GACCTTACTA GAAAAAACTC    50

AAATTCTCTG AGCCACAAGT CCTCATGGGC AAAATGTAGA TACCACCACC   100

TAACCCTGCC AATTTCCTAT CATTGTGACT ATCAAATTAA ACCACAGGCA   150

GGAAGTTGCC TTGAAAACTT TTTATAGTGT ATATTACTGT TCACATAGAT   200

NAGCAATTAA CTTTACATAT ACCCGTTTTT AAAAGATCAG TCCTGTGATT   250

AAAAGTCTGG CTGCCCTAAT TCACTTCGAT TATACATTAG GTTAAAGCCA   300

TATAAAAGAG GCACTACGTC TTCGGAGAGA TGAATGGATA TTACAAGCAG   350

TAATGTTGGC TTTGGAATAT ACACATAATG TCCACTTGAC CTCATCTATT   400

TGACACAAAA TGTAAACTAA ATTATGAGCA TCATTAGATA CCTTGGCCTT   450

TTCAAATCAC ACAGGGTCCT AGATCTNNNN NNNNNNNNNN NNNNNNNNNN   500

NNNNNNNNNN NNNNNNNNNN NNNNNNNNNN NNNNNNNNAC TTTGGGATTC   550

CTATATCTTT GTCAGCTGTC AACTTCAGTG TTTTCAGGTT AAATTCTATC   600

CATAGTCATC CCAATATACC TGCTTTAGAT GATACAACCT TCAAAAGATC   650

CGCTCTTCCT CGTAAAAAGT GGAG
```

The BLASTN program was used to compare the sequence to the UniGene and dbEST databases. No significant alignments were found in either. It was then searched against the nr database and only alignments to unnamed genomic DNA clones were found.

CAP2 was used to cluster a group of unknowns, including clone 486E11. The sequence for 486E11 was found to overlap others. These formed a contig of 1,010 residues, which is shown below:

```
                                                    SEQ ID NO: 8832
CGGACAGGTA  CCTAAAAGCA  GGCTGTGCAC  TAGGGACCTA  GTGACCTTAC       50

TAGAAAAAAC  TCAAATTCTC  TGAGCCACAA  GTCCTCATGG  GCAAAATGTA      100

GATACCACCA  CCTAACCCTG  CCAATTTCCT  ATCATTGTGA  CTATCAAATT      150

AAACCACAGG  CAGGAAGTTG  CCTTGAAAAC  TTTTTATAGT  GTATATTACT      200

GTTCACATAG  ATNAGCAATT  AACTTTACAT  ATACCCGTTT  TTAAAAGATC      250

AGTCCTGTGA  TTAAAAGTCT  GGCTGCCCTA  ATTCACTTCG  ATTATACATT      300

AGGTTAAAGC  CATATAAAAG  AGGCACTACG  TCTTCGGAGA  GATGAATGGA      350

TATTACAAGC  AGTAATTTTG  GCTTTGGAAT  ATACACATAA  TGTCCACTTG      400

ACCTCATCTA  TTTGACACAA  AATGTAAACT  AAATTATGAG  CATCATTAGA      450

TACCTTGGGC  CTTTTCAAAT  CACACAGGGT  CCTAGATCTG  NNNNNNNNNN      500

NNNNNNNNNN  NNNNNNNNNN  NNNNNNNNNN  NNNNNNNNNN  NNNNNNNNNN      550

NACTTTGGAT  TCTTATATCT  TTGTCAGCTG  TCAACTTCAG  TGTTTTCAGG      600

NTAAATTCTA  TCCATAGTCA  TCCCAATATA  CCTGCTTTAG  ATGATACAAA      650

CTTCAAAAGA  TCCGGCTCTC  CCTCGTAAAA  CGTGGAGGAC  AGACATCAAG      700

GGGGTTTTCT  GAGTAAAGAA  AGGCAACCGC  TCGGCAAAAA  CTCACCCTGG      750

CACAACAGGA  NCGAATATAT  ACAGACGCTG  ATTGAGCGTT  TTGCTCCATC      800

TTCACTTCTG  TTAAATGAAG  ACATTGATAT  CTAAAATGCT  ATGAGTCTAA      850

CTTTGTAAAA  TTAAAATAGA  TTTGTAGTTA  TTTTTCAAAA  TGAAATCGAA      900

AAGATACAAG  TTTTGAAGGC  AGTCTCTTTT  TCCACCCTGC  CCCTCTAGTG      950

TGTTTTACAC  ACTTCTCTGG  CCACTCCAAC  AGGGAAGCTG  GTCCAGGGCC     1000

ATTATACAGG
```

The sequence of the CAP2 contig was used in a BLAST search of the human genome. 934 out of 1,010 residues aligned to a region of chromosome 21. A gap of 61 residues divided the aligned region into two smaller fragments. The sequence of this region, plus 100 kilobases on each side of it, was downloaded and analyzed using the Genscan site at MIT, with the following settings:
Organism: vertebrate
Suboptimal exon cutoff: 1.00 (no suboptimal exons)
Print options: Predicted CDS and peptides The fragment was found to fall within one of several predicted genes in the chromosome region. The bases corresponding to the predicted gene, including its predicted introns, were saved as a separate file and used to search GenBank again with BLASTN to find any ESTs or UniGene clusters identified by portions of the sequence not included in the original unknown fragment. The nr database contained no significant matches. At least 100 significant matches to various parts of the predicted gene were found in the dbEST database, but all of them were to unnamed cDNA clones. Comparison to UniGene produced fewer significant matches, but all matches were to unnamed cDNAs.

The peptide sequence predicted by Genscan was also saved. Multiple types of analyses were performed on it using the resources mentioned in Table 3. BLASTP and TBLASTN were used to search the TrEMBL protein database at the web site expasy.ch/sprot and the GenBank nr database located at the web site ncbi.nlm.hih.gov/BLAST/), which includes data from the SwissProt, PIR, PRF, and PDB databases. No significant matches were found in any of these, so no gene identity or tertiary structure was discovered.

The peptide sequence was also searched for similarity to known domains and motifs using BLASTP with the Prosite, Blocks, Pfam, and ProDom databases. The searches produced no significant alignments to known domains. BLASTP comparison to the PRINTS database produced an alignment to the P450 protein family, but with a low probability of accuracy (e=6.9).

Two methods were used to predict secondary structure—the Garnier/Osguthorpe/Robson model and the Chou-Fasman model. The two methods differed somewhat in their results, but both produced representations of the peptide sequence with helical and sheet regions and locations of turns.

Antigenicity was plotted as a graph with amino acid number in the sequence on the x-axis and hydrophilicity on the y-axis. Several areas of antigenicity were observed, but only one with antigenicity greater than 2. Hydrophobicity was plotted in the same way. Only one region, from approximately residue 135 to residue 150, had notable hydrophobicity. TMpred, accessed through ExPASy, was used to predict transmembrane helices. No regions of the peptide sequence were predicted with reasonable confidence to be membrane-spanning helices.

NNPSL predicted that the putative protein would be found either in the nucleus (expected prediction accuracy=51.1%) or secreted from the cell (expected prediction accuracy=91.4%).

Example 7

Preparation of a Leukocyte cDNA Array Comprising a Candidate Gene Library

Candidate genes and gene sequences for leukocyte expression profiling were identified through methods described elsewhere in this document. Candidate genes are used to obtain or design probes for peripheral leukocyte expression profiling in a variety of ways.

A cDNA microarray carrying 384 probes was constructed using sequences selected from the cDNA libraries described in example 1. cDNAs were selected from T-cell libraries, PBMC libraries and buffy coat libraries. A listing of the cDNA fragments used is given in Table 8.

96-Well PCR

Plasmids were isolated in 96-well format and PCR was performed in 96-well format. A master mix was made that contain the reaction buffer, dNTPs, forward and reverse primer and DNA polymerase was made. 99 ul of the master mix was aliquoted into 96-well plate. 1 ul of plasmid (1-2 ng/ul) of plasmid was added to the plate. The final reaction concentration was 10 mM Tris pH 8.3, 3.5 mM MgCl2, 25 mM KCl, 0.4 mM dNTPs, 0.4 uM M13 forward primer, 0.4 M13 reverse primer, and 10 U of Taq Gold (Applied Biosystems). The PCR conditions were:

Step 1 95C for 10 min
Step 2 95C for 15 sec
Step 3 56C for 30 sec
Step 4 72C for 2 min 15 seconds
Step 5 go to Step 2 39 times
Step 6 72C for 10 minutes
Step 7 4C for ever.

PCR Purification

PCR purification was done in a 96-well format. The ArrayIt (Telechem International, Inc.) PCR purification kit was used and the provided protocol was followed without modification. Before the sample was evaporated to dryness, the concentration of PCR products was determined using a spectrophotometer. After evaporation, the samples were re-suspended in 1× Micro Spotting Solution (ArrayIt) so that the majority of the samples were between 0.2-1.0 ug/ul.

Array Fabrication

Spotted cDNA microarrays were then made from these PCR products by ArrayIt using their protocols. Each fragment was spotted 3 times onto each array.

Candidate genes and gene sequences for leukocyte expression profiling were identified through methods described elsewhere in this document. Those candidate genes are used for peripheral leukocyte expression profiling. The candidate libraries can used to obtain or design probes for expression profiling in a variety of ways.

Oligonucleotide probes are also prepared using the DNA sequence information for the candidate genes identified by differential hybridization screening (listed in Table 3 and the sequence listing) and/or the sequence information for the genes identified by database mining (listed in Table 2) is used to design complimentary oligonucleotide probes. Oligo probes are designed on a contract basis by various companies (for example, Compugen, Mergen, Affymetrix, Telechem), or designed from the candidate sequences using a variety of parameters and algorithms as indicated at located at the web site genome.wi.mit.edu/cgi-bin/primer/primer3.cgi. Briefly, the length of the oligonucleotide to be synthesized is determined, preferably greater than 18 nucleotides, generally 18-24 nucleotides, 24-70 nucleotides and, in some circumstances, more than 70 nucleotides. The sequence analysis algorithms and tools described above are applied to the sequences to mask repetitive elements, vector sequences and low complexity sequences. Oligonucleotides are selected that are specific to the candidate nucleotide sequence (based on a Blast n search of the oligonucleotide sequence in question against gene sequences databases, such as the Human Genome Sequence, UniGene, dbEST or the non-redundant database at NCBI), and have <50% G content and 25-70% G+C content. Desired oligonucleotides are synthesized using well-known methods and apparatus, or ordered from a company (for example Sigma). Oligonucleotides are spotted onto microarrays. Alternatively, oligonucleotides are synthesized directly on the array surface, using a variety of techniques (Hughes et al. 2001, Yershov et al. 1996, Lockhart et al 1996).

Example 8

Preparation of RNA from Mononuclear Cells for Expression Profiling

Blood was isolated from the subject for leukocyte expression profiling using the following methods:

Two tubes were drawn per patient. Blood was drawn from either a standard peripheral venous blood draw or directly from a large-bore intra-arterial or intravenous catheter inserted in the femoral artery, femoral vein, subclavian vein or internal jugular vein. Care was taken to avoid sample contamination with heparin from the intravascular catheters, as heparin can interfere with subsequent RNA reactions.

For each tube, 8 ml of whole blood was drawn into a tube (CPT, Becton-Dickinson order #362753) containing the anticoagulant Citrate, 25° C. density gradient solution (e.g. Ficoll, Percoll) and a polyester gel barrier that upon centrifugation was permeable to RBCs and granulocytes but not to mononuclear cells. The tube was inverted several times to mix the blood with the anticoagulant. The tubes were centrifuged at 1750×g in a swing-out rotor at room temperature for 20 minutes. The tubes were removed from the centrifuge and inverted 5-10 times to mix the plasma with the mononuclear cells, while trapping the RBCs and the granulocytes beneath the gel barrier. The plasma/mononuclear cell mix was decanted into a 15 ml tube and 5 ml of phosphate-buffered saline (PBS) is added. The 15 ml tubes were spun for 5 minutes at 1750×g to pellet the cells. The supernatant was discarded and 1.8 ml of RLT lysis buffer is added to the mononuclear cell pellet. The buffer and cells were pipetted up and down to ensure complete lysis of the pellet. The cell lysate was frozen and stored until it is convenient to proceed with isolation of total RNA.

Total RNA was purified from the lysed mononuclear cells using the Qiagen Rneasy Miniprep kit, as directed by the manufacturer (10/99 version) for total RNA isolation, including homogenization (Qiashredder columns) and on-column DNase treatment. The purified RNA was eluted in 50 ul of water. The further use of RNA prepared by this method is described in Example 11, 24, and 23.

Some samples were prepared by a different protocol, as follows:

Two 8 ml blood samples were drawn from a peripheral vein into a tube (CPT, Becton-Dickinson order #362753) containing anticoagulant (Citrate), 25° C. density gradient solution (Ficoll) and a polyester gel barrier that upon centrifugation is permeable to RBCs and granulocytes but not to mononuclear cells. The mononuclear cells and plasma remained above the barrier while the RBCs and granulocytes were trapped below. The tube was inverted several times to mix the blood with the anticoagulant, and the tubes were subjected to centrifugation at 1750×g in a swing-out rotor at room temperature for 20 min. The tubes were removed from the centrifuge, and the clear plasma layer above the cloudy mononuclear cell layer was aspirated and discarded. The cloudy mononuclear cell layer was aspirated, with care taken to rinse all of the mononuclear cells from the surface of the gel barrier with PBS (phosphate buffered saline). Approximately 2 mls of mononuclear cell suspension was transferred to a 2 ml microcentrifuge tube, and centrifuged for 3 min. at 16,000 rpm in a microcentrifuge to pellet the cells. The supernatant was discarded and 1.8 ml of RLT lysis buffer (Qiagen) were added to the mononuclear cell pellet, which lysed the cells and inactivated Rnases. The cells and lysis buffer were pipetted up and down to ensure complete lysis of the pellet. Cell lysate was frozen and stored until it was convenient to proceed with isolation of total RNA.

RNA samples were isolated from 8 mL of whole blood. Yields ranged from 2 ug to 20 ug total RNA for 8 mL blood. A260/A280 spectrophotometric ratios were between 1.6 and 2.0, indicating purity of sample. 2 ul of each sample were run on an agarose gel in the presence of ethidium bromide. No degradation of the RNA sample and no DNA contamination was visible.

In some cases, specific subsets of mononuclear cells were isolated from peripheral blood of human subjects. When this was done, the StemSep cell separation kits (manual version 6.0.0) were used from StemCell Technologies (Vancouver, Canada). This same protocol can be applied to the isolation of T cells, CD4 T cells, CD8 T cells, B cells, monocytes, NK cells and other cells. Isolation of cell types using negative selection with antibodies may be desirable to avoid activation of target cells by antibodies.

Example 9

Preparation of Universal Control RNA for Use in Leukocyte Expression Profiling

Control RNA was prepared using total RNA from Buffy coats and/or total RNA from enriched mononuclear cells isolated from Buffy coats, both with and without stimulation with ionomycin and PMA. The following control RNAs were prepared:
Control 1: Buffy Coat Total RNA
Control 2: Mononuclear cell Total RNA
Control 3: Stimulated buffy coat Total RNA
Control 4: Stimulated mononuclear Total RNA
Control 5: 50% Buffy coat Total RNA/50% Stimulated buffy coat Total RNA
Control 6: 50% Mononuclear cell Total RNA/50% Stimulated Mononuclear Total RNA Some samples were prepared using the following protocol: Buffy coats from 38 individuals were obtained from Stanford Blood Center. Each buffy coat is derived from ~350 mL whole blood from one individual. 10 ml buffy coat was removed from the bag, and placed into a 50 ml tube. 40 ml of Buffer EL (Qiagen) was added, the tube was mixed and placed on ice for 15 minutes, then cells were pelleted by centrifugation at 2000×g for 10 minutes at 4° C. The supernatant was decanted and the cell pellet was re-suspended in 10 ml of Qiagen Buffer EL. The tube was then centrifuged at 2000×g for 10 minutes at 4° C. The cell pellet was then re-suspended in 20 ml TRIZOL (GibcoBRL) per Buffy coat sample, the mixture was shredded using a rotary homogenizer, and the lysate was then frozen at −80° C. prior to proceeding to RNA isolation.

Other control RNAs were prepared from enriched mononuclear cells prepared from Buffy coats. Buffy coats from Stanford Blood Center were obtained, as described above. 10 ml buffy coat was added to a 50 ml polypropylene tube, and 10 ml of phosphate buffer saline (PBS) was added to each tube. A polysucrose (5.7 g/dL) and sodium diatrizoate (9.0 g/dL) solution at a 1.077+/−0.0001 g/ml density solution of equal volume to diluted sample was prepared (Histopaque 1077, Sigma cat. no 1077-1). This and all subsequent steps were performed at room temperature. 15 ml of diluted buffy coat/PBS was layered on top of 15 ml of the histopaque solution in a 50 ml tube. The tube was centrifuged at 400×g for 30 minutes at room temperature. After centrifugation, the upper layer of the solution to within 0.5 cm of the opaque interface containing the mononuclear cells was discarded. The opaque interface was transferred into a clean centrifuge tube. An equal volume of PBS was added to each tube and centrifuged at 350×g for 10 minutes at room temperature. The supernatant was discarded. 5 ml of Buffer EL (Qiagen) was used to resuspend the remaining cell pellet and the tube was centrifuged at 2000×g for 10 minutes at room temperature. The supernatant was discarded. The pellet was resuspended in 20 ml of TRIZOL (GibcoBRL) for each individual buffy coat that was processed. The sample was homogenized using a rotary homogenizer and frozen at −80C until RNA was isolated.

RNA was isolated from frozen lysed Buffy coat samples as follows: frozen samples were thawed, and 4 ml of chloroform was added to each buffy coat sample. The sample was mixed by vortexing and centrifuged at 2000×g for 5 minutes. The aqueous layer was moved to new tube and then repurified by using the RNeasy Maxi RNA clean up kit, according to the manufacturer's instruction (Qiagen, PN 75162). The yield, purity and integrity were assessed by spectrophotometer and gel electrophoresis.

Some samples were prepared by a different protocol, as follows. The further use of RNA prepared using this protocol is described in Example 23.

50 whole blood samples were randomly selected from consented blood donors at the Stanford Medical School Blood Center. Each buffy coat sample was produced from ~350 mL of an individual's donated blood. The whole blood sample was centrifuged at ~4,400×g for 8 minutes at room temperature, resulting in three distinct layers: a top layer of plasma, a second layer of buffy coat, and a third layer of red blood cells. 25 ml of the buffy coat fraction was obtained and diluted with an equal volume of PBS (phosphate buffered saline). 30 ml of diluted buffy coat was layered onto 15 ml of sodium diatrizoate solution adjusted to a density of 1.077+/− 0.001 g/ml (Histopaque 1077, Sigma) in a 50 mL plastic tube. The tube was spun at 800 g for 10 minutes at room temperature. The plasma layer was removed to the 30 ml mark on the tube, and the mononuclear cell layer removed into a new tube and washed with an equal volume of PBS, and collected by centrifugation at 2000 g for 10 minutes at room temperature. The cell pellet was resuspended in 10 ml of Buffer EL (Qiagen) by vortexing and incubated on ice for 10 minutes to remove any remaining erthythrocytes. The mononuclear cells were spun at 2000 g for 10 minutes at 4 degrees Celsius. The cell pellet was lysed in 25 ml of a phenol/guanidinium thiocyanate solution (TRIZOL Reagent, Invitrogen). The sample was homogenized using a PowerGene 5 rotary homogenizer (Fisher Scientific) and Omini disposable generator probes (Fisher Scientific). The Trizol lysate was frozen at −80 degrees C. until the next step.

The samples were thawed out and incubated at room temperature for 5 minutes. 5 ml chloroform was added to each sample, mixed by vortexing, and incubated at room temperature for 3 minutes. The aqueous layers were transferred to new 50 ml tubes. The aqueous layer containing total RNA was further purified using the Qiagen RNeasy Maxi kit (PN 75162), per the manufacturer's protocol (October 1999). The columns were eluted twice with 1 ml Rnase-free water, with a minute incubation before each spin. Quantity and quality of RNA was assessed using standard methods. Generally, RNA was isolated from batches of 10 buffy coats at a time, with an average yield per buffy coat of 870 μg, and an estimated total yield of 43.5 mg total RNA with a 260/280 ratio of 1.56 and a 28S/18S ratio of 1.78.

Quality of the RNA was tested using the Agilent 2100 Bioanalyzer using RNA 6000 microfluidics chips. Analysis of the electrophorgrams from the Bioanalyzer for five different batches demonstrated the reproducibility in quality between the batches.

Total RNA from all five batches were combined and mixed in a 50 ml tube, then aliquoted as follows: 2×10 ml aliquots in 15 ml tubes, and the rest in 100 μl aliquots in 1.5 ml microcentrifuge tubes. The aliquots gave highly reproducible results with respect to RNA purity, size and integrity. The RNA was stored at −80° C.

Test Hybridization of Reference RNA.

When compared with BC38 and Stimulated mononuclear reference samples, the R50 performed as well, if not better than the other reference samples as shown in FIG. 4. In an analysis of hybridizations, where the R50 targets were fluorescently labeled with Cy-5 using methods described herein and the amplified and labeled aRNA was hybridized (as in example 23) to the oligonucleotide array described in examples 20-22. The R50 detected 97.3% of probes with a Signal to Noise ratio (S/N) of greater than three and 99.9% of probes with S/N greater than one.

Example 10

RNA Labeling and Hybridization to a Leukocyte cDNA Array of Candidate Nucleotide Sequences Comparison of Guanine-Silica to Acid-Phenol RNA Purification (GSvsAP)

These data are from a set of 12 hybridizations designed to identify differences between the signal strength from two different RNA purification methods. The two RNA methods used were guanidine-silica (GS, Qiagen) and acid-phenol (AP, Trizol, Gibco BRL). Ten tubes of blood were drawn from each of four people. Two were used for the AP prep, the other eight were used for the GS prep. The protocols for the leukocyte RNA preps using the AP and GS techniques were completed as described here:

Guanidine-Silica (GS) Method:

For each tube, 8 ml blood was drawn into a tube containing the anticoagulant Citrate, 25° C. density gradient solution and a polyester gel barrier that upon centrifugation is permeable to RBCs and granulocytes but not to mononuclear cells. The mononuclear cells and plasma remained above the barrier while the RBCs and granulocytes were trapped below. CPT tubes from Becton-Dickinson (#362753) were used for this purpose. The tube was inverted several times to mix the blood with the anticoagulant. The tubes were immediately centrifuged @ 1750×g in a swinging bucket rotor at room temperature for 20 min. The tubes were removed from the centrifuge and inverted 5-10 times. This mixed the plasma with the mononuclear cells, while the RBCs and the granulocytes remained trapped beneath the gel barrier. The plasma/mononuclear cell mix was decanted into a 15 ml tube and 5 ml of phosphate-buffered saline (PBS) was added. The 15 ml tubes are spun for 5 minutes at 1750×g to pellet the cells. The supernatant was discarded and 1.8 ml of RLT lysis buffer (guanidine isothyocyanate) was added to the mononuclear cell pellet. The buffer and cells were pipetted up and down to ensure complete lysis of the pellet. The cell lysate was then processed exactly as described in the Qiagen Rneasy Miniprep kit protocol (10/99 version) for total RNA isolation (including steps for homogenization (Qiashredder columns) and on-column DNase treatment. The purified RNA was eluted in 50 ul of water.

Acid-Phenol (AP) Method:

For each tube, 8 ml blood was drawn into a tube containing the anticoagulant Citrate, 25° C. density gradient solution and a polyester gel barrier that upon centrifugation is permeable to RBCs and granulocytes but not to mononuclear cells. The mononuclear cells and plasma remained above the barrier while the RBCs and granulocytes were trapped below. CPT tubes from Becton-Dickinson (#362753) were used for this purpose. The tube was inverted several times to mix the blood with the anticoagulant. The tubes were immediately centrifuged @ 1750×g in a swinging bucket rotor at room temperature for 20 min. The tubes were removed from the centrifuge and inverted 5-10 times. This mixed the plasma with the mononuclear cells, while the RBCs and the granulocytes remained trapped beneath the gel barrier. The plasma/mononuclear cell mix was decanted into a 15 ml tube and 5 ml of phosphate-buffered saline (PBS) was added. The 15 ml tubes are spun for 5 minutes @ 1750×g to pellet the cells. The supernatant was discarded and the cell pellet was lysed using 0.6 mL Phenol/guanidine isothyocyanate (e.g. Trizol reagent, GibcoBRL). Subsequent total RNA isolation proceeded using the manufacturers protocol.

RNA from each person was labeled with either Cy3 or Cy5, and then hybridized in pairs to the mini-array. For instance, the first array was hybridized with GS RNA from one person (Cy3) and GS RNA from a second person (Cy5).

Techniques for labeling and hybridization for all experiments discussed here were completed as detailed above in example 10. Arrays were prepared as described in example 7.

RNA isolated from subject samples, or control Buffy coat RNA, were labeled for hybridization to a cDNA array. Total RNA (up to 100 μg) was combined with 2 μl of 100 μM solution of an Oligo (dT) 12-18 (GibcoBRL) and heated to 70° C. for 10 minutes and place on ice. Reaction buffer was added to the tube, to a final concentration of 1×RT buffer (GibcoBRL), 10 mM DTT (GibcoBRL), 0.1 mM unlabeled dATP, dTTP, and dGTP, and 0.025 mM unlabeled dCTP, 200 pg of CAB (*A. thaliana* photosystem I chlorophyll a/b binding protein), 200 pg of RCA (*A. thaliana* RUBISCO activase), 0.25 mM of Cy-3 or Cy-5 dCTP, and 400 U Superscript II RT (GibcoBRL).

The volumes of each component of the labeling reaction were as follows: 20 μl of 5×RT buffer; 10 μl of 100 mM DTT; 1 μl of 10 mM dNTPs without dCTP; 0.5 μl of 5 mM CTP; 13 μl of H20; 0.02 μl of 10 ng/μl CAB and RCA; 1 μl of 40 Units/μl RNAseOUT Recombinant Ribonuclease Inhibitor (GibcoBRL); 2.5 µl of 1.0 mM Cy-3 or Cy-5 dCTP; and 2.0 µl of 200 Units/µl of Superscript II RT. The sample was vortexed and centrifuged. The sample was incubated at 4° C. for 1 hour for first strand cDNA synthesis, then heated at 70° C. for 10 minutes to quench enzymatic activity. 1 µl of 10 mg/ml of Rnase A was added to degrade the RNA strand, and the sample was incubated at 37° C. for 30 minutes.

Next, the Cy-3 and Cy-5 cDNA samples were combined into one tube. Unincorporated nucleotides were removed using QIAquick RCR purification protocol (Qiagen), as directed by the manufacturer. The sample was evaporated to dryness and resuspended in 5 µl of water. The sample was mixed with hybridization buffer containing 5×SSC, 0.2% SDS, 2 mg/ml Cot-1 DNA (GibcoBRL), 1 mg/ml yeast tRNA (GibcoBRL), and 1.6 ng/µl poly dA40-60 (Pharmacia). This mixture was placed on the microarray surface and a glass cover slip was placed on the array (Corning). The microarray glass slide was placed into a hybridization chamber (ArrayIt). The chamber was then submerged in a water bath overnight at 62° C. The microarray was removed from the cassette and the cover slip was removed by repeatedly submerging it to a wash buffer containing 1×SSC, and 0.1% SDS. The microarray slide was washed in 1×SSC/0.1% SDS for 5 minutes. The slide was then washed in 0.1% SSC/0.1% SDS for 5 minutes. The slide was finally washed in 0.1×SSC for 2 minutes. The slide was spun at 1000 rpm for 2 minutes to dry out the slide, then scanned on a microarray scanner (Axon Instruments, Union City, Calif.).

Six hybridizations with 20 µg of RNA were performed for each type of RNA preparation (GS or AP). Since both the Cy3 and the Cy5 labeled RNA are from test preparations, there are six data points for each GS prepped, Cy3-labeled RNA and six for each GS-prepped, Cy5-labeled RNA. The mini array hybridizations were scanned on and Axon Instruments scanner using GenPix 3.0 software. The data presented were derived as follows. First, all features flagged as "not found" by the software were removed from the dataset for individual hybridizations. These features are usually due to high local background or other processing artifacts. Second, the median fluorescence intensity minus the background fluorescence intensity was used to calculate the mean background subtracted signal for each dye for each hybridization. In FIG. 4, the mean of these means across all six hybridizations is graphed (n=6 for each column). The error bars are the SEM. This experiment shows that the average signal from AP prepared RNA is 47% of the average signal from GS prepared RNA for both Cy3 and Cy5.

Generation of Expression Data for Leukocyte Genes from Peripheral Leukocyte Samples Six hybridizations were performed with RNA purified from human blood leukocytes using the protocols given above. Four of the six were prepared using the GS method and 2 were prepared using the AP method. Each preparation of leukocyte RNA was labeled with Cy3 and 10 µg hybridized to the mini-array. A control RNA was batch labeled with Cy5 and 10 µg hybridized to each mini-array together with the Cy3-labeled experimental RNA.

The control RNA used for these experiments was Control 1: Buffy Coat RNA, as described above. The protocol for the preparation of that RNA is reproduced here:

Buffy Coat RNA Isolation:

Buffy coats were obtained from Stanford Blood Center (in total 38 individual buffy coats were used. Each buffy coat is derived from ~350 mL whole blood from one individual. 10 ml buffy coat was taken and placed into a 50 ml tube and 40 ml of a hypoclorous acid (HOCl) solution (Buffer EL from Qiagen) was added. The tube was mixed and placed on ice for 15 minutes. The tube was then centrifuged at 2000×g for 10 minutes at 4° C. The supernatant was decanted and the cell pellet was re-suspended in 10 ml of hypochlorous acid solution (Qiagen Buffer EL). The tube was then centrifuged at 2000×g for 10 minutes at 4° C. The cell pellet was then re-suspended in 20 ml phenol/guanidine thiocyanate solution (TRIZOL from GibcoBRL) for each individual buffy coat that was processed. The mixture was then shredded using a rotary homogenizer. The lysate was then frozen at −80° C. prior to proceeding to RNA isolation.

The arrays were then scanned and analyzed on an Axon Instruments scanner using GenePix 3.0 software. The data presented were derived as follows. First, all features flagged as "not found" by the software were removed from the dataset for individual hybridizations. Second, control features were used to normalize the data for labeling and hybridization variability within the experiment. The control features are cDNA for genes from the plant, *Arabidopsis thaliana*, that were included when spotting the mini-array. Equal amounts of RNA complementary to two of these cDNAs were added to each of the samples before they were labeled. A third was pre-labeled and equal amounts were added to each hybridization solution before hybridization. Using the signal from these genes, we derived a normalization constant ($L_j$) according to the following formula:

$$L_j = \frac{\sum_{i=1}^{N} BGSS_{j,i}}{\frac{\sum_{j=1}^{K} \frac{\sum_{i=1}^{N} BGSS_{j,i}}{N}}{K}}$$

where $BGSS_i$ is the signal for a specific feature as identified in the GenePix software as the median background subtracted signal for that feature, N is the number of *A. thaliana* control features, K is the number of hybridizations, and L is the normalization constant for each individual hybridization.

Using the formula above, the mean over all control features of a particular hybridization and dye (eg Cy3) was calculated. Then these control feature means for all Cy3 hybridizations were averaged. The control feature mean in one hybridization divided by the average of all hybridizations gives a normalization constant for that particular Cy3 hybridization.

The same normalization steps were performed for Cy3 and Cy5 values, both fluorescence and background. Once normalized, the background Cy3 fluorescence was subtracted from the Cy3 fluorescence for each feature. Values less than 100 were eliminated from further calculations since low values caused spurious results.

Figure 5:
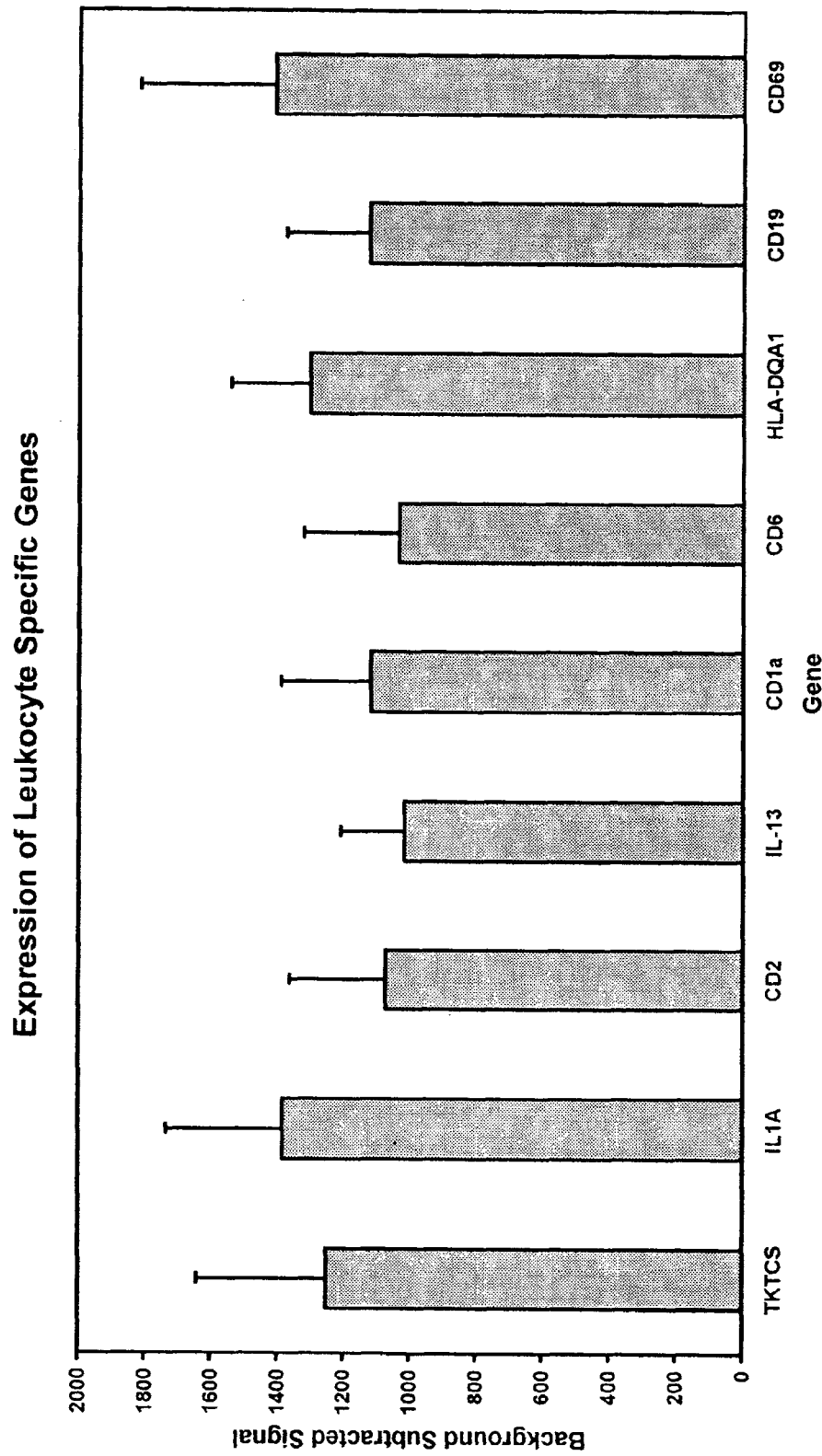
FIG. 5 shows the average background subtracted signal for each of nine leukocyte-specific genes on a mini array. This average is for 3-6 of the above-described hybridizations for each gene. The error bars are the SEM.

FIG. 5 shows the average background subtracted signal for each of nine leukocyte-specific genes on the mini array. This average is for 3-6 of the above-described hybridizations for each gene. The error bars are the SEM. FIG. 3: The ratio of Cy3 to Cy5 signal is shown for a number of genes. This ratio corrects for variability among hybridizations and allows comparison between experiments done at different times. The ratio is calculated as the Cy3 background subtracted signal divided by the Cy5 background subtracted signal. Each bar is the average for 3-6 hybridizations. The error bars are SEM.

Together, these results show that we can measure expression levels for genes that are expressed specifically in sub-populations of leukocytes. These expression measurements were made with only 10 μg of leukocyte total RNA that was labeled directly by reverse transcription. The signal strength can be increased by improved labeling techniques that amplify either the starting RNA or the signal fluorescence. In addition, scanning techniques with higher sensitivity can be used.

Figure 6:
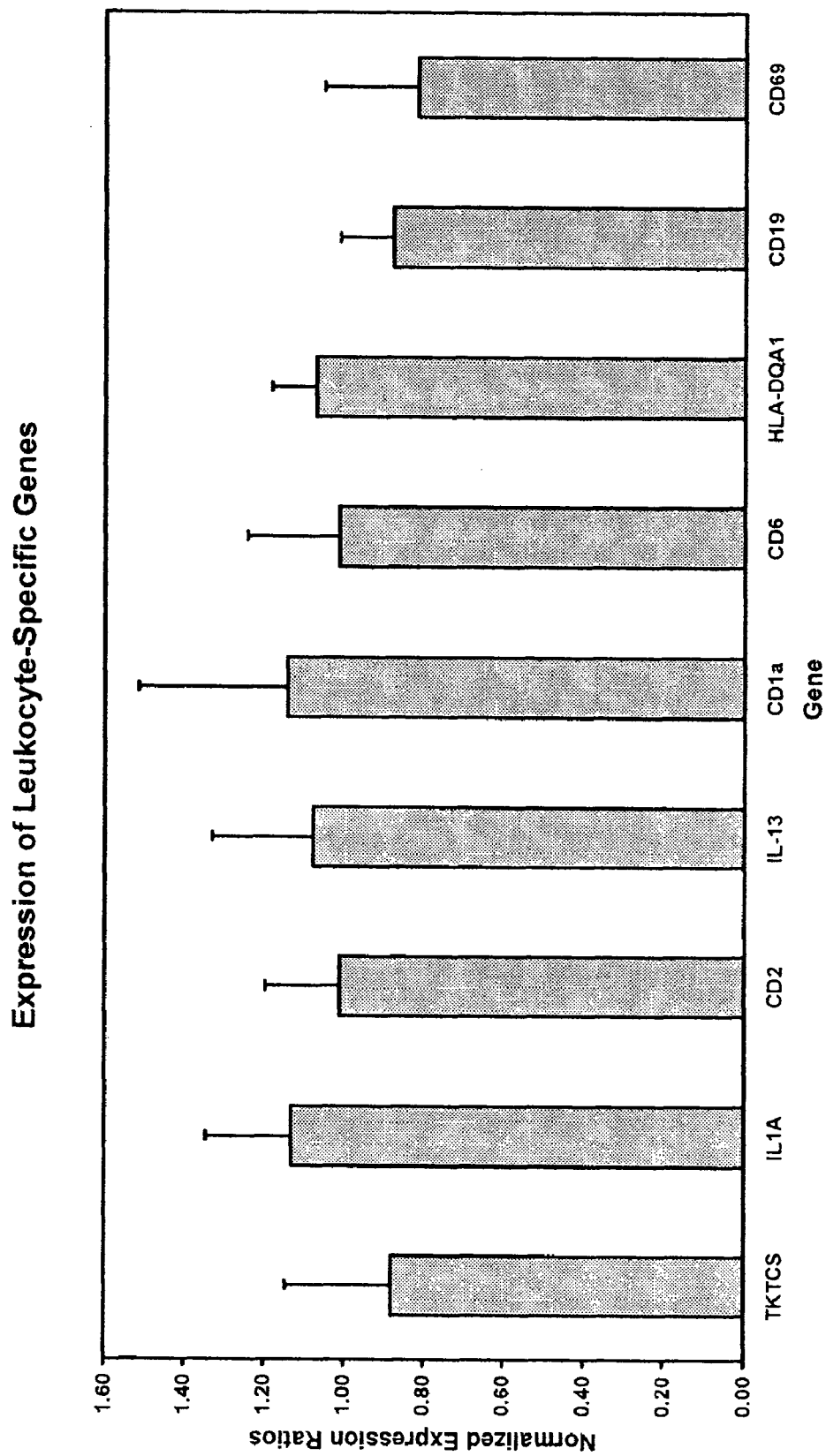
FIG. 6 shows the ratio of Cy3 to Cy5 signal for a number of genes. After normalization, this ratio corrects for variability among hybridizations and allows comparison between experiments done at different times. The ratio is calculated as the Cy3 background subtracted signal divided by the Cy5 background subtracted signal. Each bar is the average for 3-6 hybridizations. The error bars are SEM.
Figure 7:
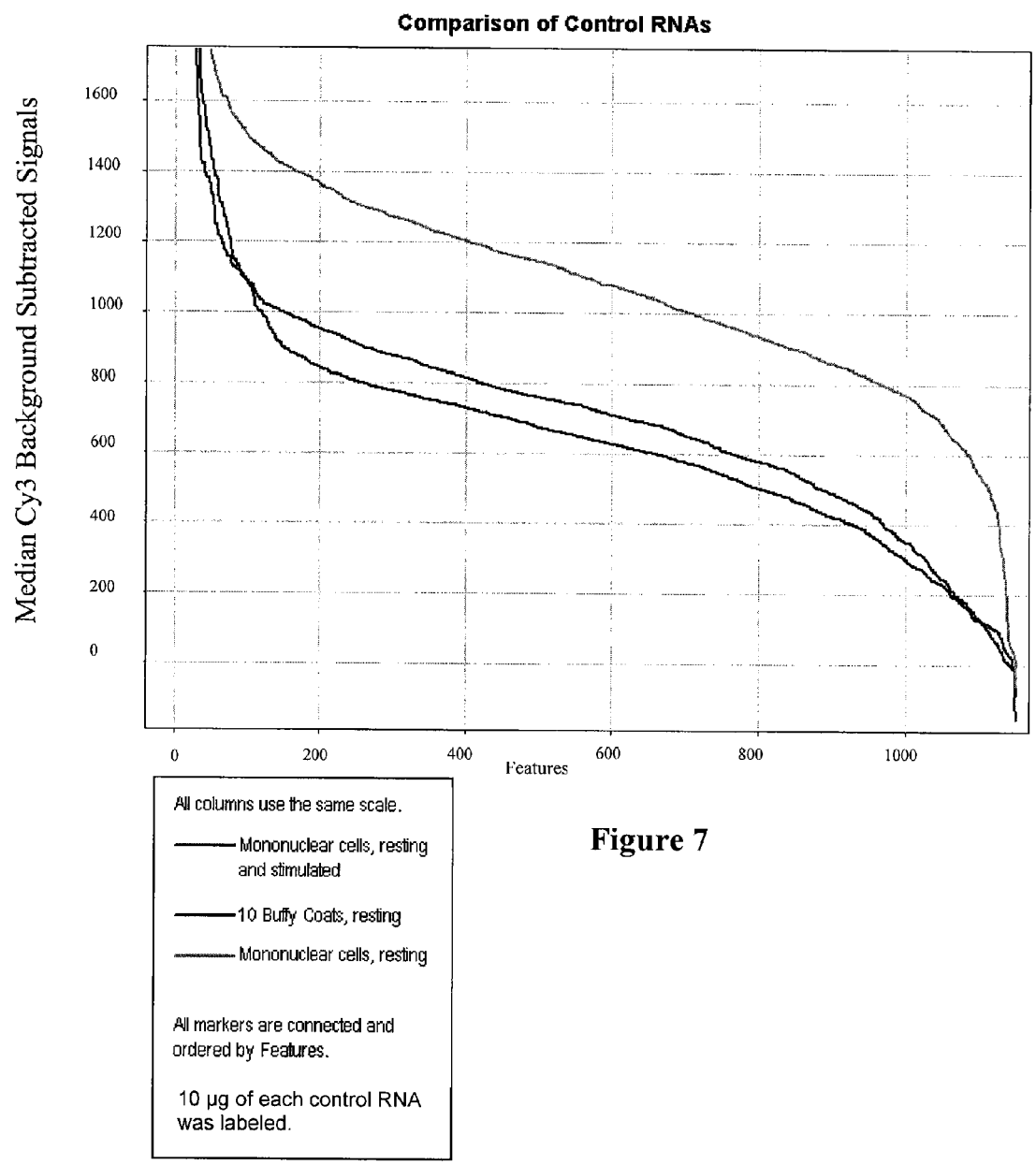
FIG. 7 shows data median Cy3 background subtracted signals for control RNAs using mini arrays.

Genes in FIGS. 5 and 6:

| Gene Name/Description | GenBank Accession Number | Gene Name Abbreviation |
|---|---|---|
| T cell-specific tyrosine kinase Mrna | L10717 | TKTCS |
| Interleukin 1 alpha (IL 1) mRNA, complete cds | NM_000575 | IL1A |
| T-cell surface antigen CD2 (T11) mRNA, complete cds | M14362 | CD2 |
| Interleukin-13 (IL-13) precursor gene, complete cds | U31120 | IL-13 |
| Thymocyte antigen CD1a mRNA, complete cds | M28825 | CD1a |
| CD6 mRNA for T cell glycoprotein CDS | NM_006725 | CD6 |
| MHC class II HLA-DQA1 mRNA, complete cds | U77589 | HLA-DQA1 |
| Granulocyte colony-stimulating factor | M28170 | CD19 |
| Homo sapiens CD69 antigen | NM_001781 | CD69 |

Example 11

Clinical Study to Identify Diagnostic Gene Sets Useful in Diagnosis and Treatment of Cardiac Allograft Recipients An observational study was conducted in which a prospective cohort of cardiac transplant recipients were analyzed for associations between clinical events or rejection grades and expression of a leukocyte candidate nucleotide sequence library. Patients were identified at 4 cardiac transplantation centers while on the transplant waiting list or during their routing post-transplant care. All adult cardiac transplant recipients (new or re-transplants) who received an organ at the study center during the study period or within 3 months of the start of the study period were eligible. The first year after transplantation is the time when most acute rejection occurs and it is thus important to study patients during this period. Patients provided informed consent prior to study procedures.

Peripheral blood leukocyte samples were obtained from all patients at the following time points: prior to transplant surgery (when able), the same day as routinely scheduled screening biopsies, upon evaluation for suspected acute rejection (urgent biopsies), on hospitalization for an acute complication of transplantation or immunosuppression, and when Cytomegalovirus (CMV) infection was suspected or confirmed. Samples were obtained through a standard peripheral vein blood draw or through a catheter placed for patient care (for example, a central venous catheter placed for endocardial biopsy). When blood was drawn from a intravenous line, care was taken to avoid obtaining heparin with the sample as it can interfere with downstream reactions involving the RNA. Mononuclear cells were prepared from whole blood samples as described in Example 8. Samples were processed within 2 hours of the blood draw and DNA and serum were saved in addition to RNA. Samples were stored at −80° C. or on dry ice and sent to the site of RNA preparation in a sealed container with ample dry ice. RNA was isolated from subject samples as described in Example 8 and hybridized to a candidate library of differentially expressed leukocyte nucleotide sequences, as further described in Examples 20-22. Methods used for amplification, labeling, hybridization and scanning are described in Example 23. Analysis of human transplant patient mononuclear cell RNA hybridized to a microarray and identification of diagnostic gene sets is shown in Example 24.

From each patient, clinical information was obtained at the following time points: prior to transplant surgery (when available), the same day as routinely scheduled screening biopsies, upon evaluation for suspected acute rejection (e.g., urgent biopsies), on hospitalization for an acute complication of transplantation or immunosuppression, and when Cytomegalovirus (CMV) infection was suspected or confirmed. Data was collected directly from the patient, from the patient's medical record, from diagnostic test reports or from computerized hospital databases. It was important to collect all information pertaining to the study clinical correlates (diagnoses and patient events and states to which expression data is correlated) and confounding variables (diagnoses and patient events and states that may result in altered leukocyte gene expression. Examples of clinical data collected are: patient sex, date of birth, date of transplant, race, requirement for prospective cross match, occurrence of pre-transplant diagnoses and complications, indication for transplantation, severity and type of heart disease, history of left ventricular assist devices, all known medical diagnoses, blood type, HLA type, viral serologies (including CMV, Hepatitis B and C, HIV and others), serum chemistries, white and red blood cell counts and differentials, CMV infections (clinical manifestations and methods of diagnosis), occurrence of new cancer, hemodynamic parameters measured by catheterization of the right or left heart (measures of graft function), results of echocardiography, results of coronary angiograms, results of intravascular ultrasound studies (diagnosis of transplant vasculopathy), medications, changes in medications, treatments for rejection, and medication levels. Information was also collected regarding the organ donor, including demographics, blood type, HLA type, results of screening cultures, results of viral serologies, primary cause of brain death, the need for inotropic support, and the organ cold ischemia time.

Of great importance was the collection of the results of endocardial biopsy for each of the patients at each visit. Biopsy results were all interpreted and recorded using the international society for heart and lung transplantation (ISHLT) criteria, described below. Biopsy pathological grades were determined by experienced pathologists at each center.

| ISHLT Criteria | | |
|---|---|---|
| Grade | Finding | Rejection Severity |
| 0 | No lymphocytic infiltrates | None |
| 1A | Focal (perivascular or interstitial lymphocytic infiltrates without necrosis) | Borderline mild |
| 1B | Diffuse but sparse lymphocytic infiltrates without necrosis | Mild |
| 2 | One focus only with aggressive lymphocytic infiltrate and/or myocyte damage | Mild, focal moderate |
| 3A | Multifocal aggressive lymphocytic infiltrates and/or myocardial damage | Moderate |
| 3B | Diffuse inflammatory lymphocytic infiltrates with necrosis | Borderline Severe |
| 4 | Diffuse aggressive polymorphous lymphocytic infiltrates with edema hemorrhage and vasculitis, with necrosis | Severe |

Because variability exists in the assignment of ISHLT grades, it was important to have a centralized and blinded reading of the biopsy slides by a single pathologist. This was arranged for all biopsy slides associated with samples in the analysis. Slides were obtained and assigned an encoded number. A single pathologist then read all slides from all centers and assigned an ISHLT grade. Grades from the single pathologist were then compared to the original grades derived from the pathologists at the study centers. For the purposes of correlation analysis of leukocyte gene expression to biopsy grades, the centralized reading information was used in a variety of ways (see Example 24 for more detail). In some analyses, only the original reading was used as an outcome. In other analyses, the result from the centralized reader was used as an outcome. In other analyses, the highest of the 2 grades was used. For example, if the original assigned grade was 0 and the centralized reader assigned a 1A, then 1A was the grade used as an outcome. In some analyses, the highest grade was used and then samples associated with a Grade 1A reading were excluded from the analysis. In some analyses, only grades with no disagreement between the 2 readings were used as outcomes for correlation analysis.

Clinical data was entered and stored in a database. The database was queried to identify all patients and patient visits that meet desired criteria (for example, patients with >grade II biopsy results, no CMV infection and time since transplant<12 weeks).

The collected clinical data (disease criteria) is used to define patient or sample groups for correlation of expression data. Patient groups are identified for comparison, for example, a patient group that possesses a useful or interesting clinical distinction, versus a patient group that does not possess the distinction. Examples of useful and interesting patient distinctions that can be made on the basis of collected clinical data are listed here:

1. Rejection episode of at least moderate histologic grade, which results in treatment of the patient with additional corticosteroids, anti-T cell antibodies, or total lymphoid irradiation.
2. Rejection with histologic grade 2 or higher.
3. Rejection with histologic grade<2.
4. The absence of histologic rejection and normal or unchanged allograft function (based on hemodynamic measurements from catheterization or on echocardiographic data).
5. The presence of severe allograft dysfunction or worsening allograft dysfunction during the study period (based on hemodynamic measurements from catheterization or on echocardiographic data).
6. Documented CMV infection by culture, histology, or PCR, and at least one clinical sign or symptom of infection.
7. Specific graft biopsy rejection grades
8. Rejection of mild to moderate histologic severity prompting augmentation of the patient's chronic immunosuppressive regimen
9. Rejection of mild to moderate severity with allograft dysfunction prompting plasmaphoresis or a diagnosis of "humoral" rejection
10. Infections other than CMV, esp. Epstein Barr virus (EBV)
11. Lymphoproliferative disorder (also called, post-transplant lymphoma)
12. Transplant vasculopathy diagnosed by increased intimal thickness on intravascular ultrasound (IVUS), angiography, or acute myocardial infarction.
13. Graft Failure or Retransplantation
14. All cause mortality
15. Grade 1A or higher rejection as defined by the initial biopsy reading.
16. Grade 1B or higher rejection as defined by the initial biopsy reading.
17. Grade 1A or higher rejection as defined by the centralized biopsy reading.
18. Grade 1B or higher rejection as defined by the centralized biopsy reading.
19. Grade 1A or higher rejection as defined by the highest of the initial and centralized biopsy reading.
20. Grade 1B or higher rejection as defined by the highest of the initial and centralized biopsy reading.
21. Any rejection>Grade 2 occurring in patient at any time in the post-transplant course.

Expression profiles of subject samples are examined to discover sets of nucleotide sequences with differential expression between patient groups, for example, by methods describes above and below.

Non-limiting examples of patient leukocyte samples to obtain for discovery of various diagnostic nucleotide sets are as follows:

a. Leukocyte set to avoid biopsy or select for biopsy:
   Samples: Grade 0 vs. Grades 1-4
b. Leukocyte set to monitor therapeutic response:
   Examine successful vs. unsuccessful drug treatment.
   Samples:
   Successful: Time 1: rejection, Time 2: drug therapy Time 3: no rejection
   Unsuccessful: Time 1: rejection, Time 2: drug therapy; Time 3: rejection
c. Leukocyte set to predict subsequent acute rejection.
   Biopsy may show no rejection, but the patient may develop rejection shortly thereafter. Look at profiles of patients who subsequently do and do not develop rejection.
   Samples:
   Group 1 (Subsequent rejection): Time 1: Grade 0; Time 2: Grade>0
   Group 2 (No subsequent rejection): Time 1: Grade 0; Time 2: Grade 0
   Focal rejection may be missed by biopsy. When this occurs the patient may have a Grade 0, but actually has rejection. These patients may go on to have damage to the graft etc.
   Samples:
   Non-rejectors: no rejection over some period of time
   Rejectors: an episode of rejection over same period
d. Leukocyte set to diagnose subsequent or current graft failure:
   Samples:
   Echocardiographic or catheterization data to define worsening function over time and correlate to profiles.
e. Leukocyte set to diagnose impending active CMV:
   Samples:
   Look at patients who are CMV IgG positive. Compare patients with subsequent (to a sample) clinical CMV infection verses no subsequent clinical CMV infection.
f. Leukocyte set to diagnose current active CMV:
   Samples:
   Analyze patients who are CMV IgG positive. Compare patients with active current clinical CMV infection vs. no active current CMV infection.

Upon identification of a nucleotide sequence or set of nucleotide sequences that distinguish patient groups with a high degree of accuracy, that nucleotide sequence or set of nucleotide sequences is validated, and implemented as a diagnostic test. The use of the test depends on the patient groups that are used to discover the nucleotide set. For example, if a set of nucleotide sequences is discovered that have collective expression behavior that reliably distinguishes patients with no histological rejection or graft dysfunction from all others, a diagnostic is developed that is used to screen patients for the need for biopsy. Patients identified as having no rejection do not need biopsy, while others are subjected to a biopsy to further define the extent of disease. In another example, a diagnostic nucleotide set that determines continuing graft rejection associated with myocyte necrosis (>grade I) is used to determine that a patient is not receiving adequate treatment under the current treatment regimen. After increased or altered immunosuppressive therapy, diagnostic profiling is conducted to determine whether continuing graft rejection is progressing. In yet another example, a diagnostic nucleotide set(s) that determine a patient's rejection status and diagnose cytomegalovirus infection is used to balance immunosuppressive and anti-viral therapy.

The methods of this example are also applicable to cardiac xenograft monitoring.

Example 12

Identification of Diagnostic Nucleotide Sets for Kidney and Liver Allograft Rejection Diagnostic tests for rejection are identified using patient leukocyte expression profiles to identify a molecular signature correlated with rejection of a transplanted kidney or liver. Blood, or other leukocyte source, samples are obtained from patients undergoing kidney or liver biopsy following liver or kidney transplantation, respectively. Such results reveal the histological grade, i.e., the state and severity of allograft rejection. Expression profiles are obtained from the samples as described above, and the expression profile is correlated with biopsy results. In the case of kidney rejection, clinical data is collected corresponding to urine output, level of creatine clearance, and level of serum creatine (and other markers of renal function). Clinical data collected for monitoring liver transplant rejection includes, biochemical characterization of serum markers of liver damage and function such as SGOT, SGPT, Alkaline phosphatase, GGT, Bilirubin, Albumin and Prothrombin time.

Leukocyte nucleotide sequence expression profiles are collected and correlated with important clinical states and outcomes in renal or hepatic transplantation. Examples of useful clinical correlates are given here:

1. Rejection episode of at least moderate histologic grade, which results in treatment of the patient with additional corticosteriods, anti-T cell antibodies, or total lymphoid irradiation.

2. The absence of histologic rejection and normal or unchanged allograft function (based on tests of renal or liver function listed above).

3. The presence of severe allograft dysfunction or worsening allograft dysfunction during the study period (based on tests of renal and hepatic function listed above).

4. Documented CMV infection by culture, histology, or PCR, and at least one clinical sign or symptom of infection.

5. Specific graft biopsy rejection grades

6. Rejection of mild to moderate histologic severity prompting augmentation of the patient's chronic immunosuppressive regimen 7. Infections other than CMV, esp. Epstein Barr virus (EBV)

8. Lymphoproliferative disorder (also called, post-transplant lymphoma)

9. Graft Failure or Retransplantation

10. Need for hemodialysis or other renal replacement therapy for renal transplant patients.

11. Hepatic encephalopathy for liver transplant recipients.

12. All cause mortality

Subsets of the candidate library (or of a previously identified diagnostic nucleotide set), are identified, according to the above procedures, that have predictive and/or diagnostic value for kidney or liver allograft rejection.

Example 13

Identification of Diagnostic Nucleotide Sequences Sets for Use in the Diagnosis, Prognosis, Risk Stratification, and Treatment of Atherosclerosis, Stable Angina Pectoris, and Acute Coronary Syndrome Prediction of Complications of Atherosclerosis: Angina Pectoris.

Over 50 million in the US have atherosclerotic coronary artery disease (CAD). Almost all adults have some atherosclerosis. The most important question is who will develop complications of atherosclerosis. Patients with angiographically-confirmed atherosclerosis are enrolled in a study, and followed over time. Leukocyte expression profiles are taken at the beginning of the study, and routinely thereafter. Some patients develop angina and others do not. Expression profiles are correlated with development of angina, and subsets of the candidate library (or a previously identified diagnostic nucleotide set) are identified, according to the above procedures, that have predictive and/or diagnostic value for angina pectoris.

Alternatively, patients are followed by serial angiography. Profiles are collected at the first angiography, and at a repeat angiography at some future time (for example, after 1 year). Expression profiles are correlated with progression of disease, measured, for example, by decrease in vessel lumen diameter. Subsets of the candidate library (or a previously identified diagnostic nucleotide set) are identified, according to the above procedures, that have predictive and/or diagnostic value for progression of atherosclerosis.

Prediction and/or Diagnosis of Acute Coronary Syndrome

The main cause of death due to coronary atherosclerosis is the occurrence of acute coronary syndromes: myocardial infarction and unstable angina. Patients with at a very high risk of acute coronary syndrome (e.g., patients with a history of acute coronary syndrome, patients with atherosclerosis, patients with multiple traditional risk factors, clotting disorders or lupus) are enrolled in a prospective study. Leukocyte expression profiles are taken at the beginning of the study period and patients are monitored for the occurrence of unstable angina and/or myocardial infarction. Standard criteria for the occurrence of an event are used (serum enzyme elevation, EKG, nuclear imaging or other), and the occurrence of these events can be collected from the patient, the patient's physician, the medical record or medical database. Expression profiles (taken at the beginning of the study) are correlated with the occurrence of an acute event. Subsets of the candidate library (or a previously identified diagnostic nucleotide set) are identified, according to the above procedures, that have predictive value for occurrence of an acute event.

In addition, expression profiles (taken at the time that an acute event occurs) are correlated with the occurrence of an acute event. Subsets of the candidate library (or a previously identified diagnostic nucleotide set) are identified, according to the above procedures, that have diagnostic value for occurrence of an acute event.

Risk Stratification: Occurrence of Coronary Artery Disease

The established and classic risks for the occurrence of coronary artery disease and complications of that disease are: cigarette smoking, diabetes, hypertension, hyperlipidemia and a family history of early atherosclerosis. Obesity, sedentary lifestyle, syndrome X, cocaine use, chronic hemodialysis and renal disease, radiation exposure, endothelial dysfunction, elevated plasma homocysteine, elevated plasma lipoprotein a, and elevated CRP. Infection with CMV and chlamydia infection are less well established, controversial or putative risk factors for the disease. These risk factors can be assessed or measured in a population.

Leukocyte expression profiles are measured in a population possessing risk factors for the occurrence of coronary artery disease. Expression profiles are correlated with the presence of one or more risk factors (that may correlate with future development of disease and complications). Subsets of the candidate library (or a previously identified diagnostic nucleotide set) are identified, according to the above procedures, that have predictive value for the development of coronary artery disease.

Additional examples of useful correlation groups in cardiology include:

1. Samples from patients with a high risk factor burden (e.g., smoking, diabetes, high cholesterol, hypertension, family history) versus samples from those same patients at different times with fewer risks, or versus samples from different patients with fewer or different risks.

2. Samples from patients during an episode of unstable angina or myocardial infarction versus paired samples from those same patients before the episode or after recovery, or from different patients without these diagnoses.

3. Samples from patients (with or without documented atherosclerosis) who subsequently develop clinical manifestations of atherosclerosis such as stable angina, unstable angina, myocardial infarction, or stroke versus samples from patients (with or without atherosclerosis) who do not develop these manifestations over the same time period.

4. Samples from patients who subsequently respond to a given medication or treatment regimen versus samples from those same or different patients who subsequently do not respond to a given medication or treatment regimen.

Example 14

Identification of Diagnostic Nucleotide Sets for Use in Diagnosing and Treating Restenosis Restenosis is the re-narrowing of a coronary artery after an angioplasty. Patients are identified who are about to, or have recently undergone angioplasty. Leukocyte expression profiles are measured before the angioplasty, and at 1 day and 1-2 weeks after angioplasty or stent placement. Patients have a follow-up angiogram at 3 months and/or are followed for the occurrence of clinical restenosis, e.g., chest pain due to re-narrowing of the artery, that is confirmed by angiography. Expression profiles are compared between patients with and without restenosis, and candidate nucleotide profiles are correlated with the occurrence of restenosis. Subsets of the candidate library (or a previously identified diagnostic nucleotide set) are identified, according to the above procedures, that have predictive value for the development of restenosis.

Example 15

Identification of Diagnostic Nucleotide Sets for Use in Monitoring Treatment and/or Progression of Congestive Heart Failure CHF effects greater than 5 million individuals in the US and the prevalence of this disorder is growing as the population ages. The disease is chronic and debilitating. Medical expenditures are huge due to the costs of drug treatments, echocardiograms and other tests, frequent hospitalization and cardiac transplantation. The primary causes of CHF are coronary artery disease, hypertension and idiopathic cardiomyopathy. Congestive heart failure is the number one indication for heart transplantation.

There is ample recent evidence that congestive heart failure is associated with systemic inflammation. A leukocyte test with the ability to determine the rate of progression and the adequacy of therapy is of great interest. Patients with severe CHF are identified, e.g. in a CHF clinic, an inpatient service, or a CHF study or registry (such as the cardiac transplant waiting list/registry). Expression profiles are taken at the beginning of the study and patients are followed over time, for example, over the course of one year, with serial assessments performed at least every three months. Further profiles are taken at clinically relevant end-points, for example: hospitalization for CHF, death, pulmonary edema, worsening of Ejection Fraction or increased cardiac chamber dimensions determined by echocardiography or another imaging test, and/or exercise testing of hemodynamic measurements. Clinical data is collected from patients if available, including:

Serial C-Reactive Protein (CRP), other serum markers, echocardiography (e.g., ejection fraction or another echocardiographic measure of cardiac function), nuclear imaging, NYHA functional classes, hospitalizations for CHF, quality of life measures, renal function, transplant listing, pulmonary edema, left ventricular assist device use, medication use and changes.

Expression profiles correlating with progression of CHF are identified. Expression profiles predicting disease progression, monitoring disease progression and response to treatment, and predicting response to a particular treatment(s) or class of treatment(s) are identified. Subsets of the candidate library (or a previously identified diagnostic nucleotide set) are identified, according to the above procedures, that have predictive value for the progression of CHF. Such diagnostic nucleotide sets are also useful for monitoring response to treatment for CHF.

Example 16

Identification of Diagnostic Nucleotide Sets for Use in Monitoring Treatment and/or Progression of Rheumatoid Arthritis Rheumatoid arthritis (hereinafter, "RA") is a chronic and debilitating inflammatory arthritis. The diagnosis of RA is made by clinical criteria and radiographs. A new class of medication, TNF blockers, are effective, but the drugs are expensive, have side effects and not all patients respond to treatment. In addition, relief of disease symptoms does not always correlate with inhibition of joint destruction. For these reasons, an alternative mechanism for the titration of therapy is needed.

An observational study was conducted in which a cohort of patients meeting American College of Rheumatology (hereinafter "ARC") criteria for the diagnosis of RA was identified. Arnett et al. (1988) *Arthritis Rheum* 31:315-24. Patients gave informed consent and a peripheral blood mononuclear cell RNA sample was obtained by the methods as described herein. When available, RNA samples were also obtained from surgical specimens of bone or synovium from effected joints, and synovial fluid.

From each patient, the following clinical information was obtained if available:

Demographic information; information relating to the ACR criteria for RA; presence or absence of additional diagnoses of inflammatory and non-inflammatory conditions; data from laboratory test, including complete blood counts with differentials, CRP, ESR, ANA, Serum IL6, Soluble CD40 ligand, LDL, HDL, Anti-DNA antibodies, rheumatoid factor, C3, C4, serum creatinine and any medication levels; data from surgical procedures such as gross operative findings and pathological evaluation of resected tissues and biopsies; information on pharmacological therapy and treatment changes; clinical diagnoses of disease "flare"; hospitalizations; quantitative joint exams; results from health assessment questionnaires (HAQs); other clinical measures of patient symptoms and disability; physical examination results and radiographic data assessing joint involvement, synovial thickening, bone loss and erosion and joint space narrowing and deformity.

From these data, measures of improvement in RA are derived as exemplified by the ACR 20% and 50% response/improvement rates (Felson et al. 1996). Measures of disease activity over some period of time is derived from these data as are measures of disease progression. Serial radiography of effected joints is used for objective determination of progression (e.g., joint space narrowing, peri-articular osteoporosis, synovial thickening). Disease activity is determined from the clinical scores, medical history, physical exam, lab studies, surgical and pathological findings.

The collected clinical data (disease criteria) is used to define patient or sample groups for correlation of expression data. Patient groups are identified for comparison, for example, a patient group that possesses a useful or interesting clinical distinction, verses a patient group that does not possess the distinction. Examples of useful and interesting patient distinctions that can be made on the basis of collected clinical data are listed here:

1. Samples from patients during a clinically diagnosed RA flare versus samples from these same or different patients while they are asymptomatic.

2. Samples from patients who subsequently have high measures of disease activity versus samples from those same or different patients who have low subsequent disease activity.

3. Samples from patients who subsequently have high measures of disease progression versus samples from those same or different patients who have low subsequent disease progression.

4. Samples from patients who subsequently respond to a given medication or treatment regimen versus samples from those same or different patients who subsequently do not respond to a given medication or treatment regimen (for example, TNF pathway blocking medications).

5. Samples from patients with a diagnosis of osteoarthritis versus patients with rheumatoid arthritis.

6. Samples from patients with tissue biopsy results showing a high degree of inflammation versus samples from patients with lesser degrees of histological evidence of inflammation on biopsy.

Expression profiles correlating with progression of RA are identified. Subsets of the candidate library (or a previously identified diagnostic nucleotide set) are identified, according to the above procedures, that have predictive value for the progression of RA.

Diagnostic nucleotide set(s) are identified which predict respond to TNF blockade. Patients are profiled before and during treatment with these medications. Patients are followed for relief of symptoms, side effects and progression of joint destruction, e.g., as measured by hand radiographs. Expression profiles correlating with response to TNF blockade are identified. Subsets of the candidate library (or a previously identified diagnostic nucleotide set) are identified, according to the above procedures that have predictive value for response to TNF blockade.

Example 17

Identification of a Diagnostic Nucleotide Set for Diagnosis of Cytomegalovirus

Cytomegalovirus is a very important cause of disease in immunocompromised patients, for example, transplant patients, cancer patients, and AIDS patients. The virus can cause inflammation and disease in almost any tissue (particularly the colon, lung, bone marrow and retina). It is increasingly important to identify patients with current or impending clinical CMV disease, particularly when immunosuppressive drugs are to be used in a patient, e.g. for preventing transplant rejection.

Leukocytes are profiled in patients with active CMV, impending CMV, or no CMV. Expression profiles correlating with diagnosis of active or impending CMV are identified. Subsets of the candidate library (or a previously identified diagnostic nucleotide set) are identified, according to the above procedures that have predictive value for the diagnosis of active or impending CMV. Diagnostic nucleotide set(s) identified with predictive value for the diagnosis of active or impending CMV may be combined, or used in conjunction with, cardiac, liver and/or kidney allograft-related diagnostic gene set(s) (described in Examples 12 and 24).

In addition, or alternatively, CMV nucleotide sequences are obtained, and a diagnostic nucleotide set is designed using CMV nucleotide sequence. The entire sequence of the organism is known and all CMV nucleotide sequences can be isolated and added to the library using the sequence information and the approach described below. Known expressed genes are preferred. Alternatively, nucleotide sequences are selected to represent groups of CMV genes that are coordinately expressed (immediate early genes, early genes, and late genes) (Spector et al. 1990, Stamminger et al. 1990).

Oligonucleotides were designed for CMV genes using the oligo design procedures of Example 21. Probes were designed using the 14 gene sequences shown here and were included on the array described in examples 20-22:

| | | |
|---|---|---|
| Cytomegalovirus (CMV) | HCMVTRL2 (IRL2) | 1893 . . . 2240 |
| Accession #X17403 | HCMVTRL7 (IRL7) | complement (6595 . . . 6843) |
| | HCMVUL21 | complement (26497 . . . 27024) |
| | HCMVUL27 | complement (32831 . . . 34657) |
| | HCMVUL33 | 43251 . . . 44423 |
| | HCMVUL54 | complement (76903 . . . 80631) |
| | HCMVUL75 | complement (107901 . . . 110132) |
| | HCMVUL83 | complement (119352 . . . 121037) |

-continued

| | |
|---|---|
| HCMVUL106 | complement (154947 . . . 155324) |
| HCMVUL109 | complement (157514 . . . 157810) |
| HCMVUL113 | 161503 . . . 162800 |
| HCMVUL122 | complement (169364 . . . 170599) |
| HCMVUL123 (last exon at 3'-end) | complement (171006 . . . 172225) |
| HCMVUS28 | 219200 . . . 220171 |

Diagnostic nucleotide set(s) for expression of CMV genes is used in combination with diagnostic leukocyte nucleotide sets for diagnosis of other conditions, e.g. organ allograft rejection.

Using the techniques described in example 8 mononuclear samples from 180 cardiac transplant recipients (enrolled in the study described in Example 11) were used for expression profiling with the leukocyte arrays. Of these samples 15 were associated with patients who had a diagnosis of primary or reactivation CMV made by culture, PCR or any specific diagnostic test.

After preparation of RNA, amplification, labeling, hybridization, scanning, feature extraction and data processing were done as described in Example 23 using the oligonucleotide microarrays described in Examples 20-22.

The resulting log ratio of expression of Cy3 (patient sample)/Cy5 (R50 reference RNA) was used for analysis. Significance analysis for microarrays (SAM, Tusher 2001, see Example 26) was applied to determine which genes were most significantly differentially expressed between these 15 CMV patients and the 165 non-CMV patients (Table 11A). 12 genes were identified with a 0% FDR and 6 with a 0.1% FDR. Some genes are represented by more than one oligonucleotide on the array and for 2 genes, multiple oligonucleotides from the same gene are called significant (SEQ IDs: 5559, 6308: eomesodermin and 1685, 2428, 4113, 6059: small inducible cytokine A4).

Clinical variables were also included in the significance analysis. For example, the white blood cell count and the number of weeks post transplant (for the patient at the time the sample was obtained) were available for most of the 180 samples. The log of these variables was taken and the variables were then used in the significance analysis described above with the gene expression data. Both the white blood cell count (0.1% FDR) and the weeks post transplant (0% FDR) appeared to correlate with CMV status. CMV patients were more likely to have samples associated with later post transplant data and the lower white blood cell counts.

These genes and variables can be used alone or in association with other genes or variables or with other genes to build a diagnostic gene set or a classification algorithm using the approaches described herein.

Primers for real-time PCR validation were designed for some of these genes as described in Example 25 and listed in Table 11B and the sequence listing. Using the methods described in example 25, primers for Granzyme B were designed and used to validate expression findings from the arrays. 6 samples were tested (3 from patients with CMV and 3 from patients without CMV). The gene was found to be differentially expressed between the patients with and without CMV (see example 25 for full description). This same approach can be used to validate other diagnostic genes by real-time PCR.

Diagnostic nucleotide sets can also be identified for a variety of other viral diseases (Table 1) using this same approach.

Example 18

Identification of a Diagnostic Nucleotide Set for Diagnosis of Cytomegalovirus

Cytomegalovirus is a very important cause of disease in immunosuppressed patients, for example, transplant patients, cancer patients, and AIDS patients. The virus can cause inflammation and disease in almost any tissue (particularly the colon, lung, bone marrow and retina). It is increasingly important to identify patients with current or impending clinical CMV disease, particularly when immunosuppressive drugs are to be used in a patient, e.g. for preventing transplant rejection.

Leukocytes are profiled in patients with active CMV, impending CMV, or no CMV. Expression profiles correlating with diagnosis of active or impending CMV are identified. Subsets of the candidate library (or a previously identified diagnostic nucleotide set) are identified, according to the above procedures, that have predictive value for the diagnosis of active or impending CMV. Diagnostic nucleotide set(s) identified with predictive value for the diagnosis of active or impending CMV may be combined, or used in conjunction with, cardiac, liver and/or kidney allograft-related diagnostic gene set(s) (described in Examples 11 and 12).

In addition, or alternatively, CMV nucleotide sequences are obtained, and a diagnostic nucleotide set is designed using CMV nucleotide sequence. The entire sequence of the organism is known and all CMV nucleotide sequences can be isolated and added to the library using the sequence information and the approach described below. Known expressed genes are preferred. Alternatively, nucleotide sequences are selected to represent groups of CMV genes that are coordinately expressed (immediate early genes, early genes, and late genes) (Spector et al. 1990, Stamminger et al. 1990).

CMV nucleotide sequences were isolated as follows: Primers were designed to amplify known expressed CMV genes, based on the publicly available sequence of CMV strain AD 169 (Genbank LOCUS: HEHCMVCG 229354 bp; DEFINITION Human cytomegalovirus strain AD169 complete genome; ACCESSION X17403; VERSION X17403.1 GI:59591). The following primer were used to PCR amplify nucleotide sequences from 175 ng of AD 169 viral genomic DNA (Advance Biotechnologies Incorporated) as a template:

| CMV GENE | | PRIMER SEQUENCES | SEQ. ID. NO: |
|---|---|---|---|
| UL21 | 5' | atgtggccgcttctgaaaaac | 8771 |
| UL21 | 3' | tcatggggtggggacgggg | 8772 |
| UL33 | 5' | gtacgcgctgctgggtcatg | 8773 |
| UL33 | 3' | tcatacccgctgaggttatg | 8774 |
| UL54 | 5' | cacggacgacgacgctgacg | 8775 |
| UL54 | 3' | gtacggcagaaaagccggctc | 8776 |
| UL55 | 5' | caccaaagacacgtcgttacag | 8777 |
| UL55 | 3' | tcagacgttctcttcttcgtcg | 8778 |
| UL75 | 5' | cagcggcgctcaacatttcac | 8779 |
| UL75 | 3' | tcagcatgtcttgagcatgcgg | 8780 |

-continued

| CMV GENE | PRIMER SEQUENCES | SEQ. ID. NO: |
|---|---|---|
| UL80 5' | cctccccaactactactaccg | 8781 |
| UL80 3' | ttactcgagcttattgagcgcag | 8782 |
| UL83 5' | cacgtcgggcgttatgacac | 8783 |
| UL83 3' | tcaacctcggtgcttttggg | 8784 |
| UL97 5' | ctgtctgctcattctggcgg | 8785 |
| UL97 3' | ttactcggggaacagttggcg | 8786 |
| UL106 5' | atgatgaccgaccgcacgga | 8787 |
| UL106 3' | tcacggtggctcgatacactg | 8788 |
| UL107 5' | aagcttccttacagcataactgt | 8789 |
| UL107 3' | ccttataacatgtattttgaaaaattg | 8790 |
| UL109 5' | atgatacacgactaccactgg | 8791 |
| UL109 3' | ttacgagcaagagttcatcacg | 8792 |
| UL112 5' | ctgcgtgtcctcgctgggt | 8793 |
| UL112 3' | tcacgagtccactcggaaagc | 8794 |
| UL113 5' | ctcgtcttcttcggctccac | 8795 |
| UL113 3' | ttaatcgtcgaaaaacgccgcg | 8796 |
| UL122 5' | gatgcttgtaacgaaggcgtc | 8797 |
| UL122 3' | ttactgagacttgttcctcagg | 8798 |
| UL123 5' | gtagcctacactttggccacc | 8799 |
| UL123 3' | ttactggtcagccttgcttcta | 8800 |
| IRL2 5' | acgtccctggtagacggg | 8801 |
| IRL2 3' | ttataagaaaagaagcacaagctc | 8802 |
| IRL3 5' | atgtattgttttctttttttacagaaag | 8803 |
| IRL3 3' | ttatattattatcaaaacgaaaaacag | 8804 |
| IRL4 5' | cttctccttccttaatctcgg | 8805 |
| IRL4 3' | ctatacggagatcgcggtcc | 8806 |
| IRL5 5' | atgcatacatacacgcgtgcat | 8807 |
| IRL5 3' | ctaccatataaaaacgcagggg | 8808 |
| IRL7 5' | atgaaagcaagaggcagccg | 8809 |
| IRL7 3' | tcataaggtaacgatgctactttt | 8810 |
| IRL13 5' | atggactggcgatttacggtt | 8811 |
| IRL13 3' | ctacattgtgccatttctcagt | 8812 |
| US2 5' | atgaacaatctctggaaagcctg | 8813 |
| US2 3' | tcagcacacgaaaaaccgcatc | 8814 |
| US3 5' | atgaagccggtgttggtgctc | 8815 |
| US3 3' | ttaaataaatcgcagacgggcg | 8816 |
| US6 5' | atggatctcttgattcgtctcg | 8817 |
| US6 3' | tcaggagccacaacgtcgaatc | 8818 |

-continued

| CMV GENE | PRIMER SEQUENCES | SEQ. ID. NO: |
|---|---|---|
| US11 5' | cgcaaaacgctactggctcc | 8819 |
| US11 3' | tcaccactggtccgaaaacatc | 8820 |
| US18 5' | tacggctggtccgtcatcgt | 8821 |
| US18 3' | ttacaacaagctgaggagactc | 8822 |
| US27 5' | atgaccacctctacaaataatcaaac | 8823 |
| US27 3' | gtagaaacaagcgttgagtccc | 8824 |
| US28 5' | cgttgcggtgtctcagtcg | 8825 |
| US28 3' | tcatgctgtggtaccaggata | 8826 |

The PCR reaction conditions were 10 mM Tris pH 8.3, 3.5 mM MgCl2, 25 mM KCl, 200 uM dNTP's, 0.2 uM primers, and 5 Units of Taq Gold. The cycle parameters were as follows:

1. 95° C. for 30 sec
2. 95° C. for 15 sec
3. 56° C. for 30 sec
4. 72° C. for 2 min
5. go to step 2, 29 times
6. 72° C. for 2 min
7. 4° C. forever PCR products were gel purified, and DNA was extracted from the agarose using the QiaexII gel purification kit (Qiagen). PCR product was ligated into the T/A cloning vector p-GEM-T-Easy (Promega) using 3 ul of gel purified PCR product and following the Promega protocol. The products of the ligation reaction were transformed and plated as described in the p-GEM protocol. White colonies were picked and grow culture in LB-AMP medium. Plasmid was prepared from these cultures using Qiagen Miniprep kit (Qiagen). Restriction enzyme digested plasmid (Not I and EcoRI) was examined after agarose gel electrophoresis to assess insert size. When the insert was the predicted size, the plasmid was sequenced by well-known techniques to confirm the identity of the CMV gene. Using forward and reverse primers that are complimentary to sequences flanking the insert cloning site (M13F and M13R), the isolated CMV gene was amplified and purified as described above. Amplified cDNAs were used to create a microarray as described above. In addition, 50 mer oligonucleotides corresponding the CMV genes listed above were designed, synthesized and placed on a microarray using methods described elsewhere in the specification.

Alternatively, oligonucleotide sequences are designed and synthesized for oligonucleotide array expression analysis from CMV genes as described in examples 20-22.

Diagnostic nucleotide set(s) for expression of CMV genes is used in combination with diagnostic leukocyte nucleotide sets for diagnosis of other conditions, e.g. organ allograft rejection.

Example 19

Identification of Diagnostic Nucleotide Sets for Monitoring Response to Statins

HMG-CoA reductase inhibitors, called "Statins," are very effective in preventing complications of coronary artery disease in either patients with coronary disease and high cholesterol (secondary prevention) or patients without known coronary disease and with high cholesterol (primary prevention). Examples of Statins are (generic names given) pravistatin, atorvastatin, and simvastain. Monitoring response to Statin therapy is of interest. Patients are identified who are on or are about to start Statin therapy. Leukocytes are profiled in patients before and after initiation of therapy, or in patients already being treated with Statins. Data is collected corresponding to cholesterol level, markers of inflammation (e.g., C-Reactive Protein and the Erythrocyte Sedimentation Rate), measures of endothelial function (e.g., improved forearm resistance or coronary flow reserve) and clinical endpoints (new stable angina, unstable angina, myocardial infarction, ventricular arrhythmia, claudication). Patient groups can be defined based on their response to Statin therapy (cholesterol, clinical endpoints, endothelial function). Expression profiles correlating with response to Statin treatment are identified. Subsets of the candidate library (or a previously identified diagnostic nucleotide set) are identified, according to the above procedures, that have predictive value for the response to Statins. Members of candidate nucleotide sets with expression that is altered by Statins are disease target nucleotides sequences.

Example 20

Probe Selection for a 24,000 Feature Array

This Example describes the compilation of almost 8,000 unique genes and ESTs using sequences identified from the sources described below. The sequences of these genes and ESTs were used to design probes, as described in the following Example.

Tables 3A, 3B and 3C list the sequences identified in the subtracted leukocyte expression libraries. All sequences that were identified as corresponding to a known RNA transcript were represented at least once, and all unidentified sequences were represented twice—once by the sequence on file and again by the complementary sequence—to ensure that the sense (or coding) strand of the gene sequence was included.

Table 3A. Table 3A contained all those sequences in the subtracted libraries of example 1 that matched sequences in GenBank's nr, EST_Human, and UniGene databases with an acceptable level of confidence. All the entries in the table representing the sense strand of their genes were grouped together and all those representing the antisense strand were grouped. A third group contained those entries whose strand could not be determined. Two complementary probes were designed for each member of this third group.

Table 3B and 3C. Table 3B and 3C contained all those sequences in the leukocyte expression subtracted libraries of example 1 that did not match sequences in GenBank's nr, EST_Human, and UniGene databases with an acceptable level of confidence, but which had a high probability of representing real mRNA sequences. Sequences in Table 3B did not match anything in the databases above but matched regions of the human genome draft and were spatially clustered along it, suggesting that they were exons, rather than genomic DNA included in the library by chance. Sequences in Table 3C also aligned well to regions of the human genome draft, but the aligned regions were interrupted by genomic DNA, meaning they were likely to be spliced transcripts of multiple exon genes.

Table 3B lists 510 clones and Table 3C lists 48 clones that originally had no similarity with any sequence in the public databases. Blastn searches conducted after the initial filing have identified sequences in the public database with high similarity (E values less than 1e–40) to the sequences determined for these clones. Table 3B contained 272 clones and Table 3C contained 25 clones that were found to have high similarity to sequences in dbEST. The sequences of the similar dbEST clones were used to design probes. Sequences from clones that contained no similar regions to any sequence in the database were used to design a pair of complementary probes.

Probes were designed from database sequences that had the highest similarity to each of the sequenced clones in Tables 3A, 3B, and 3C. Based on BLASTn searches the most similar database sequence was identified by locus number and the locus number was submitted to GenBank using batch Entrez located at the web site ncbi.nlm.nih.gov/entrez/batchentrez.cgi?db=Nucleotide to obtain the sequence for that locus. The GenBank entry sequence was used because in most cases it was more complete or was derived from multi-pass sequencing and thus would likely have fewer errors than the single pass cDNA library sequences. When only UniGene cluster IDs were available for genes of interest, the respective sequences were extracted from the UniGene_unique database, build 137, downloaded from NCBI (ftp://ncbi.nlm.nih-.gov/repository/UniGene/). This database contains one representative sequence for each cluster in UniGene.

| Summary of library clones used in array probe design | | | |
|---|---|---|---|
| Table | Sense Strand | Antisnese Strand | Strand Undetermined |
| 3A | 3621 | 763 | 124 |
| 3B | 142 | 130 | 238 |
| 3C | 19 | 6 | 23 |
| Totals | 3782 | 899 | 385 |

Literature Searches

Example 2 describes searches of literature databases. We also searched for research articles discussing genes expressed only in leukocytes or involved in inflammation and particular disease conditions, including genes that were specifically expressed or down-regulated in a disease state. Searches included, but were not limited to, the following terms and various combinations of theses terms: inflammation, atherosclerosis, rheumatoid arthritis, osteoarthritis, lupus, SLE, allograft, transplant, rejection, leukocyte, monocyte, lymphocyte, mononuclear, macrophage, neutrophil, eosinophil, basophil, platelet, congestive heart failure, expression, profiling, microarray, inflammatory bowel disease, asthma, RNA expression, gene expression, granulocyte.

A UniGene cluster ID or GenBank accession number was found for each gene in the list. The strand of the corresponding sequence was determined, if possible, and the genes were divided into the three groups: sense (coding) strand, antisense strand, or strand unknown. The rest of the probe design process was carried out as described above for the sequences from the leukocyte subtracted expression library.

Database Mining

Database mining was performed as described in Example 2. In addition, the Library Browser at the NCBI UniGene web site ncbi.nlm.nih.gov/UniGene/lbrowse.cgi?ORG= Hs& DISPLAY=ALL was used to identify genes that are specifically expressed in leukocyte cell populations. All expression libraries available at the time were examined and those derived from leukocytes were viewed individually. Each library viewed through the Library Browser at the UniGene web site contains a section titled "Shown below are UniGene clusters of special interest only" that lists genes that are either highly represented or found only in that library. Only the genes in this section were downloaded from each library. Alternatively, every sequence in each library is downloaded and then redundancy between libraries is reduced by discarding all UniGene cluster IDs that are represented more than once. A total of 439 libraries were downloaded, containing 35,819 genes, although many were found in more than one library. The most important libraries from the remaining set were separated and 3,914 genes remained. After eliminating all redundancy between these libraries and comparing the remaining genes to those listed in Tables 3A, 3B and 3C, the set was reduced to 2,573 genes in 35 libraries as shown in Table 9. From these, all genes in first 30 libraries were used to design probes. A random subset of genes was used from Library Lib.376, "Activated_T-cells_XX". From the last four libraries, a random subset of sequences listed as "ESTs, found only in this library" was used.

Angiogenesis Markers 215 sequences derived from an angiogenic endothelial cell subtracted cDNA library obtained from Stanford University were used for probe design. Briefly, using well known subtractive hybridization procedures, (as described in, e.g., U.S. Pat. Nos. 5,958,738; 5,589,339; 5,827,658; 5,712,127; 5,643,761; 5,565,340) modified to normalize expression by suppressing over-representation of abundant RNA species while increasing representation of rare RNA species, a library was produced that is enriched for RNA species (messages) that are differentially expressed between test (stimulated) and control (resting) HUVEC populations. The subtraction/suppression protocol was performed as described by the kit manufacturer (Clontech, PCR-select cDNA Subtraction Kit).

Pooled primary HUVECs (Clonetics) were cultured in 15% FCS, M199 (GibcoBRL) with standard concentrations of Heparin, Penicillin, Streptomycin, Glutamine and Endothelial Cell Growth Supplement. The cells were cultured on 1% gelatin coated 10 cm dishes. Confluent HUVECs were photographed under phase contrast microscopy. The cells formed a monolayer of flat cells without gaps. Passage 2-5 cells were used for all experiments. Confluent HUVECs were treated with trypsin/EDTA and seeded onto collagen gels. Collagen gels were made according to the protocol of the Collagen manufacturer (Becton Dickinson Labware). Collagen gels were prepared with the following ingredients: Rat tail collagen type I (Collaborative Biomedical) 1.5 mg/mL, mouse laminin (Collaborative Biomedical) 0.5 mg/mL, 10% 10× media 199 (Gibco BRL). 1N NaOH, 10×PBS and sterile water were added in amounts recommended in the protocol. Cell density was measured by microscopy. $1.2 \times 10^6$ cells were seeded onto gels in 6-well, 35 mm dishes, in 5% FCS M199 media. The cells were incubated for 2 hrs at 37 C with 5% $CO2$. The media was then changed to the same media with the addition of VEGF (Sigma) at 30 ng/mL media. Cells were cultured for 36 hrs. At 12, 24 and 36 hrs, the cells were observed with phase contrast microscopy. At 36 hours, the cells were observed elongating, adhering to each other and forming lumen structures. At 12 and 24 hrs media was aspirated and refreshed. At 36 hrs, the media was aspirated, the cells were rinsed with PBS and then treated with Collagenase (Sigma) 2.5 mg/mL PBS for 5 min with active agitation until the collagen gels were liquefied. The cells were then centrifuged at 4C, 2000 g for 10 min. The supernatant was removed and the cells were lysed with 1 mL Trizol Reagent (Gibco) per $5 \times 10^6$ cells. Total RNA was prepared as specified in the Trizol instructions for use. mRNA was then isolated as described in the micro-fast track mRNA isolation protocol from Invitrogen. This RNA was used as the tester RNA for the subtraction procedure.

Ten plates of resting, confluent, p4 HUVECs, were cultured with 15% FCS in the M199 media described above. The media was aspirated and the cells were lysed with 1 mL Trizol and total RNA was prepared according to the Trizol protocol. mRNA was then isolated according to the micro-fast track mRNA isolation protocol from Invitrogen. This RNA served as the control RNA for the subtraction procedure.

The entire subtraction cloning procedure was carried out as per the user manual for the Clontech PCR Select Subtraction Kit. The cDNAs prepared from the test population of HUVECs were divided into "tester" pools, while cDNAs prepared from the control population of HUVECs were designated the "driver" pool. cDNA was synthesized from the tester and control RNA samples described above. Resulting cDNAs were digested with the restriction enzyme RsaI. Unique double-stranded adapters were ligated to the tester cDNA. An initial hybridization was performed consisting of the tester pools of cDNA (with its corresponding adapter) and an excess of the driver cDNA. The initial hybridization results in a partial normalization of the cDNAs such that high and low abundance messages become more equally represented following hybridization due to a failure of driver/tester hybrids to amplify.

A second hybridization involved pooling unhybridized sequences from the first hybridization together with the addition of supplemental driver cDNA. In this step, the expressed sequences enriched in the two tester pools following the initial hybridization can hybridize. Hybrids resulting from the hybridization between members of each of the two tester pools are then recovered by amplification in a polymerase chain reaction (PCR) using primers specific for the unique adapters. Again, sequences originating in a tester pool that form hybrids with components of the driver pool are not amplified. Hybrids resulting between members of the same tester pool are eliminated by the formation of "panhandles" between their common 5' and 3' ends. The subtraction was done in both directions, producing two libraries, one with clones that are upregulated in tube-formation and one with clones that are down-regulated in the process.

The resulting PCR products representing partial cDNAs of differentially expressed genes were then cloned (i.e., ligated) into an appropriate vector according to the manufacturer's protocol (pGEM-Teasy from Promega) and transformed into competent bacteria for selection and screening. Colonies (2180) were picked and cultured in LB broth with 50 ug/mL ampicillin at 37C overnight. Stocks of saturated LB+50 ug/mL ampicillin and 15% glycerol in 96-well plates were stored at −80C. Plasmid was prepared from 1.4 mL saturated LB broth containing 50 ug/mL ampicillin. This was done in a 96 well format using commercially available kits according to the manufacturer's recommendations (Qiagen 96-turbo prep).

2 probes to represent 22 of these sequences required, therefore, a total of 237 probes were derived from this library.

Viral Genes

Several viruses may play a role in a host of disease including inflammatory disorders, atherosclerosis, and transplant rejection. Table 10 lists the viral genes represented by oligonucleotide probes on the microarray. Low-complexity regions in the sequences were masked using RepeatMasker before using them to design probes.

Strand Selection

It was necessary to design sense oligonucleotide probes because the labeling and hybridization protocol to be used with the microarray results in fluorescently-labeled antisense cRNA. All of the sequences we selected to design probes could be divided into three categories:
  (1) Sequences known to represent the sense strand
  (2) Sequences known to represent the antisense strand
  (3) Sequences whose strand could not be easily determined from their descriptions It was not known whether the sequences from the leukocyte subtracted expression library were from the sense or antisense strand. GenBank sequences are reported with sequence given 5' to 3', and the majority of the sequences we used to design probes came from accession numbers with descriptions that made it clear whether they represented sense or antisense sequence. For example, all sequences containing "mRNA" in their descriptions were understood to be the sequences of the sense mRNA, unless otherwise noted in the description, and all IMAGE Consortium clones are directionally cloned and so the direction (or sense) of the reported sequence can be determined from the annotation in the GenBank record.

For accession numbers representing the sense strand, the sequence was downloaded and masked and a probe was designed directly from the sequence. These probes were selected as close to the 3' end as possible. For accession numbers representing the antisense strand, the sequence was downloaded and masked, and a probe was designed complementary to this sequence. These probes were designed as close to the 5' end as possible (i.e., complementary to the 3' end of the sense strand).

Minimizing Probe Redundancy.

Multiple copies of certain genes or segments of genes were included in the sequences from each category described above, either by accident or by design. Reducing redundancy within each of the gene sets was necessary to maximize the number of unique genes and ESTs that could be represented on the microarray.

Three methods were used to reduce redundancy of genes, depending on what information was available. First, in gene sets with multiple occurrences of one or more UniGene numbers, only one occurrence of each UniGene number was kept. Next, each gene set was searched by GenBank accession numbers and only one occurrence of each accession number was conserved. Finally, the gene name, description, or gene symbol were searched for redundant genes with no UniGene number or different accession numbers. In reducing the redundancy of the gene sets, every effort was made to conserve the most information about each gene.

We note, however, that the UniGene system for clustering submissions to GenBank is frequently updated and UniGene cluster IDs can change. Two or more clusters may be combined under a new cluster ID or a cluster may be split into several new clusters and the original cluster ID retired. Since the lists of genes in each of the gene sets discussed were assembled at different times, the same sequence may appear in several different sets with a different UniGene ID in each.

Sequences from Table 3A were treated differently. In some cases, two or more of the leukocyte subtracted expression library sequences aligned to different regions of the same GenBank entry, indicating that these sequences were likely to be from different exons in the same gene transcript. In these cases, one representative library sequence corresponding to each presumptive exon was individually listed in Table 3A.

Compilation.

After redundancy within a gene set was sufficiently reduced, a table of approximately 8,000 unique genes and ESTs was compiled in the following manner. All of the entries in Table 3A were transferred to the new table. The list of genes produced by literature and database searches was added, eliminating any genes already contained in Table 3A. Next, each of the remaining sets of genes was compared to the table and any genes already contained in the table were deleted from the gene sets before appending them to the table.

|  | Probes |
|---|---|
| Subtracted Leukocyte Expression Library |  |
| Table 3A | 4,872 |
| Table 3B | 796 |
| Table 3C | 85 |
| Literature Search Results | 494 |
| Database Mining | 1,607 |
| Viral genes |  |
| a. CMV | 14 |
| b. EBV | 6 |
| c. HHV 6 | 14 |
| d. Adenovirus | 8 |
| Angiogenesis markers: 215, 22 of which needed two probes | 237 |
| *Arabidopsis thaliana* genes | 10 |
| Total sequences used to design probes | 8,143 |

Example 21

Design of Oligonucleotide Probes

By way of example, this section describes the design of four oligonucleotide probes using Array Designer Ver 1.1 (Premier Biosoft International, Palo Alto, Calif.). The major steps in the process are given first.

1. Obtain best possible sequence of mRNA from GenBank. If a full-length sequence reference sequence is not available, a partial sequence is used, with preference for the 3' end over the 5' end. When the sequence is known to represent the antisense strand, the reverse complement of the sequence is used for probe design. For sequences represented in the subtracted leukocyte expression library that have no significant match in GenBank at the time of probe design, our sequence is used.

2. Mask low complexity regions and repetitive elements in the sequence using an algorithm such as RepeatMasker.

3. Use probe design software, such as Array Designer, version 1.1, to select a sequence of 50 residues with specified physical and chemical properties. The 50 residues nearest the 3' end constitute a search frame. The residues it contains are tested for suitability. If they don't meet the specified criteria, the search frame is moved one residue closer to the 5' end, and the 50 residues it now contains are tested. The process is repeated until a suitable 50-mer is found.
4. If no such 50-mer occurs in the sequence, the physical and chemical criteria are adjusted until a suitable 50-mer is found.

Compare the probe to dbEST, the UniGene cluster set, and the assembled human genome using the BLASTn search tool at NCBI to obtain the pertinent identifying information and to verify that the probe does not have significant similarity to more than one known gene.

Clone 40H12

Clone 40H12 was sequenced and compared to the nr, dbEST, and UniGene databases at NCBI using the BLAST search tool. The sequence matched accession number NM_002310, a 'curated RefSeq project' sequence, see Pruitt et al. (2000) *Trends Genet.* 16:44-47, encoding leukemia inhibitory factor receptor (LIFR) mRNA with a reported E value of zero. An E value of zero indicates there is, for all practical purposes, no chance that the similarity was random based on the length of the sequence and the composition and size of the database. This sequence, cataloged by accession number NM_002310, is much longer than the sequence of clone 40H12 and has a poly-A tail. This indicated that the sequence cataloged by accession number NM_002310 is the sense strand and a more complete representation of the mRNA than the sequence of clone 40H12, especially at the 3' end. Accession number "NM_002310" was included in a text file of accession numbers representing sense strand mRNAs, and sequences for the sense strand mRNAs were obtained by uploading a text file containing desired accession numbers as an Entrez search query using the Batch Entrez web interface and saving the results locally as a FASTA file. The following sequence was obtained, and the region of alignment of clone 40H12 is outlined:

(SEQ ID NO: 8827)

```
CTCTCTCCCAGAACGTGTCTCTGCTGCAAGGCACCGGGCCCTTTCGCTCTGCAGAACTGC
ACTTGCAAGACCATTATCAACTCCTAATCCCAGCTCAGAAAGGGAGCCTCTGCGACTCAT
TCATCGCCCTCCAGGACTGACTGCATTGCACAGATGATGGATATTTACGTATGTTTGAAA
CGACCATCCTGGATGGTGGACAATAAAAGAATGAGGACTGCTTCAAATTTCCAGTGGCTG
TTATCAACATTTATTCTTCTATATCTAATGAATCAAGTAAATAGCCAGAAAAAGGGGGCT
CCTCATGATTTGAAGTGTGTAACTAACAATTTGCAAGTGTGGAACTGTTCTTGGAAAGCA
CCCTCTGGAACAGGCCGTGGTACTGATTATGAAGTTTGCATTGAAAACAGGTCCCGTTCT
TGTTATCAGTTGGAGAAAACCAGTATTAAAATTCCAGCTCTTTCACATGGTGATTATGAA
ATAACAATAAATTCTCTACATGATTTTGGAAGTTCTACAAGTAAATTCACACTAAATGAA
CAAAACGTTTCCTTAATTCCAGATACTCCAGAGATCTTGAATTTGTCTGCTGATTTCTCA

ACCTCTACATTATACCTAAAGTGGAACGACAGGGGTTCAGTTTTTCCACACCGCTCAAAT
GTTATCTGGGAAATTAAAGTTCTACGTAAAGAGAGTATGGAGCTCGTAAAATTAGTGACC
CACAACACAACTCTGAATGGCAAAGATACACTTCATCACTGGAGTTGGGCCTCAGATATG
CCCTTGGAATGTGCCATTCATTTTGTGGAAATTAGATGCTACATTGACAATCTTCATTTT
TCTGGTCTCGAAGAGTGGAGTGACTGGAGCCCTGTGAAGAACATTTCTTGGATACCTGAT
TCTCAGACTAAGGTTTTTCCTCAAGATAAAGTGATACTTGTAGGCTCAGACATAACATTT
TGTTGTGTGAGTCAAGAAAAAGTGTTATCAGCACTGATTGGCCATACAAACTGCCCCTTG
ATCCATCTTGATGGGGAAAATGTTGCAATCAAGATTCGTAATATTTCTGTTTCTGCAAGT
AGTGGAACAAATGTAGTTTTTACAACCGAAGATAACATATTTGGAACCGTTATTTTTGCT
GGATATCCACCAGATACTCCTCAACAACTGAATTGTGAGACACATGATTTAAAAGAAATT

ATATGTAGTTGGAATCCAGGAAGGGTGACAGCGTTGGTGGGCCCACGTGCTACAAGCTAC
ACTTTAGTTGAAAGTTTTTCAGGAAAATATGTTAGACTTAAAAGAGCTGAAGCACCTACA
AACGAAAGCTATCAATTATTATTTCAAATGCTTCCAAATCAAGAAATATATAATTTTACT
TTGAATGCTCACAATCCGCTGGGTCGATCACAATCAACAATTTTAGTTAATATAACTGAA
AAAGTTTATCCCCATACTCCTACTTCATTCAAAGTGAAGGATATTAATTCAACAGCTGTT
AAACTTTCTTGGCATTTACCAGGCAACTTTGCAAAGATTAATTTTTTATGTGAAATTGAA
ATTAAGAAATCTAATTCAGTACAAGAGCAGCGGAATGTCACAATCAAAGGAGTAGAAAAT
TCAAGTTATCTTGTTGCTCTGGACAAGTTAAATCCATACACTCTATATACTTTTCGGATT

CGTTGTTCTACTGAAACTTTCTGGAAATGGAGCAAATGGAGCAATAAAAAACAACATTTA
ACAACAGAAGCCAGTCCTTCAAAGGGGCCTGATACTTGGAGAGAGTGGAGTTCTGATGGA
AAAAATTTAATAATCTATTGGAAGCCTTTACCCATTAATGAAGCTAATGGAAAAATACTT
TCCTACAATGTATCGTGTTCATCAGATGAGGAAACACAGTCCCTTTCTGAAATCCCTGAT
CCTCAGCACAAAGCAGAGATACGACTTGATAAGAATGACTACATCATCAGCGTAGTGGCT
AAAAATTCTGTGGGCTCATCACCACCTTCCAAAATAGCGAGTATGGAAATTCCAAATGAT
GATCTCAAAATAGAACAAGTTGTTGGGATGGGAAAGGGGATTCTCCTCACCTGGCATTAC
GACCCCAACATGACTTGCGACTACGTCATTAAGTGGTGTAACTCGTCTCGGTCGGAACCA
TGCCTTATGGACTGGAGAAAAGTTCCCTCAAACAGCACTGAAACTGTAATAGAATCTGAT
GAGTTTCGACCAGGTATAAGATATAATTTTTTCCTGTATGGATGCAGAAATCAAGGATAT

CAATTATTACGCTCCATGATTGGATATATAGAAGAATTGGCTCCCATTGTTGCACCAAAT
TTTACTGTTGAGGATACTTCTGCAGATTCGATATTAGTAAAATGGGAAGACATTCCTGTG
GAAGAACTTAGAGGCTTTTTAAGAGGATATTTGTTTTACTTTGGAAAAGGAGAAAGAGAC
ACATCTAAGATGAGGGTTTTAGAATCAGGTCGTTCTGACATAAAAGTTAAGAATATTACT
GACATATCCCAGAAGACACTGAGAATTGCTGATCTTCAAGGTAAAACAAGTTACCACCTG
GTCTTGCGAGCCTATACAGATGGTGGAGTGGGCCCGGAGAAGAGTATGTATGTGGTGACA
AAGGAAAATTCTGTGGGATTAATTATTGCCATTCTCATCCCAGTGGCAGTGGCTGTCATT
GTTGGAGTGGTGACAAGTATCCTTTGCTATCGGAAACGAGAATGGATTAAAGAAACCTTC
TACCCTGATATTCCAAATCCAGAAAACTGTAAAGCATTACAGTTTCAAAAGAGTGTCTGT

GAGGGAAGCAGTGCTCTTAAAACATTGGAAATGAATCCTTGTACCCCAAATAATGTTGAG
GTTCTGGAAACTCGATCAGCATTTCCTAAAATAGAAGATACAGAAATAATTTCCCCAGTA
GCTGAGCGTCCTGAAGATCGCTCTGATGCAGAGCCTGAAAACCATGTGGTTGTGTCCTAT
TGTCCACCCATCATTGAGGAAGAAATACCAAACCCAGCCGCAGATGAAGCTGGAGGGACT
GCACAGGTTATTTACATTGATGTTCAGTCGATGTATCAGCCTCAAGCAAAACCAGAAGAA
GAACAAGAAAATGACCCTGTAGGAGGGGCAGGCTATAAGCCACAGATGCACCTCCCCATT
AATTCTACTGTGGAAGATATAGCTGCAGAAGAGGACTTAGATAAAACTGCGGGTTACAGA
CCTCAGGCCAATGTAAATACATGGAATTTAGTGTCTCCAGACTCTCCTAGATCCATAGAC
AGCAACAGTGAGATTGTCTCATTTGGAAGTCCATGCTCCATTAATTCCCGACAATTTTTG
```

-continued

```
ATTCCTCCTAAAGATGAAGACTCTCCTAAATCTAATGGAGGAGGGTGGTCCTTTACAAAC
TTTTTTCAGAACAAACCAAACGATTAACAGTGTCACCGTGTCACTTCAGTCAGCCATCTC
AATAAGCTCTTACTGCTAGTGTTGCTACATCAGCACTGGGCATTCTTGGAGGGATCCTGT
GAAGTATTGTTAGGAGGTGAACTTCACTACATGTTAAGTTACACTGAAAGTTCATGTGCT
TTTAATGTAGTCTAAAAGCCAAAGTATAGTGACTCAGAATCCTCAATCCACAAAACTCAA
GATTGGGAGCTCTTTGTGATCAAGCCAAAGAATTCTCATGTACTCTACCTTCAAGAAGCA
TTTCAAGGCTAATACCTACTTGTACGTACATGTAAAACAAATCCCGCCGCAACTGTTTTC
TGTTCTGTTGTTTGTGGTTTTCTCATATGTATACTTGGTGGAATTGTAAGTGGATTTGCA
GGCCAGGGAGAAAATGTCCAAGTAACAGGTGAAGTTTATTTGCCTGACGTTTACTCCTTT
CTAGATGAAAACCAAGCACAGATTTTAAAACTTCTAAGATTATTCTCCTCTATCCACAGC
ATTCACAAAAATTAATATAATTTTTAATGTAGTGACAGCGATTTAGTGTTTTGTTTGATA

AAGTATGCTTATTTCTGTGCCTACTGTATAATGGTTATCAAACAGTTGTCTCAGGGGTAC
AAACTTTGAAAACAAGTGTGACACTGACCAGCCCAAATCATAATCATGTTTTCTTGCTGT
GATAGGTTTTGCTTGCCTTTTCATTATTTTTTAGCTTTTATGCTTGCTTCCATTATTTCA
GTTGGTTGCCCTAATATTTAAAATTTACACTTCTAAGACTAGAGACCCACATTTTTTAAA
AATCATTTTATTTTGTGATACAGTGACAGCTTTATATGAGCAAATTCAATATTATTCATA
AGCATGTAATTCCAGTGACTTACTATGTGAGATGACTACTAAGCAATATCTAGCAGCGTT
AGTTCCATATAGTTCTGATTGGATTTCGTTCCTCCTGAGGAGACCATGCCGTTGAGCTTG
GCTACCCAGGCAGTGGTGATCTTTGACACCTTCTGGTGGATGTTCCTCCCACTCATGAGT
CTTTTCATCATGCCACATTATCTGATCCAGTCCTCACATTTTTAAATATAAAACTAAAGA
GAGAATGCTTCTTACAGGAACAGTTACCCAAGGGCTGTTTCTTAGTAACTGTCATAAACT
GATCTGGATCCATGGGCATACCTGTGTTCGAGGTGCAGCAATTGCTTGGTGAGCTGTGCA
GAATTGATTGCCTTCAGCACAGCATCCTCTGCCCACCCTTGTTTCTCATAAGCGATGTCT
GGAGTGATTGTGGTTCTTGGAAAAGCAGAAGGAAAAACTAAAAAGTGTATCTTGTATTTT
CCCTGCGCTCAGGTTGCCTATGTATTTTACCTTTTCATATTTAAGGCAAAAGTACTTGAA

AATTTTAAGTGTCCGAATAAGATATGTCTTTTTTGTTTGTTTTTTTGGTTGGTTGTTTG
TTTTTTATCATCTGAGATTCTGTAATGTATTTGCAAATAATGGATCAATTAATTTTTTTT
GAAGCTCATATTGTATCTTTTTAAAAACCATGTTGTGGAAAAAAGCCAGAGTGACAAGTG
ACAAAATCTATTTAGGAACTCTGTGTATGAATCCTGATTTTAACTGCTAGGATTCAGCTA
AATTTCTGAGCTTTATGATCTGTGGAAATTTGGAATGAAATCGAATTCATTTTGTACATA
CATAGTATATTAAAACTATATAATAGTTCATAGAAATGTTCAGTAATGAAAAAATATATC
CAATCAGAGCCATCCCGAAAAAAAAAAAAAAA
```

The FASTA file, including the sequence of NM_002310, was masked using the RepeatMasker web interface (Smit, AFA & Green, P RepeatMasker at http://ftp.genome.washington.edu/RM/RepeatMasker.html, Smit and Green). Specifically, during masking, the followingtypes of sequences were replaced with "N's": SINE/MIR & LINE/L2, LINE/L1, LTR/MaLR, LTR/Retroviral, Alu, and other low informational content sequences such as simple repeats. Below is the sequence following masking:

(SEQ ID NO: 8828)
```
CTCTCTCCCAGAACGTGTCTCTGCTGCAAGGCACCGGGCCCTTTCGCTCTGCAGAACTGC
ACTTGCAAGACCATTATCAACTCCTAATCCCAGCTCAGAAAGGGAGCCTCTGCGACTCAT
TCATCGCCCTCCAGGACTGACTGCATTGCACAGATGATGGATATTTACGTATGTTTGAAA
CGACCATCCTGGATGGTGGACAATAAAAGAATGAGGACTGCTTCAAATTTCCAGTGGCTG
TTATCAACATTTATTCTTCTATATCTAATGAATCAAGTAAATAGCCAGAAAAAGGGGGCT
CCTCATGATTTGAAGTGTGTAACTAACAATTTGCAAGTGTGGAACTGTTCTTGGAAAGCA
CCCTCTGGAACAGGCCGTGGTACTGATTATGAAGTTTGCATTGAAAACAGGTCCCGTTCT
TGTTATCAGTTGGAGAAAACCAGTATTAAAATTCCAGCTCTTTCACATGGTGATTATGAA

ATAACAATAAATTCTCTACATGATTTTGGAAGTTCTACAAGTAAATTCACACTAAATGAA
CAAAACGTTTCCTTAATTCCAGATACTCCAGAGATCTTGAATTTGTCTGCTGATTTCTCA
ACCTCTACATTATACCTAAAGTGGAACGACAGGGGTTCAGTTTTTCCACACCGCTCAAAT
GTTATCTGGGAAATTAAAGTTCTACGTAAAGAGAGTATGGAGCTCGTAAAATTAGTGACC
CACAACACAACTCTGAATGGCAAAGATACACTTCATCACTGGAGTTGGGCCTCAGATATG
CCCTTGGAATGTGCCATTCATTTTGTGGAAATTAGATGCTACATTGACAATCTTCATTTT
TCTGGTCTCGAAGAGTGGAGTGACTGGAGCCCTGTGAAGAACATTTCTTGGATACCTGAT
TCTCAGACTAAGGTTTTTCCTCAAGATAAAGTGATACTTGTAGGCTCAGACATAACATTT
TGTTGTGTGAGTCAAGAAAAAGTGTTATCAGCACTGATTGGCCATACAAACTGCCCCTTG

ATCCATCTTGATGGGGAAATGTTGCAATCAAGATTCGTAATATTTCTGTTTCTGCAAGT
AGTGGAACAAATGTAGTTTTTACAACCGAAGATAACATATTTGGAACCGTTATTTTTGCT
GGATATCCACCAGATACTCCTCAACAACTGAATTGTGAGACACATGATTTAAAAGAAATT
ATATGTAGTTGGAATCCAGGAAGGGTGACAGCGTTGGTGGGCCCACGTGCTACAAGCTAC
ACTTTAGTTGAAAGTTTTTCAGGAAAATATGTTAGACTTAAAAGAGCTGAAGCACCTACA
AACGAAAGCTATCAATTATTATTTCAAATGCTTCCAAATCAAGAAATATATAATTTTACT
TTGAATGCTCACAATCCGCTGGGTCGATCACAATCAACAATTTTAGTTAATATAACTGAA
AAAGTTTATCCCCATACTCCTACTTCATTCAAAGTGAAGGATATTAATTCAACAGCTGTT

AAACTTTCTTGGCATTTACCAGGCAACTTTGCAAAGATTAATTTTTTATGTGAAATTGAA
ATTAAGAAATCTAATTCAGTACAAGAGCAGCGGAATGTCACAATCAAAGGAGTAGAAAAT
TCAAGTTATCTTGTTGCTCTGGACAAGTTAAATCCATACACTCTATATACTTTTCGGATT
CGTTGTTCTACTGAAACTTTCTGGAAATGGAGCAAATGGAGCAATAAAAAACAACATTTA
ACAACAGAAGCCAGTCCTTCAAAGGGGCCTGATACTTGGAGAGAGTGGAGTTCTGATGGA
AAAAATTTAATAATCTATTGGAAGCCTTTACCCATTAATGAAGCTAATGGAAAAATACTT
TCCTACAATGTATCGTGTTCATCAGATGAGGAAACACAGTCCCTTTCTGAAATCCCTGAT
CCTCAGCACAAAGCAGAGATACGACTTGATAAGAATGACTACATCATCAGCGTAGTGGCT
```

-continued

```
AAAAATTCTGTGGGCTCATCACCACCTTCCAAAATAGCGAGTATGGAAATTCCAAATGAT
GATCTCAAAATAGAACAAGTTGTTGGGATGGGAAAGGGGATTCTCCTCACCTGGCATTAC
GACCCCAACATGACTTGCGACTACGTCATTAAGTGGTGTAACTCGTCTCGGTCGGAACCA
TGCCTTATGGACTGGAGAAAAGTTCCCTCAAACAGCACTGAAACTGTAATAGAATCTGAT
GAGTTTCGACCAGGTATAAGATATAATTTTTTCCTGTATGGATGCAGAAATCAAGGATAT
CAATTATTACGCTCCATGATTGGATATATAGAAGAATTGGCTCCCATTGTTGCACCAAAT
TTTACTGTTGAGGATACTTCTGCAGATTCGATATTAGTAAAATGGGAAGACATTCCTGTG
GAAGAACTTAGAGGCTTTTTAAGAGGATATTTGTTTTACTTTGGAAAAGGACAAAGAGAC

ACATCTAAGATGAGGGTTTTAGAATCAGGTCGTTCTGACATAAAAGTTAAGAATATTACT
GACATATCCCAGAAGACACTGAGAATTGCTGATCTTCAAGGTAAAACAAGTTACCACCTG
GTCTTGCGAGCCTATACAGATGGTGGAGTGGGCCCGGAGAAGAGTATGTATGTGGTGACA
AAGGAAAATTCTGTGGGATTAATTATTGCCATTCTCATCCCAGTGGCAGTGGCTGTCATT
GTTGGAGTGGTGACAAGTATCCTTTGCTATCGGAAACGAGAATGGATTAAAGAAACCTTC
TACCCTGATATTCCAAATCCAGAAAACTGTAAAGCATTACAGTTTCAAAAGAGTGTCTGT
GAGGGAAGCAGTGCTCTTAAAACATTGGAAATGAATCCTTGTACCCCAAATAATGTTGAG
GTTCTGGAAACTCGATCAGCATTTCCTAAAATAGAAGATACAGAAATAATTTCCCCAGTA
GCTGAGCGTCCTGAAGATCGCTCTGATGCAGAGCCTGAAAACCATGTGGTTGTGTCCTAT
TGTCCACCCATCATTGAGGAAGAAATACCAAACCCAGCCGCAGATGAAGCTGGAGGGACT
GCACAGGTTATTTACATTGATGTTCAGTCGATGTATCAGCCTCAAGCAAAACCAGAAGAA
GAACAAGAAAATGACCCTGTAGGAGGGGCAGGCTATAAGCCACAGATGCACCTCCCCATT
AATTCTACTGTGGAAGATATAGCTGCAGAAGAGGACTTAGATAAAACTGCGGGTTACAGA
CCTCAGGCCAATGTAAATACATGGAATTTAGTGTCTCCAGACTCTCCTAGATCCATAGAC
AGCAACAGTGAGATTGTCTCATTTGGAAGTCCATGCTCCATTAATTCCCGACAATTTTTG
ATTCCTCCTAAAGATGAAGACTCTCCTAAATCTAATGGAGGAGGGTGGTCCTTTACAAAC
TTTTTTCAGAACAAACCAAACGATTAACAGTGTCACCGTGTCACTTCAGTCAGCCATCTC
AATAAGCTCTTACTGCTAGTGTTGCTACATCAGCACTGGGCATTCTTGGAGGGATCCTGT
GAAGTATTGTTAGGAGGTGAACTTCACTACATGTTAAGTTACACTGAAAGTTCATGTGCT

TTTAATGTAGTCTAAAAGCCAAAGTATAGTGACTCAGAATCCTCAATCCACAAAACTCAA
GATTGGGAGCTCTTTGTGATCAAGCCAAAGAATTCTCATGTACTCTACCTTCAAGAAGCA
TTTCAAGGCTAATACCTACTTGTACGTACATGTAAAACAAATCCCGCCGCAACTGTTTTC
TGTTCTGTTGTTTGTGGTTTTCTCATATGTATACTTGGTGGAATTGTAAGTGGATTTGCA
GGCCAGGGAGAAAATGTCCAAGTAACAGGTGAAGTTTATTTGCCTGACGTTTACTCCTTT
CTAGATGAAAACCAAGCACAGATTTTAAAACTTCTAAGATTATTCTCCTCTATCCACAGC
ATTCACNNNNNNNNNNNNNNNNNNNNNNNGTAGTGACAGCGATTTAGTGTTTTGTTTGATA
AAGTATGCTTATTTCTGTGCCTACTGTATAATGGTTATCAAACAGTTGTCTCAGGGGTAC
AAACTTTGAAAACAAGTGTGACACTGACCAGCCCAAAT CATAATCATGTTTTCTTGCTG
TGATAGGTTTTGCTTGCCTTTTCATTATTTTTTAGCTTTTATGCTTGCTTCCATTATTT
CAGTTGGTTGCCCTAATATTTAAAATTTACACTTCTAAGACTAGAGACCCACATTTTTT
AAAAATCATTTTATTTTGTGATACAGTGACAGCTTTATATGAGCAAATTCAATATTATT

CATAAGCATGTAATTCCAGTGACTTACTATGTGAGATGACTACTAAGCAATATCTAGCA
GCGTTAGTTCCATATAGTTCTGATTGGATTTCGTTCCTCCTGAGGAGACCATGCCGTTG
AGCTTGGCTACCCAGGCAGTGGTGATCTTTGACACCTTCTGGTGGATGTTCCTCCCACT
CATGAGTCTTTTCATCATGCCACATTATCTGATCCAGTCCTCACATTTTTAAATATAAA
ACTAAAGAGAGAATGCTTCTTACAGGAACAGTTACCCAAGGGCTGTTTCTTAGTAACTG
TCATAAACTGATCTGGATCCATGGGCATACCTGTGTTCGAGGTGCAGCAATTGCTTGGT
GAGCTGTGCAGAATTGATTGCCTTCAGCACAGCATCCTCTGCCCACCCTTGTTTCTCAT
AAGCGATGTCTGGAGTGATTGTGGTTCTTGGAAAAGCAGAAGGAAAAACTAAAAAGTGT
ATCTTGTATTTTCCCTGCC CTCAGGTTGCCTATGTATTTTACCTTTTCATATTTAAGGC
AAAAGTACTTGAAAATTTTAAGTGTCCGAATAAGATATGTCTTTTTTGTTTGTTTTTTT
GGTTGGTTGTTTGTTTTTATCATCTGAGATTCTGTAATGTATTTGCAAATAATGGATCA
ATTAATTTTTTTTGAAGCTCATATTGTATCTTTTTAAAAACCATGTTGTGGAAAAAAGCC
AGAGTGACAAGTGACAAAATCTATTTAGGAACTCTGTGTATGAATCCTGATTTTAACTGC
TAGGATTCAGCTAAATTTCTGAGCTTTATGATCTGTGGAAATTTGGAATGAAATCGAATT
CATTTTGTACATACATAGTATATTAAAACTATATAATAGTTCAT AGAAATGTTCAGTAAT
GAAAAATATATCCAATCAGAGCCATCCCGAAAA AAAAAAAAAAA
```

The length of this sequence was determined using batch, automated computational methods and the sequence, as sense strand, its length, and the desired location of the probe sequence near the 3' end of the mRNA was submitted to Array Designer Ver 1.1 (Premier Biosoft International, Palo Alto, Calif.). Search quality was set at 100%, number of best probes set at 1, length range set at 50 base pairs, Target Tm set at 75 C. degrees plus or minus 5 degrees, Hairpin max deltaG at 6.0-kcal/mol., Self dimmer max deltaG at 6.0-kcal/mol, Run/repeat (dinucleotide) max length set at 5, and Probe site minimum overlap set at 1. When none of the 49 possible probes met the criteria, the probe site would be moved 50 base pairs closer to the 5' end of the sequence and resubmitted to Array Designer for analysis. When no possible probes met the criteria, the variation on melting temperature was raised to plus and minus 8 degrees and the number of identical base-pairs in a run increased to 6 so that a probe sequence was produced.

In the sequence above, using the criteria noted above, Array Designer Ver 1.1 designed a probe corresponding to oligonucleotide number 2280 in Table 8 and is indicated by underlining in the sequence above. It has a melting temperature of 68.4 degrees Celsius and a max run of 6 nucleotides and represents one of the cases where the criteria for probe design in Array Designer Ver 1.1 were relaxed in order to obtain an oligonucleotide near the 3' end of the mRNA (Low melting temperature was allowed).

Clone 463D12

Clone 463D12 was sequenced and compared to the nr, dbEST, and UniGene databases at NCBI using the BLAST search tool. The sequence matched accession number AI184553, an EST sequence with the definition line "qd60a05.x1 Soares_testis_NHT *Homo sapiens* cDNA clone IMAGE:1733840 3' similar to gb:M29550 PROTEIN PHOSPHATASE 2B CATALYTIC SUBUNIT 1 (HUMAN); mRNA sequence." The E value of the alignment was $1.00 \times 10^{-118}$. The GenBank sequence begins with a poly-T region, suggesting that it is the antisense strand, read 5' to 3'. The beginning of this sequence is complementary to the 3' end of the mRNA sense strand. The accession number for this sequence was included in a text file of accession numbers representing antisense sequences. Sequences for antisense strand mRNAs were obtained by uploading a text file containing desired accession numbers as an Entrez search query using the Batch Entrez web interface and saving the results locally as a FASTA file. The following sequence was obtained, and the region of alignment of clone 463D12 is outlined:

The sequence was submitted to Array Designer as described above, however, the desired location of the probe was indicated at base pair 50 and if no probe met the criteria, moved in the 3' direction. The complementary sequence from Array Designer was used, because the original sequence was antisense. The oligonucleotide designed by Array Designer corresponds to oligonucleotide number 4342 in Table 8 and is complementary to the underlined sequence above. The probe has a melting temperature of 72.7 degrees centigrade and a max run of 4 nucleotides.

Clone 72D4

Clone 72D4 was sequenced and compared to the nr, dbEST, and UniGene databases at NCBI using the BLAST search tool. No significant matches were found in any of these databases. When compared to the human genome draft, significant alignments were found to three consecutive regions of the reference sequence NT_008060, as depicted below, suggesting that the insert contains three spliced exons of an unidentified gene.

```
                                                    (SEQ ID NO: 8829)
TTTTTTTTTTTTTTCTTAAATAGCATTTATTTTCTCTCAAAAAGCCTATTATGTACTAAC
AAGTGTTCCTCTAAATTAGAAAGGCATCACTACTAAAATTTTATACATATTTTTATATA
AGAGAAGGAATATTGGGTTACAATCTGAATTTCTCTTTATGATTTCTCTTAAAGTATAGA
ACAGCTATTAAAATGACTAATATTGCTAAAATGAAGGCTACTAAATTTCCCCAAGAATTT
CGGTGGAATGCCCAAAAATGGTGTTAAGATATGCAGAAGGGCCCATTTCAAGCAAAGCAA
TCTCTCCACCCCTTCATAAAAGATTTAAGCTAAAAAAAAAAAAAAAAGAAGAAAATCCA
ACAGCTGAAGACATTGGGCTATTTATAAATCTTCTCCCAGTCCCCCAGACAGCCTCACA
TGGGGGCTGTAAACAGCTAACTAAAATATCTTTGAGACTCTTATGTCCACACCCACTGA
CACAAGGAGAGCTGTAACCACAGTGAAACTAGACTTTGCTTTCCTTTAGCAAGTATGTG
CCTATGATAGTAAACTGGAGTAAATGTAACAGTAATAAAACAAATTTTTTTTAAAAATA
AAAATTATACCTTTTTCTCCAACAAACGGTAAAGACCACGTGAAGACATCCATAAAATTA
GGCAACCAGTAAAGATGTGGAGAACCAGTAAACTGTCGAAATTCATCACATTATTTTCAT
ACTTTAATACAGCAGCTTTAATTATTGGAGAACATCAAAGTAATTAGGTGCCGAAAAACA
TTGTTATTAATGAAGGGAACCCCTGACGTTTGACCTTTTCTGTACCATCTATAGCCCTGG
ACTTGA
```

The FASTA file, including the sequence of AA184553, was then masked using the RepeatMasker web interface, as shown below. The region of alignment of clone 463D12 is outlined.

```
Masked version of 463D12 sequence        (SEQ ID NO: 8830)
TTTTTTTTTTTTTTCTTAAATAGCATTTATTTTCTCTCAAAAAGCCTATTATGTACTAAC
AAGTGTTCCTCTAAATTAGAAAGGCATCACTACNNNNNNNNNNNNNNNNNNNNNNNNNNN
NGAGAAGGAATATTGGGTTACAATCTGAATTTCTCTTTATGATTTCTCTTAAAGTATAGA
ACAGCTATTAAAATGACTAATATTGCTAAAATGAAGGCTACTAAATTTCCCCAAGAATTT
CGGTGGAATGCCCAAAAATGGTGTTAAGATATGCAGAAGGGCCCATTTCAAGCAAAGCAA
TCTCTCCACCCCTTCATAAAAGATTTAAGCTAAAAAAAAAAAAAAAAGAAGAAAATCCA
ACAGCTGAAGACATTGGGCTATTTATAAATCTTCTCCCAGTCCCCCAGACAGCCTCACA
TGGGGGCTGTAAACAGCTAACTAAAATATCTTTGAGACTCTTATGTCCACACCCACTGA
CACAAGGAGAGCTGTAACCACAGTGAAACTAGACTTTGCTTTCCTTTAGCAAGTATGTG
CCTATGATAGTAAACTGGAGTAAATGTAACAGNNNNNNNNNNNNNNNNNNNNNNNNNNNN
NNNNNNNNNCCTTTTCTCCAACAAACGGTAAAGACCACGTGAAGACATCCATAAAATTA
GGCAACCAGTAAAGATGTGGAGAACCAGTAAACTGTCGAAATTCATCACATTATTTTCAT
ACTTTAATACAGCAGCTTTAATTATTGGAGAACATCAAAGTAATTAGGTGCCGAAAAACA
TTGTTATTAATGAAGGGAACCCCTGACGTTTGACCTTTTCTGTACCATCTATAGCCCTGG
ACTTGA
```

| Residue numbers on clone 72D4 sequence | Matching residue numbers on NT_008060 |
|---|---|
| 1-198 | 478646-478843 |
| 197-489 | 479876-480168 |
| 491-585 | 489271-489365 |

Because the reference sequence contains introns and may represent either the coding or noncoding strand for this gene, BioCardia's own sequence file was used to design the oligonucleotide. Two complementary probes were designed to ensure that the sense strand was represented. The sequence of the insert in clone 72D4 is shown below, with the three putative exons outlined.

(SEQ ID NO: 8545)

```
CAGGTCACACAGCACATCAGTGGCTACATGTGAGCTCAGACCTGGGTCTGCT
GCTGTCTGTCTTCCCAATATCCATGACCTTGACTGATGCAGGTGTCTAGGGAT
ACGTCCATCCCCGTCCTGCTGGAGCCCAGAGCACGGAAGCCTGGCCCTCCGA
GGAGACAGAAGGGAGTGTCGGACACCATGACGAGAGCTTGGCAGAATAAAT
AACTTCTTTAAACAATTTTACGGCATGAAGAAATCTGGACCAGTTTATTAAAT
GGGATTTCTGCCACAAACCTTGGAAGAATCACATCATCTTANNCCCAAGTGA
AAACTGTGTTGCGTAACAAAGAACATGACTGCGCTCCACACATACATCATTG
CCCGGCGAGGCGGGACACAAGTCAACGACGGAACACTTGAGACAGGCCTAC
AACTGTGCACGGGTCAGAAGCAAGTTTAAGCCATACTTGCTGCAGTGAGACT
ACATTTCTGTCTATAGAAGATACCTGACTTGATCTGTTTTTCAGCTCCAGTTC
CCAGATGTGCGTGTTGTGGTCCCCAAGTATCACCTTCCAATTTCTGGGAGCA
GTGCTCTGGCCGGATCCTTGCCGCGCGGATAAAAAC
```

The sequence was submitted to RepeatMasker, but no repetitive sequences were found. The sequence shown above was used to design the two 50-mer probes using Array Designer as described above. The probes are shown in bold typeface in the sequence depicted below. The probe in the sequence is oligonucleotide number 6415 (SEQ ID NO: 6415) in Table 8 and the complementary probe is oligonucleotide number 6805 (SEQ ID NO:6805).

CAGGTCACACAGCACATCAGTGGCTACATGTGAGCTCAGACCTGGGTCTG

CTGCTGTCTGTCTTCCCAATATCCATGACCTTGACTGATGCAGGTGTCTA

GGGATACGTCCATCCCCGTCCTGCTGGAGCCCAGAGCACGGAAGCCTGGC

CCTCCGAGGAGACAGAAGGGAGTGTCGGACACCATGACGAGAGCTTGGCA

GAATAAATAACTTCTTTAAACAATTTTACGGCTAGAAGAAATCTGGACCA

GTTTATTAAATGGGATTTCTGCCACAAACCTTGGAAGAATCACATCATCT

TANNCCCAAGTGAAAACTGTGTTGCGTAACAAAGAACATGACTGCGCTCC

ACACATACATCATTGCCCGGCGAGGCGGGACACAAGTCAACGACGGAACA

CTTGAGACAGGCCTACAACTGTGCACGGGTCAGAAGCAAGTTTAAGCCAT

ACTTGCTGCAGTGAGACTACATTTCTGTCTATAGAAGATACCTGACTTGA

TCTGTTTTTCAGCTCCAGTTCCCAGATGTGC

(SEQ ID NO: 6805)
←----3'-GTCAAGGGTCTACACGGTGTTGTGGTCCCCAAGTATCACCTT

CCAATTTCTGGGAG---→CACAACACCAGGGGTTCATAGTGGAAGGTTAAA

G-5'

-continued (SEQ ID NO: 8545)
CAGTGCTCTGGCCGGATCCTTGCCGCGCGGATAAAAACT---→

Confirmation of Probe Sequence

Following probe design, each probe sequence was confirmed by comparing the sequence against dbEST, the UniGene cluster set, and the assembled human genome using BLASTn at NCBI. Alignments, accession numbers, gi numbers, UniGene cluster numbers and names were examined and the most common sequence used for the probe. The final probe set was compiled into Table 8.

Example 22

Production of an Array of 8000 Spotted 50 mer Oligonucleotides

We produced an array of 8000 spotted 50 mer oligonucleotides. Examples 20 and 21 exemplify the design and selection of probes for this array.

Sigma-Genosys (The Woodlands, Tex.) synthesized unmodified 50-mer oligonucleotides using standard phosphoramidite chemistry, with a starting scale of synthesis of 0.05 μmole (see, e.g., R. Meyers, ed. (1995) *Molecular Biology and Biotechnology: A Comprehensive Desk Reference*). Briefly, to begin synthesis, a 3' hydroxyl nucleoside with a dimethoxytrityl (DMT) group at the 5' end was attached to a solid support. The DMT group was removed with trichloroacetic acid (TCA) in order to free the 5'-hydroxyl for the coupling reaction. Next, tetrazole and a phosphoramidite derivative of the next nucleotide were added. The tetrazole protonates the nitrogen of the phosphoramidite, making it susceptible to nucleophilic attack. The DMT group at the 5'-end of the hydroxyl group blocks further addition of nucleotides in excess. Next, the inter-nucleotide linkage was converted to a phosphotriester bond in an oxidation step using an oxidizing agent and water as the oxygen donor. Excess nucleotides were filtered out and the cycle for the next nucleotide was started by the removal of the DMT protecting group. Following the synthesis, the oligo was cleaved from the solid support. The oligonucleotides were desalted, resuspended in water at a concentration of 100 or 200 μM, and placed in 96-deep well format. The oligonucleotides were re-arrayed into Whatman Uniplate 384-well polyproylene V bottom plates. The oligonucleotides were diluted to a final concentration 30 µM in 1× Micro Spotting Solution Plus (Telechem/arrayit.com, Sunnyvale, Calif.) in a total volume of 15 µl. In total, 8,031 oligonucleotides were arrayed into twenty-one 384-well plates.

Arrays were produced on Telechem/arrayit.com Super amine glass substrates (Telechem/arrayit.com), which were manufactured in 0.1 mm filtered clean room with exact dimensions of 25×76×0.96 mm. The arrays were printed using the Virtek Chipwriter with a Telechem 48 pin Micro Spotting Printhead. The Printhead was loaded with 48 Stealth SMP3B TeleChem Micro Spotting Pins, which were used to print oligonucleotides onto the slide with the spot size being 110-115 microns in diameter.

Example 23

Amplification, Labeling, and Hybridization of Total RNA to an Oligonucleotide Microarray Amplification, labeling, hybridization and scanning Samples consisting of at least 2 µg of intact total RNA were further processed for array hybridization. Amplification and labeling of total RNA samples was performed in three successive enzymatic reactions. First, a single-stranded DNA copy of the RNA was made (hereinafter, "ss-cDNA"). Second, the ss-cDNA was used as a template for the complementary DNA strand, producing double-stranded cDNA (hereinafter, "ds-cDNA, or cDNA"). Third, linear amplification was performed by in vitro transcription from a bacterial $T_7$ promoter. During this step, fluorescent-conjugated nucleotides were incorporated into the amplified RNA (hereinafter, "aRNA").

The first strand cDNA was produced using the Invitrogen kit (Superscript II). The first strand cDNA was produced in a reaction composed of 50 mM Tris-HCl (pH 8.3), 75 mM KCl, and 3 mM $MgCl_2$ (1× First Strand Buffer, Invitrogen), 0.5 mM dGTP, 0.5 mM dATP, 0.5 mM dTTP, 0.5 mM dCTP, 10 mM DTT, 10 U reverse transcriptase (Superscript II, Invitrogen, #18064014), 15 U RNase inhibitor (RNAGuard, Amersham Pharmacia, #27-0815-01), 5 µM T7T24 primer (5'-GGCCAGTGAATTGTAATACGACTCACTATAGGGAGG CGGTTTTTTTTTTTT TTTTTTTTTTTT-3'), (SEQ ID NO:8831) and 2 µg of selected sample total RNA. Several purified, recombinant control mRNAs from the plant *Arabidopsis thaliana* were added to the reaction mixture: 2-20 pg of the following genes CAB, RCA, LTP4, NAC1, RCP1, XCP2, RBCL, LTP6, TIM, and PRKase (Stratagene, #252201, #252202, #252204, #252208, #252207, #252206, #252203, #252205, #252209, #252210 respectively). The control RNAs allow the estimate of copy numbers for individual mRNAs in the clinical sample because corresponding sense oligonucleotide probes for each of these plant genes are present on the microarray. The final reaction volume of 20 µl was incubated at 42° C. for 60 min.

For synthesis of the second cDNA strand, DNA polymerase and RNase were added to the previous reaction, bringing the final volume to 150 µl. The previous contents were diluted and new substrates were added to a final concentration of 20 mM Tris-HCl (pH 7.0) (Fisher Scientific, Pittsburgh, Pa. #BP1756-100), 90 mM KCl (Teknova, Half Moon Bay, Calif., #0313-500), 4.6 mM $MgCl_2$ (Teknova, Half Moon Bay, Calif., #0304-500), 10 mM $(NH_4)_2SO_4$ (Fisher Scientific #A702-500) (1× Second Strand buffer, Invitrogen), 0.266 mM dGTP, 0.266 mM dATP, 0.266 mM dTTP, 0.266 mM dCTP, 40 U *E. coli* DNA polymerase (Invitrogen, #18010-025), and 2 U RNaseH (Invitrogen, #18021-014). The second strand synthesis took place at 16° C. for 120 minutes.

Following second-strand synthesis, the ds-cDNA was purified from the enzymes, dNTPs, and buffers before proceeding to amplification, using phenol-chloroform extraction followed by ethanol precipitation of the cDNA in the presence of glycogen.

Alternatively, a silica-gel column is used to purify the cDNA (e.g. Qiaquick PCR cleanup from Qiagen, #28104). The cDNA was collected by centrifugation at >10,000×g for 30 minutes, the supernatant is aspirated, and 150 µl of 70% ethanol, 30% water was added to wash the DNA pellet. Following centrifugation, the supernatant was removed, and residual ethanol was evaporated at room temperature.

Linear amplification of the cDNA was performed by in vitro transcription of the cDNA. The cDNA pellet from the step described above was resuspended in 7.4 µl of water, and in vitro transcription reaction buffer was added to a final volume of 20 µl containing 7.5 mM GTP, 7.5 mM ATP, 7.5 mM TTP, 2.25 mM CTP, 1.025 mM Cy3-conjugated CTP (Perkin Elmer; Boston, Mass., #NEL-580), 1× reaction buffer (Ambion, Megascript Kit, Austin, Tex. and #1334) and 1% $T_7$ polymerase enzyme mix (Ambion, Megascript Kit, Austin, Tex. and #1334). This reaction was incubated at 37° C. overnight. Following in vitro transcription, the RNA was purified from the enzyme, buffers, and excess NTPs using the RNeasy kit from Qiagen (Valencia, Calif.; #74106) as described in the vendor's protocol. A second elution step was performed and the two eluates were combined for a final volume of 60 µl. RNA is quantified using an Agilent 2100 bioanalyzer with the RNA 6000 nano LabChip.

Reference RNA was prepared as described above, except Cy5-CTP was incorporated instead of Cy3CTP. Reference RNA from five reactions, each reaction started with 2 ug total RNA, was pooled together and quantitated as described above.

Hybridization to an Array

RNA was prepared for hybridization as follows: for an 18 mm×55 mm array, 20 µg of amplified RNA (aRNA) was combined with 20 µg of reference aRNA. The combined sample and reference aRNA was concentrated by evaporating the water to 10 µl in a vacuum evaporator. The sample was fragmented by heating the sample at 95° C. for 30 minutes to fragment the RNA into 50-200 bp pieces. Alternatively, the combined sample and reference aRNA was concentrated by evaporating the water to 5 µl in a vacuum evaporator. Five µl of 20 mM zinc acetate was added to the aRNA and the mix incubated at 60° C. for 10 minutes. Following fragmentation, 40 µl of hybridization buffer was added to achieve final concentrations of 5×SSC and 0.20% SDS with 0.1 µg/ul of Cot-1 DNA (Invitrogen) as a competitor DNA. The final hybridization mix was heated to 98° C., and then reduced to 50° C. at 0.1° C. per second.

Alternatively, formamide is included in the hybridization mixture to lower the hybridization temperature.

The hybridization mixture was applied to a pre-heated 65° C. microarray, surface, covered with a glass coverslip (Corning, #2935-246), and placed on a pre-heated 65° C. hybridization chamber (Telechem, AHC-10). 15 ul of 5×SSC was placed in each of the reservoir in the hybridization chamber and the chamber was sealed and placed in a water bath at 62° C. for overnight (16-20 hrs). Following incubation, the slides were washed in 2×SSC, 0.1% SDS for five minutes at 30° C., then in 2×SSC for five minutes at 30° C., then in 2×SSC for another five minutes at 30° C., then in 0.2×SSC for two minutes at room temperature. The arrays were spun at 1000×g for 2 minutes to dry them. The dry microarrays are then scanned by methods described above.

The microarrays were imaged on the Agilent (Palo Alto, Calif.) scanner G2565AA. The scan settings using the Agilent software were as follows: for the PMT Sensitivity (100% Red and 100% Green); Scan Resolution (10 microns); red and green dye channels; used the default scan region for all slides in the carousel; using the largest scan region; scan date for Instrument ID; and barcode for Slide ID. The full image produced by the Agilent scanner was flipped, rotated, and split into two images (one for each signal channel) using TIFFSplitter (Agilent, Palo Alto, Calif.). The two channels are the output at 532 nm (Cy3-labeled sample) and 633 nm (Cy5-labeled R50). The individual images were loaded into GenePix 3.0 (Axon Instruments, Union City, Calif.) for feature extraction, each image was assigned an excitation wavelength corresponding the file opened; Red equals 633 nm and Green equals 532 nm. The setting file (gal) was opened and the grid was laid onto the image so that each spot in the grid overlapped with >50% of the feature. Then the GenePix software was used to find the features without setting minimum threshold value for a feature. For features with low signal intensity, GenePix reports "not found". For all features, the diameter setting was adjusted to include only the feature if necessary.

The GenePix software determined the median pixel intensity for each feature ($F_i$) and the median pixel intensity of the local background for each feature ($B_i$) in both channels. The standard deviation ($SDF_i$ and $SDB_i$) for each is also determined. Features for which GenePix could not discriminate the feature from the background were "flagged" as described below.

Following feature extraction into a .gpr file, the header information of the .gpr file was changed to carry accurate information into the database. An Excel macro was written to change the headers. The steps in that macro were:
1. Open .gpr file.
2. Check the value in the first row, first column. If it is "ATF", then the header has likely already been reformatted. The file is skipped and the user is alerted. Otherwise, proceed through the following steps.
3. Store the following values in variables.
   a. Name of .tif image file: parsed from row 11.
   b. SlideID: parsed from name of .tif image file.
   c. Version of the feature extraction software: parsed from row 25
   d. GenePix Array List file: parsed from row 6
   e. GenePix Settings file: parsed from row 5
4. Delete rows 1-8, 10-12, 20, 22, and 25.
5. Arrange remaining values in rows 15-29.
6. Fill in rows 1-14 with the following:
   Row 1: ScanID (date image file was last modified, formatted as yyyy.mm.dd-hh.mm.ss)
   Row 2: SlideID, from stored value
   Row 3: Name of person who scanned the slide, from user input
   Row 4: Image file name, from stored value
   Row 5: Green PMT setting, from user input
   Row 6: Red PMT setting, from user input
   Row 7: ExtractID (date .gpr file was created, formatted as yyyy.mm.dd-hh.mm.ss)
   Row 8: Name of person who performed the feature extraction, from user input
   Row 9: Feature extraction software used, from stored value
   Row 10: Results file name (same as the .gpr file name)
   Row 11: GenePix Array List file, from stored value
   Row 12: GenePix Settings file, from stored value
   Row 13: StorageCD, currently left blank
   Row 14: Extraction comments, from user input (anything about the scanning or feature extraction of the image the user feels might be relevant when selecting which hybridizations to include in an analysis)

Pre-Processing with Excel Templates

Following analysis of the image and extraction of the data, the data from each hybridization was pre-processed to extract data that was entered into the database and subsequently used for analysis. The complete GPR file produced by the feature extraction in GenePix was imported into an excel file pre-processing template. The same excel template was used to process each GPR file. The template performs a series of calculations on the data to differentiate poor features from others and to combine triplicate feature data into a single data point for each probe.

Each GPR file contained 31 rows of header information, followed by rows of data for 24093 features. The last of these rows was retained with the data. Rows 31 through the end of the file were imported into the excel template. Each row contained 43 columns of data. The only columns used in the pre-processing were: Oligo ID, F633 Median (median value from all the pixels in the feature for the Cy5 dye), B633 Median (the median value of all the pixels in the local background of the selected feature for Cy5), B633 SD (the standard deviation of the values for the pixels in the local background of the selected feature for Cy5), F532 Median (median value from all the pixels in the feature for the Cy3 dye), B532 Median (the median value of all the pixels in the local background of the selected feature for Cy3), B532 SD (the standard deviation of the values for the pixels in the local background of the selected feature for Cy3), and Flags. The GenePix Flags column contains the flags set during feature extraction. "−75" indicates there were no features printed on the array in that position, "−50" indicates that GenePix could not differentiate the feature signal from the local background, and "−100" indicates that the user marked the feature as bad.

Once imported, the rows with −75 flags were deleted. Then the median of B633 SD and B532 SD were calculated over all features with a flag value of "0". The minimum values of B633 Median and B532 Median were identified, considering only those values associated with a flag value of "0". For each feature, the signal to noise ratio (S/N) was calculated for both dyes by taking the fluorescence signal minus the local background (BGSS) and dividing it by the standard deviation of the local background:

$$S/N = \frac{F_i - B_i}{SDB_i}$$

If the S/N was less than 3, then an adjusted background-subtracted signal was calculated as the fluorescence minus the minimum local background on the slide. An adjusted S/N was then calculated as the adjusted background subtracted signal divided by the median noise over all features for that channel. If the adjusted S/N was greater than three and the original S/N were less than three, a flag of 25 was set for the Cy5 channel, a flag of 23 was set for the Cy3 channel, and if both met these criteria, then a flag of 20 was set. If both the adjusted S/N and the original S/N were less than three, then a flag of 65 was set for Cy5, 63 set for Cy3, and 60 set if both dye channels had an adjusted S/N less than three. All signal to noise calculations, adjusted background-subtracted signal, and adjusted S/N were calculated for each dye channel. If the BGSS value was greater than or equal to 64000, a flag was set to indicate saturation; 55 for Cy5, 53 for Cy3, 50 for both.

The BGSS used for further calculations was the original BGSS if the original S/N was greater than or equal to three. If the original S/N ratio was less than three and the adjusted S/N ratio was greater than or equal to three, then the adjusted BGSS was used. If the adjusted S/N ratio was less than three, then the adjusted BGSS was used, but with knowledge of the flag status.

To facilitate comparison among arrays, the Cy3 and Cy5 data were scaled to have a median of 1. For each dye channel, the median value of all features with flags=0, 20, 23, or 25 was calculated. The BGSS for each dye in each feature was then divided by this median value. The Cy3/Cy5 ratio was calculated for each feature using the scaled BGSS:

$$R_n = \frac{Cy3S_i}{Cy5S_i}$$

The flag setting for each feature was used to determine the expression ratio for each probe, a combination of three features. If all three features had flag settings in the same category (categories=negatives, 0 to 25, 50-55, and 60-65), then the average and CV of the three feature ratios was calculated. If the CV of all three features was less than 15, the average was used. If the CV was greater than 15, then the CV of each combination of two of the features was calculated and the two features with the lowest CV were averaged. If none of the combinations of two features had a CV less than 15, then the median ratio of the three features was used as the probe feature.

If the three features do not have flags in the same category, then the features with the best quality flags were used (0>25>23>20>55>53>50>65>63>60). Features with negative flags were never used. When the best flags were two features in the same category, the average was used. If a single feature had a better flag category than the other two then that feature was used.

Once the probe expression ratio was calculated from the three features, the log of the ratio was taken as described below and stored for use in analyzing the data. Whichever features were used to calculate the probe value, the worst of the flags from those features was carried forward and stored as the flag value for that probe. 2 different data sets can be used for analysis. Flagged data uses all values, including those with flags. Filtered data sets are created by removing flagged data from the set before analysis.

Example 24

Identification of Diagnostic Nucleotide Sets for Diagnosis of Cardiac Allograft Rejection Genes were identified which have expression patterns useful for the diagnosis and monitoring of cardiac allograft rejection. Further, sets of genes that work together in a diagnostic algorithm for allograft rejection were identified. Patients, patient clinical data and patient samples used in the discovery of markers below were derived from a clinical study described in example 11.

The collected clinical data is used to define patient or sample groups for correlation of expression data. Patient groups are identified for comparison, for example, a patient group that possesses a useful or interesting clinical distinction, verses a patient group that does not possess the distinction. Measures of cardiac allograft rejection are derived from the clinical data described above to divide patients (and patient samples) into groups with higher and lower rejection activity over some period of time or at any one point in time. Such data are rejection grade as determined from pathologist reading of the cardiac biopsies and data measuring progression of end-organ damage, including depressed left ventricular dysfunction (decreased cardiac output, decreased ejection fraction, clinical signs of low cardiac output) and usage of inotropic agents (Kobashigawa 1998).

Expression profiles correlating with occurrence of allograft rejection are identified, including expression profiles corresponding to end-organ damage and progression of end-organ damage. Expression profiles are identified predicting allograft rejection, and response to treatment or likelihood of response to treatment. Subsets of the candidate library (or a previously identified diagnostic nucleotide set) are identified, that have predictive value for the presence of allograft rejection or prediction of allograft rejection or end organ damage.

Identification of a Diagnostic Nucleotide Set for Diagnosis of Cardiac Allograft Acute Rejection Mononuclear RNA samples were collected from patients who had recently undergone a cardiac allograft transplantation using the protocol described in example 8. The allograft rejection status at the time of sample collection was determined by examination of cardiac biopsies as described in example 11.

180 samples were included in the analysis. Each patient sample was associated with a biopsy and clinical data collected at the time of the sample. The cardiac biopsies were graded by a pathologist at the local center and by a centralized pathologist who read the biopsy slides from all four local centers in a blinded manner. Biopsy grades included 0, 1A, 1B, 2, 3A, and 3B. No grade 4 rejection was identified. Dependent variables were developed based on these grades using either the local center pathology reading or the higher of the two readings, local or centralized. The dependent variables used for correlation of gene expression profiles with cardiac allograft rejection are shown in Table 13. Dependent variables are used to create classes of samples corresponding to the presence or absence of rejection.

Clinical data were also used to determine criteria for including samples in the analysis. The strictest inclusion criteria required that samples be from patients who did not have a bacterial or viral infection, were at least two weeks post cardiac transplant and were not currently admitted to the hospital. A second inclusion criteria (inclusion 2) reduced the post-transplant criteria to 1 week and eliminated the hospital admission criteria.

After preparation of RNA (example 8), amplification, labeling, hybridization, scanning, feature extraction and data processing were done as described in Example 23, using the oligonucleotide microarrays described in Examples 20-22. The resulting log ratio of expression of Cy3 (patient sample)/Cy5 (R50 reference RNA) was used for analysis. This dataset is called the "static" data. A second type of dataset, referenced, was derived from the first. These datasets compared the gene expression log ratio in each sample to a baseline sample from the same patient using the formula:

ref log ratio=(log ratio$_{sample}$)−(log ratio$_{baseline}$)

Two referenced datasets were used, named "0 HG" and "Best 0". The baseline for 0 HG was a Grade 0 sample from the same patient as the sample, using the highest grade between the centralized and local pathologists. The baseline for Best 0 was a Grade 0 sample from the same patient as the sample, using both the local and centralized reader biopsy grade data. When possible a Grade 0 prior to the sample was used as the baseline in both referenced datasets.

The datasets were also divided into subsets to compare analysis between two subsets of roughly half of the data. The types of subsets constructed were as follows. First half/second half subsets were the first half of the samples and the second half of the samples from a dataset ordered by sample number. Odd/even subsets used the same source, a dataset ordered by sample number, but the odd subset consisted of every $2^{nd}$ sample starting with the first and the even subset consisted of every $2^{nd}$ sample starting with the second sample, Center 14/other subsets were the same datasets, divided by transplant hospital. The center 14 subset consisted of all samples from patients at center 14, while the other subset consisted of all samples from the other three centers (12, 13, and 15).

Initially, significance analysis for microarrays (SAM, Tusher 2001, Example 26) was used to discover genes that were differentially expressed between the rejection and no-rejection groups. Ninety-six different combinations of dependent variables, inclusion criteria, static/referenced, and data subsets were used in SAM analysis to develop the primary lists of genes significantly differentially expressed between rejection and no-rejection. The most significant of these genes were chosen based on the following criteria. Tier 1 (A1, in Table 12A) genes were those which appeared with an FDR of less than 20% in identical analyses in two independent subsets. Tier 2 (A2 in Table 12A) genes were those which appeared in the top 20 genes on the list with an FDR less than 20% more than 50% of the time over all dependent variables with the inclusion criteria, and static/referenced constant. Tier 3 genes were those that appeared more than 50% of the time with an FDR less than 20% more than 50% of the time over all dependent variables with the inclusion criteria, and static/referenced constant. The genes that were identified by the analysis as statistically differentially expressed between rejection and no rejection are shown in Table 12A.

SAM chooses genes as significantly different based on the magnitude of the difference between the groups and the variation among the samples within each group. An example of the difference between some Grade 0 and some Grade 3A samples for 9 genes is show in FIG. 9A.

Additionally, many of these same combinations were used in the Supervised Harvesting of Expression Trees (SHET, Hastie et al. 2001) algorithm (see example 26) to identify markers that the algorithm chose as the best to distinguish between the rejection and no rejection classes using a bias factor of 0.01. The top 20 or 30 terms were taken from the SHET output and among all comparisons in either the static or referenced data the results were grouped. Any gene found in the top 5 terms in more than 50% of the analyses was selected to be in group B1 (Table 12A). The occurrences of each gene were tabulated over all SHET analysis (for either static or referenced data) and the 10 genes that occurred the most were selected to be in group B2 (Table 12A).

An additional classification method used was CART (Salford Systems, San Diego, example 26). Either the static or referenced dataset was reduced to only the genes for which expression values (log ratios) were present in at least 80% of the samples. These data were used in CART with the default settings, using the Symmetric Gini algorithm. Each of the dependent variables was used with both the full sample set and the strict inclusion criteria. Two groups of genes were identified. Group C1 were those genes that were a primary splitter ($1^{st}$ decision node). Group C2 genes were the 10 genes that occurred as splitters the most often over all these analyses.

Two other classification models were developed and their best genes identified as markers of cardiac allograft rejection. Group D genes were identified from a set of 59 samples, referenced data, local biopsy reading grade, using logistic regression. Group E genes were identified from the primary static dataset using a K-nearest neighbor classification algorithm.

Both hierarchical clustering (Eisen et al. 1998) and CART were used to identify surrogates for each identified marker as shown in Table 12C. Hierarchical clustering surrogates are genes co-expressed in these and were chosen from the nearest branches of the dendrogram. CART surrogates were identified by CART as the surrogates for those genes chosen as primary splitters at decision nodes.

Primers for real-time PCR validation were designed for each of the marker genes as described in Example 25 and are listed in Table 12B.

CART was used to build a decision tree for classification of samples as rejection or no-rejection using the gene expression data from the arrays. The analysis identified sets of genes that can be used together to accurately identify samples derived from cardiac allograft transplant patients. The set of genes and the identified threshold expression levels for the decision tree are referred to as a "models". This model can be used to predict the rejection state of an unknown sample. The input data were the static expression data (log ratio) and the referenced expression data (log ratio referenced to the best available grade 0 from either the centralized reader or the local reader) for 139 of our top marker genes.

These two types of expression data were entered into the CART software as independent variables. The dependent variable was rejection state, defined for this model as no rejection=grade 0 and rejection=grade 3A. Samples were eliminated from consideration in the training set if they were from patients with either bacterial or viral infection or were from patients who were less than two weeks post-transplant. The method used was Symmetric Gini, allowing linear combinations of independent variables. The costs were set to 1 for both false negatives and false positives and the priors were set equal for the two states. No penalties were assessed for missing data, however the marker genes selected have strong representation across the dataset. 10-fold cross validation was used to test the model. Settings not specified remained at the default values.

The model shown in FIG. 9B is based on decisions about expression values at three nodes, each a different marker gene. The cost assigned to this model is 0.292, based on the priors being equal, the costs set to 1 for each type of error, and the results from the 10-fold cross validation.

In the training set, no rejection samples were misclassified (sensitivity=100%) and only 1 no-rejection sample was misclassified (specificity=94.4%). Following 10-fold cross validation, 2 rejection samples were misclassified (sensitivity=87.5%) and 3 no-rejection samples were misclassified (specificity=83.3%). The CART software assigns surrogate markers for each decision node. For this model, the surrogates are shown in FIG. 9C and Table 12C.

These genes can be used alone or in association with other genes or variables to build a diagnostic gene set or a classification algorithm. These genes can be used in association with known gene markers for rejection (such as those identified in the prior art) to provide a diagnostic algorithm.

Example 25

Real-Time PCR Validation of Array Expression Results

In examples 17 and 24, leukocyte gene expression was used to discover expression markers and diagnostic gene sets for clinical outcomes. It is desirable to validate the gene expression results for each gene using a more sensitive and quantitative technology such as real-time PCR. Further, it is possible for the diagnostic nucleotide sets to be implemented as a diagnostic test as a real-time PCR panel. Alternatively, the quantitative information provided by real-time PCR validation can be used to design a diagnostic test using any alternative quantitative or semi-quantitative gene expression technology.

To validate the results of the microarray experiments we used real-time, or kinetic, PCR. In this type of experiment the amplification product is measured during the PCR reaction. This enables the researcher to observe the amplification before any reagent becomes rate limiting for amplification. In kinetic PCR the measurement is of $C_T$ (threshold cycle) or $C_P$ (crossing point). This measurement ($C_T=C_P$) is the point at which an amplification curve crosses a threshold fluorescence value. The threshold is set to a point within the area where all of the reactions were in their linear phase of amplification. When measuring $C_T$, a lower $C_T$ value is indicative of a higher amount of starting material since an earlier cycle number means the threshold was crossed more quickly.

Several fluorescence methodologies are available to measure amplification product in real-time PCR. Taqman (Applied BioSystems, Foster City, Calif.) uses fluorescence resonance energy transfer (FRET) to inhibit signal from a probe until the probe is degraded by the sequence specific binding and Taq 3' exonuclease activity. Molecular Beacons (Stratagene, La Jolla, Calif.) also use FRET technology, whereby the fluorescence is measured when a hairpin structure is relaxed by the specific probe binding to the amplified DNA. The third commonly used chemistry is Sybr Green, a DNA-binding dye (Molecular Probes, Eugene, Oreg.). The more amplified product that is produced, the higher the signal. The Sybr Green method is sensitive to non-specific amplification products, increasing the importance of primer design and selection. Other detection chemistries can also been used, such as ethedium bromide or other DNA-binding dyes and many modifications of the fluorescent dye/quencher dye Taqman chemistry.

Initially, samples are chosen for validation, which have already been used for microarray based expression analysis. They are also chosen to represent important disease classes or disease criteria. For the first steps of this example (primer design, primer endpoint testing, and primer efficiency testing) we examined β-actin and β-GUS. These genes are considered "housekeeping" genes because they are required for maintenance in all cells. They are commonly used as a reference that is expected to not change with experimental treatment. We chose these two particular genes as references because they varied the least in expression across 5 mRNA samples examined by real-time PCR.

The inputs for real time PCR reaction are gene-specific primers, cDNA from specific patient samples, and the standard reagents. The cDNA was produced from mononuclear RNA (prepared as in example 8) by reverse transcription using OligodT primers (Invitrogen, 18418-012) and random hexamers (Invitrogen, 48190-011) at a final concentration of 0.5 ng/μl and 3 ng/μl respectively. For the first strand reaction mix, 1.45 μg/μl of total RNA (R50, universal leukocyte reference RNA as described in Example 9) and 1 μl of the Oligo dT/Random Hexamer Mix, were added to water to a final volume of 11.5 μl. The sample mix was then placed at 70° C. for 10 minutes. Following the 70° C. incubation, the samples were chilled on ice, spun down, and 88.5 μl of first strand buffer mix dispensed into the reaction tube. The final first strand buffer mix produced final concentrations of 1× first strand buffer (Invitrogen, Y00146, Carlsbad, Calif.), 0.01 mM DTT (Invitrogen, Y00147), 0.1 mM dATP (NEB, N0440S, Beverly, Mass.), 0.1 mM dGTP (NEB, N0442S), 0.1 mM dTTP (NEB, N0443S), 0.1 mM dCTP (NEB, N0441S), 2 U of reverse transcriptase (Superscript II, Invitrogen, 18064-014), and 0.18 U of RNase inhibitor (RNAGaurd Amersham Pharmacia, 27-0815-01, Piscataway, N.J.). The reaction was incubated at 42° C. for 1 hour. After incubation the enzyme was heat inactivated at 70° C. for 15 minutes, 1 μl of RNAse H added to the reaction tube, and incubated at 37° C. for 20 minutes.

Primer Design

Two methods were used to design primers. The first was to use the software, Primer Express™ and recommendations for primer design that are provided with the GeneAmp® 7700 Sequence Detection System supplied by Applied BioSystems (Foster City, Calif.). The second method used to design primers was the PRIMER3 ver 0.9 program that is available from the Whitehead Research Institute, Cambridge, Mass. at the web site genome.wi.mit.edu/genome_software/other/primer3.html. The program can also be accessed on the World Wide Web at the web site genome.wi.mit.edu/cgi-bin/primer/primer3_www.cgi. Primers and Taqman/hybridization probes were designed as described below using both programs.

The Primer Express literature explains that primers should be designed with a melting temperature between 58 and 60 degrees C. while the Taqman probes should have a melting temperature of 68 to 70 under the salt conditions of the supplied reagents. The salt concentration is fixed in the software. Primers should be between 15 and 30 basepairs long. The primers should produce and amplicon in size between 50 and 150 base pairs, have a C-G content between 20% and 80%, have no more than 4 identical base pairs next to one another, and no more than 2 C's and G's in the last 5 bases of the 3' end. The probe cannot have a G on the 5' end and the strand with the fewest G's should be used for the probe.

Primer3 has a large number of parameters. The defaults were used for all except for melting temperature and the optimal size of the amplicon was set at 100 bases. One of the most critical is salt concentration as it affects the melting temperature of the probes and primers. In order to produce primers and probes with melting temperatures equivalent to Primer Express, a number of primers and probes designed by Primer Express were examined using PRIMER3. Using a salt concentration of 50 mM these primers had an average melting temperature of 3.7 degrees higher than predicted by Primer Express. In order to design primers and probes with equivalent melting temperatures as Primer Express using PRIMER3, a melting temperature of 62.7 plus/minus 1.0 degree was used in PRIMER3 for primers and 72.7 plus/minus 1.0 degrees for probes with a salt concentration of 50 mM.

The C source code for Primer3 was downloaded and complied on a Sun Enterprise 250 server using the GCC complier. The program was then used from the command line using a input file that contained the sequence for which we wanted to design primers and probes along with the input parameters as described by help files that accompany the software. Using scripting it was possible to input a number of sequences and automatically generate a number of possible probes and primers.

Primers for β-Actin (Beta Actin, Genbank Locus: NM_001101) and β-GUS: glucuronidase, beta, (GUSB, Genbank Locus: NM_000181), two reference genes, were designed using both methods and are shown here as examples:

The first step was to mask out repetitive sequences found in the mRNA sequences using RepeatMasker program that can be accessed at: the web site repeatmasker.genome.washington.edu/cgi-bin/RepeatMasker (Smit, AFA & Green, P "RepeatMasker" at the web site ftp.genome.washington.edu/RM/RepeatMasker.html).

The last 500 basepairs on the last 3' end of masked sequence was then submitted to PRIMER3 using the following exemplary input file:

| | |
|---|---|
| PRIMER_SEQUENCE ID=> | ACTB Beta Actin |
| PRIMER_EXPLAIN_FLAG = | 1 |
| PRIMER_MISPRIMING_LIBRARY = | |
| SEQUENCE = TTGGCTTGACTCAGGATTTAAAAACTGGAACGGTGAAGG TGACAGCAGTCGGTTGGACGAGCATCCCCCAAAGTTCACAATGTGGCCGA GGACTTTGATTGCACATTGTTGTTTTTAATAGTCATTCCAAATATGAGA TGCATTGTTACAGGAAGTCCCTTGCCATCCTAAAAGCACCCCACTTCTCT CTAAGGAGAATGGCCCAGTCCTCTCCCAAGTCCACACAGGGGAGGGATAG CATTGCTTTCGTGTAAATTATGTAATGCAAAATTTTTTAATCTTCGCCT TAATCTTTTTATTTTGTTTTATTTTGAATGATGAGCCTTCGTGCCCCCC CTTCCCCCTTTTTTCCCCCAACTTGAGATGTATGAAGGCTTTTGGTCTCC CTGGGAGTGGGTGGAGGCAGCCGGGCTTACCTGTACACTGACTTGAGACC AGTTGAATAAAAGTGCACACCTTA (SEQ ID NO: 9191) | |
| PRIMER_PRODUCT_OPT_SIZE = | 100 |
| PRIMER_NUM_RETURN = | 100 |
| PRIMER_MAX_END_STABILITY = | 9.0 |
| PRIMER_MAX_MISPRIMING = | 12.00 |
| PRIMER_PAIR_MAX_MISPRIMING = | 24.00 |
| PRIMER_MIN_SIZE = | 18 |
| PRIMER_OPT_SIZE = | 20 |
| PRIMER_MAX_SIZE = | 32 |
| PRIMER_MIN_TM = | 61.7 |
| PRIMER_OPT_TM = | 62.7 |
| PRIMER_MAX_TM = | 63.7 |
| PRIMER_MAX_DIFF_TM = | 100.0 |
| PRIMER_MIN_GC = | 20.0 |
| PRIMER_MAX_GC = | 80.0 |

-continued

| | |
|---|---|
| PRIMER_SELF_ANY = | 8.00 |
| PRIMER_SELF_END = | 3.00 |
| PRIMER_NUM_NS_ACCEPTED = | 0 |
| PRIMER_MAX_POLY_X = | 4 |
| PRIMER_OUTSIDE_PENALTY = | 0 |
| PRIMER_GC_CLAMP = | 0 |
| PRIMER_SALT_CONC = | 50.0 |
| PRIMER_DNA_CONC = | 50.0 |
| PRIMER_LIBERAL_BASE = | 1 |
| PRIMER_MIN_QUALITY = | 0 |
| PRIMER_MIN_END_QUALITY = | 0 |
| PRIMER_QUALITY_RANGE_MIN = | 0 |
| PRIMER_QUALITY_RANGE_MAX = | 100 |
| PRIMER_WT_TM_LT = | 1.0 |
| PRIMER_WT_TM_GT = | 1.0 |
| PRIMER_WT_SIZE_LT = | 1.0 |
| PRIMER_WT_SIZE_GT = | 1.0 |
| PRIMER_WT_GC_PERCENT_LT = | 0.0 |
| PRIMER_WT_GC_PERCENT_GT = | 0.0 |
| PRIMER_WT_COMPL_ANY = | 0.0 |
| PRIMER_WT_COMPL_END = | 0.0 |
| PRIMER_WT_NUM_NS = | 0.0 |
| PRIMER_WT_REP_SIM = | 0.0 |
| PRIMER_WT_SEQ_QUAL = | 0.0 |
| PRIMER_WT_END_QUAL = | 0.0 |
| PRIMER_WT_POS_PENALTY = | 0.0 |
| PRIMER_WT_END_STABILITY = | 0.0 |
| PRIMER_PAIR_WT_PRODUCT_SIZE_LT = | 0.05 |
| PRIMER_PAIR_WT_PRODUCT_SIZE_GT = | 0.05 |
| PRIMER_PAIR_WT_PRODUCT_TM_LT = | 0.0 |
| PRIMER_PAIR_WT_PRODUCT_TM_GT = | 0.0 |
| PRIMER_PAIR_WT_DIFF_TM = | 0.0 |
| PRIMER_PAIR_WT_COMPL_ANY = | 0.0 |
| PRIMER_PAIR_WT_COMPL_END = | 0.0 |
| PRIMER_PAIR_WT_REP_SIM = | 0.0 |
| PRIMER_PAIR_WT_PR_PENALTY = | 1.0 |
| PRIMER_PAIR_WT_IO_PENALTY = | 0.0 |
| PRIMER_INTERNAL_OLIGO_MIN_SIZE = | 18 |
| PRIMER_INTERNAL_OLIGO_OPT_SIZE = | 20 |
| PRIMER_INTERNAL_OLIGO_MAX_SIZE = | 35 |

```
PRIMER_INTERNAL_OLIGO_MIN_TM    =    71.7
PRIMER_INTERNAL_OLIGO_OPT_TM    =    72.7
PRIMER_INTERNAL_OLIGO_MAX_TM    =    73.7
PRIMER_INTERNAL_OLIGO_MIN_GC    =    20.0
PRIMER_INTERNAL_OLIGO_MAX_GC    =    80.0
PRIMER_INTERNAL_OLIGO_SELF_ANY  =    12.00
PRIMER_INTERNAL_OLIGO_SELF_END  =    12.00
PRIMER_INTERNAL_OLIGO_NUM_NS    =    0
PRIMER_INTERNAL_OLIGO_MAX_POLY_X =   5
PRIMER_INTERNAL_OLIGO_MISHYB_LIBRARY =
PRIMER_INTERNAL_OLIGO_MAX_MISHYB =   12.00
PRIMER_INTERNAL_OLIGO_MIN_QUALITY =  0
PRIMER_INTERNAL_OLIGO_SALT_CONC =    50.0
PRIMER_INTERNAL_OLIGO_DNA_CONC  =    50.0
PRIMER_IO_WT_TM_LT              =    1.0
PRIMER_IO_WT_TM_GT              =    1.0
PRIMER_IO_WT_SIZE_LT            =    1.0
PRIMER_IO_WT_SIZE_GT            =    1.0
PRIMER_IO_WT_GC_PERCENT_LT      =    0.0
PRIMER_IO_WT_GC_PERCENT_GT      =    0.0
PRIMER_IO_WT_COMPL_ANY          =    0.0
PRIMER_IO_WT_NUM_NS             =    0.0
PRIMER_IO_WT_REP_SIM            =    0.0
PRIMER_IO_WT_SEQ_QUAL           =    0.0
PRIMER_TASK                     =    pick_pcr_
                                     primers_
                                     and_hyb_
                                     probe
PRIMER_PRODUCT_SIZE_RANGE       =    50-150
PRIMER_FIRST_BASE_INDEX         =    1
PRIMER_PICK_ANYWAY              =    1
=
PRIMER_SEQUENCE_ID =>                GUSB
PRIMER_EXPLAIN_FLAG             =    1
PRIMER_MISPRIMING_LIBRARY       =
                                        (SEQ ID NO: 9192)
SEQUENCE = GAAGAGTACCAGAAAAGTCTGCTAGAGCAGTACCATCTG
GGTCTGGATCAAAAACGCAGAAAATATGTGGTTGGAGAGCTCATTTGGAA
TTTTGCCGATTTCATGACTGAACAGTCACCGACGAGAGTGCTGGGGAATA
AAAGGGGATCTTCACTCGGCAGAGACAACCAAAAAGTGCAGCGTTCCTT
TTGCGAGAGAGATACTGGAAGATTGCCAATGAAACCAGGTATCCCCACTC
AGTAGCCAAGTCACAATGTTTGGAAAACAGCCCGTTTACTTGAGCAAGAC
TGATACCACCTGCGTGTCCCTTCCTCCCCGAGTCAGGGCGACTTCCACAG
CAGCAGAACAAGTGCCTCCTGGACTGTTCACGGCAGACCAGAACGTTTCT
GGCCTGGGTTTTGTGGTCATCTATTCTAGCAGGGAACACTAAAGGTGGAA
ATAAAAGATTTTCTATTATGGAAATAAAGAGTTGGCATGAAAGTCGCTAC
TG
PRIMER_PRODUCT_OPT_SIZE         =    100
PRIMER_NUM_RETURN               =    100
PRIMER_MAX_END_STABILITY        =    9.0
PRIMER_MAX_MISPRIMING           =    12.00
PRIMER_PAIR_MAX_MISPRIMING      =    24.00
PRIMER_MIN_SIZE                 =    18
PRIMER_OPT_SIZE                 =    20
PRIMER_MAX_SIZE                 =    32
PRIMER_MIN_TM                   =    61.7
PRIMER_OPT_TM                   =    62.7
PRIMER_MAX_TM                   =    63.7
PRIMER_MAX_DIFF_TM              =    100.0
PRIMER_MIN_GC                   =    20.0
PRIMER_MAX_GC                   =    80.0
PRIMER_SELF_ANY                 =    8.00
PRIMER_SELF_END                 =    3.00
PRIMER_NUM_NS_ACCEPTED          =    0
PRIMER_MAX_POLY_X               =    4
PRIMER_OUTSIDE_PENALTY          =    0
PRIMER_GC_CLAMP                 =    0
PRIMER_SALT_CONC                =    50.0
PRIMER_DNA_CONC                 =    50.0
PRIMER_LIBERAL_BASE             =    1
PRIMER_MIN_QUALITY              =    0
PRIMER_MIN_END_QUALITY          =    0
PRIMER_QUALITY_RANGE_MIN        =    0
PRIMER_QUALITY_RANGE_MAX        =    100
PRIMER_WT_TM_LT                 =    1.0
PRIMER_WT_TM_GT                 =    1.0
PRIMER_WT_SIZE_LT               =    1.0
PRIMER_WT_SIZE_GT               =    1.0
PRIMER_WT_GC_PERCENT_LT         =    0.0
PRIMER_WT_GC_PERCENT_GT         =    0.0
PRIMER_WT_COMPL_ANY             =    0.0
PRIMER_WT_COMPL_END             =    0.0
```

```
-continued
PRIMER_WT_NUM_NS =                        0.0
PRIMER_WT_REP_SIM =                       0.0
PRIMER_WT_SEQ_QUAL =                      0.0
PRIMER_WT_END_QUAL =                      0.0
PRIMER_WT_POS_PENALTY =                   0.0
PRIMER_WT_END_STABILITY =                 0.0
PRIMER_PAIR_WT_PRODUCT_SIZE_LT =          0.05
PRIMER_PAIR_WT_PRODUCT_SIZE_GT =          0.05
PRIMER_PAIR_WT_PRODUCT_TM_LT =            0.0
PRIMER_PAIR_WT_PRODUCT_TM_GT =            0.0
PRIMER_PAIR_WT_DIFF_TM =                  0.0
PRIMER_PAIR_WT_COMPL_ANY =                0.0
PRIMER_PAIR_WT_COMPL_END =                0.0
PRIMER_PAIR_WT_REP_SIM =                  0.0
PRIMER_PAIR_WT_PR_PENALTY =               1.0
PRIMER_PAIR_WT_IO_PENALTY =               0.0
PRIMER_INTERNAL_OLIGO_MIN_SIZE =          18
PRIMER_INTERNAL_OLIGO_OPT_SIZE =          20
PRIMER_INTERNAL_OLIGO_MAX_SIZE =          35
PRIMER_INTERNAL_OLIGO_MIN_TM =            71.7
PRIMER_INTERNAL_OLIGO_OPT_TM =            72.7
PRIMER_INTERNAL_OLIGO_MAX_TM =            73.7
PRIMER_INTERNAL_OLIGO_MIN_GC =            20.0
PRIMER_INTERNAL_OLIGO_MAX_GC =            80.0
PRIMER_INTERNAL_OLIGO_SELF_ANY =          12.00
PRIMER_INTERNAL_OLIGO_SELF_END =          12.00
PRIMER_INTERNAL_OLIGO_NUM_NS =            0
PRIMER_INTERNAL_OLIGO_MAX_POLY_X =        5
PRIMER_INTERNAL_OLIGO_MISHYB_LIBRARY =
PRIMER_INTERNAL_OLIGO_MAX_MISHYB =        12.00
PRIMER_INTERNAL_OLIGO_MIN_QUALITY =       0
PRIMER_INTERNAL_OLIGO_SALT_CONC =         50.0
PRIMER_INTERNAL_OLIGO_DNA_CONC =          50.0
PRIMER_IO_WT_TM_LT =                      1.0
PRIMER_IO_WT_TM_GT =                      1.0
PRIMER_IO_WT_SIZE_LT =                    1.0
PRIMER_IO_WT_SIZE_GT =                    1.0
PRIMER_IO_WT_GC_PERCENT_LT =              0.0
PRIMER_IO_WT_GC_PERCENT_GT =              0.0
PRIMER_IO_WT_COMPL_ANY =                  0.0
```

```
-continued
PRIMER_IO_WT_NUM_NS =                     0.0
PRIMER_IO_WT_REP_SIM =                    0.0
PRIMER_IO_WT_SEQ_QUAL =                   0.0
PRIMER_TASK =                             pick_pcr_
                                          primers_
                                          and_hyb_
                                          probe
PRIMER_PRODUCT_SIZE_RANGE =               50-150
PRIMER_FIRST_BASE_INDEX =                 1
PRIMER_PICK_ANYWAY =                      1
=
```

After running PRIMER3, 100 sets of primers and probes were generated for ACTB and GUSB. From this set, nested primers were chosen based on whether both left primers could be paired with both right primers and a single Taqman probe could be used on an insert of the correct size. With more experience we have decided not use the mix and match approach to primer selection and just use several of the top pairs of predicted primers.

For ACTB this turned out to be:

```
                                                      (SEQ ID NO: 9174)
    Forward 75        CACAATGTGGCCGAGGACTT, (SEQ ID NO: 9175)
    Forward 80        TGTGGCCGAGGACTTTGATT, (SEQ ID NO: 9176)
    Reverse 178       TGGCTTTTAGGATGGCAAGG,
    and (SEQ ID NO: 9177)
    Reverse 168       GGGGGCTTAGTTTGCTTCCT.
```

Upon testing, the F75 and R178 pair worked best.

For GUSB the following primers were chosen:

```
                                                      (SEQ ID NO: 9178)
    Forward 59        AAGTGCAGCGTTCCTTTTGC, (SEQ ID NO: 9179)
    Forward 65        AGCGTTCCTTTTGCGAGAGA, (SEQ ID NO: 9180)
    Reverse 158       CGGGCTGTTTTCCAAACATT,
    and (SEQ ID NO: 9181)
    Reverse 197       GAAGGGACACGCAGGTGGTA.
```

No combination of these GUSB pairs worked well.

In addition to the primer pairs above, Primer Express predicted the following primers for GUSB: Forward 178 TACCACCTGCGTGTCCCTTC (SEQ ID NO: 9182) and Reverse 242 GAGGCACTTGTTCTGCTGCTG (SEQ ID NO: 9183). This pair of primers worked to amplify the GUSB mRNA.

The parameters used to predict these primers in Primer Express were:

Primer Tm: min 58, Max=60, opt 59, max difference=2 degrees

Primer GC: min=20% Max=80% no 3' G/C clamp

Primer: Length: min=9 max=40 opt=20

Amplicon: min Tm=0 max Tm=85
 min=50 bp max=150 bp

Probe: Tm 10 degrees>primers, do not begin with a G on 5' end

Other: max base pair repeat=3
 max number of ambiguous residues 0
 secondary structure: max consec bp 4, max total bp=8
 Uniqueness: max consec match=9
  max % match=75
  max 3' consecutive match=7

Granzyme B is an important marker of CMV infection and transplant rejection. Tables 13 A and B.

For Granzyme B the following sequence (NM_004131) was used as input for Primer3:

```
                                         (SEQ ID NO: 9184)
GGGGACTCTGGAGGCCCTCTTGTGTGTAACAAGGTGGCCCAGGGCATTGT

CTCCTATGGACGAAACAATGGCATGCCTCCACGAGCCTGCACCAAAGTCT

CAAGCTTTGTACACTGGATAAAGAAAACCATGAAACGCTACTAACTACAG

GAAGCAAACTAAGCCCCGCTGTAATGAAACACCTTCTCTGGAGCCAAGT

CCAGATTTACACTGGGAGAGGTGCCAGCAACTGAATAAATACCTCTCCCA

GTGTAAATCTGGAGCCAAGTCCAGATTTACACTGGGAGAGGTGCCAGCAA

CTGAATAAATACCTCTTAGCTGAGTGG
```

For Granzyme B the following primers were chosen for testing:

```
                       (SEQ ID NO: 9185)
Forward 81    ACGAGCCTGCACCAAAGTCT (SEQ ID NO: 9186)
Forward 63    AAACAATGGCATGCCTCCAC (SEQ ID NO: 9187)
Reverse 178   TCATTACAGCGGGGCTTAG (SEQ ID NO: 9188)
Reverse 168   GGGGGCTTAGTTTGCTTCCT
```

Testing demonstrated that F81 and R178 worked well.

Using this approach, multiple primers were designed for genes that were shown to have expression patterns that correlated with clinical data in examples 17 and 24. These primer pairs are shown in Tables 13B and 14B and are added to the sequence listing. Primers can be designed from any region of a target gene using this approach.

Primer Endpoint Testing

Primers were first tested to examine whether they would produce the correct size product without non-specific amplification. The standard real-time PCR protocol was used without the Rox and Sybr green dyes. Each primer pair was tested on cDNA made from universal mononuclear leukocyte reference RNA that was produced from 50 individuals as described in Example 9 (R50).

The PCR reaction consisted of 1× RealTime PCR Buffer (Ambion, Austin, Tex.), 3 mM MgCl2 (Applied BioSystems, B02953), 0.2 mM dATP (NEB), 0.2 mM dTTP (NEB), 0.2 mM dCTP (NEB), 0.2 mM dGTP (NEB), 1.25 U AmpliTaq Gold (Applied BioSystems, Foster City, Calif.), 0.3 µM of each primer to be used (Sigma Genosys, The Woodlands, Tex.), 5 µl of the R50 reverse-transcription reaction and water to a final volume of 19 µl.

Following 40 cycles of PCR, one microliter of the product was examined by agarose gel electrophoresis and on an Agilent Bioanalyzer, DNA 1000 chip (Palo Alto, Calif.). Results for 2 genes are shown in FIG. 11. From the primer design and the sequence of the target gene, one can calculate the expected size of the amplified DNA product. Only primer pairs with amplification of the desired product and minimal amplification of contaminants were used for real-time PCR. Primers that produced multiple products of different sizes are likely not specific for the gene of interest and may amplify multiple genes or chromosomal loci.

Primer Optimization/Efficiency

Once primers passed the end-point PCR, the primers were tested to determine the efficiency of the reaction in a real-time PCR reaction. cDNA was synthesized from starting total RNA as described above. A set of 5 serial dilutions of the R50 reverse-transcribed cDNA (as described above) were made in water: 1:10, 1:20, 1:40, 1:80, and 1:160.

The Sybr Green real-time PCR reaction was performed using the Taqman PCR Reagent kit (Applied BioSystems, Foster City, Calif., N808-0228). A master mix was made that consisted of all reagents except the primes and template. The final concentration of all ingredients in the reaction was 1× Taqman Buffer A (Applied BioSystems), 2 mM MgCl2 (Applied BioSystems), 200 µM dATP (Applied BioSystems), 200 µM dCTP (Applied BioSystems), 200 µM dGTP (Applied BioSystems), 400 µM dUTP (Applied BioSystems), 1:400,000 diluted Sybr Green dye (Molecular Probes), 1.25 U AmpliTaq Gold (Applied BioSystems). The master mix for 92 reactions was made to a final volume of 2112 µl. 1012 µl of PCR master mix was dispensed into two, light-tight tubes. Each β-Actin primer F75 and R178 (Genosys), was added to one tube of PCR master mix and Each β-GUS primer F178 and R242 (Genosys), was added to the other tube of PCR master mix to a final primer concentration of 300 nM, and a final volume of 1035 µl per reaction tube. 45 µl of the β-Actin master mix was dispensed into 23 wells, in a 96 well plate (Applied BioSystems). 45 µl of the β-GUS master mix was dispensed into 23 wells, in a 96 well plate (Applied BioSystems). 5 µl of the template dilution series was dispensed into triplicate wells for each primer. The reaction was run on an ABI 7700 Sequence Detector (Applied BioSystems).

The Sequence Detector v1.7 software was used to analyze the fluorescent signal from each well. A threshold value was selected that allowed most of the amplification curves to cross the threshold during the linear phase of amplification. The cycle number at which each amplification curve crossed the threshold ($C_T$) was recorded and the file transferred to MS Excel for further analysis. The $C_T$ values for triplicate wells were averaged. The data were plotted as a function of the $\log_{10}$ of the calculated starting concentration of RNA. The starting RNA concentration for each cDNA dilution was determined based on the original amount of RNA used in the RT reaction, the dilution of the RT reaction, and the amount used (5 µl) in the real-time PCR reaction. For each gene, a linear regression line was plotted through all of the dilutions series points. The slope of the line was used to calculate the efficiency of the reaction for each primer set using the equation:

$$E=10^{(-1/slope)}$$

Using this equation (Pfaffl 2001), the efficiency for these β-actin primers is 2.28 and the efficiency for these β-GUS primers is 2.14 (FIG. 12). This efficiency was used when comparing the expression levels among multiple genes and multiple samples. This same method was used to calculate reaction efficiency for primer pairs for each gene we studied.

Assay and Results

Once primers were designed and tested and efficiency analysis was completed, primers were used examine expression of a single gene among many clinical samples. The basic design was to examine expression of both the experimental gene and a reference gene in each sample and, at the same time, in a control sample. The control sample we used was the universal mononuclear leukocyte reference RNA described in example 9 (R50).

In this example, three patient samples from patients with known CMV infection were compared to three patient samples from patients with no diagnosis of CMV infection based on standard diagnostic algorithms for active CMV infection (including viral PCR assays, serologies, culture and other tests). cDNA was made from all six RNA samples and the R50 control as described above. The cDNA was diluted 1:10 in water and 5 µl of this dilution was used in the 50 µl PCR reaction. Each 96-well plate consisted of 32 reactions, each done in triplicate. There were 17 templates and 3 primer sets. The three primer sets were β-GUS, β-Actin, and Granzyme B. The β-GUS and β-Actin primers are shown above and the Granzyme B primers were:

```
F81:   ACGAGCCTGCACCAAAGT,     SEQ ID NO: 9189

R178:  TCATTACAGCGGGGCTT,      SEQ ID NO: 9190
```

Each of the three primer sets was used to measure template levels in 8 templates: the six experimental samples, R50, and water (no-template control). The β-GUS primers were also used to measure template levels a set of 8 templates identical except for the absence of the reverse transcriptase enzyme in the cDNA synthesis reaction (−RT). The real-time PCR reactions were performed as described above in "primer optimization/efficiency".

The β-GUS amplification with +RT and −RT cDNA synthesis reaction templates were compared to measure the amount of genomic DNA contamination of the patient RNA sample (FIG. 10A). The only source of amplifiable material in the −RT cDNA synthesis reaction is contaminating genomic DNA. Separation by at least four $C_T$ between the −RT and +RT for each sample was required to consider the sample useful for analysis of RNA levels. Since a $C_T$ decrease of one is a two-fold increase in template, a difference of four $C_T$ would indicate that genomic DNA contamination level in the +RT samples was 6.25% of the total signal. Since we used these reactions to measure 30% or greater differences, a 6% contamination would not change the result.

For samples with sufficiently low genomic DNA contamination the data were used to identify differences in gene expression by measuring RNA levels. $C_T$ values from the triplicate wells for each reaction were averaged and the coefficient of variation (CV) determined. Samples with high CV (>2%) were examined and outlier reaction wells were discarded from further analysis. The average of the wells for each sample was taken as the $C_T$ value for each sample. For each gene, the $\Delta C_T$ was the R50 control $C_T$ minus the sample $C_T$. The equation below was then used to identify an expression ratio compared to a reference gene (β-Actin) and control sample (R50) for Granzyme B expression in each experimental sample (Pfaffl, M. W. 2001). E is the amplification efficiency determined above.

$$\text{ratio} = \frac{(E_{target})^{\Delta C_T target(control-sample)}}{(E_{ref})^{\Delta C_T ref(control-sample)}}$$

The complete experiment was performed in duplicate and the average of the two ratios taken for each gene. When β-Actin was used as the reference gene, the data show that Granzyme B is expressed at 25-fold higher levels in mononuclear cell RNA from patients with CMV than from patients without CMV (FIG. 10B). In this graph, each circle represents a patient sample and the black bars are the average of the three samples in each category.

Example 26

Correlation and Classification Analysis

After generation and processing of expression data sets from microarrays as described in Example 23, a log ratio value is used for most subsequent analysis. This is the logarithm of the expression ratio for each gene between sample and universal reference. The processing algorithm assigns a number of flags to data that are of low signal to noise or are in some other way of uncertain quality. Correlation analysis can proceed with all the data (including the flagged data) or can be done on filtered data sets where the flagged data is removed from the set. Filtered data should have less variability and may result in more significant results. Flagged data contains all information available and may allow discovery of genes that are missed with the filtered data set.

In addition to expression data, clinical data are included in the analysis. Continuous variables, such as the ejection fraction of the heart measured by echocardiography or the white blood cell count can be used for correlation analysis. In some cases, it may be desirable to take the logarithm of the values before analysis. These variables can be included in an analysis along with gene expression values, in which case they are treated as another "gene". Sets of markers can be discovered that work to diagnose a patient condition and these can include both genes and clinical parameters. Categorical variables such as male or female can also be used as variables for correlation analysis. For example, the sex of a patient may be an important splitter for a classification tree.

Clinical data are used as supervising vectors for the significance or classification analysis. In this case, clinical data associated with the samples are used to divide samples in to clinically meaningful diagnostic categories for correlation or classification analysis. For example, pathologic specimens from kidney biopsies can be used to divide lupus patients into groups with and without kidney disease. A third or more categories can also be included (for example "unknown" or "not reported"). After generation of expression data and definition of using supervising vectors, correlation, significance and classification analysis is used to determine which set of genes are most appropriate for diagnosis and classification of patients and patient samples.

Significance Analysis for Microarrays (SAM)

Significance analysis for microarrays (SAM) (Tusher 2001) is a method through which genes with a correlation between their expression values and the response vector are statistically discovered and assigned a statistical significance. The ratio of false significant to significant genes is the False Discovery Rate (FDR). This means that for each threshold there are a set of genes which are called significant, and the FDR gives a confidence level for this claim. If a gene is called differentially expressed between 2 classes by SAM, with a FDR of 5%, there is a 95% chance that the gene is actually differentially expressed between the classes. SAM takes into account the variability and large number of variables of microarrays. SAM will identify genes that are most globally differentially expressed between the classes. Thus, important genes for identifying and classifying outlier samples or patients may not be identified by SAM.

After generation of data from patient samples and definition of categories using clinical data as supervising vectors, SAM is used to detect genes that are likely to be differentially expressed between the groupings. Those genes with the highest significance can be validated by real-time PCR (Example 25) or can be used to build a classification algorithm as described here.

Classification

Supervised harvesting of expression trees (Hastie et al. 2001) identifies genes or clusters that best distinguish one class from all the others on the data set. The method is used to identify the genes/clusters that can best separate one class versus all the others for datasets that include two or more classes from each other. This algorithm can be used to identify genes that are used to create a diagnostic algorithm. Genes that are identified can be used to build a classification tree with algorithms such as CART.

CART is a decision tree classification algorithm (Breiman 1984). From gene expression and or other data, CART can develop a decision tree for the classification of samples. Each node on the decision tree involves a query about the expression level of one or more genes or variables. Samples that are above the threshold go down one branch of the decision tree and samples that are not go down the other branch. Genes from expression data sets can be selected for classification building using CART by significant differential expression in SAM analysis (or other significance test), identification by supervised tree-harvesting analysis, high fold change between sample groups, or known relevance to classification of the target diseases. In addition, clinical data can also be used as variables for CART that are of know importance to the clinical question or are found to be significant predictors by multivariate analysis or some other technique. CART identifies surrogates for each splitter (genes that are the next best substitute for a useful gene in classification). Analysis is performed in CART by weighting misclassification costs to optimize desired performance of the assay. For example, it may be most important the sensitivity of a test for a given diagnosis be near 100% while specificity is less important.

Once a set of genes and expression criteria for those genes have been established for classification, cross validation is done. There are many approaches, including a 10 fold cross validation analysis in which 10% of the training samples are left out of the analysis and the classification algorithm is built with the remaining 90%. The 10% are then used as a test set for the algorithm. The process is repeated 10 times with 10% of the samples being left out as a test set each time. Through this analysis, one can derive a cross validation error which helps estimate the robustness of the algorithm for use on prospective (test) samples. When a gene set is established for a diagnosis with a low cross validation error, this set of genes is tested using samples that were not included in the initial analysis (test samples). These samples may be taken from archives generated during the clinical study. Alternatively, a new prospective clinical study can be initiated, where samples are obtained and the gene set is used to predict patient diagnoses.

Lengthy table referenced here

US07829286-20101109-T00001

Please refer to the end of the specification for access instructions.

Lengthy table referenced here

US07829286-20101109-T00002

Please refer to the end of the specification for access instructions.

Lengthy table referenced here

US07829286-20101109-T00003

Please refer to the end of the specification for access instructions.

Lengthy table referenced here

US07829286-20101109-T00004

Please refer to the end of the specification for access instructions.

Lengthy table referenced here

US07829286-20101109-T00005

Please refer to the end of the specification for access instructions.

Lengthy table referenced here

US07829286-20101109-T00006

Please refer to the end of the specification for access instructions.

Lengthy table referenced here

US07829286-20101109-T00007

Please refer to the end of the specification for access instructions.

Lengthy table referenced here

US07829286-20101109-T00008

Please refer to the end of the specification for access instructions.

Lengthy table referenced here
US07829286-20101109-T00009
Please refer to the end of the specification for access instructions.

Lengthy table referenced here
US07829286-20101109-T00010
Please refer to the end of the specification for access instructions.

Lengthy table referenced here
US07829286-20101109-T00011
Please refer to the end of the specification for access instructions.

Lengthy table referenced here
US07829286-20101109-T00012
Please refer to the end of the specification for access instructions.

Lengthy table referenced here
US07829286-20101109-T00013
Please refer to the end of the specification for access instructions.

Lengthy table referenced here
US07829286-20101109-T00014
Please refer to the end of the specification for access instructions.

Lengthy table referenced here
US07829286-20101109-T00015
Please refer to the end of the specification for access instructions.

Lengthy table referenced here
US07829286-20101109-T00016
Please refer to the end of the specification for access instructions.

Lengthy table referenced here
US07829286-20101109-T00017
Please refer to the end of the specification for access instructions.

Lengthy table referenced here
US07829286-20101109-T00018
Please refer to the end of the specification for access instructions.

Lengthy table referenced here
US07829286-20101109-T00019
Please refer to the end of the specification for access instructions.

Lengthy table referenced here
US07829286-20101109-T00020
Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US07829286B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07829286B2). An electronic copy of the "Sequence Listing" will also be available from the USPTO upon request and payment of the fee set forth in 37 CFR 1.19(b)(3).

We claim:

1. A method of diagnosing or monitoring cardiac transplant rejection in a patient, comprising detecting the expression level of a nucleic acid in said patient to diagnose or monitor cardiac transplant rejection in said patient wherein said nucleic acid comprises the nucleotide sequence SEQ ID NO: 176.

2. The method of claim 1 wherein said expression level is detected by measuring the RNA level expressed by said nucleic acid.

3. The method of claim 2, further including isolating RNA from said patient prior to detecting said RNA level expressed by said nucleic acid.

4. The method of claim 2 wherein said RNA level is detected by PCR.

5. The method of claim 2 wherein said RNA level is detected by hybridization.

6. The method of claim 2 wherein said RNA level is detected by hybridization to an oligonucleotide.

7. The method of claim 6 wherein said oligonucleotide comprises DNA, RNA, cDNA, PNA, genomic DNA, or synthetic oligonucleotides.

* * * * *